United States Patent
Moon et al.

(10) Patent No.: US 11,219,673 B2
(45) Date of Patent: Jan. 11, 2022

(54) COMPOSITIONS AND METHODS FOR DELIVERY OF BIOMACROMOLECULE AGENTS

(71) Applicant: The Regents of the University of Michigan, Ann Arbor, MI (US)

(72) Inventors: James J. Moon, Ann Arbor, MI (US); Rui Kuai, Ann Arbor, MI (US); Anna A. Schwendeman, Ann Arbor, MI (US); Jutaek Nam, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 15/561,374

(22) PCT Filed: Mar. 25, 2016

(86) PCT No.: PCT/US2016/024233
§ 371 (c)(1),
(2) Date: Sep. 25, 2017

(87) PCT Pub. No.: WO2016/154544
PCT Pub. Date: Sep. 29, 2016

(65) Prior Publication Data
US 2018/0078625 A1    Mar. 22, 2018

Related U.S. Application Data

(60) Provisional application No. 62/248,908, filed on Oct. 30, 2015, provisional application No. 62/138,186, filed on Mar. 25, 2015.

(51) Int. Cl.

| | |
|---|---|
| *A61K 47/69* | (2017.01) |
| *A61K 39/00* | (2006.01) |
| *A61K 9/127* | (2006.01) |
| *A61K 31/713* | (2006.01) |
| *A61K 47/54* | (2017.01) |
| *A61K 31/712* | (2006.01) |
| *C12N 15/11* | (2006.01) |
| *A61K 31/7088* | (2006.01) |
| *A61K 45/06* | (2006.01) |
| *C12N 15/113* | (2010.01) |

(52) U.S. Cl.
CPC .......... *A61K 39/0011* (2013.01); *A61K 9/127* (2013.01); *A61K 31/7088* (2013.01); *A61K 31/712* (2013.01); *A61K 31/713* (2013.01); *A61K 39/00111* (2018.08); *A61K 39/001106* (2018.08); *A61K 39/001132* (2018.08); *A61K 39/001151* (2018.08); *A61K 39/001156* (2018.08); *A61K 39/001157* (2018.08); *A61K 39/001162* (2018.08); *A61K 39/001164* (2018.08); *A61K 39/001166* (2018.08); *A61K 39/001176* (2018.08); *A61K 39/001181* (2018.08); *A61K 39/001182* (2018.08); *A61K 39/001184* (2018.08); *A61K 39/001186* (2018.08); *A61K 39/001188* (2018.08); *A61K 39/001189* (2018.08); *A61K 39/001191* (2018.08); *A61K 39/001192* (2018.08); *A61K 39/001193* (2018.08); *A61K 39/001194* (2018.08); *A61K 39/001195* (2018.08); *A61K 39/001197* (2018.08); *A61K 45/06* (2013.01); *A61K 47/554* (2017.08); *A61K 47/6917* (2017.08); *C12N 15/111* (2013.01); *C12N 15/113* (2013.01); *C12N 2310/14* (2013.01); *C12N 2310/3515* (2013.01); *C12N 2320/32* (2013.01)

(58) Field of Classification Search
CPC .................................................. A61K 39/0011
See application file for complete search history.

(56) References Cited

U.S. PATENT DOCUMENTS

| | | | |
|---|---|---|---|
| 6,004,925 A * | 12/1999 | Dasseux | ............ A61K 38/1709 514/21.3 |
| 8,598,339 B2 | 12/2013 | Timmermann et al. | |
| 8,747,869 B2 | 6/2014 | Irvine | |
| 9,115,402 B2 * | 8/2015 | Hacohen | ............ C12Q 1/6886 |
| 2002/0012998 A1 | 1/2002 | Gonda et al. | |
| 2003/0008827 A1 | 1/2003 | Dasseux et al. | |

(Continued)

FOREIGN PATENT DOCUMENTS

| | | |
|---|---|---|
| EP | 0092453 | 9/1987 |
| WO | 2002/057780 | 7/2002 |

(Continued)

OTHER PUBLICATIONS

Stano et al (Biomaterials, 2013, 34: 4339-4346).*

(Continued)

*Primary Examiner* — Sean E Aeder

(74) *Attorney, Agent, or Firm* — Casimir Jones, S.C.; Robert A. Goetz

(57) ABSTRACT

The present invention relates to nanoparticles complexed with biomacromolecule agents configured for treating, preventing or ameliorating various types of disorders, and methods of synthesizing the same. In particular, the present invention is directed to compositions comprising nanoparticles (e.g., synthetic high density lipoprotein (sHDL)) carrying biomacromolecule agents (e.g., nucleic acid, peptides, glycolipids, etc.), methods for synthesizing such nanoparticles, as well as systems and methods utilizing such nanoparticles (e.g., in diagnostic and/or therapeutic settings).

7 Claims, 34 Drawing Sheets
Specification includes a Sequence Listing.

(56) References Cited

U.S. PATENT DOCUMENTS

| | | | |
|---|---|---|---|
| 2004/0157253 | A1 | 8/2004 | Xu et al. |
| 2005/0226950 | A1 | 10/2005 | Sangwan |
| 2006/0154867 | A1 | 7/2006 | Sokoloff et al. |
| 2007/0110813 | A1 | 5/2007 | Ingenito et al. |
| 2009/0104268 | A1 | 4/2009 | Himmler et al. |
| 2009/0209458 | A1 | 8/2009 | Hawiger et al. |
| 2011/0065644 | A1 | 3/2011 | Xiet et al. |
| 2011/0305719 | A1 | 12/2011 | Naziruddin et al. |
| 2012/0016009 | A1 | 1/2012 | Fitzgerald et al. |
| 2012/0021050 | A1 | 1/2012 | Zhou et al. |
| 2012/0129916 | A1 | 5/2012 | Peer |
| 2012/0196815 | A1 | 8/2012 | Timmermann |
| 2012/0232005 | A1 | 9/2012 | Dasseux et al. |
| 2013/0034599 | A1 | 2/2013 | Thaxton et al. |
| 2013/0197055 | A1 | 8/2013 | Kamens et al. |
| 2014/0038894 | A1 | 2/2014 | Corrigan et al. |
| 2014/0045950 | A1 | 2/2014 | Lacko et al. |
| 2014/0121263 | A1 | 5/2014 | Fitzgerald et al. |
| 2014/0199241 | A1 | 7/2014 | Yedgar |
| 2016/0101170 | A1 | 4/2016 | Hacohen et al. |

FOREIGN PATENT DOCUMENTS

| | | |
|---|---|---|
| WO | WO 03/099261 | 12/2003 |
| WO | WO 2004/018066 | 3/2004 |
| WO | 2009/051837 | 4/2009 |
| WO | 2009/143280 | 11/2009 |
| WO | 2010/009277 | 1/2010 |
| WO | 2011/143656 | 11/2011 |
| WO | WO 2012/149563 | 11/2012 |
| WO | WO 2013/126776 | 8/2013 |
| WO | 2014/168874 | 10/2014 |
| WO | WO 2015/034360 | 3/2015 |
| WO | WO 2016/011049 | 1/2016 |
| WO | 2017/223085 | 12/2017 |

OTHER PUBLICATIONS

Gyongyossy-Issa et al (Archives of Biochemistry and Biophysics, 1998, 353(1): 101-108).*

Antipina, Maria N. et al. "Studies of nanoscale structural ordering in planar DNA complexes with amphiphilic mono- and polycations" Surface Science, 2003, vols. 532-535, pp. 1025-1033.

Ambardekar et al. "The Modification of siRNA with 3/ Cholesterol to Increase Nuclease Protection and Suppression of Native mRNA by Select siRNA Polyplexes" Biomaterials, Feb. 2011, vol. 32, No. 5, pp. 1-20.

Banchereau J, et al., "Dendritic cells as therapeutic vaccines against cancer." Nat Rev Immunol. 2005;5(4):296-306.

Chen et al. "Enhanced Nasal Mucosal Delivery and Immunogenicity of Anti-Caries DNA Vaccine through Incorporation of Anionic Liposomes in Chitosan/DNA Complexes" PLOS One, Aug. 2013, vol. 8, Issue 8, 1-13.

Eliaz et al., "Liposome-encapsulated Doxorubicin Targeted to CD44" 2001, Cancer Res. 61:2592-2601.

Fan et al. "Cationic liposome-hyaluronic acid hybrid nanoparticles for intranasal vaccination with subunit antigens" Journal of Controlled Release, Apr. 11, 2015, vol. 208, pp. 121-129.

Fourcade, J. et al. "Immunization with analogue peptide in combination with CpG and Montanide expands tumor antigen-specific CD8+ T cells in melanoma patients" J. Immunother. 31, 781-791 (2008).

Ghaghada et al. "High-resolution Vascular Imaging of the Rat Spine Using Liposomal Blood Pool MR Agent" American Journal of Neuroradiology. Jan. 2007; vol. 28, No. 1; pp. 48-53, p. 48, col. 2, paragraph 2.

Holland et al., "Poly(ethylene glycol)—Lipid Conjugates Regulate the Calium-Induced Fusion of Liposomes Composed of Phosphatidylethanolamine and Phosphatidylserine" 1996, Biochem. 35:2618-2624.

Hutcheon et al., "Controlled destabilization of a liposomal drug delivery system enhances mitoxantrone antitumor activity." 1999, Biotechnol. 17:775-779.

International Search Report & Written Opinion, International Patent Application No. PCT/US2016/024233, dated Aug. 29, 2016.

International Search Report & Written Opinion, International Patent Application No. PCT/US2017/014070, dated Aug. 3, 2017.

International Search Report & Written Opinion, International Patent Application No. PCT/US2017/038333, dated Nov. 24, 2017.

International Search Report & Written Opinion, International Patent Application No. PCT/US2017/040404, dated Feb. 2, 2016.

International Search Report, International Patent Application No. PCT/US2016/015404, dated Apr. 11, 2016.

International Search Report, International Patent Application No. PCT/US2016/062250, dated Mar. 30, 2017.

Kreiter, S. et al. "Mutant MHC class II epitopes drive therapeutic immune responses to cancer" Nature 520, 692-696 (2015).

Marrache et al. Biodegradable Synthetic High-Density Lipoprotein Nanoparticles for Atherosclerosis, Proceedings of the Naitonal Academy of Sciences of the United States of America. May 13, 2013; vol. 110, No. 23, pp. 9445-9450.

Matsuo K, et al., "A low-invasive and effective transcutaneous immunization system using a novel dissolving microneedle array for soluble and particulate antigens." J Control Release. 2012;161(1):10-7.

Mero et al. "Hyaluronic Acid Bioconjugates for the Delivery of Bioactive Molecules," Polymers, Jan. 30, 2014, vol. 6, pp. 346-369.

Moon et al. "Interbilayer-Crosslinked Multilameller Vesicles as Synthetic Vaccines for Potent Humoral and Cellular Immune Responses" Nat. Mater. Mar. 1, 2011, vol. 10, No. 3, pp. 243-251.

O'Brien et al., "Polymerization of Preformed Self-Organized Assemblies" 1998, Acc. Chem. Res. 31:861-868.

Papahadjopoulos D. et al., "Sterically stabilised liposomes: Improvements in pharmacokinetics, tissue disposition and anti-tumour therapeutic efficacy."1991, Proc. Natl. Acad. Sci. 88:11460-11464.

Ringsdorf et al., "Molecular Architecture and Function of Polymeric Oriented Systems: Models for the Study of Organization, Surface Recognition, and Dynamics of Biomembranes" 1988, Angew. Chem. Int. Ed. 27:113-158.

Ruponen et al. "Interactions of polymeric and liposomal gene delivery systems with extracellular glycosaminoglycans: physicochemical and transfection studes" Biochimica et Biophysica Acta (1999) 1415, 331-341.

Saade F, et al., "A novel hepatitis B vaccine containing Advax, a polysaccharide adjuvant derived from delta inulin, induces robust humoral and cellular immunity with minimal reactogenicity in preclinical testing." Vaccine. 2013;31(15):1999-2007.

Sahdev et al. "Biomaterials for Nanoparticle Vaccine Delivery Systems," Pharm. Res. Oct. 16, 2014, vol. 31, No. 10, pp. 2563-2582.

Schmitz T, et al. "Synthesis and characterization of a chitosan-N-acetyl cysteine conjugate." Int J Pharm. 2008;347(1-2):79-85.

Schumacher, T.N. & Schreiber, R.D. "Neoantigens in cancer immunotherapy." Science 348, 69-74 (2015).

Silvius et al., "Interbilayer transfer of phospholipid-anchored macromolecules via monomer diffusion." 1993, Biochem. 32:3153-3161.

Speiser, D.E. et al. "Rapid and strong human CD8+ T cell responses to vaccination with peptide, IFA, and CpG oligodeoxynucleotide 7909." J. Clin. Invest. 115, 739-746 (2005).

Torchilin, 2005, "Recent advances with liposomes as pharmaceutical carriers." Nat. Rev. Drug Discov. 4:145-160.

Yadav, M. et al. "Predicting immunogenic tumour mutations by combining mass spectrometry and exome sequencing." Nature 515, 572-576 (2014).

European Search Report, EP Patent Application No. 16769774.7, dated Jan. 30, 2019.

Rajasagi, M. et al. "Systematic identification of personal tumor-specific neoantigens in chronic lymphocytic leukemia" Blood, vol. 124, No. 3, Jun. 2, 2014, pp. 453-462.

Zhao, Yannan et al. "Mimicry of High-Density Lipoprotein: Functional Peptide-Lipid Nanoparticles Based on Multivalent Peptide

(56) References Cited

OTHER PUBLICATIONS

Constructs", Journal of the American Chemical Society, vol. 135, No. 36, Aug. 2013, pp. 13414-13424.

Tatsuya, Murakami "Phospholipid nanodisc engineering for drug delivery systems" Biotechnology Journal, vol. 7, No. 6, Jun. 2012, pp. 762-767.

* cited by examiner

FIG. 1F
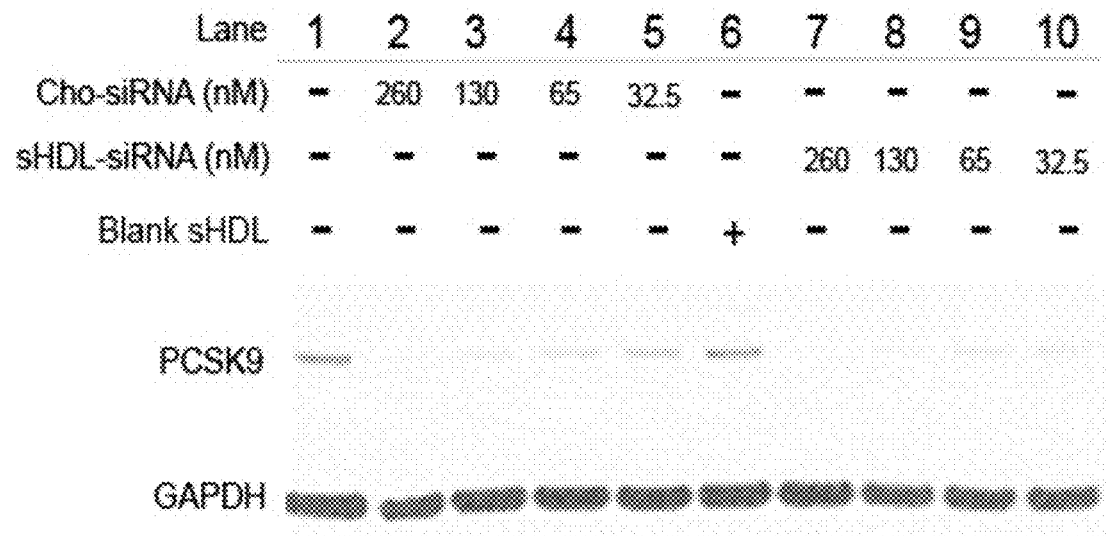
FIG. 2A                              FIG. 2B
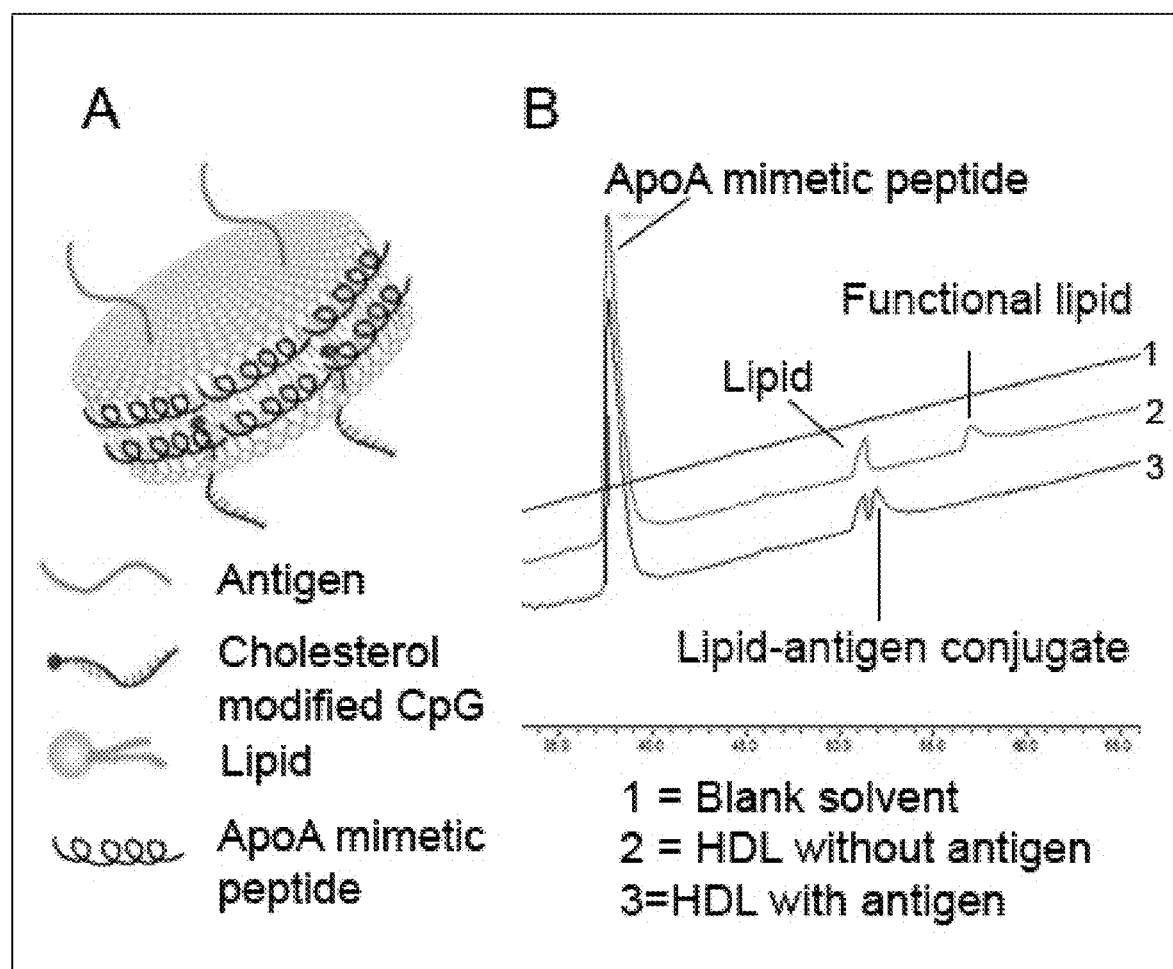

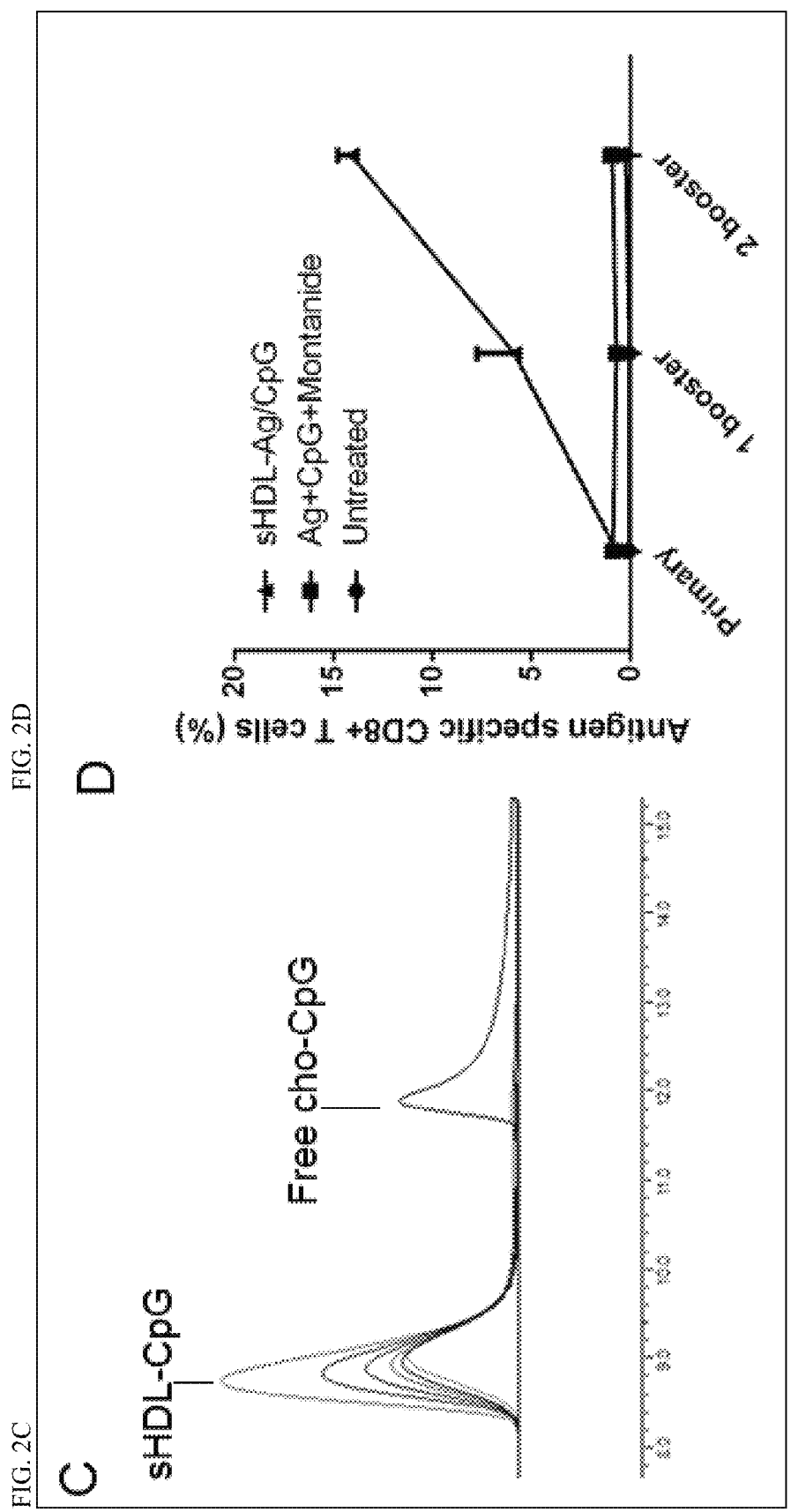

FIG. 4
Homogeneous particle size of sHDL-Ag/CpG as analyzed by cryoEM and dynamic light scattering
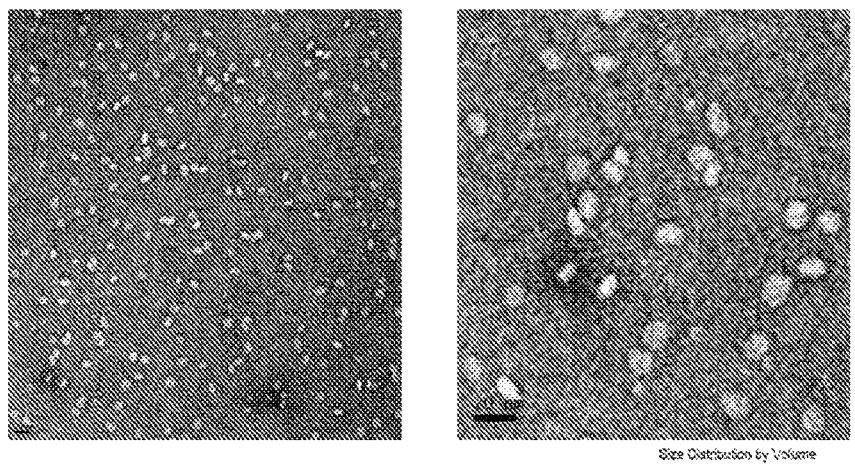
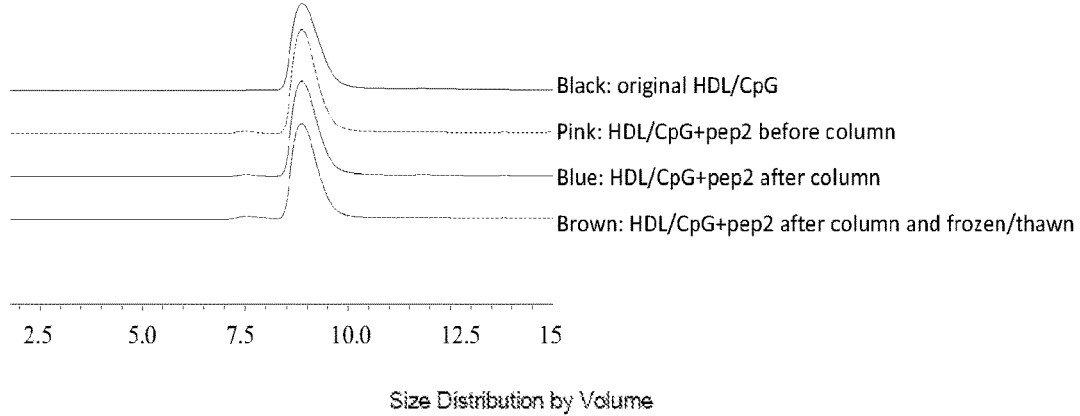
Black: original HDL/CpG
Pink: HDL/CpG+pep2 before column
Blue: HDL/CpG+pep2 after column
Brown: HDL/CpG+pep2 after column and frozen/thawn
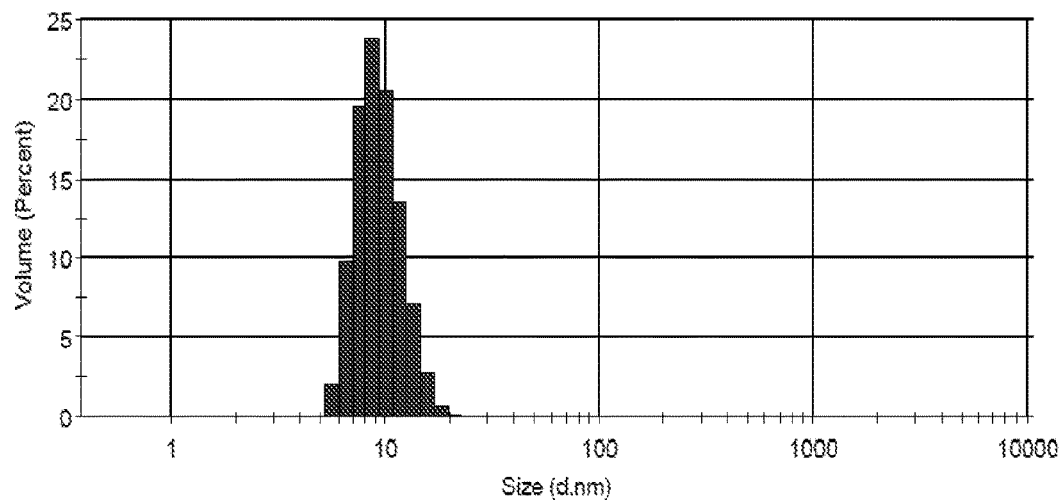

Compared with free soluble form, alpha-GalCer delivered via sHDL significantly enhances CD1d presentation on antigen-presenting cells sHDL was better than free aGC, but similar to liposomes; DOTAP didn't significantly affect the result.

Lyophilization offers a convenient method of large-scale synthesis of sHDL loaded with alpha-GalCer.

Effect of sHDL preparation method on aGC-CD1d level

FIG. 13 a

| | Sample ID | Sequence | Size (d. nm) | PDI |
|---|---|---|---|---|
| (SEQ ID NO: 4) | 22A | PVLDLFRELLNELLEALKQKLK | 10.6 ± 0.2 | 0.18 ± 0.01 |
| (SEQ ID NO: 75) | 22A-1 | PVLDEFREKLNEELEALKQKLK | N.D. | N.D. |
| (SEQ ID NO: 1) | 22A-2 | PVLDLFRELLNELLEZLKQKLK | 25.6 ± 2.7 | 0.28 ± 0.10 |
| (SEQ ID NO: 15) | 22A-3 | PVLDLFRELWNELLEALKQKLK | 13.5 ± 0.5 | 0.25 ± 0.03 |
| (SEQ ID NO: 28) | 22A-4 | PVLDLFRELLNELWEALKQKLK | 14.3 ± 0.2 | 0.29 ± 0.01 |
| (SEQ ID NO: 35) | 22A-5 | PVLDWFRELLNELLEALKQKLK | 20.2 ± 2.2 | 0.27 ± 0.06 |
| (SEQ ID NO: 54) | 22A-6 | PVLDLFRELLNEWLEALKQKLK | 13.9 ± 0.2 | 0.29 ± 0.01 |
| (SEQ ID NO: 79) | 22A-7 | PVLDEFRELLNELLEALKQKLK | 13.6 ± 1.8 | 0.38 ± 0.10 |
| (SEQ ID NO: 106) | 22A-8 | PVLDLFREKLNEELEALKQKLK | N.D. | N.D. |
| (SEQ ID NO: 99) | 22A-9 | KLKQKLAELLENLLERFLDLVP | N.D. | N.D. |
| (SEQ ID NO: 4) | 22A-10 | PVLDLFRELLNELLEALKQKLK (D-amino acids) | 10.8 ± 0.3 | 0.19 ± 0.01 |

4°C (stored for one month)

b

| | | | | | | |
|---|---|---|---|---|---|---|
| DOPC | + | - | - | - | - | - |
| POPC | - | + | - | - | - | - |
| DMPC | - | - | + | - | + | - |
| DPPC | - | - | - | + | - | + |
| 22A | + | + | + | + | - | - |

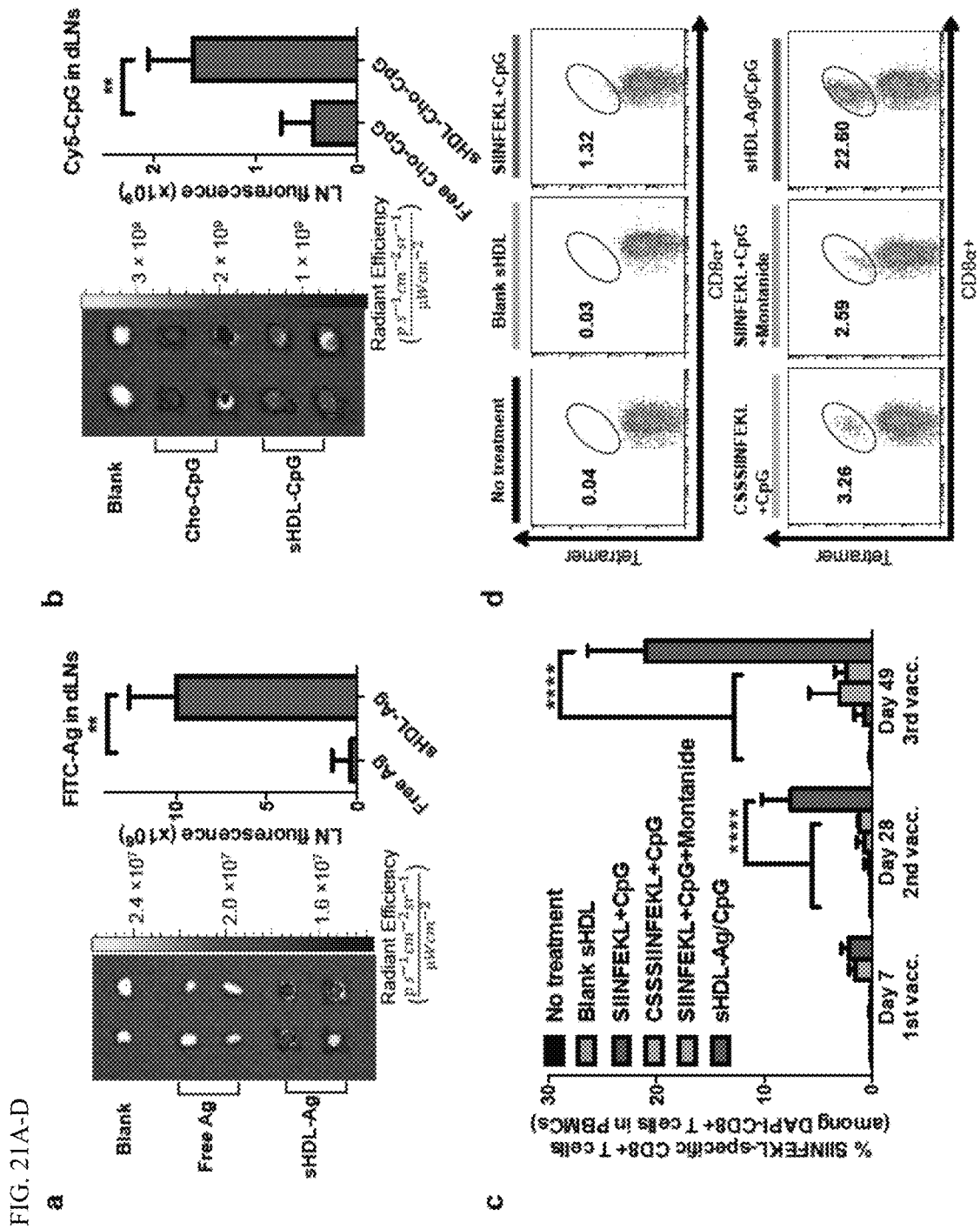
FIG. 21A-D

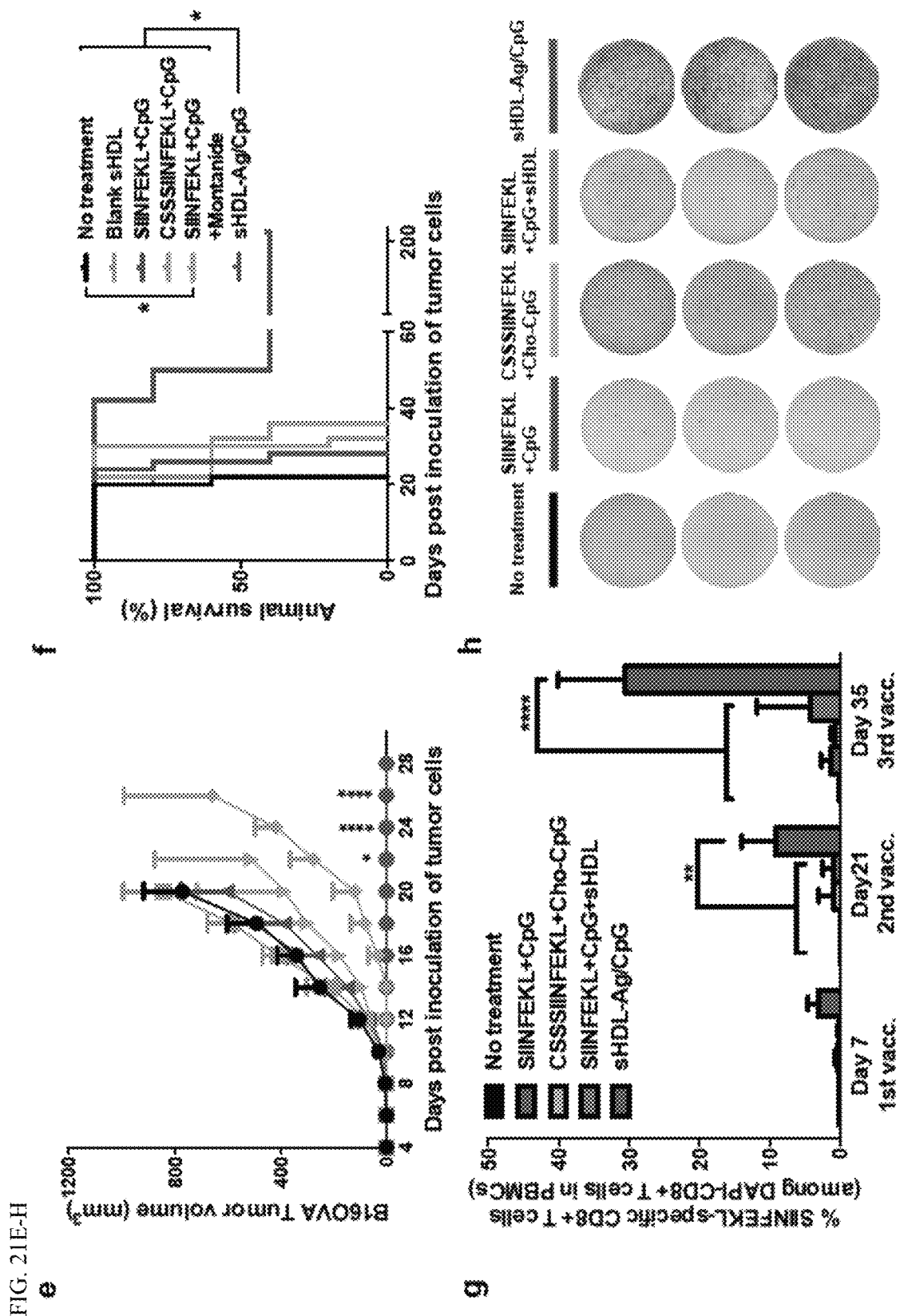
FIG. 21E-H

FIG. 27A
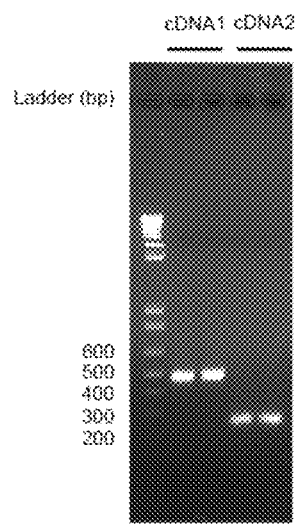
FIG. 27B-C
WT: GCCAGTATGACCAACAGGGAGCTCATG (SEQ ID NO: 337)
WT peptide: A  S  M  T  N  R  E  L  M  (SEQ ID NO: 338)
Mutant: GCCAGTATGACCAACATGGAGCTCATG (SEQ ID NO: 339)
Mutant peptide: A  S  M  T  N  M  E  L  M  (SEQ ID NO: 340)
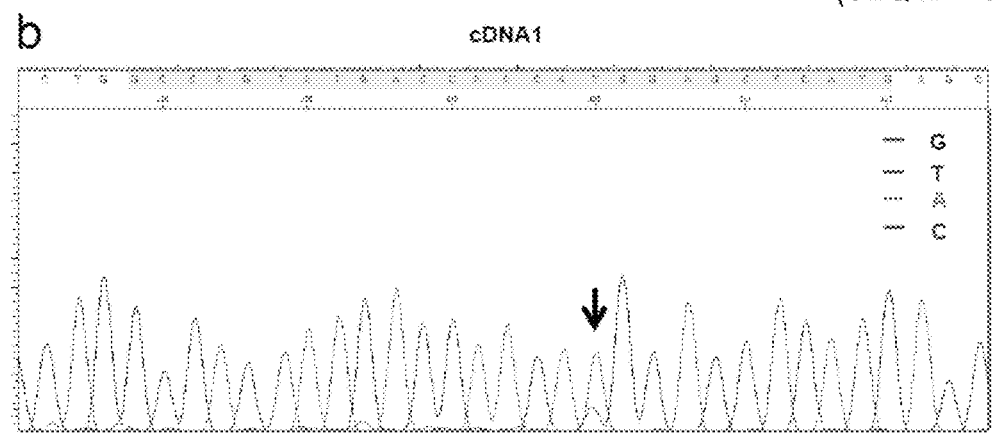
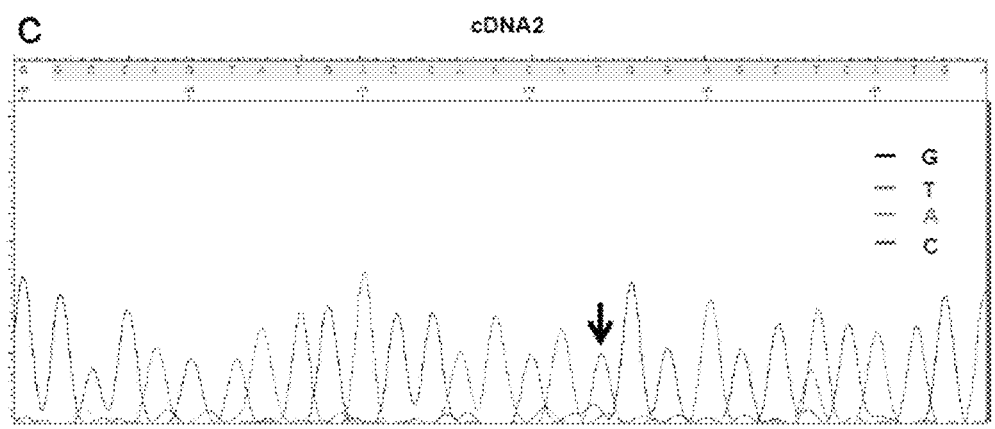

COMPOSITIONS AND METHODS FOR DELIVERY OF BIOMACROMOLECULE AGENTS

CROSS REFERENCE TO RELATED APPLICATIONS

The present invention is a national stage of International (PCT) Patent Application Serial No. PCT/US2016/024233, filed Mar. 25, 2016, which claims the priority benefit of U.S. Provisional Patent Application 62/138,186, filed Mar. 25, 2015 and U.S. Provisional Patent Application 62/248,908, filed Oct. 30, 2015 which are incorporated by reference in their entireties.

STATEMENT REGARDING FEDERALLY SPONSORED RESEARCH OR DEVELOPMENT

This invention was made with government support under AI097291 awarded by the National Institutes of Health. The Government has certain rights in the invention.

FIELD OF THE INVENTION

The present invention relates to nanoparticles complexed with biomacromolecule agents configured for treating, preventing or ameliorating various types of disorders, and methods of synthesizing the same. In particular, the present invention is directed to compositions comprising nanoparticles (e.g., synthetic high density lipoprotein (sHDL)) carrying biomacromolecule agents (e.g., nucleic acid, peptides, glycolipids, etc.), methods for synthesizing such nanoparticles, as well as systems and methods utilizing such nanoparticles (e.g., in diagnostic and/or therapeutic settings).

BACKGROUND OF THE INVENTION

Peptide and nucleic acid based drugs have tremendous potential as the next generation therapeutics. Despite their huge potential, their clinical translation has been challenging, partially due to lack of drug delivery platforms that can efficiently deliver the drugs to the site of action while protecting the cargo materials against enzymatic degradation in vivo. One prime example is in the area of cancer vaccines; numerous clinical trials have been performed using defined tumor associated antigen peptides, but they have failed to demonstrate clinical efficacy because soluble peptides do not sufficiently reach the site of action (e.g., lymphoid tissues) and fail to generate strong immune responses.

Improved compositions and techniques for stable and targeted delivery (e.g., in vitro or in vivo) of biomacromolcules (e.g., peptides, nucleic acids, glycolipids) are needed.

SUMMARY

Despite the tremendous potential of peptide-based cancer vaccines, their efficacy has been limited in humans. Recent innovations in tumor exome sequencing have signaled the new era of "personalized" immunotherapy with patient-specific neo-antigens (see, e.g., Yadav, M. et al. Nature 515, 572-576 (2014); Kreiter, S. et al. Nature 520, 692-696 (2015); Schumacher, T. N. & Schreiber, R. D. Science 348, 69-74 (2015)), but a general methodology for stimulating strong CD8α+ cytotoxic T lymphocyte (CTL) responses remains lacking. Experiments conducted during the course of developing embodiments for the present invention demonstrated that preformed high density lipoprotein-mimicking nanodiscs can be readily coupled with antigen (Ag) peptides and adjuvants, producing stable, ultrasmall nanoparticles that markedly improve Ag/adjuvant co-delivery to lymphoid organs and achieved sustained Ag presentation on dendritic cells. Strikingly, it was shown that these nanodiscs elicited up to 41-fold greater frequency of CTLs than soluble vaccines and even 9-fold greater than perhaps the strongest adjuvant in clinical trials (i.e. CpG in Montanide) (see, e.g., Speiser, D. E. et al. J. Clin. Invest. 115, 739-746 (2005); Fourcade, J. et al. J. Immunother. 31, 781-791 (2008)). Moreover, it was shown that the nanodisc platform can be easily adapted to neoantigens, generating potent anti-tumor immunity. Such results represent a new powerful approach for cancer immunotherapy and more broadly, suggest a general strategy for personalized nanomedicine.

Such results have significant clinical importance, as these nanodiscs, with an established manufacturing procedure and excellent safety profiles in humans, can drastically improve co-delivery of antigens and adjuvants to LNs, sustain antigen presentation on DCs, and drive T-cell responses with potent anti-tumor efficacy. As the majority of tumor mutations are unique to each patient, cancer vaccines would require a personalized approach (see, e.g., Yadav, M. et al. Nature 515, 572-576 (2014); Kreiter, S. et al. Nature 520, 692-696 (2015); Schumacher, T. N. & Schreiber, R. D. Science 348, 69-74 (2015)). Coupled with the recent technical innovations in neo-antigen screening, this approach provides powerful yet facile strategies for producing cancer vaccines designed for each patient. Furthermore, this platform technology is generally applicable for personalized therapeutics with a wide range of bioactive molecules and imaging agents.

Accordingly, in certain embodiments, the present invention provides methods for making a personalized neoplasia vaccine for a subject diagnosed as having a neoplasia. The present invention is not limited to particular methods for making a personalized neoplasia vaccine for a subject diagnosed as having a neoplasia. In some embodiments, such methods comprise obtaining a biological sample of the neoplasia from the subject; identifying a plurality of mutations in the neoplasia; analyzing the plurality of mutations to identify one or more neo-antigenic mutations predicted to encode neo-antigenic peptides, the neo-antigenic mutations selected from the group consisting of missense mutations, neoORF mutations, and any combination thereof; and producing a personalized neoplasia vaccine, wherein the personalized neoplasia vaccine comprises a microparticle or nanoparticle complexed with one or more neo-antigenic peptides specific for the analyzed and identified neo-antigenic mutations predicted to encode neo-antigenic peptides. In some embodiments, the nanoparticle is further complexed or admixed with an adjuvant. In some embodiments, the identifying further comprises sequencing the genome, transcriptome, or proteome of the neoplasia.

In some embodiments, the size of the microparticle is between 0.5 microns to 100 microns.

In some embodiments, the one or more neo-antigenic peptides range from about 5 to about 50 amino acids in length. In some embodiments, the one or more neo-antigenic mutations peptides range from about 15 to about 35 amino acids in length. In some embodiments, the one or more neo-antigenic peptides range from about 18 to about 30 amino acids in length. In some embodiments, the one or more neo-antigenic peptides range from about 6 to about 15 amino acids in length.

In some embodiments, the adjuvant is selected from the group consisting of CPG, polyIC, poly-ICLC, 1018 ISS, aluminum salts, Amplivax, AS15, BCG, CP-870, 893, CpG7909, CyaA, dSLIM, GM-CSF, IC30, IC31, Imiquimod, ImuFact IMP321, IS Patch, ISS, ISCOMATRIX, Juvlmmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel®, vector system, PLGA microparticles, imiquimod, resiquimod, gardiquimod, 3M-052, SRL172, Virosomes and other Virus-like particles, YF-17D, VEGF trap, beta-glucan, Pam3Cys, Aquila's QS21 stimulon, vadimezan, and AsA404 (DMXAA). In some embodiments, the adjuvant is any derivative of an adjuvant (e.g., cholesterol-modified CpG).

The methods are not limited to a particular nanoparticle. In some embodiments, the average size of the nanoparticle is between 6 to 500 nm. In some embodiments, the nanoparticle is a sHDL nanoparticle. In some embodiments, the sHDL nanoparticle comprises a mixture of at least one phospholipid and at least one HDL apolipoprotein or apolipoprotein mimetic. In some embodiments, the average size of the nanoparticle is between 6 to 500 nm. In some embodiments, the average particle size of the sHDL nanoparticle is between 6-70 nm.

In some embodiments, the phospholipid is selected from the group consisting of dipalmitoylphosphatidylcholine (DPPC), dioleoyl-sn-glycero-3-phosphoethanolamine-N-[3-(2-pyridyldithio) propionate] (DOPE-PDP), 1,2-dipalmitoyl-sn-glycero-3-phosphothioethanol, 1,2-di-(9Z-octadecenoyl)-sn-glycero-3-phosphoethanolamine-N-[4-(p-maleimidophenyl)butyramide], 1,2-dihexadecanoyl-sn-glycero-3-phosphoethanolamine-N-[4-(p-maleimidophenyl)butyramide], 1,2-dihexadecanoyl-sn-glycero-3-phosphoethanolamine-N-[4-(p-maleimidomethyl)cyclohexane-carboxamide], 1,2-di-(9Z-octadecenoyl)-sn-glycero-3-phosphoethanolamine-N-[4-(p-maleimidomethyl)cyclohexane-carboxamide], phosphatidylcholine, phosphatidylinositol, phosphatidylserine, phosphatidylethanolamine, and combinations thereof.

In some embodiments, the HDL apolipoprotein is selected from the group consisting of apolipoprotein A-I (apo A-I), apolipoprotein A-II (apo A-II), apolipoprotein A4 (apo A4), apolipoprotein Cs (apo Cs), and apolipoprotein E (apo E). In some embodiments, the HDL apolipoprotein mimetic is an ApoA-I mimetic. In some embodiments, the ApoA-I mimetic is described by any of SEQ ID NOs: 1-336.

In certain embodiments, the present invention provides methods for treating a subject diagnosed as having a neoplasia with a personalized neoplasia vaccine. The present invention is not limited to particular methods for treating a subject diagnosed as having a neoplasia with a personalized neoplasia vaccine. In some embodiments, such methods comprise obtaining a biological sample of the neoplasia from the subject; identifying one or more mutations in the neoplasia; analyzing the plurality of mutations to identify one or more neo-antigenic mutations predicted to encode expressed neo-antigenic peptides, the neo-antigenic mutations selected from the group consisting of missense mutations, neoORF mutations, and any combination thereof; producing a personalized neoplasia vaccine, wherein the personalized neoplasia vaccine comprises a microparticle or nanoparticle complexed with one or more neo-antigenic peptides specific for the analyzed and identified neo-antigenic mutations predicted to encode neo-antigenic peptides; and administering the personalized neoplasia vaccine to the subject, thereby treating the neoplasia. In some embodiments, the personalized neoplasia vaccine is coadministered with an adjuvant. In some embodiments, the nanoparticle is further complexed or admixed with an adjuvant. In some embodiments, the identifying further comprises sequencing the genome, transcriptome, or proteome of the neoplasia.

In some embodiments, the one or more neo-antigenic peptides range from about 5 to about 50 amino acids in length. In some embodiments, the one or more neo-antigenic mutations peptides range from about 15 to about 35 amino acids in length. In some embodiments, the one or more neo-antigenic peptides range from about 18 to about 30 amino acids in length. In some embodiments, the one or more neo-antigenic peptides range from about 6 to about 15 amino acids in length.

In some embodiments, the adjuvant is selected from the group consisting of CPG, polyIC, poly-ICLC, 1018 ISS, aluminum salts, Amplivax, AS15, BCG, CP-870, 893, CpG7909, CyaA, dSLIM, GM-CSF, IC30, IC31, Imiquimod, ImuFact IMP321, IS Patch, ISS, ISCOMATRIX, Juvlmmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel®, vector system, PLGA microparticles, imiquimod, resiquimod, gardiquimod, 3M-052, SRL172, Virosomes and other Virus-like particles, YF-17D, VEGF trap, beta-glucan, Pam3Cys, Aquila's QS21 stimulon, vadimezan, and AsA404 (DMXAA). In some embodiments, the adjuvant is any derivative of an adjuvant (e.g., cholesterol-modified CpG).

The methods are not limited to a particular nanoparticle. In some embodiments, the average size of the nanoparticle is between 6 to 500 nm. In some embodiments, the nanoparticle is a sHDL nanoparticle. In some embodiments, the sHDL nanoparticle comprises a mixture of at least one phospholipid and at least one HDL apolipoprotein or apolipoprotein mimetic. In some embodiments, the average particle size of the sHDL nanoparticle is between 6-70 nm.

In some embodiments, the phospholipid is selected from the group consisting of dipalmitoylphosphatidylcholine (DPPC), dioleoyl-sn-glycero-3-phosphoethanolamine-N-[3-(2-pyridyldithio) propionate] (DOPE-PDP), 1,2-dipalmitoyl-sn-glycero-3-phosphothioethanol, 1,2-di-(9Z-octadecenoyl)-sn-glycero-3-phosphoethanolamine-N-[4-(p-maleimidophenyl)butyramide], 1,2-dihexadecanoyl-sn-glycero-3-phosphoethanolamine-N-[4-(p-maleimidophenyl)butyramide], 1,2-dihexadecanoyl-sn-glycero-3-phosphoethanolamine-N-[4-(p-maleimidomethyl)cyclohexane-carboxamide], 1,2-di-(9Z-octadecenoyl)-sn-glycero-3-phosphoethanolamine-N-[4-(p-maleimidomethyl)cyclohexane-carboxamide], phosphatidylcholine, phosphatidylinositol, phosphatidylserine, phosphatidylethanolamine, and combinations thereof.

In some embodiments, the HDL apolipoprotein is selected from the group consisting of apolipoprotein A-I (apo A-I), apolipoprotein A-II (apo A-II), apolipoprotein A4 (apo A4), apolipoprotein Cs (apo Cs), and apolipoprotein E (apo E). In some embodiments, the HDL apolipoprotein mimetic is an ApoA-I mimetic. In some embodiments, the ApoA-I mimetic is described by any of SEQ ID NOs: 1-336.

In some embodiments, the personalized neoplasia vaccine is coadministered with an an anti-immunosuppressive or immuno stimulatory agent. In some embodiments, the anti-immunosuppressive or immuno stimulatory agent is selected from the group consisting of anti-CTLA antibody, anti-PD-1, anti-PD-L1, anti-TIM-3, anti-BTLA, anti-VISTA, anti-LAG3, anti-CD25, anti-CD27, anti-CD28, anti-CD137, anti-OX40, anti-GITR, anti-ICOS, anti-TIGIT, and inhibitors of IDO.

In certain embodiments, the present invention provides a composition comprising a microparticle or nanoparticle complexed with one or more neo-antigenic peptides, wherein each of the one or more neo-antigenic peptides is specific for a neo-antigenic mutation identified from a neoplasia biological sample obtained from a subject. In some embodiments, the subject is a human being.

In some embodiments, the size of the microparticle is between 0.5 microns to 100 microns. In some embodiments, the average size of the nanoparticle is between 6 to 500 nm.

In some embodiments, the one or more neo-antigenic peptides range from about 5 to about 50 amino acids in length. In some embodiments, the one or more neo-antigenic peptides range from about 15 to about 35 amino acids in length. In some embodiments, the one or more neo-antigenic peptides range from about 18 to about 30 amino acids in length. In some embodiments, the one or more neo-antigenic peptides range from about 6 to about 15 amino acids in length.

In some embodiments, the nanoparticle is further complexed or admixed with an adjuvant. In some embodiments, the adjuvant is selected from the group consisting of CPG, polyIC, poly-ICLC, 1018 ISS, aluminum salts, Amplivax, AS15, BCG, CP-870, 893, CpG7909, CyaA, dSLIM, GM-CSF, IC30, IC31, Imiquimod, ImuFact IMP321, IS Patch, ISS, ISCOMATRIX, Juvlmmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel®, vector system, PLGA microparticles, imiquimod, resiquimod, gardiquimod, 3M-052, SRL172, Virosomes and other Virus-like particles, YF-17D, VEGF trap, beta-glucan, Pam3Cys, Aquila's QS21 stimulon, vadimezan, and AsA404 (DMXAA). In some embodiments, the adjuvant is any derivative of an adjuvant (e.g., cholesterol-modified CpG).

In some embodiments, the nanoparticle is a sHDL nanoparticle. In some embodiments, the sHDL nanoparticle comprises a mixture of at least one phospholipid and at least one HDL apolipoprotein or apolipoprotein mimetic. In some embodiments, the HDL apolipoprotein is selected from the group consisting of apolipoprotein A-I (apo apolipoprotein A-II (apo A-II), apolipoprotein A4 (apo A4), apolipoprotein Cs (apo Cs), and apolipoprotein E (apo E). In some embodiments, the phospholipid is selected from the group consisting of dipalmitoylphosphatidylcholine (DPPC), dioleoyl-sn-glycero-3-phosphoethanolamine-N-[3-(2-pyridyldithio) propionate] (DOPE-PDP), 1,2-dipalmitoyl-sn-glycero-3-phosphothioethanol, 1,2-di-(9Z-octadecenoyl)-sn-glycero-3-phosphoethanolamine-N-[4-(p-maleimidophenyl)butyramide], 1,2-dihexadecanoyl-sn-glycero-3-phosphoethanolamine-N-[4-(p-maleimidophenyl) butyramide], 1,2-dihexadecanoyl-sn-glycero-3-phosphoethanolamine-N-[4-(p-maleimidomethyl) cyclohexane-carboxamide], 1,2-di-(9Z-octadecenoyl)-sn-glycero-3-phosphoethanolamine-N-[4-(p-maleimidomethyl)cyclohexane-carboxamide], phosphatidylcholine, phosphatidylinositol, phosphatidylserine, phosphatidylethanolamine, and combinations thereof. In some embodiments, the HDL apolipoprotein mimetic is an ApoA-I mimetic. In some embodiments, the ApoA-I mimetic is described by any of SEQ ID NOs: 1-336. In some embodiments, the average particle size of the sHDL nanoparticle is between 6-70 nm.

Moreover, the present invention relates to nanoparticles complexed with biomacromolecule agents configured for treating, preventing or ameliorating various types of disorders, and methods of synthesizing the same. In particular, the present invention is directed to compositions comprising synthetic high density lipoprotein (sHDL) nanoparticles carrying biomacromolecule agents (e.g., nucleic acid, peptides, glycolipids, etc.), methods for synthesizing such sHDL nanoparticles, as well as systems and methods utilizing such sHDL nanoparticles (e.g., in diagnostic and/or therapeutic settings).

As such, in certain embodiments, the present invention provides methods for inhibiting a target gene in a cell, comprising introducing into the cell a composition comprising siRNA encapsulated within a sHDL nanoparticle, wherein the siRNA is capable of inhibiting the target gene by RNA interference, wherein the siRNA comprises two RNA strands that are complementary to each other. In some embodiments, the siRNA is modified with cholesterol at the 3' sense strand. In some embodiments, the cell is in vivo, in vitro, or ex vivo. In some embodiments, the cell is within a human being. In some embodiments, an imaging agent is encapsulated within the sHDL nanoparticle.

In certain embodiments, the present invention provides methods for reducing serum LDL-C levels in patient, comprising administering to the patient a therapeutically effective amount of a pharmaceutical composition comprising a PCSK9 siRNA encapsulated within a nanoparticle, wherein the PCSK9 siRNA is capable of inhibiting the PCSK9 gene by RNA interference, wherein the PCSK9 siRNA comprises two RNA strands that are complementary to each other, wherein inhibiting of the PCSK9 gene results in reduction of serum LDL-C levels in the patient. In some embodiments, the patient is a human patient. In some embodiments, the PCSK9 siRNA is modified with cholesterol at the 3' sense strand. In some embodiments, an imaging agent is encapsulated within the nanoparticle. In some embodiments, the nanoparticle is selected from the group consisting of sHDL nanoparticle, fullerenes, endohedral metallofullerenes buckyballs, trimetallic nitride templated endohedral metallofullerenes, single-walled and multi-walled carbon nanotubes, branched and dendritic carbon nanotubes, gold nanorods, silver nanorods, single-walled and multi-walled boron/nitrate nanotubes, carbon nanotube peapods, carbon nanohorns, carbon nanohorn peapods, liposomes, nanoshells, dendrimers, microparticles, quantum dots, superparamagnetic nanoparticles, nanorods, cellulose nanoparticles, glass and polymer micro- and nano-spheres, biodegradable PLGA micro- and nano-spheres, gold nanoparticles, silver nanoparticles, carbon nanoparticles, iron nanoparticles, a modified micelle. In some embodiments, the nanoparticle is a sHDL nanoparticle.

In certain embodiments, the present invention provides methods for treating coronary heart disease in a patient through reducing serum LDL-C levels in the patient, comprising administering to the patient a therapeutically effective amount of a pharmaceutical composition comprising a PCSK9 siRNA encapsulated within a nanoparticle, wherein the PCSK9 siRNA is capable of inhibiting the PCSK9 gene by RNA interference, wherein the PCSK9 siRNA comprises two RNA strands that are complementary to each other, wherein inhibiting of the PCSK9 gene results in reduction of serum LDL-C levels. In some embodiments, the patient is a human patient. In some embodiments, the PCSK9 siRNA is modified with cholesterol at the 3' sense strand. In some embodiments, an imaging agent is encapsulated within the nanoparticle. In some embodiments, the nanoparticle is selected from the group consisting of sHDL nanoparticle, fullerenes, endohedral metallofullerenes buckyballs, trimetallic nitride templated endohedral metallofullerenes, single-walled and multi-walled carbon nanotubes, branched and dendritic carbon nanotubes, gold nanorods, silver nanorods, single-walled and multi-walled boron/nitrate nanotubes, carbon nanotube peapods, carbon nanohorns, carbon nanohorn peapods, liposomes, nanoshells, dendrimers, microparticles, quantum dots, superparamagnetic nanoparticles, nanorods, cellulose nanoparticles, glass and polymer micro- and nano-spheres, biodegradable PLGA micro- and nano-spheres, gold nanoparticles, silver nanoparticles, carbon nanoparticles, iron nanoparticles, a modified micelle. In some embodiments, the nanoparticle is a sHDL nanoparticle. In some embodiments, the sHDL nanoparticle comprises a mixture of at least one phospholipid and at least one HDL apolipoprotein or apolipoprotein mimetic.

In certain embodiments, the present invention provides methods for inducing a natural killer T cell-mediated immune response in a cell comprising exposing the cell to a composition comprising an αGalCer glycolipid encapsulated within a nanoparticle, wherein such exposure results in the induction of a natural killer T cell-mediated immune response. In some embodiments, the cell is an in vivo cell, an ex vivo cell, or an in vitro cell. In some embodiments, the nanoparticle is selected from the group consisting of sHDL nanoparticle, fullerenes, endohedral metallofullerenes buckyballs, trimetallic nitride templated endohedral metallofullerenes, single-walled and multi-walled carbon nanotubes, branched and dendritic carbon nanotubes, gold nanorods, silver nanorods, single-walled and multi-walled boron/nitrate nanotubes, carbon nanotube peapods, carbon nanohorns, carbon nanohorn peapods, liposomes, nanoshells, dendrimers, microparticles, quantum dots, superparamagnetic nanoparticles, nanorods, cellulose nanoparticles, glass and polymer micro- and nano-spheres, biodegradable PLGA micro- and nano-spheres, gold nanoparticles, silver nanoparticles, carbon nanoparticles, iron nanoparticles, a modified micelle. In some embodiments, the nanoparticle is a sHDL nanoparticle.

In certain embodiments, the present invention provides methods for inducing an immune response to an antigen comprising administering to a subject in need an effective amount of a composition comprising an nanoparticle, wherein the antigen is complexed with the nanoparticle, wherein an adjuvant is complexed or admixed with the nanoparticle.

In some embodiments, the antigen is against PCSK9. In some embodiments, the antigen is against gp100 melanoma. In some embodiments, the antigen is selected from the group consisting of a peptide based antigen, a protein based antigen, a polysaccharide based antigen, a saccharide based antigen, a lipid based antigen, a glycolipid based antigen, a nucleic acid based antigen, an inactivated organism based antigen, an attenuated organism based antigen, a viral antigen, a bacterial antigen, a parasite antigen, an antigen derived from an allergen, and a tumor antigen. In some embodiments, the antigen is a tumor antigen selected from the group consisting of alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triosephosphate isomeras, Bage-1, Gage 3,4,5,6,7, GnTV, Herv-K-mel, Lage-1, Mage-A1,2,3, 4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGS), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS.

In some embodiments, the adjuvant is a dendritic cell targeting molecule. In some embodiments, the adjuvant is CpG. In certain embodiments, the present invention provides methods for inducing an immune response to an antigen comprising administering to a subject in need an effective amount of a composition comprising a nanoparticle, wherein the antigen is complexed with the nanoparticle. In some embodiments, the antigen is against PCSK9. In some embodiments, the nanoparticle is further complexed or admixed with an adjuvant. In some embodiments, the nanoparticle is co-administered with an adjuvant.

In some embodiments, the nanoparticle is selected from the group consisting of sHDL nanoparticle, fullerenes, endohedral metallofullerenes buckyballs, trimetallic nitride templated endohedral metallofullerenes, single-walled and multi-walled carbon nanotubes, branched and dendritic carbon nanotubes, gold nanorods, silver nanorods, single-walled and multi-walled boron/nitrate nanotubes, carbon nanotube peapods, carbon nanohorns, carbon nanohorn peapods, liposomes, nanoshells, dendrimers, microparticles, quantum dots, superparamagnetic nanoparticles, nanorods, cellulose nanoparticles, glass and polymer micro- and nano-spheres, biodegradable PLGA micro- and nano-spheres, gold nanoparticles, silver nanoparticles, carbon nanoparticles, iron nanoparticles, a modified micelle. In some embodiments, the nanoparticle is a sHDL nanoparticle.

In some embodiments, the adjuvant is a dendritic cell targeting molecule. In some embodiments, the adjuvant is CpG. In some embodiments, the adjuvant is selected from the group consisting of CPG, polyIC, poly-ICLC, 1018 ISS, aluminum salts, Amplivax, AS15, BCG, CP-870, 893, CpG7909, CyaA, dSLIM, GM-CSF, IC30, IC31, Imiquimod, ImuFact IMP321, IS Patch, ISS, ISCOMATRIX, Juvlmmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel®, vector system, PLGA microparticles, imiquimod, resiquimod, gardiquimod, 3M-052, SRL172, Virosomes and other Virus-like particles, YF-17D, VEGF trap, beta-glucan, Pam3Cys, Aquila's QS21 stimulon, vadimezan, and AsA404 (DMXAA). In some embodiments, the adjuvant is any derivative of an adjuvant (e.g., cholesterol-modified CpG).

In some embodiments, the antigen is conjugated to the outer surface of the nanoparticle. In some embodiments, the adjuvant is conjugated to the outer surface of the nanoparticle. In some embodiments, the adjuvant is encapsulated within the nanoparticle.

In some embodiments, the composition is co-administered with a chemotherapeutic agent. In some embodiments, the chemotherapeutic agent is one or more of the following: aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol®), pilocarpine, prochloroperazine, rituximab, tamoxifen, taxol, topotecan hydrochloride, trastuzumab, vinblastine, vincristine and vinorelbine tartrate.

In certain embodiments, the present invention provides compositions comprising a nanoparticle, wherein an antigen is complexed with the nanoparticle. In some embodiments, the nanoparticle is further complexed or admixed with an adjuvant.

In some embodiments, the antigen is derived from a self-antigen.

In some embodiments, the antigen is against PCSK9. In some embodiments, the antigen is against gp100 melanoma. In some embodiments, the antigen is selected from the group consisting of a peptide based antigen, a protein based antigen, a polysaccharide based antigen, a saccharide based antigen, a lipid based antigen, a glycolipid based antigen, a nucleic acid based antigen, an inactivated organism based antigen, an attenuated organism based antigen, a viral antigen, a bacterial antigen, a parasite antigen, an antigen derived from an allergen, and a tumor antigen. In some embodiments, the antigen is a tumor antigen selected from the group consisting of alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triosephosphate isomeras, Bage-1, Gage 3,4,5,6,7, GnTV, Herv-K-mel, Lage-1, Mage-A1,2,3, 4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGS), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS.

In some embodiments, the adjuvant is a dendritic cell targeting molecule. In some embodiments, the adjuvant is an immunostimulatory agent that activates dendritic cells. In some embodiments, the adjuvant is CpG. In some embodiments, the adjuvant is selected from the group consisting of CPG, polyIC, poly-ICLC, 1018 ISS, aluminum salts, Amplivax, AS15, BCG, CP-870, 893, CpG7909, CyaA, dSLIM, GM-CSF, IC30, IC31, Imiquimod, ImuFact IMP321, IS Patch, ISS, ISCOMATRIX, Juvlmmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel®, vector system, PLGA microparticles, imiquimod, resiquimod, gardiquimod, 3M-052, SRL172, Virosomes and other Virus-like particles, YF-17D, VEGF trap, beta-glucan, Pam3Cys, Aquila's QS21 stimulon, vadimezan, and AsA404 (DMXAA). In some embodiments, the adjuvant is any derivative of an adjuvant (e.g., cholesterol-modified CpG).

In some embodiments, the antigen is conjugated to the outer surface of the nanoparticle. In some embodiments, the adjuvant is conjugated to the outer surface of the nanoparticle. In some embodiments, the adjuvant is encapsulated within the nanoparticle.

In some embodiments, the nanoparticle is selected from the group consisting of sHDL nanoparticle, fullerenes, endohedral metallofullerenes buckyballs, trimetallic nitride templated endohedral metallofullerenes, single-walled and multi-walled carbon nanotubes, branched and dendritic carbon nanotubes, gold nanorods, silver nanorods, single-walled and multi-walled boron/nitrate nanotubes, carbon nanotube peapods, carbon nanohorns, carbon nanohorn peapods, liposomes, nanoshells, dendrimers, microparticles, quantum dots, superparamagnetic nanoparticles, nanorods, cellulose nanoparticles, glass and polymer micro- and nanospheres, biodegradable PLGA micro- and nano-spheres, gold nanoparticles, silver nanoparticles, carbon nanoparticles, iron nanoparticles, a modified micelle. In some embodiments, the nanoparticle is a sHDL nanoparticle.

In certain embodiments, the present invention provides comprising siRNA encapsulated within a nanoparticle, wherein the siRNA is capable of inhibiting a target gene by RNA interference, wherein the siRNA comprises two RNA strands that are complementary to each other. In some embodiments, the siRNA is modified with cholesterol at the 3' sense strand. In some embodiments, an imaging agent is encapsulated within the nanoparticle.

In some embodiments, the nanoparticle is selected from the group consisting of sHDL nanoparticle, fullerenes, endohedral metallofullerenes buckyballs, trimetallic nitride templated endohedral metallofullerenes, single-walled and multi-walled carbon nanotubes, branched and dendritic carbon nanotubes, gold nanorods, silver nanorods, single-walled and multi-walled boron/nitrate nanotubes, carbon nanotube peapods, carbon nanohorns, carbon nanohorn peapods, liposomes, nanoshells, dendrimers, microparticles, quantum dots, superparamagnetic nanoparticles, nanorods, cellulose nanoparticles, glass and polymer micro- and nanospheres, biodegradable PLGA micro- and nano-spheres, gold nanoparticles, silver nanoparticles, carbon nanoparticles, iron nanoparticles, a modified micelle. In some embodiments, the nanoparticle is a sHDL nanoparticle.

In certain embodiments, the present invention provides comprising a PCSK9 siRNA encapsulated within a nanoparticle, wherein the PCSK9 siRNA is capable of inhibiting the PCSK9 gene by RNA interference, wherein the PCSK9 siRNA comprises two RNA strands that are complementary to each other. In some embodiments, the PCSK9 siRNA is modified with cholesterol at the 3' sense strand. In some embodiments, an imaging agent is encapsulated within the nanoparticle.

In some embodiments, the average size of the nanoparticle is between 6 to 500 nm.

In some embodiments, the nanoparticle is selected from the group consisting of sHDL nanoparticle, fullerenes, endohedral metallofullerenes buckyballs, trimetallic nitride templated endohedral metallofullerenes, single-walled and multi-walled carbon nanotubes, branched and dendritic carbon nanotubes, gold nanorods, silver nanorods, single-walled and multi-walled boron/nitrate nanotubes, carbon nanotube peapods, carbon nanohorns, carbon nanohorn peapods, liposomes, nanoshells, dendrimers, microparticles, quantum dots, superparamagnetic nanoparticles, nanorods, cellulose nanoparticles, glass and polymer micro- and nanospheres, biodegradable PLGA micro- and nano-spheres, gold nanoparticles, silver nanoparticles, carbon nanoparticles, iron nanoparticles, a modified micelle. In some embodiments, the nanoparticle is a sHDL nanoparticle.

In certain embodiments, the present invention provides comprising an αGalCer glycolipid encapsulated within a nanoparticle.

Such methods and compositions are not limited to particular size, type or kind of nanoparticles. In some embodiments, the nanoparticle is selected from the group consisting of sHDL nanoparticle, fullerenes, endohedral metallofullerenes buckyballs, trimetallic nitride templated endohedral metallofullerenes, single-walled and multi-walled carbon nanotubes, branched and dendritic carbon nanotubes, gold nanorods, silver nanorods, single-walled and multi-walled boron/nitrate nanotubes, carbon nanotube peapods, carbon nanohorns, carbon nanohorn peapods, liposomes, nanoshells, dendrimers, microparticles, quantum dots, superparamagnetic nanoparticles, nanorods, cellulose nanoparticles, glass and polymer micro- and nano-spheres, biodegradable PLGA micro- and nano-spheres, gold nanoparticles, silver nanoparticles, carbon nanoparticles, iron nanoparticles, a modified micelle.

In some embodiments, the nanoparticle is a sHDL nanoparticle. In some embodiments, the sHDL nanoparticle comprises a mixture of at least one phospholipid and at least one HDL apolipoprotein or apolipoprotein mimetic.

In some embodiments, the HDL apolipoprotein is selected from the group consisting of apolipoprotein A-I (apo A-I), apolipoprotein A-II (apo A-II), apolipoprotein A4 (apo A4), apolipoprotein Cs (apo Cs), and apolipoprotein E (apo E). In some embodiments, the HDL apolipoprotein is selected from preproapoliprotein, preproApoA-I, proApoA-I, ApoA-I, preproApoA-II, proApoA-II, ApoA-II, preproApoA-1V, proApoA-1V, ApoA-IV, ApoA-V, preproApoE, proApoE, ApoE, preproApoA-1Milano, proApoA-IMilano ApoA-1Milano preproApoA-IParis, proApoA-IParis, and ApoA-IParis and peptide mimetics of these proteins mixtures thereof.

In some embodiments, the phospholipid is selected from the group consisting of dipalmitoylphosphatidylcholine (DPPC), dioleoyl-sn-glycero-3-phosphoethanolamine-N-[3-(2-pyridyldithio) propionate] (DOPE-PDP), 1,2-dipalmitoyl-sn-glycero-3-phosphothioethanol, 1,2-di-(9Z-octadecenoyl)-sn-glycero-3-phosphoethanolamine-N-[4-(p-maleimidophenyl)butyramide], 1,2-dihexadecanoyl-sn-glycero-3-phosphoethanolamine-N-[4-(p-maleimidophenyl)butyramide], 1,2-dihexadecanoyl-sn-glycero-3-phosphoethanolamine-N-[4-(p-maleimidomethyl)cyclohexane-carboxamide], 1,2-di-(9Z-octadecenoyl)-sn-glycero-3-phosphoethanolamine-N-[4-(p-maleimidomethyl)cyclohexane-carboxamide], phosphatidylcholine, phosphatidylinositol, phosphatidylserine, phosphatidylethanolamine, and combinations thereof.

In some embodiments, the HDL apolipoprotein mimetic is an ApoA-I mimetic. In some embodiments, the ApoA-I mimetic is described by any of SEQ ID NOs: 1-336. In some embodiments, the average particle size of the sHDL nanoparticle is between 6-70 nm.

In certain embodiments, the present invention provides methods for inducing an immune response to one or more antigens comprising administering to a subject in need an effective amount of a composition comprising a nanoparticle, wherein the one or more antigens is complexed with the nanoparticle, wherein an adjuvant is complexed with the nanoparticle. In certain embodiments, the present invention provides compositions comprising nanoparticle, wherein one or more antigens is complexed with the nanoparticle, wherein an adjuvant is complexed with the nanoparticle. In some embodiments, the average size of the nanoparticle is between 6 to 500 nm.

In some embodiments, the one or more antigens is against PCSK9, M30, M27, Adpgk, and ASMTNMELM. In some embodiments, the one or more antigens are conjugated to the outer surface of the nanoparticle.

In some embodiments, the adjuvant is selected from the group consisting of CPG, polyIC, poly-ICLC, 1018 ISS, aluminum salts, Amplivax, AS15, BCG, CP-870, 893, CpG7909, CyaA, dSLIM, GM-CSF, IC30, IC31, Imiquimod, ImuFact IMP321, IS Patch, ISS, ISCOMATRIX, Juvlmmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel®, vector system, PLGA microparticles, imiquimod, resiquimod, gardiquimod, 3M-052, SRL172, Virosomes and other Virus-like particles, YF-17D, VEGF trap, beta-glucan, Pam3Cys, Aquila's QS21 stimulon, vadimezan, and AsA404 (DMXAA). In some embodiments, the adjuvant is any derivative of an adjuvant (e.g., cholesterol-modified CpG). In some embodiments, the adjuvant is conjugated to the outer surface of the nanoparticle. In some embodiments, the adjuvant is encapsulated within the nanoparticle.

In some embodiments, the nanoparticle is selected from the group consisting of sHDL nanoparticle, fullerenes, endohedral metallofullerenes buckyballs, trimetallic nitride templated endohedral metallofullerenes, single-walled and multi-walled carbon nanotubes, branched and dendritic carbon nanotubes, gold nanorods, silver nanorods, single-walled and multi-walled boron/nitrate nanotubes, carbon nanotube peapods, carbon nanohorns, carbon nanohorn peapods, liposomes, nanoshells, dendrimers, microparticles, quantum dots, superparamagnetic nanoparticles, nanorods, cellulose nanoparticles, glass and polymer micro- and nano-spheres, biodegradable PLGA micro- and nano-spheres, gold nanoparticles, silver nanoparticles, carbon nanoparticles, iron nanoparticles, a modified micelle.

In some embodiments, the nanoparticle is a sHDL nanoparticle. In some embodiments, the nanoparticle is sHDL, wherein the sHDL nanoparticle comprises a mixture of at least one phospholipid and at least one HDL apolipoprotein or apolipoprotein mimetic.

In some embodiments, the HDL apolipoprotein is selected from the group consisting of apolipoprotein A-I (apo A-I), apolipoprotein A-II (apo A-II), apolipoprotein A4 (apo A4), apolipoprotein Cs (apo Cs), and apolipoprotein E (apo E), wherein the phospholipid is selected from the group consisting of dipalmitoylphosphatidylcholine (DPPC), dioleoyl-sn-glycero-3-phosphoethanolamine-N-[3-(2-pyridyldithio) propionate] (DOPE-PDP), 1,2-dipalmitoyl-sn-glycero-3-phosphothioethanol, 1,2-di-(9Z-octadecenoyl)-sn-glycero-3-phosphoethanolamine-N-[4-(p-maleimidophenyl)butyramide], 1,2-dihexadecanoyl-sn-glycero-3-phosphoethanolamine-N-[4-(p-maleimidophenyl)butyramide], 1,2-dihexadecanoyl-sn-glycero-3-phosphoethanolamine-N-[4-(p-maleimidomethyl)cyclohexane-carboxamide], 1,2-di-(9Z-octadecenoyl)-sn-glycero-3-phosphoethanolamine-N-[4-(p-maleimidomethyl)cyclohexane-carboxamide], phosphatidylcholine, phosphatidylinositol, phosphatidylserine, phosphatidylethanolamine, and combinations thereof.

In some embodiments, the HDL apolipoprotein mimetic is an ApoA-I mimetic, wherein the thiol-reactive phospholipid is dioleoyl-sn-glycero-3-phosphoethanolamine-N-[3-(2-pyridyldithio) propionate] (DOPE-PDP). In some embodiments, the ApoA-I mimetic is described by any of SEQ ID NOs: 1-336.

Additional embodiments will be apparent to persons skilled in the relevant art based on the teachings contained herein.

BRIEF DESCRIPTION OF THE DRAWINGS

FIG. 2: (A) Schematic of antigens and adjuvants-loaded sHDL; (B) Addition of antigens to functional lipids containing sHDL led to the formation of lipid-antigen conjugates as measured by HPLC; (C) The Cho-CpG could be quantitatively incorporated into sHDL as measured by GPC; (D) Co-localized delivery of antigens (Ag) and adjuvants (CpG) by sHDL led to more potent cellular response than the mixture of antigens and adjuvants in montanide.

FIG. 4 shows homogenous particle size of sHDL-Ag/CpG as analyzed by cryoEM and dynamic light scattering.

FIG. 13: Effect of 22A variants and lipids on the formation of sHDL nanodisc. a, DMPC (containing 4% mol DOPE-PDP) and different 22A mutants were used to prepare sHDL. In addition to 22A that we have used throughout this study, several other 22A variants, including 22A composed of D-amino acids, formed homogeneous sHDL nanodiscs (as analyzed by dynamic light scattering) that remained stable up to one month at 4° C. N.D., not determined due to aggregation. b, Synthesis of sHDL requires phospholipids with high transition temperature (Tm) and ApoA-mimetic peptides. DPPC and DMPC (Tm=41° C. and 24° C., respectively) but not POPC or DOPC (Tm=−2° C. and −17° C., respectively), formed homogeneous sHDL in the presence of 22A and 4 mol % DOPE-PDP.

FIG. 21: Vaccine nanodiscs for LN-targeting of Ag and adjuvants and elicitation of CTL responses. a-b, C57BL/6 mice were administered subcutaneously at tail base with a, 31 nmol FITC-tagged Ag (CSSSIINFEK$_{(FITC)}$L) or b, 2.3 nmol Cho-CpG (20% labeled by Cy5) in free soluble or sHDL form, and fluorescence signal in the draining inguinal LNs were quantified with IVIS after 24 h. c-f, C57BL/6 mice were immunized with the indicated formulations (15.5 nmol Ag peptide and 2.3 nmol CpG) on days 0, 21, and 42. c, The frequency of SIINFEKL-specific CD8α+ T-cells in peripheral blood was measured 7 days post each immunization by flow-cytometry analysis of tetramer+CD8α+ T-cells, and d, their representative scatter plots on day 49 are shown. e-f, On day 50, pre-vaccinated animals were challenged with subcutaneous flank injection of 2×10$^5$ B16OVA cells. e, Tumor growth and f, overall survival are shown. g-h, C57BL/6 mice were immunized with the indicated formulations in a biweekly interval. Shown are g, percent of SIINFEKL-specific CD8α+ T-cells among PBMCs and h, ELISPOT analysis of IFN-γ spot-forming cells among splenocytes after ex vivo restimulation with SIINFEKL on day 42. The data show mean±SD from a representative experiment (n=4-5) from 2-3 independent experiments. * $p<0.05$,  $p<0.01$, * $p<0.001$, and **** $p<0.0001$, analyzed by (a-b) two-tailed unpaired Student's t test, (c, e, g) two-way ANOVA with Tukey's HSD post-test, or (f) log-rank (Mantel-Cox) test. Asterisks in panel e indicate statistically significant differences between sHDL-Ag/CpG and SIINFEKL+CpG+Montanide.

FIGS. 27A-C: cDNA sequencing of MC-38 cells for mutated Adpgk neoantigen. Two different lengths (485 bp and 250 bp) of cDNA for the neoantigen Adpgk mRNA (amino acid sequence ASMTNMELM (SEQ ID NO: 341)) were prepared by using two different sets of primers. The sequence of cDNA was analyzed by DNA sequencing. Shown are A, two different lengths of cDNA bands on agarose gel and the results of Sanger DNA sequencing for B, 485 bp cDNA and C, 250 bp cDNA. Arrows indicate the mutation of G→T.

Figure 28:
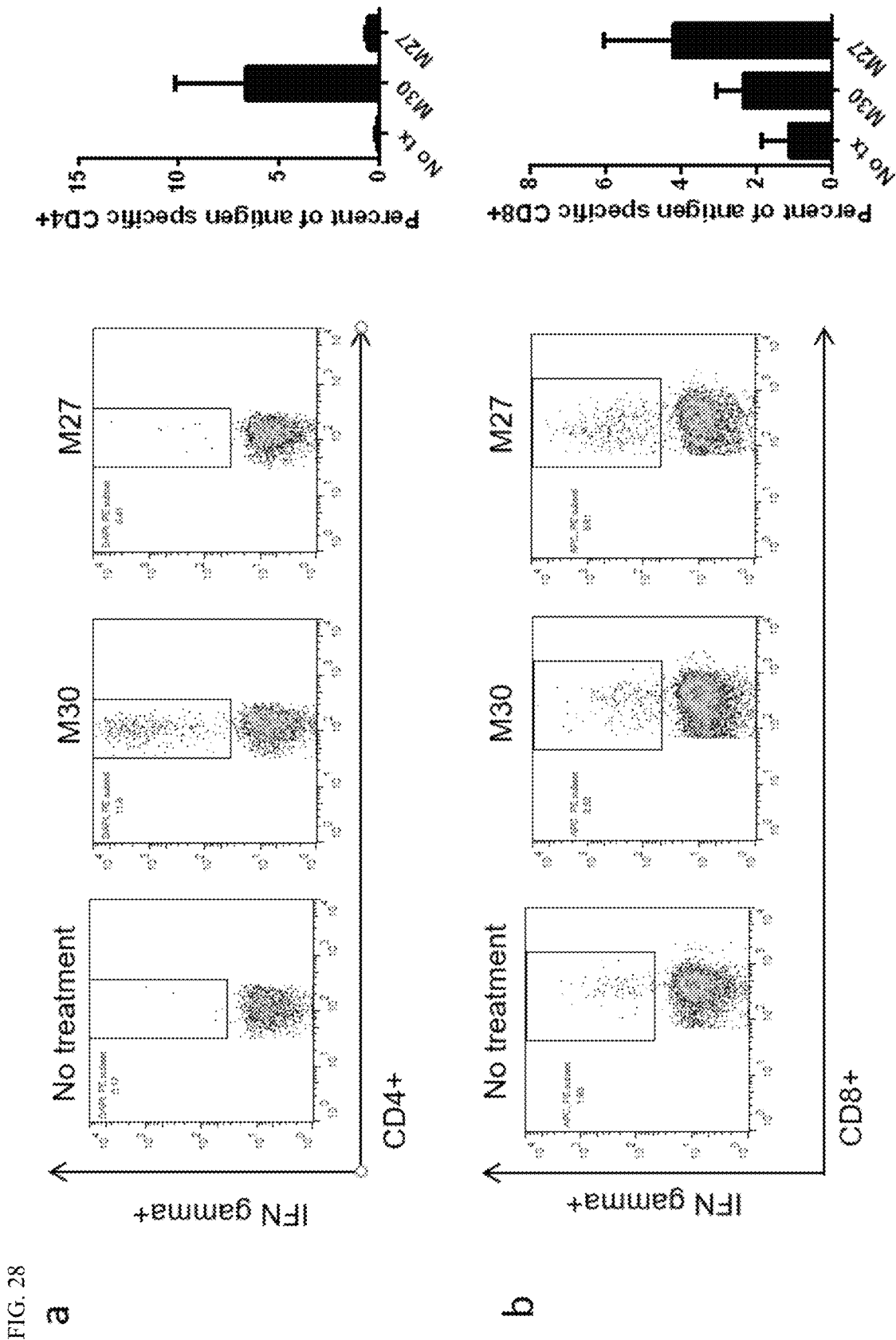

FIG. 28: Nanodisc-based vaccination with multivalent neo-antigen peptides elicited strong CD4+ and CD8+ T cell responses. (a) PBMCs from mice vaccinated with sHDL-M30/M27/CpG showed strong IFN gamma secretion from CD4+ T cells upon restimulation by M30 peptide. (b) PBMCs from mice vaccinated with sHDL-M30/M27/CpG showed strong IFN gamma secretion from CD8+ T cells upon restimulation by M27 peptide. Data represent mean±SD (n=3-4).

Figure 29:
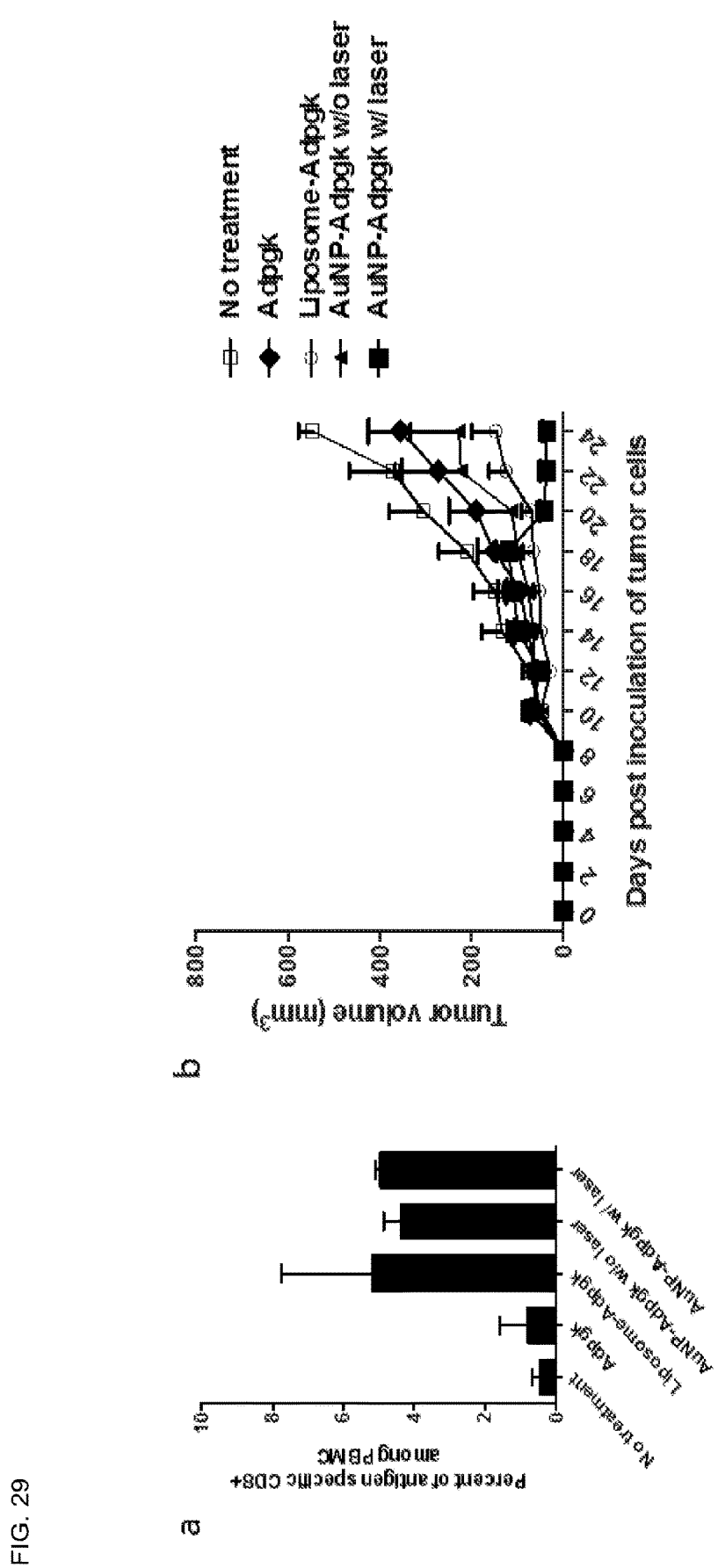

FIG. 29: Nanoparticle formulations improve CD8+ T cell responses and therapeutic effect of neo-antigen peptide vaccination. C57BL/6 mice were inoculated with tumor cells ($1 \times 10^5$ MC38 cells per mouse) on the right flank by subcutaneous injection on day 0. Mice were vaccinated on days 10 and 17 with 15.5 nmol of ASMTNMELM and 2.3 nmol of CpG in either soluble for liposomal forms. AuNP (gold nanoparticles) groups were immunized on day 10 and exposed to laser or not on day 11, followed by tetramer staining on day 17. (a) Percent of antigen specific CD8+ T cells among PBMCs elicited by different formulations on day 7 post last vaccination. (b) Tumor growth curves for indicated formulations. Data represent mean±SD (n=3-5).

DEFINITIONS

To facilitate an understanding of the present invention, a number of terms and phrases are defined below:

As used here, the term "lipids" refer to fatty substances that are insoluble in water and include fats, oils, waxes, and related compounds. They may be either made in the blood (endogenous) or ingested in the diet (exogenous). Lipids are essential for normal body function and whether produced from an exogenous or endogenous source, they must be transported and then released for use by the cells. The production, transportation and release of lipids for use by the cells is referred to as lipid metabolism. While there are several classes of lipids, two major classes are cholesterol and triglycerides. Cholesterol may be ingested in the diet and manufactured by the cells of most organs and tissues in the body, primarily in the liver. Cholesterol can be found in its free form or, more often, combined with fatty acids as what is called cholesterol esters.

As used herein the term, "lipoproteins" refer to spherical compounds that are structured so that water-insoluble lipids are contained in a partially water-soluble shell. Depending on the type of lipoprotein, the contents include varying amounts of free and esterified cholesterol, triglycerides and apoproteins or apolipoproteins. There are five major types of lipoproteins, which differ in function and in their lipid and apoprotein content and are classified according to increasing density: (i) chylomicrons and chylomicron remnants, (ii) very low density lipoproteins ("VLDL"), (iii) intermediate-density lipoproteins ("IDL"), (iv) low-density lipoproteins ("LDL"), and (v) high-density lipoproteins ("HDL"). Cholesterol circulates in the bloodstream as particles associated with lipoproteins.

As used herein, the term "HDL" or "high density lipoprotein" refers to high-density lipoprotein. HDL comprises a complex of lipids and proteins in approximately equal amounts that functions as a transporter of cholesterol in the blood. HDL is mainly synthesized in and secreted from the liver and epithelial cells of the small intestine. Immediately after secretion, HDL is in a form of a discoidal particle containing apolipoprotein A-I (also called apoA-I) and phospholipid as its major constituents, and also called nascent HDL. This nascent HDL receives, in blood, free cholesterol from cell membranes of peripheral cells or produced in the hydrolysis course of other lipoproteins, and forms mature spherical HDL while holding, at its hydrophobic center, cholesterol ester converted from said cholesterol by the action of LCAT (lecithin cholesterol acyltransferase). HDL plays an extremely important role in a lipid metabolism process called "reverse cholesterol transport", which takes, in blood, cholesterol out of peripheral tissues and transports it to the liver. High levels of HDL are associated with a decreased risk of atherosclerosis and coronary heart disease (CHD) as the reverse cholesterol transport is considered one of the major mechanisms for HDL's prophylactic action on atherosclerosis.

As used herein, the terms "synthetic HDL," "sHDL," "reconstituted HDL", or "rHDL" refer to a particle structurally analogous to native HDL, composed of a lipid or lipids in association with at least one of the proteins of HDL, preferably Apo A-I or a mimetic thereof, and which exhibits all of the known physiological functions of HDL. Typically, the components of sHDL may be derived from blood, or produced by recombinant technology.

As used herein, the term "complexed" is used in its broadest sense. Examples of complexed include but are not limited to chemical conjugation, surface adsorption, internal loading, as well as physical mixture of antigen and adjuvant molecules.

As used herein, the terms "biological biomacromolecule" or "biomacromolecule" as used herein refer to a molecule with a molecular mass exceeding 1 kDa which can be isolated from an organism or from cellular culture, e.g., eukaryotic (e.g., mammalian) cell culture or prokaryotic (e.g., bacterial) cell culture. In some embodiments, the use of the term refers to polymers, e.g., biopolymers such as nucleic acids (such as DNA, RNA), polypeptides (such as proteins), carbohydrates, and lipids. In some embodiments, the term "biomacromolecule" refers to a protein. In some embodiments, the term "biomacromolecule" refers to a recombinant protein or a fusion protein. In some embodiments, the protein is soluble. In some embodiments, the biomacromolecule is an antibody, e.g., a monoclonal antibody.

As used herein, the term "antigen" is defined herein as a molecule which contains one or more epitopes that will stimulate a hosts immune system to make a cellular antigen-specific immune response, and/or a humoral antibody response. Antigens can be peptides, proteins, polysaccharides, saccharides, lipids, nucleic acids, and combinations thereof. The antigen can be derived from a virus, bacterium, parasite, plant, protozoan, fungus, tissue or transformed cell such as a cancer or leukemic cell and can be a whole cell or immunogenic component thereof, e.g., cell wall components. An antigen may be an oligonucleotide or polynucleotide which expresses an antigen. Antigens can be natural or synthetic antigens, for example, haptens, polyepitopes, flanking epitopes, and other recombinant or synthetically derived antigens (see, e.g., Bergmann, et al., Eur. J. Immunol., 23:2777-2781 (1993); Bergmann, et al., J. Immunol., 157:3242-3249 (1996); Suhrbier, Immunol. and Cell Biol., 75:402-408 (1997)).

As used herein, the term "neo-antigen" or "neo-antigenic" means a class of tumor antigens that arises from a tumor-specific mutation(s) which alters the amino acid sequence of genome encoded proteins.

As used herein, the term "tumor-specific antigen" is defined herein as an antigen that is unique to tumor cells and does not occur in or on other cells in the body.

As used herein, the term "tumor-associated antigen" is defined herein as an antigen that is not unique to a tumor cell and is also expressed in or on a normal cell under conditions that fail to induce an immune response to the antigen.

As used herein, the term "adjuvant" is defined herein as a substance increasing the immune response to other antigens when administered with other antigens. Adjuvants are also referred to herein as "immune potentiators" and "immune modulators".

As used herein, the term "antigen-presenting cells" are defined herein as highly specialized cells that can process antigens and display their peptide fragments on the cell surface together with molecules required for lymphocyte activation. The major antigen-presenting cells for T cells are dendritic cells, macrophages and B cells. The major antigen-presenting cells for B cells are follicular dendritic cells.

As used herein, the term "cross-presentation" is defined herein as the ability of antigen-presenting cells to take up, process and present extracellular antigens with MHC class I molecules to CD8 T cells (cytotoxic T cells). This process induces cellular immunity against most tumors and against viruses that do not infect antigen-presenting cells. Cross-presentation is also required for induction of cytotoxic immunity by vaccination with protein antigens, for example in tumor vaccination.

As used herein, the terms "immunologic", "immunological" or "immune" response is the development of a humoral and/or a cellular response directed against an antigen.

As used herein, the term "kit" refers to any delivery system for delivering materials. In the context of the sHDL nanoparticles as described herein (e.g., compositions comprising a sHDL nanoparticle encapsulating siRNA) (e.g., compositions comprising an sHDL nanoparticle configured to activate an immune response), such delivery systems include systems that allow for the storage, transport, or delivery of such compositions and/or supporting materials (e.g., written instructions for using the materials, etc.) from one location to another. For example, kits include one or more enclosures (e.g., boxes) containing the necessary agents and/or supporting materials. As used herein, the term "fragmented kit" refers to delivery systems comprising two or more separate containers that each contain a subportion of the total kit components. The containers may be delivered to the intended recipient together or separately. For example, a first container may contain a composition comprising an sHDL nanoparticle or the ingredients necessary to synthesize such an sHDL nanoparticle, while a second container contains a second agent (e.g., siRNA, an antigen, an adjuvant) (e.g., an antibiotic or spray applicator). Indeed, any delivery system comprising two or more separate containers that each contains a subportion of the total kit components are included in the term "fragmented kit." In contrast, a "combined kit" refers to a delivery system containing all of the components necessary to synthesize and utilize any of the sHDL nanoparticles as described (e.g., in a single box housing each of the desired components). The term "kit" includes both fragmented and combined kits.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

As used herein, the term "drug" or "therapeutic agent" is meant to include any molecule, molecular complex or substance administered to an organism for diagnostic or therapeutic purposes, including medical imaging, monitoring, contraceptive, cosmetic, nutraceutical, pharmaceutical and prophylactic applications. The term "drug" is further meant to include any such molecule, molecular complex or substance that is chemically modified and/or operatively attached to a biologic or biocompatible structure.

As used herein, the term "solvent" refers to a medium in which a reaction is conducted. Solvents may be liquid but are not limited to liquid form. Solvent categories include but are not limited to nonpolar, polar, protic, and aprotic.

DETAILED DESCRIPTION OF THE INVENTION

The present invention relates to nanoparticles complexed with biomacromolecule agents configured for treating, preventing or ameliorating various types of disorders, and methods of synthesizing the same. In particular, the present invention is directed to compositions comprising nanoparticles (e.g., synthetic high density lipoprotein (sHDL)) carrying biomacromolecule agents (e.g., nucleic acid, peptides, glycolipids, etc.), methods for synthesizing such nanoparticles, as well as systems and methods utilizing such nanoparticles (e.g., in diagnostic and/or therapeutic settings).

Nanoparticles

The present invention is not limited to specific types or kinds of nanoparticles for complexing with biomacromolecule agents configured for treating, preventing or ameliorating various types of disorders.

Examples of nanoparticles include, but are not limited to, fullerenes (a.k.a. $C_{60}$, $C_{70}$, $C_{76}$, $C_{80}$, $C_{84}$), endohedral metallofullerenes (EMI's) buckyballs, which contain additional atoms, ions, or clusters inside their fullerene cage), trimetallic nitride templated endohedral metallofullerenes (TNT EMEs, high-symmetry four-atom molecular cluster endohedrals, which are formed in a trimetallic nitride template within the carbon cage), single-walled and multi-walled carbon nanotubes, branched and dendritic carbon nanotubes, gold nanorods, silver nanorods, single-walled and multi-walled boron/nitrate nanotubes, carbon nanotube peapods (nanotubes with internal metallo-fullerenes and/or other internal chemical structures), carbon nanohorns, carbon nanohorn peapods, liposomes, nanoshells, dendrimers, quantum dots, superparamagnetic nanoparticles, nanorods, and cellulose nanoparticles. The particle embodiment can also include microparticles with the capability to enhance effectiveness or selectivity. Other non-limiting exemplary nanoparticles include glass and polymer micro- and nano-spheres, biodegradable PLGA micro- and nano-spheres, gold, silver, carbon, and iron nanoparticles.

In some embodiments, the nanoparticle is a modified micelle. In these embodiments, the modified micelle comprises polyol polymers modified to contain a hydrophobic polymer block. The term "hydrophobic polymer block" as used in the present disclosure indicates a segment of the polymer that on its own would be hydrophobic. The term "micelle" as used herein refers to an aggregate of molecules dispersed in a liquid. A typical micelle in aqueous solution forms an aggregate with the hydrophilic "head" regions in contact with surrounding solvent, sequestering the hydrophobic single tail regions in the micelle centre. In some embodiments the head region may be, for example, a surface region of the polyol polymer while the tail region may be, for example, the hydrophobic polymer block region of the polyol polymer.

The invention further encompasses use of particles on the micrometer scale in addition to the nanometer scale. Where microparticles are used, it is preferred that they are relatively small, on the order of 1-50 micrometers. For ease of discussion, the use herein of "nanoparticles" encompasses true nanoparticles (sizes of from about 1 nm to about 1000 nm), microparticles (e.g., from about 1 micrometer to about 50 micrometers), or both.

Examples of nanoparticles include, by way of example and without limitation, paramagnetic nanoparticles, super-paramagnetic nanoparticles, metal nanoparticles, fullerene-like materials, inorganic nanotubes, dendrimers, dendrimers with covalently attached metal chelates, nanofibers, nano-horns, nano-onions, nanorods, nanoropes and quantum dots. In some embodiments, a nanoparticle is a metal nanoparticle (for example, a nanoparticle of gold, palladium, platinum, silver, copper, nickel, cobalt, iridium, or an alloy of two or more thereof). Nanoparticles can include a core or a core and a shell, as in core-shell nanoparticles.

In some embodiments, the nanoparticles are sHDL nanoparticles. Generally, sHDL nanoparticles are composed of a mixture of HDL apolipoprotein and an amphipathic lipid.

The present invention is not limited to use of a particular type or kind of HDL apolipoprotein. HDL apolipoproteins include, for example apolipoprotein A-I (apo A-I), apolipoprotein A-II (apo A-II), apolipoprotein A4 (apo A4), apolipoprotein Cs (apo Cs), and apolipoprotein E (apo E). In some embodiments, the HDL apolipoprotein is selected from preproapolipoprotein, preproApoA-I, proApoA-I, ApoA-I, preproApoA-II, proApoA-II, ApoA-II, preproApoA-IV, proApoA-IV, ApoA-IV, ApoA-V, preproApoE, proApoE, ApoE, preproApoA-1Milano, proApoA-IMilano ApoA-1Milano preproApoA-IParis, proApoA-IParis, and ApoA-IParis and peptide mimetics of these proteins mixtures thereof. Preferably, the carrier particles are composed of Apo A-I or Apo A-II, however the use of other lipoproteins including apolipoprotein A4, apolipoprotein Cs or apolipoprotein E may be used alone or in combination to formulate carrier particle mixtures for delivery of therapeutic agents. In some embodiments, mimetics of such HDL apolipoproteins are used.

ApoA-I is synthesized by the liver and small intestine as preproapolipoprotein which is secreted as a proprotein that is rapidly cleaved to generate a mature polypeptide having 243 amino acid residues. ApoA-I consists mainly of 6 to 8 different 22 amino acid repeats spaced by a linker moiety which is often proline, and in some cases consists of a stretch made up of several residues. ApoA-I forms three types of stable complexes with lipids: small, lipid-poor complexes referred to as pre-beta-1 HDL; flattened discoidal particles containing polar lipids (phospholipid and cholesterol) referred to as pre-beta-2 HDL; and spherical particles containing both polar and nonpolar lipids, referred to as spherical or mature HDL ($HDL_3$ and $HDL_2$). Most HDL in the circulating population contain both ApoA-I and ApoA-II (the second major HDL protein).

In some embodiments, ApoA-I agonists or mimetics are provided. In some embodiments, such ApoA-I mimetics are capable of forming amphipathic α-helices that mimic the activity of ApoA-I, and have specific activities approaching or exceeding that of the native molecule. In some, the ApoA-I mimetics are peptides or peptide analogues that: form amphipathic helices (in the presence of lipids), bind lipids, form pre-β-like or HDL-like complexes, activate lecithin:cholesterol acyltransferase (LCAT), increase serum levels of HDL fractions, and promote cholesterol efflux.

The present invention is not limited to use of a particular ApoA-I mimetic. In some embodiments, any of the ApoA-I mimetics described in Srinivasa, et al., 2014 Curr. Opinion Lipidology Vol. 25(4): 304-308 are utilized. In some embodiments, any of the ApoA-I mimetics described in U.S. Patent Application Publication Nos. 20110046056 and 20130231459 are utilized.

In some embodiments, the "22A" ApoA-I mimetic is used (PVLDLFRELLNELLEALKQKLK) (SEQ ID NO: 4) (see, Examples I-IV) (see, e.g., U.S. Pat. No. 7,566,695). In some embodiments, any of the following ApoA-I mimetics shown in Table 1 as described in U.S. Pat. No. 7,566,695 are utilized:

TABLE 1

| ApoA-I mimetics | |
|---|---|
| SEQ ID NO | AMINO ACID SEQUENCE |
| (SEQ ID NO: 1) | PVLDLFRELLNELLEZLKQKLK |
| (SEQ ID NO: 2) | GVLDLFRELLNELLEALKQKLKK |
| (SEQ ID NO: 3) | PVLDLFRELLNELLEWLKQKLK |
| (SEQ ID NO: 4) | PVLDLFRELLNELLEALKQKLK |
| (SEQ ID NO: 5) | pVLDLFRELLNELLEALKQKLKK |
| (SEQ ID NO: 6) | PVLDLFRELLNEXLEALKQKLK |
| (SEQ ID NO: 7) | PVLDLFKELLNELLEALKQKLK |
| (SEQ ID NO: 8) | PVLDLFRELLNEGLEALKQKLK |
| (SEQ ID NO: 9) | PVLDLFRELGNELLEALKQKLK |
| (SEQ ID NO: 10) | PVLDLFRELLNELLEAZKQKLK |
| (SEQ ID NO: 11) | PVLDLFKELLQELLEALKQKLK |
| (SEQ ID NO: 12) | PVLDLFRELLNELLEAGKQKLK |

TABLE 1-continued

ApoA-I mimetics

| SEQ ID NO | AMINO ACID SEQUENCE |
|---|---|
| (SEQ ID NO: 13) | GVLDLFRELLNEGLEALKQKLK |
| (SEQ ID NO: 14) | PVLDLFRELLNELLEALOQOLO |
| (SEQ ID NO: 15) | PVLDLFRELWNELLEALKQKLK |
| (SEQ ID NO: 16) | PVLDLLRELLNELLEALKQKLK |
| (SEQ ID NO: 17) | PVLELFKELLQELLEALKQKLK |
| (SEQ ID NO: 18) | GVLDLFRELLNELLEALKQKLK |
| (SEQ ID NO: 19) | pVLDLFRELLNEGLEALKQKLK |
| (SEQ ID NO: 20) | PVLDLFREGLNELLEALKQKLK |
| (SEQ ID NO: 21) | pVLDLFRELLNELLEALKQKLK |
| (SEQ ID NO: 22) | PVLDLFRELLNELLEGLKQKLK |
| (SEQ ID NO: 23) | PLLELFKELLQELLEALKQKLK |
| (SEQ ID NO: 24) | PVLDLFRELLNELLEALQKKLK |
| (SEQ ID NO: 25) | PVLDFFRELLNEXLEALKQKLK |
| (SEQ ID NO: 26) | PVLDLFRELLNELLELLKQKLK |
| (SEQ ID NO: 27) | PVLDLFRELLNELZEALKQKLK |
| (SEQ ID NO: 28) | PVLDLFRELLNELWEALKQKLK |
| (SEQ ID NO: 29) | AVLDLFRELLNELLEALKQKLK |
| (SEQ ID NO: 30) | PVLDLPRELLNELLEALKQKLK[1] |
| (SEQ ID NO: 31) | PVLDLFLELLNEXLEALKQKLK |
| (SEQ ID NO: 32) | XVLDLFRELLNELLEALKQKLK |
| (SEQ ID NO: 33) | PVLDLFREKLNELLEALKQKLK |
| (SEQ ID NO: 34) | PVLDZFRELLNELLEALKQKLK |
| (SEQ ID NO: 35) | PVLDWFRELLNELLEALKQKLK |
| (SEQ ID NO: 36) | PLLELLKELLQELLEALKQKLK |
| (SEQ ID NO: 37) | PVLDLFREWLNELLEALKQKLK |
| (SEQ ID NO: 38) | PVLDLFRELLNEXLEAWKQKLK |
| (SEQ ID NO: 39) | PVLDLFRELLEELLKALKKKLK |
| (SEQ ID NO: 40) | PVLDLFNELLRELLEALQKKLK |
| (SEQ ID NO: 41) | PVLDLWRELLNEXLEALKQKLK |
| (SEQ ID NO: 42) | PVLDEFREKLNEXWEALKQKLK |
| (SEQ ID NO: 43) | PVLDEFREKLWEXLEALKQKLK |
| (SEQ ID NO: 44) | pvldefreklneXlealkqklk |
| (SEQ ID NO: 45) | PVLDEFREKLNEXLEALKQKLK |
| (SEQ ID NO: 46) | PVLDEFREKLNEXLEALKQKLK |
| (SEQ ID NO: 47) | ~VLDLFRELLNEGLEALKQKLK |
| (SEQ ID NO: 48) | pVLDLFRELLNELLEALKQKLK |
| (SEQ ID NO: 49) | PVLDLFRNLLEKLLEALEQKLK |
| (SEQ ID NO: 50) | PVLDLFRELLWEXLEALKQKLK |
| (SEQ ID NO: 51) | PVLDLFWELLNEXLEALKQKLK |
| (SEQ ID NO: 52) | PVWDEFREKLNEXLEALKQKLK |
| (SEQ ID NO: 53) | WLDLFRELLNELLEALKQKLK |
| (SEQ ID NO: 54) | PVLDLFRELLNEWLEALKQKLK |
| (SEQ ID NO: 55) | P~~~LFRELLNELLEALKQKLK |
| (SEQ ID NO: 56) | PVLDLFRELLNELLEALKQKKK |
| (SEQ ID NO: 57) | PVLDLFRNLLEELLKALEQKLK |
| (SEQ ID NO: 58) | PVLDEFREKLNEXLEALKQKL~ |
| (SEQ ID NO: 59) | LVLDLFRELLNELLEALKQKLK |
| (SEQ ID NO: 60) | PVLDLFRELLNELLEALKQ~~~ |
| (SEQ ID NO: 61) | PVLDEFRWKLNEXLEALKQKLK |
| (SEQ ID NO: 62) | PVLDEWREKLNEXLEALKQKLK |
| (SEQ ID NO: 63) | PVLDFFREKLNEXLEALKQKLK |
| (SEQ ID NO: 64) | PWLDEFREKLNEXLEALKQKLK |
| (SEQ ID NO: 65) | ~VLDEFREKLNEXLEALKQKLK |
| (SEQ ID NO: 66) | PVLDLFRNLLEELLEALQKKLK |
| (SEQ ID NO: 67) | ~VLDLFRELLNELLEALKQKLK |
| (SEQ ID NO: 68) | PVLDEFRELLKEXLEALKQKLK |
| (SEQ ID NO: 69) | PVLDEFRKKLNEXLEALKQKLK |
| (SEQ ID NO: 70) | PVLDEFRELLYEXLEALKQKLK |
| (SEQ ID NO: 71) | PVLDEFREKLNELXEALKQKLK |
| (SEQ ID NO: 72) | PVLDLFRELLNEXLWALKQKLK |
| (SEQ ID NO: 73) | PVLDEFWEKLNEXLEALKQKLK |
| (SEQ ID NO: 74) | PVLDKFREKLNEXLEALKQKLK |
| (SEQ ID NO: 75) | PVLDEFREKLNEELEALKQKLK |
| (SEQ ID NO: 76) | PVLDEFRELLFEXLEALKQKLK |
| (SEQ ID NO: 77) | PVLDEFREKLNKXLEALKQKLK |
| (SEQ ID NO: 78) | PVLDEFRDKLNEXLEALKQKLK |
| (SEQ ID NO: 79) | PVLDEFRELLNELLEALKQKLK |
| (SEQ ID NO: 80) | PVLDLFERLLNELLEALQKKLK |
| (SEQ ID NO: 81) | PVLDEFREKLNWXLEALKQKLK |
| (SEQ ID NO: 82) | ~~LDEFREKLNEXLEALKQKLK |
| (SEQ ID NO: 83) | PVLDEFREKLNEXLEALWQKLK |
| (SEQ ID NO: 84) | PVLDEFREKLNELLEALKQKLK |
| (SEQ ID NO: 85) | P~LDLFRELLNELLEALKQKLK |
| (SEQ ID NO: 86) | PVLELFERLLDELLNALQKKLK |
| (SEQ ID NO: 87) | pllellkellqellealkqklk |
| (SEQ ID NO: 88) | PVLDKFRELLNEXLEALKQKLK |

TABLE 1-continued

ApoA-I mimetics

| SEQ ID NO | AMINO ACID SEQUENCE |
|---|---|
| (SEQ ID NO: 89) | PVLDEFREKLNEXLWALKQKLK |
| (SEQ ID NO: 90) | ~~~DEFREKLNEXLEALKQKLK |
| (SEQ ID NO: 91) | PVLDEFRELLNEXLEALKQKLK |
| (SEQ ID NO: 92) | PVLDEFRELYNEXLEALKQKLK |
| (SEQ ID NO: 93) | PVLDEFREKLNEXLKALKQKLK |
| (SEQ ID NO: 94) | PVLDEFREKLNEALEALKQKLK |
| (SEQ ID NO: 95) | PVLDLFRELLNLXLEALKQKLK |
| (SEQ ID NO: 96) | pvldlfrellneXlealkqklk |
| (SEQ ID NO: 97) | PVLDLFRELLNELLE~~~~~~~ |
| (SEQ ID NO: 98) | PVLDLFRELLNEELEALKQKLK |
| (SEQ ID NO: 99) | KLKQKLAELLENLLERFLDLVP |
| (SEQ ID NO: 100) | pvldlfrellnellealkqklk |
| (SEQ ID NO: 101) | PVLDLFRELLNWXLEALKQKLK |
| (SEQ ID NO: 102) | PVLDLFRELLNLXLEALKEKLK |
| (SEQ ID NO: 103) | PVLDEFRELLNEELEALKQKLK |
| (SEQ ID NO: 104) | P~~~~~~~LLNELLEALKQKLK |
| (SEQ ID NO: 105) | PAADAFREAANEAAEAAKQKAK |
| (SEQ ID NO: 106) | PVLDEFREKLNEELEALKQKLK |
| (SEQ ID NO: 107) | klkqklaellenllerfldlvp |
| (SEQ ID NO: 108) | PVLDLFRWLLNEXLEALKQKLK |
| (SEQ ID NO: 109) | PVLDEFREKLNERLEALKQKLK |
| (SEQ ID NO: 110) | PVLDEFREKLNEXXEALKQKLK |
| (SEQ ID NO: 111) | PVLDEFREKLWEXWEALKQKLK |
| (SEQ ID NO: 112) | PVLDEFREKLNEXSEALKQKLK |
| (SEQ ID NO: 113) | PVLDEFREKLNEPLEALKQKLK |
| (SEQ ID NO: 114) | PVLDEFREKLNEXMEALKQKLK |
| (SEQ ID NO: 115) | PKLDEFREKLNEXLEALKQKLK |
| (SEQ ID NO: 116) | PHLDEFREKLNEXLEALKQKLK |
| (SEQ ID NO: 117) | PELDEFREKLNEXLEALKQKLK |
| (SEQ ID NO: 118) | PVLDEFREKLNEXLEALEQKLK |
| (SEQ ID NO: 119) | PVLDEFREKLNEELEAXKQKLK |
| (SEQ ID NO: 120) | PVLDEFREKLNEELEXLKQKLK |
| (SEQ ID NO: 121) | PVLDEFREKLNEELEALWQKLK |
| (SEQ ID NO: 122) | PVLDEFREKLNEELEWLKQKLK |
| (SEQ ID NO: 123) | QVLDLFRELLNELLEALKQKLK |
| (SEQ ID NO: 124) | PVLDLFOELLNELLEALOQOLO |
| (SEQ ID NO: 125) | NVLDLFRELLNELLEALKQKLK |
| (SEQ ID NO: 126) | PVLDLFRELLNELGEALKQKLK |
| (SEQ ID NO: 127) | PVLDLFRELLNELLELLKQKLK |
| (SEQ ID NO: 128) | PVLDLFRELLNELLEFLKQKLK |
| (SEQ ID NO: 129) | PVLELFNDLLRELLEALQKKLK |
| (SEQ ID NO: 130) | PVLELFNDLLRELLEALKQKLK |
| (SEQ ID NO: 131) | PVLELFKELLNELLDALRQKLK |
| (SEQ ID NO: 132) | PVLDLFRELLENLLEALQKKLK |
| (SEQ ID NO: 133) | PVLELFERLLEDLLQALNKKLK |
| (SEQ ID NO: 134) | PVLELFERLLEDLLKALNOKLK |
| (SEQ ID NO: 135) | DVLDLFRELLNELLEALKQKLK |
| (SEQ ID NO: 136) | PALELFKDLLQELLEALKQKLK |
| (SEQ ID NO: 137) | PVLDLFRELLNEGLEAZKQKLK |
| (SEQ ID NO: 138) | PVLDLFRELLNEGLEWLKQKLK |
| (SEQ ID NO: 139) | PVLDLFRELWNEGLEALKQKLK |
| (SEQ ID NO: 140) | PVLDLFRELLNEGLEALOQOLO |
| (SEQ ID NO: 141) | PVLDFFRELLNEGLEALKQKLK |
| (SEQ ID NO: 142) | PVLELFRELLNEGLEALKQKLK |
| (SEQ ID NO: 143) | PVLDLFRELLNEGLEALKQKLK* |
| (SEQ ID NO: 144) | pVLELFENLLERLLDALQKKLK |
| (SEQ ID NO: 145) | GVLELFENLLERLLDALQKKLK |
| (SEQ ID NO: 146) | PVLELFENLLERLLDALQKKLK |
| (SEQ ID NO: 147) | PVLELFENLLERLFDALQKKLK |
| (SEQ ID NO: 148) | PVLELFENLLERLGDALQKKLK |
| (SEQ ID NO: 149) | PVLELFENLWERLLDALQKKLK |
| (SEQ ID NO: 150) | PLLELFENLLERLLDALQKKLK |
| (SEQ ID NO: 151) | PVLELFENLGERLLDALQKKLK |
| (SEQ ID NO: 152) | PVFELFENLLERLLDALQKKLK |
| (SEQ ID NO: 153) | AVLELFENLLERLLDALQKKLK |
| (SEQ ID NO: 154) | PVLELFENLLERGLDALQKKLK |
| (SEQ ID NO: 155) | PVLELFLNLWERLLDALQKKLK |
| (SEQ ID NO: 156) | PVLELFLNLLERLLDALQKKLK |
| (SEQ ID NO: 157) | PVLEFFENLLERLLDALQKKLK |
| (SEQ ID NO: 158) | PVLELFLNLLERLLDWLQKKLK |
| (SEQ ID NO: 159) | PVLDLFENLLERLLDALQKKLK |
| (SEQ ID NO: 160) | PVLELFENLLERLLDWLQKKLK |
| (SEQ ID NO: 161) | PVLELFENLLERLLEALQKKLK |
| (SEQ ID NO: 162) | PVLELFENWLERLLDALQKKLK |
| (SEQ ID NO: 163) | PVLELFENLLERLWDALQKKLK |
| (SEQ ID NO: 164) | PVLELFENLLERLLDAWQKKLK |

TABLE 1-continued

ApoA-I mimetics

| SEQ ID NO | AMINO ACID SEQUENCE |
|---|---|
| (SEQ ID NO: 165) | PVLELFENLLERLLDLLQKKLK |
| (SEQ ID NO: 166) | PVLELFLNLLEKLLDALQKKLK |
| (SEQ ID NO: 167) | PVLELFENGLERLLLDALQKKLK |
| (SEQ ID NO: 168) | PVLELFEQLLEKLLLDALQKKLK |
| (SEQ ID NO: 169) | PVLELFENLLEKLLDALQKKLK |
| (SEQ ID NO: 170) | PVLELFENLLEOLLDALQOOLO |
| (SEQ ID NO: 171) | PVLELFENLLEKLLDLLQKKLK |
| (SEQ ID NO: 172) | PVLELFLNLLERLGDALQKKLK |
| (SEQ ID NO: 173) | PVLDLFDNLLDRLLDLLNKKLK |
| (SEQ ID NO: 174) | pvlelfenllerlldalqkklk |
| (SEQ ID NO: 175) | PVLELFENLLERLLELLNKKLK |
| (SEQ ID NO: 176) | PVLELWENLLERLLDALQKKLK |
| (SEQ ID NO: 177) | GVLELFLNLLERLLDALQKKLK |
| (SEQ ID NO: 178) | PVLELFDNLLEKLLEALQKKLR |
| (SEQ ID NO: 179) | PVLELFDNLLERLLDALQKKLK |
| (SEQ ID NO: 180) | PVLELFDNLLDKLLDALQKKLR |
| (SEQ ID NO: 181) | PVLELFENLLERWLDALQKKLK |
| (SEQ ID NO: 182) | PVLELFENLLEKLLEALQKKLK |
| (SEQ ID NO: 183) | PLLELFENLLEKLLDALQKKLK |
| (SEQ ID NO: 184) | PVLELFLNLLERLLDAWQKKLK |
| (SEQ ID NO: 185) | PVLELFENLLERLLDALQOOLO |
| (SEQ ID NO: 186) | PVLELFEQLLERLLDALQKKLK |
| (SEQ ID NO: 187) | PVLELFENLLERLLDALNKKLK |
| (SEQ ID NO: 188) | PVLELFENLLDRLLDALQKKLK |
| (SEQ ID NO: 189) | DVLELFENLLERLLDALQKKLK |
| (SEQ ID NO: 190) | PVLEFWDNLLDKLLDALQKKLR |
| (SEQ ID NO: 191) | PVLDLLRELLEELKQKLK* |
| (SEQ ID NO: 192) | PVLDLFKELLEELKQKLK* |
| (SEQ ID NO: 193) | PVLDLFRELLEELKQKLK* |
| (SEQ ID NO: 194) | PVLELFRELLEELKQKLK* |
| (SEQ ID NO: 195) | PVLELFKELLEELKQKLK* |
| (SEQ ID NO: 196) | PVLDLFRELLEELKNKLK* |
| (SEQ ID NO: 197) | PLLDLFRELLEELKQKLK* |
| (SEQ ID NO: 198) | GVLDLFRELLEELKQKLK* |
| (SEQ ID NO: 199) | PVLDLFRELWEELKQKLK* |
| (SEQ ID NO: 200) | NVLDLFRELLEELKQKLK* |
| (SEQ ID NO: 201) | PLLDLFKELLEELKQKLK* |
| (SEQ ID NO: 202) | PALELFKDLLEELRQKLR* |
| (SEQ ID NO: 203) | AVLDLFRELLEELKQKLK* |
| (SEQ ID NO: 204) | PVLDFFRELLEELKQKLK* |
| (SEQ ID NO: 205) | PVLDLFREWLEELKQKLK* |
| (SEQ ID NO: 206) | PLLELLKELLEELKQKLK* |
| (SEQ ID NO: 207) | PVLELLKELLEELKQKLK* |
| (SEQ ID NO: 208) | PALELFKDLLEELRQRLK* |
| (SEQ ID NO: 209) | PVLDLFRELLNELLQKLK |
| (SEQ ID NO: 210) | PVLDLFRELLEELKQKLK |
| (SEQ ID NO: 211) | PVLDLFRELLEELOQOLO* |
| (SEQ ID NO: 212) | PVLDLFOELLEELOQOLK* |
| (SEQ ID NO: 213) | PALELFKDLLEEFRQRLK* |
| (SEQ ID NO: 214) | pVLDLFRELLEELKQKLK* |
| (SEQ ID NO: 215) | PVLDLFRELLEEWKQKLK* |
| (SEQ ID NO: 216) | PVLELFKELLEELKQKLK |
| (SEQ ID NO: 217) | PVLDLFRELLELLKQKLK |
| (SEQ ID NO: 218) | PVLDLFRELLNELLQKLK* |
| (SEQ ID NO: 219) | PVLDLFRELLNELWQKLK |
| (SEQ ID NO: 220) | PVLDLFRELLEELQKKLK |
| (SEQ ID NO: 221) | DVLDLFRELLEELKQKLK* |
| (SEQ ID NO: 222) | PVLDAFRELLEALLQLKK |
| (SEQ ID NO: 223) | PVLDAFRELLEALAQLKK |
| (SEQ ID NO: 224) | PVLDLFREGWEELKQKLK |
| (SEQ ID NO: 225) | PVLDAFRELAEALAQLKK |
| (SEQ ID NO: 226) | PVLDAFRELGEALLQLKK |
| (SEQ ID NO: 227) | PVLDLFRELGEELKQKLK* |
| (SEQ ID NO: 228) | PVLDLFREGLEELKQKLK* |
| (SEQ ID NO: 229) | PVLDLFRELLEEGKQKLK* |
| (SEQ ID NO: 230) | PVLELFERLLEDLQKKLK |
| (SEQ ID NO: 231) | PVLDLFRELLEKLEQKLK |
| (SEQ ID NO: 232) | PLLELFKELLEELKQKLK* |
| (SEQ ID NO: 233) | LDDLLQKWAEAFNQLLKK |
| (SEQ ID NO: 234) | EWLKAFYEKVLEKLKELF* |
| (SEQ ID NO: 235) | EWLEAFYKKVLEKLKELF* |
| (SEQ ID NO: 236) | DWLKAFYDKVAEKLKEAF* |
| (SEQ ID NO: 237) | DWFKAFYDKVFEKFKEFF |
| (SEQ ID NO: 238) | GIKKFLGSIWKFIKAFVG |
| (SEQ ID NO: 239) | DWFKAFYDKVAEKFKEAF |
| (SEQ ID NO: 240) | DWLKAFYDKVAEKLKEAF |

TABLE 1-continued

ApoA-I mimetics

| SEQ ID NO | AMINO ACID SEQUENCE |
|---|---|
| (SEQ ID NO: 241) | DWLKAFYDKVFEKFKEFF |
| (SEQ ID NO: 242) | EWLEAFYKKVLEKLKELP |
| (SEQ ID NO: 243) | DWFKAFYDKFFEKFKEFF |
| (SEQ ID NO: 244) | EWLKAFYEKVLEKLKELF |
| (SEQ ID NO: 245) | EWLKAEYEKVEEKLKELF* |
| (SEQ ID NO: 246) | EWLKAEYEKVLEKLKELF* |
| (SEQ ID NO: 247) | EWLKAFYKKVLEKLKELF* |
| (SEQ ID NO: 248) | PVLDLFRELLEQKLK* |
| (SEQ ID NO: 249) | PVLDLFRELLEELKQK* |
| (SEQ ID NO: 250) | PVLDLFRELLEKLKQK* |

TABLE 1-continued

ApoA-I mimetics

| SEQ ID NO | AMINO ACID SEQUENCE |
|---|---|
| (SEQ ID NO: 251) | PVLDLFRELLEKLQK* |
| (SEQ ID NO: 252) | PVLDLFRELLEALKQK* |
| (SEQ ID NO: 253) | PVLDLFENLLERLKQK* |
| (SEQ ID NO: 254) | PVLDLFRELLNELKQK* |

*indicates peptides that are N-terminal acetylated and C-terminal amidated; indicates peptides that are N-terminal dansylated, sp indicates peptides that exhibited solubility problems under the experimental conditions; X is Aib, Z is Nal; O is Orn, He (%) designates percent helicity, mics designates micelles; and ~ indicates deleted amino acids.

In some embodiments, an ApoA-I mimetic having the following sequence as described in U.S. Pat. No. 6,743,778 is utilized: Asp Trp Leu Lys Ala Phe Tyr Asp Lys Val Ala Glu Lys Leu Lys Glu Ala Phe (SEQ ID NO:255).

In some embodiments, any of the following ApoA-I mimetics shown in Table 2 as described in U.S. Patent Application Publication No. 2003/0171277 are utilized:

TABLE 2

| SEQ ID NO | AMINO ACID SEQUENCE |
|---|---|
| (SEQ ID NO: 256) | D-W-L-K-A-F-Y-D-K-V-A-E-K-L-K-E-A-F |
| (SEQ ID NO: 257) | Ac-D-W-L-K-A-F-Y-D-K-V-A-E-K-L-K-E-A-F-NH$_2$ |
| (SEQ ID NO: 258) | Ac-D-W-F-K-A-F-Y-D-K-V-A-E-K-L-K-E-A-F-NH$_2$ |
| (SEQ ID NO: 259) | Ac-D-W-L-K-A-F-Y-D-K-V-A-E-K-F-K-E-A-F-NH$_2$ |
| (SEQ ID NO: 260) | Ac-D-W-F-K-A-F-Y-D-K-V-A-E-K-F-K-E-A-F-NH$_2$ |
| (SEQ ID NO: 261) | Ac-D-W-L-K-A-F-Y-D-K-V-F-E-K-F-K-E-F-F-NH$_2$ |
| (SEQ ID NO: 262) | Ac-D-W-L-K-A-F-Y-D-K-F-F-E-K-F-K-E-F-F-NH$_2$ |
| (SEQ ID NO: 263) | Ac-D-W-F-K-A-F-Y-D-K-F-F-E-K-F-K-E-F-F-NH$_2$ |
| (SEQ ID NO: 264) | Ac-D-W-L-K-A-F-Y-D-K-V-A-E-K-L-K-E-F-F-NH$_2$ |
| (SEQ ID NO: 265) | Ac-D-W-L-K-A-F-Y-D-K-V-F-E-K-F-K-E-A-F-NH$_2$ |
| (SEQ ID NO: 266) | Ac-D-W-L-K-A-F-Y-D-K-V-F-E-K-L-K-E-F-F-NH$_2$ |
| (SEQ ID NO: 267) | Ac-D-W-L-K-A-F-Y-D-K-V-A-E-K-F-K-E-F-F-NH$_2$ |
| (SEQ ID NO: 268) | Ac-D-W-L-K-A-F-Y-D-K-V-F-E-K-F-K-E-F-F-NH$_2$ |
| (SEQ ID NO: 269) | Ac-E-W-L-K-L-F-Y-E-K-V-L-E-K-F-K-E-A-F-NH$_2$ |
| (SEQ ID NO: 270) | Ac-E-W-L-K-A-F-Y-D-K-V-A-E-K-F-K-E-A-F-NH$_2$ |
| (SEQ ID NO: 271) | Ac-E-W-L-K-A-F-Y-D-K-V-A-E-K-L-K-E-F-F-NH$_2$ |
| (SEQ ID NO: 272) | Ac-E-W-L-K-A-F-Y-D-K-V-F-E-K-F-K-E-A-F-NH$_2$ |
| (SEQ ID NO: 273) | Ac-E-W-L-K-A-F-Y-D-K-V-F-E-K-L-K-E-F-F-NH$_2$ |
| (SEQ ID NO: 274) | Ac-E-W-L-K-A-F-Y-D-K-V-A-E-K-F-K-E-F-F-NH$_2$ |
| (SEQ ID NO: 275) | Ac-E-W-L-K-A-F-Y-D-K-V-F-E-K-F-K-E-F-F-NH$_2$ |
| (SEQ ID NO: 276) | AC-A-F-Y-D-K-V-A-E-K-L-K-E-A-F-NH$_2$ |
| (SEQ ID NO: 277) | Ac-A-F-Y-D-K-V-A-E-K-F-K-E-A-F-NH$_2$ |
| (SEQ ID NO: 278) | Ac-A-F-Y-D-K-V-A-E-K-F-K-E-A-F-NH$_2$ |
| (SEQ ID NO: 279) | Ac-A-F-Y-D-K-F-F-E-K-F-K-E-F-F-NH$_2$ |

TABLE 2-continued

| SEQ ID NO | AMINO ACID SEQUENCE |
|---|---|
| (SEQ ID NO: 280) | Ac-A-F-Y-D-K-F-F-E-K-F-K-E-F-F-NH$_2$ |
| (SEQ ID NO: 281) | Ac-A-F-Y-D-K-V-A-E-K-F-K-E-A-F-NH$_2$ |
| (SEQ ID NO: 282) | Ac-A-F-Y-D-K-V-A-E-K-L-K-E-F-F-NH$_2$ |
| (SEQ ID NO: 283) | Ac-A-F-Y-D-K-V-F-E-K-F-K-E-A-F-NH$_2$ |
| (SEQ ID NO: 284) | Ac-A-F-Y-D-K-V-F-E-K-L-K-E-F-F-NH$_2$ |
| (SEQ ID NO: 285) | Ac-A-F-Y-D-K-V-A-E-K-F-K-E-F-F-NH$_2$ |
| (SEQ ID NO: 286) | Ac-K-A-F-Y-D-K-V-F-E-K-F-K-E-F-NH$_2$ |
| (SEQ ID NO: 287) | Ac-L-F-Y-E-K-V-L-E-K-F-K-E-A-F-NH$_2$ |
| (SEQ ID NO: 288) | Ac-A-F-Y-D-K-V-A-E-K-F-K-E-A-F-NH$_2$ |
| (SEQ ID NO: 289) | Ac-A-F-Y-D-K-V-A-E-K-L-K-E-F-F-NH$_2$ |
| (SEQ ID NO: 290) | Ac-A-F-Y-D-K-V-F-E-K-F-K-E-A-F-NH$_2$ |
| (SEQ ID NO: 291) | Ac-A-F-Y-D-K-V-F-E-K-L-K-E-F-F-NH$_2$ |
| (SEQ ID NO: 292) | Ac-A-F-Y-D-K-V-A-E-K-F-K-E-F-F-NH$_2$ |
| (SEQ ID NO: 293) | Ac-A-F-Y-D-K-V-F-E-K-F-K-E-F-F-NH$_2$ |
| (SEQ ID NO: 294) | Ac-D-W-L-K-A-L-Y-D-K-V-A-E-K-L-K-E-A-L-NH$_2$ |
| (SEQ ID NO: 295) | Ac-D-W-F-K-A-F-Y-E-K-V-A-E-K-L-K-E-F-F-NH$_2$ |
| (SEQ ID NO: 296) | Ac-D-W-F-K-A-F-Y-E-K-F-F-E-K-F-K-E-F-F-NH$_2$ |
| (SEQ ID NO: 297) | Ac-E-W-L-K-A-L-Y-E-K-V-A-E-K-L-K-E-A-L-NH$_2$ |
| (SEQ ID NO: 298) | Ac-E-W-L-K-A-F-Y-E-K-V-A-E-K-L-K-E-A-F-NH$_2$ |
| (SEQ ID NO: 299) | Ac-E-W-F-K-A-F-Y-E-K-V-A-E-K-L-K-E-F-F-NH$_2$ |
| (SEQ ID NO: 300) | Ac-E-W-L-K-A-F-Y-E-K-V-F-E-K-F-K-E-F-F-NH$_2$ |
| (SEQ ID NO: 301) | Ac-E-W-L-K-A-F-Y-E-K-F-F-E-K-F-K-E-F-F-NH$_2$ |
| (SEQ ID NO: 302) | Ac-E-W-F-K-A-F-Y-E-K-F-F-E-K-F-K-E-F-F-NH$_2$ |
| (SEQ ID NO: 303) | Ac-D-F-L-K-A-W-Y-D-K-V-A-E-K-L-K-E-A-W-NH$_2$ |
| (SEQ ID NO: 304) | Ac-E-F-L-K-A-W-Y-E-K-V-A-E-K-L-K-E-A-W-NH$_2$ |
| (SEQ ID NO: 305) | Ac-D-F-W-K-A-W-Y-D-K-V-A-E-K-L-K-E-W-W-NH$_2$ |
| (SEQ ID NO: 306) | Ac-E-F-W-K-A-W-Y-E-K-V-A-E-K-L-K-E-W-W-NH$_2$ |
| (SEQ ID NO: 307) | Ac-D-K-L-K-A-F-Y-D-K-V-F-E-W-A-K-E-A-F-NH$_2$ |
| (SEQ ID NO: 308) | Ac-D-K-W-K-A-V-Y-D-K-F-A-E-A-F-K-E-F-L-NH$_2$ |
| (SEQ ID NO: 309) | Ac-E-K-L-K-A-F-Y-E-K-V-F-E-W-A-K-E-A-F-NH$_2$ |
| (SEQ ID NO: 310) | Ac-E-K-W-K-A-V-Y-E-K-F-A-E-A-F-K-E-F-L-NH$_2$ |
| (SEQ ID NO: 311) | Ac-D-W-L-K-A-F-V-D-K-F-A-E-K-F-K-E-A-Y-NH$_2$ |
| (SEQ ID NO: 312) | Ac-E-K-W-K-A-V-Y-E-K-F-A-E-A-F-K-E-F-L-NH$_2$ |
| (SEQ ID NO: 313) | Ac-D-W-L-K-A-F-V-Y-D-K-V-F-K-L-K-E-F-F-NH$_2$ |
| (SEQ ID NO: 314) | Ac-E-W-L-K-A-F-V-Y-E-K-V-F-L-K-E-F-F-NH$_2$ |
| (SEQ ID NO: 315) | Ac-D-W-L-R-A-F-Y-D-K-V-A-E-K-L-K-E-A-F-NH$_2$ |
| (SEQ ID NO: 316) | Ac-E-W-L-R-A-F-Y-E-K-V-A-E-K-L-K-E-A-F-NH$_2$ |
| (SEQ ID NO: 317) | Ac-D-W-L-K-A-F-Y-D-R-V-A-E-K-L-K-E-A-F-NH$_2$ |
| (SEQ ID NO: 318) | Ac-E-W-L-K-A-F-Y-E-R-V-A-E-K-L-K-E-A-F-NH$_2$ |

TABLE 2-continued

| SEQ ID NO | AMINO ACID SEQUENCE |
| --- | --- |
| (SEQ ID NO: 319) | Ac-D-W-L-K-A-F-Y-D-K-V-A-E-R-L-K-E-A-F-NH$_2$ |
| (SEQ ID NO: 320) | Ac-E-W-L-K-A-F-Y-E-K-V-A-E-R-L-K-E-A-F-NH$_2$ |
| (SEQ ID NO: 321) | Ac-D-W-L-K-A-F-Y-D-K-V-A-E-K-L-R-E-A-F-NH$_2$ |
| (SEQ ID NO: 322) | Ac-E-W-L-K-A-F-Y-E-K-V-A-E-K-L-R-E-A-F-NH$_2$ |
| (SEQ ID NO: 323) | Ac-D-W-L-K-A-F-Y-D-R-V-A-E-R-L-K-E-A-F-NH$_2$ |
| (SEQ ID NO: 324) | Ac-E-W-L-K-A-F-Y-E-R-V-A-E-R-L-K-E-A-F-NH$_2$ |
| (SEQ ID NO: 325) | Ac-D-W-L-R-A-F-Y-D-K-V-A-E-K-L-R-E-A-F-NH$_2$ |
| (SEQ ID NO: 326) | Ac-E-W-L-R-A-F-Y-E-K-V-A-E-K-L-R-E-A-F-NH$_2$ |
| (SEQ ID NO: 327) | Ac-D-W-L-R-A-F-Y-D-R-V-A-E-K-L-K-E-A-F-NH$_2$ |
| (SEQ ID NO: 328) | Ac-E-W-L-R-A-F-Y-E-R-V-A-E-K-L-K-E-A-F-NH$_2$ |
| (SEQ ID NO: 329) | Ac-D-W-L-K-A-F-Y-D-K-V-A-E-R-L-R-E-A-F-NH$_2$ |
| (SEQ ID NO: 330) | Ac-E-W-L-K-A-F-Y-E-K-V-A-E-R-L-R-E-A-F-NH$_2$ |
| (SEQ ID NO: 331) | Ac-D-W-L-R-A-F-Y-D-K-V-A-E-R-L-K-E-A-F-NH$_2$ |
| (SEQ ID NO: 332) | Ac-E-W-L-R-A-F-Y-E-K-V-A-E-R-L-K-E-A-F-NH$_2$ |

In some embodiments, an ApoA-I mimetic having the following sequence as described in U.S. Patent Application Publication No. 2006/0069030 is utilized: F-A-E-K-F-K-E-A-V-K-D-Y-F-A-K-F-W-D (SEQ ID NO:333).

In some embodiments, an ApoA-I mimetic having the following sequence as described in U.S. Patent Application Publication No. 2009/0081293 is utilized:

DWFKAFYDKVAEKFKEAF; (SEQ ID NO: 334)

DWLKAFYDKVAEKLKEAF; (SEQ ID NO: 335)

PALEDLRQGLLPVLESFKVFLSALEEYTKKLNTQ. (SEQ ID NO: 336)

Amphipathic lipids include, for example, any lipid molecule which has both a hydrophobic and a hydrophilic moiety. Examples include phospholipids or glycolipids. Examples of phospholipids which may be used in the sHDL-TA nanoparticles include but are not limited to dipalmitoylphosphatidylcholine (DPPC), dioleoyl-sn-glycero-3-phosphoethanolamine-N-[3-(2-pyridyldithio) propionate] (DOPE-PDP), 1,2-dipalmitoyl-sn-glycero-3-phosphothioethanol, 1,2-di-(9Z-octadecenoyl)-sn-glycero-3-phosphoethanolamine-N-[4-(p-maleimidophenyl) butyramide], 1,2-dihexadecanoyl-sn-glycero-3-phosphoethanolamine-N-[4-(p-maleimidophenyl) butyramide], 1,2-dihexadecanoyl-sn-glycero-3-phosphoethanolamine-N-[4-(p-maleimidomethyl) cyclohexane-carboxamide], 1,2-di-(9Z-octadecenoyl)-sn-glycero-3-phosphoethanolamine-N-[4-(p-maleimidomethyl)cyclohexane-carboxamide], phosphatidylcholine, phosphatidylinositol, phosphatidylserine, phosphatidylethanolamine, and combinations thereof. In some embodiments, the phospholipid is complexed with an imaging agent (e.g., rhodamine (Rhod)-labeled DOPE (DOPE-Rhod)). In some embodiments, the phospholipids are thiol reactive phospholipids such as, for example, Dioleoyl-sn-glycero-3-phosphoethanolamine-N-[3-(2-pyridyldithio) propionate] (DOPE-PDP), 1,2-dihexadecanoyl-sn-glycero-3-phosphothioethanol, or N-4-(p-maleimidophenyl) butyryl) dipalmitoylphosphatidylethanolamine (MPB-DPPE)).

In some embodiments, exemplary phospholipids include, but are not limited to, small alkyl chain phospholipids, egg phosphatidylcholine, soybean phosphatidylcholine, dipalmitoylphosphatidylcholine, dimyristoylphosphatidylcholine, distearoylphosphatidylcholine 1-myristoyl-2-palmitoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, dioleoylphosphatidylcholine dioleophosphatidylethanolamine, dilauroylphosphatidylglycerol phosphatidylcholine, phosphatidylserine, phosphatidylethanolamine, phosphatidylinositol, phosphatidylglycerols, diphosphatidylglycerols such as dimyristoylphosphatidylglycerol, dipalmitoylphosphatidylglycerol, distearoylphosphatidylglycerol, dioleoylphosphatidylglycerol, dimyristoylphosphatidic acid, dipalmitoylphosphatidic acid, dimyristoylphosphatidylethanolamine, dipalmitoylphosphatidylethanolamine, dimyristoylphosphatidylserine, dipalmitoylphosphatidylserine, brain phosphatidylserine, brain sphingomyelin, egg sphingomyelin, milk sphingomyelin, palmitoyl sphingomyelin, phytosphingomyelin, dipalmitoylsphingomyelin, distearoylsphingomyelin, dipalmitoylphosphatidylglycerol salt, phosphatidic acid, galactocerebroside, gangliosides, cerebrosides, dilaurylphosphatidylcholine, (1,3)-D-mannosyl-(1,3)diglyceride, aminophenylglycoside, 3-cholesteryl-6'-(glycosylthio)hexyl ether glycolipids, and cholesterol and its derivatives. Phospholipid fractions including SM and palmitoylsphingomyelin can optionally include small quantities of any type of lipid, including but not limited to lysophospholipids, sphingomyelins other than palmitoylsphingomyelin, galactocerebroside, gangliosides, cerebrosides, glycerides, triglycerides, and cholesterol and its derivatives.

In some embodiments, the sHDL nanoparticles have a molar ratio of phospholipid/HDL apolipoprotein from 2 to 250 (e.g., 10 to 200, 20 to 100, 20 to 50, 30 to 40).

Generally, the sHDL nanoparticles so formed are spherical and have a diameter of from about 5 nm to about 20 nm (e.g., 4-75 nm, 4-60 nm, 4-50 nm, 4-22 nm, 6-18 nm, 8-15 nm, 8-10 nm, etc.). In some embodiments, the sHDL nanoparticles are subjected to size exclusion chromatography to yield a more homogeneous preparation.

The present invention addresses the need for improved stable and targeted delivery (e.g., in vitro or in vivo) of biomacromolcules (e.g., peptides, nucleic acids, glycolipids). Indeed, the present invention addresses such needs through providing synthetic high density lipoprotein (sHDL) nanoparticles for stable and targeted delivery of biomacromolecules, including peptides, nucleic acids, and glycolipids.

Compared to other strategies, including conventional nanoparticle vehicles, sHDL nanoparticles have impressive biocompatibility and capacity for cargo loading. For example, the ultrasmall but tunable size (e.g., 10-20 nm) enables the sHDL nanoparticles to effectively drain to lymph nodes and deliver cargo peptide antigens and nucleic acid-based adjuvants to lymph node-resident dendritic cells, thus positioning them as an efficient platform for co-delivery of antigen and adjuvant for tumor immunotherapy. In addition, experiments conducted during the course of developing embodiments for the present invention demonstrated broad applicability of the sHDL-based approach by (1) targeting delivery of siRNA to hepatocytes, which are the natural target cells of endogenous HDL, and (2) targeting immunostimulatory glycolid (alpha-galactosyl ceramide) to antigen presenting cells.

Such experiments further demonstrated the engineering of sHDL nanoparticles prepared with phospholipids and Apolipoprotein A-I mimetic peptides and loaded with biomacromolecular drugs. To load peptide drugs on HDL nanodiscs, synthesized thiol-reactive phospholipids were utilized that allowed reduction-sensitive linkage of peptides on the surfaces of HDL nanodiscs. To load nucleic acids (including CpG motifs and siRNA), nucleic acids were modified with a cholesteryl moiety, which was shown to allow facile insertion of nucleic acids into the sHDL nanoparticles. To load glycolipids into HDL, hydrophobic interactions between glycolipids and HDL were utilized. Such experiments further demonstrated stable delivery of such cargo to target tissues in vitro and in vivo.

RNA Interference

In certain embodiments, the sHDL nanoparticles are used within RNA interference methods and systems.

RNA interference is a highly conserved mechanism triggered by double-stranded RNA (dsRNA) and able to down regulate transcript of genes homologous to the dsRNA. The dsRNA is first processed by Dicer into short duplexes of 21-23 nt, called short interfering RNAs (siRNAs). Incorporated in RNA-induced silencing complex (RISC), they are able to mediate gene silencing through cleavage of the target mRNA. "siRNA" or "small-interfering ribonucleic acid" refers to two strands of ribonucleotides which hybridize along a complementary region under physiological conditions. The siRNA molecules comprise a double-stranded region which is substantially identical to a region of the mRNA of the target gene. A region with 100% identity to the corresponding sequence of the target gene is suitable. This state is referred to as "fully complementary". However, the region may also contain one, two or three mismatches as compared to the corresponding region of the target gene, depending on the length of the region of the mRNA that is targeted, and as such may be not fully complementary. Methods to analyze and identify siRNAs with sufficient sequence identity in order to effectively inhibit expression of a specific target sequence are known in the art. A suitable mRNA target region would be the coding region. Also suitable are untranslated regions, such as the 5'-UTR, the 3'-UTR, and splice junctions as long as the regions are unique to the mRNA target and not directed to a mRNA poly A tail.

In some embodiments, siRNA encapsulated within sHDL nanoparticles are utilized conducting methods and systems involving RNA interference.

Such embodiments are not limited to a particular size or type of siRNA molecule. The length of the region of the siRNA complementary to the target, for example, may be from 15 to 100 nucleotides, 18 to 25 nucleotides, 20 to 23 nucleotides, or more than 15, 16, 17 or 18 nucleotides. Where there are mismatches to the corresponding target region, the length of the complementary region is generally required to be somewhat longer.

In certain embodiments, it is contemplated that the siRNA delivery approach using sHDL nanoparticles disclosed herein (e.g., through encapsulation of the siRNA within an sHDL nanoparticle) can be used to inhibit any gene of interest.

Figure 10:
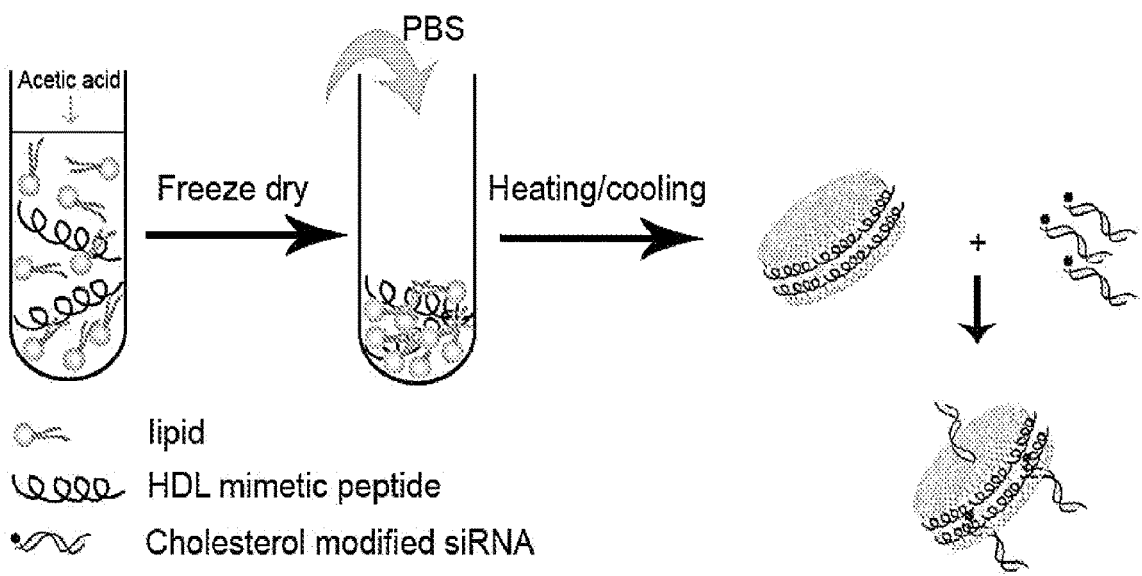
FIG. 10 presents a schematic of the lyophilization method for rapid preparation of sHDL comprising encapsulated siRNA.

The present invention is not limited to particular methods for generating sHDL nanoparticles comprising encapsulated siRNA molecules. For example, in some embodiments, lyophilization methods are used for the preparation of homogenous sHDL. In some embodiments, phospholipids and ApoA mimetic peptides are dissolved in glacial acetic acid and lyophilized. In some embodiments, loading of an siRNA molecule into the sHDL nanoparticle is facilitated through cholesterol modification of the siRNA molecule. For example, the siRNA is modified with cholesterol at the 3' sense strand (e.g., Kuwahara, H.; et al., Molecular Therapy 2011, 19 (12), 2213-2221) and an intermediate level of chemical modification will be used to stabilize siRNA in the serum without significantly compromising its silencing effect (see, e.g., Behlke, M. A., Oligonucleotides 2008, 18 (4), 305-319). In some embodiments, the lyophilized phospholipids and ApoA mimetic peptides are hydrated (e.g., hydrated in PBS (pH 7.4)) and thermocycled above and below the transition temperature (Tm) of phospholipids to form blank sHDL, which are next incubated with the cholesterol modified siRNA at room temperature for an optimal amount of time (e.g., 5, 10, 20, 25, 30, 35, 50, 80, 120, 360 minutes) to form sHDL comprising encapsulated siRNA. FIG. 10 presents a schematic of the lyophilization method for rapid preparation of sHDL comprising encapsulated siRNA.

Such embodiments are not limited to a particular manner of characterizing the sHDL comprising encapsulated siRNA. In some embodiments, the morphology of sHDL is observed by TEM. In some embodiments, the size distribution of sHDL is analyzed by dynamic light scattering (DLS) using a Malven Nanosizer instrument and GPC assay.

Such embodiments are not limited to a particular manner of assessing the delivery profile of the siRNA in vitro and in vivo. In some embodiments, labelling the siRNA molecules with an imaging agent (e.g., fluorescent dye Cy3) permits visualization of the biodistribution of siRNA molecules at the organ level and also the intracellular delivery profile. In some embodiments, RT-PCR and western blot are used to analyze the target protein at the mRNA level and protein level, respectively.

As such, in certain embodiments, the present invention provides methods for inhibiting a target gene in a cell comprising introducing into the cell a siRNA capable of inhibiting the target gene by RNA interference, wherein the siRNA comprises two RNA strands that are complementary to each other, wherein the siRNA is encapsulated within a sHDL nanoparticle. In some embodiments, the siRNA is modified with cholesterol at the 3' sense strand. In some embodiments, the cell is within a human being.

In certain embodiments, sHDL nanoparticles are provided wherein siRNAs specific for proprotein convertase subtilisin/kexin 9 (PCSK9) are encapsulated within the sHDL nanoparticle. Compelling evidence has shown that an elevated plasma level of low-density lipoprotein cholesterol (LDL-C) is a cardinal risk factor for coronary heart disease (CHD) (see, e.g., Law, M. R.; et al., British Medical Journal 2003, 326 (7404), 1423-1427; Boekholdt, S. M.; et al., Jama-Journal of the American Medical Association 2012, 307 (12), 1302-1309; Sniderman, A. D.; et al., Circulation-Cardiovascular Quality and Outcomes 2011, 4 (3), 337-U144). PCSK9 synthesized in the liver performs important roles in regulating LDL-C: PCSK9 can bind to the LDL receptor (LDLR) on hepatocytes and prevent the recycling of LDLR from lysosomes to the cell surface, and this in turn leads to the down-regulation of LDLR and increased levels of LDL-C (see, e.g., Maxwell, K. N.; et al., Proceedings of the National Academy of Sciences of the U.S. Pat. No. 2,004,101 (18), 7100-7105; Dadu, R. T.; et al., Nature Reviews Cardiology 2014, 11 (10), 563-575; Horton, J. D.; et al., Trends in Biochemical Sciences 2007, 32 (2), 71-77). Therefore PCSK9 inhibition can potentially decrease LDL-C (see, e.g., Shen, L.; et al., Pharmacological Research 2013, 73, 27-34). Therapeutic approaches under development for PCSK9 inhibition in vivo include siRNA-mediated knockdown of PCSK9 and vaccination against PCSK9 (see, e.g., Fitzgerald, K.; et al., Lancet 2014, 383 (9911), 60-68; Galabova, G.; et al., Circulation 2013, 128 (22)), but both strategies face the major challenge: how to efficiently deliver therapeutic agents to the target cells, namely hepatocytes and immune cells, respectively, in order to maximize the in vivo efficacy of each strategy.

Previously, PCSK9 siRNA has been delivered to the hepatocytes by lipid nanoparticles (see, e.g., Frank-Kamenetsky, M.; et al., Proceedings of the National Academy of Sciences of the U.S. Pat. No. 2,008,105 (33), 11915-11920) or by conjugating siRNA to N-acetylgalactosamine (GalNAc) ligands (see, e.g., Akinc, A.; et al., Molecular Therapy 2010, 18 (7), 1357-1364), which allow siRNA to be targeted to hepatocytes passively or through the recognition of Asialoglycoprotein Receptor (ASGPR) on hepatocytes. However, these conventional delivery strategies can subject the siRNA molecules to the intracellular endosomes/lysosomes pathway, in which siRNA cargo can be degraded, leading to suboptimal knockdown of PCSK9. Therefore, developing strategies that can both target the hepatocyte and bypass the endosomes/lysosomes pathway are urgently needed.

Use of sHDL nanoparticles comprising encapsulated PCSK9 siRNA molecules overcomes such limitations. Indeed, sHDL nanoparticles have similar properties to endogenous HDL, which can intrinsically target hepatocytes after i.v. injection, thus permitting direct delivery of siRNA cargoes to the cytosol of hepatocytes and knockdown of PCSK9 without going through the intracellular endosome/lysosome pathway.

In certain embodiments, sHDL comprising encapsulated PCSK9 siRNA molecules are delivered into the cytosol where they can associate with RNA-induced silencing complex (RISC) to knockdown the PCSK9 proteins (see, e.g., Chendrimada, T. P.; et al., Nature 2005, 436 (7051), 740-744; Matranga, C.; et al., Cell 2005, 123 (4), 607-620) within SR-BI expressing hepatocytes (see, e.g., Goldstein, J. L.; Brown, M. S., Arteriosclerosis Thrombosis and Vascular Biology 2009, 29 (4), 431-438; Wolfrum, C.; et al., Nature Biotechnology 2007, 25 (10), 1149-1157).

Figure 11:
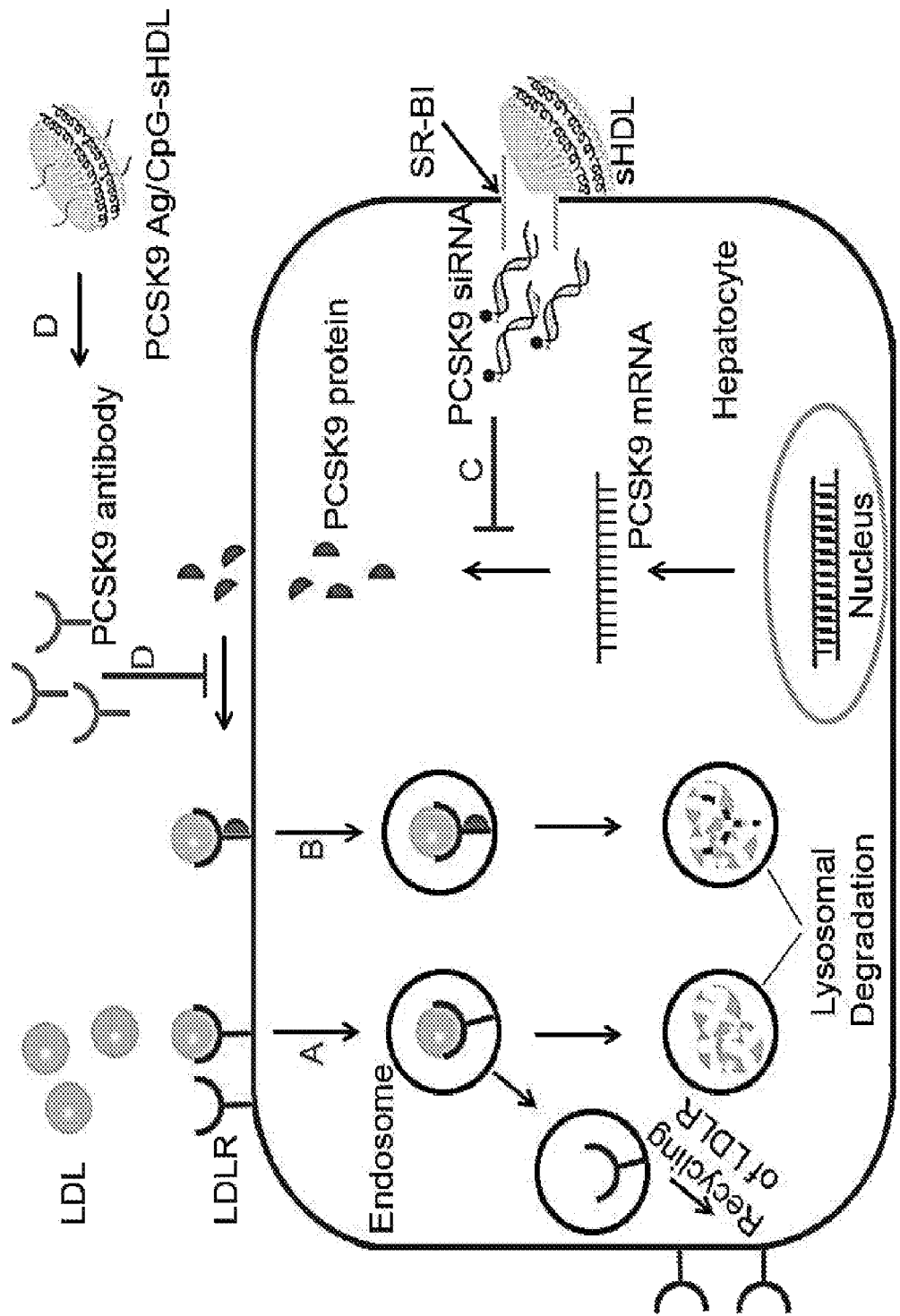
FIG. 11 shows a schematic of using sHDL to regulate PCSK9 for LDL-C management. As shown, (A) LDL is cleared by LDLR through endocytosis; (B) Binding of PCSK9 to LDLR leads to the degradation of LDLR in lysosomes and prevents the recycling of LDLR; (C) Knockdown of PCSK9 can upregulate LDLR and reduce LDL-C. (D) PCSK9 antibody induced by PCSK9 vaccine can block the interaction between PCSK9 and LDLR, thus upregulating LDLR and reducing LDL-C.

FIG. 11 shows a schematic of using sHDL to regulate PCSK9 for LDL-C management.

The present invention is not limited to use of a particular PCSK9 siRNA sequence. In some embodiments, the PCSK9 siRNA sequence is cross-reactive to murine, rat, nonhuman primate and human PCSK9 mRNA (see, e.g., Frank-Kamenetsky, et al., Proceedings of the National Academy of Sciences of the U.S. Pat. No. 2,008,105 (33), 11915-11920).

In certain embodiments, the present invention provides methods for inhibiting a PCSK9 gene in a cell comprising introducing into the cell a PCSK9 siRNA capable of inhibiting the PCSK9 gene by RNA interference, wherein the PCSK9 siRNA comprises two RNA strands that are complementary to each other, wherein the PCSK9 siRNA is encapsulated within a sHDL nanoparticle. In some embodiments, the PCSK9 siRNA is modified with cholesterol at the 3' sense strand. In some embodiments, the cell is within a human being.

In certain embodiments, the present invention provides methods for reducing serum LDL-C levels in patient (e.g., human patient), comprising administering to the patient a therapeutically effective amount of a pharmaceutical composition comprising a PCSK9 siRNA encapsulated within a sHDL nanoparticle, wherein the PCSK9 siRNA is capable of inhibiting the PCSK9 gene by RNA interference, wherein the PCSK9 siRNA comprises two RNA strands that are complementary to each other, wherein inhibiting of the PCSK9 gene results in reduction of serum LDL-C levels.

In certain embodiments, the present invention provides methods for treating coronary heart disease in a patient through reducing serum LDL-C levels in the patient, comprising administering to the patient a therapeutically effective amount of a pharmaceutical composition comprising a PCSK9 siRNA encapsulated within a sHDL nanoparticle, wherein the PCSK9 siRNA is capable of inhibiting the PCSK9 gene by RNA interference, wherein the PCSK9 siRNA comprises two RNA strands that are complementary to each other, wherein inhibiting of the PCSK9 gene results in reduction of serum LDL-C levels.

In certain embodiments, the sHDL nanoparticles are used to activate an immune response. Such embodiments are not limited to a particular manner of activating an immune response.

Immune Response Stimulation

The immune system can be classified into two functional subsystems: the innate and the acquired immune system. The innate immune system is the first line of defense against infections, and most potential pathogens are rapidly neutralized by this system before they can cause, for example, a noticeable infection. The acquired immune system reacts to molecular structures, referred to as antigens, of the intruding organism. There are two types of acquired immune reactions, which include the humoral immune reaction and the cell-mediated immune reaction. In the humoral immune reaction, antibodies secreted by B cells into bodily fluids bind to pathogen-derived antigens, leading to the elimination of the pathogen through a variety of mechanisms, e.g. complement-mediated lysis. In the cell-mediated immune reaction, T-cells capable of destroying other cells are activated. For example, if proteins associated with a disease are present in a cell, they are fragmented proteolytically to peptides within the cell. Specific cell proteins then attach themselves to the antigen or peptide formed in this manner and transport them to the surface of the cell, where they are presented to the molecular defense mechanisms, in particular T-cells, of the body. Cytotoxic T cells recognize these antigens and kill the cells that harbor the antigens.

The molecules that transport and present peptides on the cell surface are referred to as proteins of the major histocompatibility complex (MHC). MHC proteins are classified into two types, referred to as MHC class I and MHC class II. The structures of the proteins of the two MHC classes are very similar; however, they have very different functions. Proteins of MHC class I are present on the surface of almost all cells of the body, including most tumor cells. MHC class I proteins are loaded with antigens that usually originate from endogenous proteins or from pathogens present inside cells, and are then presented to naive or cytotoxic T-lymphocytes (CTLs). MHC class II proteins are present on dendritic cells, B-lymphocytes, macrophages and other antigen-presenting cells. They mainly present peptides, which are processed from external antigen sources, i.e. outside of the cells, to T-helper (Th) cells. Most of the peptides bound by the MHC class I proteins originate from cytoplasmic proteins produced in the healthy host cells of an organism itself, and do not normally stimulate an immune reaction. Accordingly, cytotoxic T-lymphocytes that recognize such self-peptide-presenting MHC molecules of class I are deleted in the thymus (central tolerance) or, after their release from the thymus, are deleted or inactivated, i.e. tolerized (peripheral tolerance). MHC molecules are capable of stimulating an immune reaction when they present peptides to non-tolerized T-lymphocytes. Cytotoxic T-lymphocytes have both T-cell receptors (TCR) and CD8 molecules on their surface. T-Cell receptors are capable of recognizing and binding peptides complexed with the molecules of MHC class I. Each cytotoxic T-lymphocyte expresses a unique T-cell receptor which is capable of binding specific MHC/peptide complexes.

The peptide antigens attach themselves to the molecules of MHC class I by competitive affinity binding within the endoplasmic reticulum, before they are presented on the cell surface. Here, the affinity of an individual peptide antigen is directly linked to its amino acid sequence and the presence of specific binding motifs in defined positions within the amino acid sequence. If the sequence of such a peptide is known, it is possible to manipulate the immune system against diseased cells using, for example, peptide vaccines.

Peptide-based cancer vaccines have been extensively investigated due to their good safety profiles and ease of manufacturing and quality control. However, their anti-tumor efficacy in clinical trials have been disappointing, a phenomenon that has been attributed to inefficient codelivery of Ag peptides and adjuvants to draining lymph nodes (dLNs), and subsequent immunological tolerance and CTL fratricide (see, e.g., Toes, R. E., et al., Proc. Natl. Acad. Sci. U.S.A. 93, 7855-7860 (1996); Su, M. W., et al., J. Immunol. 151, 658-667 (1993); Melief, C. J. & van der Burg, S. H. Nat. Rev. Cancer 8, 351-360 (2008)). Although depot-forming water-in-oil adjuvant systems can improve immunogenicity (see, e.g., Speiser, D. E. et al. J. Clin. Invest. 115, 739-746 (2005); Fourcade, J. et al. J. Immunother. 31, 781-791 (2008)), booster immunizations can cause T-cell sequestration at the vaccine site, causing T-cell exhaustion and deletion (see, e.g., Rezvani, K. et al. Haematologica 96, 432-440 (2011); Hailemichael, Y. et al. Nat. Med. 19, 465-472 (2013)). To address these issues, various nanoparticle-based vaccine systems have been evaluated in animal models (see, e.g., Reddy, S. T. et al. Nat. Biotechnol. 25, 1159-1164 (2007); Li, A. V. et al. Sci. Transl. Med. 5, 204ra130 (2013); Jeanbart, L. et al. Cancer. Immunol. Res. 2, 436-447 (2014); Xu, Z., et al., ACS Nano 8, 3636-3645 (2014); Liu, H. et al. Nature 507, 519-522 (2014); Fan, Y. & Moon, J. J. Vaccines (Basel) 3, 662-685 (2015)). However, potential safety concerns and scale-up manufacturing of nanoparticles, especially in a manner suitable for personalized therapeutics with patient-specific neo-antigens, remain as the major challenges.

Figure 12:
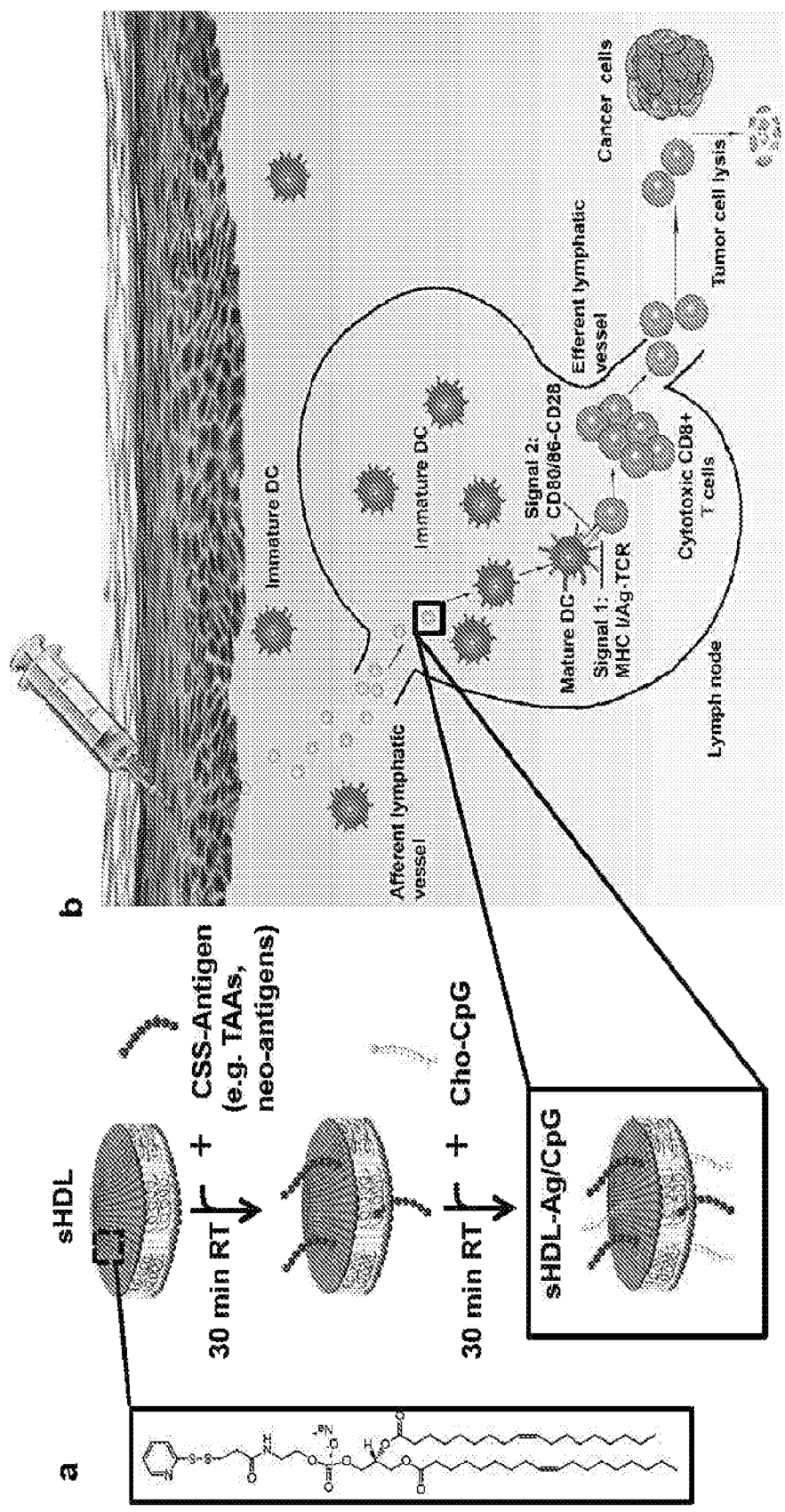
FIG. 12: Design of sHDL nanodisc platform for "personalized" cancer vaccines. a, sHDL nanodiscs, composed of phospholipids and apolipoprotein-1 mimetic peptides (22A), are engineered for co-delivery of antigen (Ag) peptides and adjuvants. Pre-formed sHDL nanodiscs displaying 4 mol % DOPE-PDP (insert) are mixed with cysteine-modified Ag peptides, including tumor-associated antigens (TAAs) and tumor-specific mutated neo-antigens identified via tumor exome DNA sequencing, and subsequent incubation with cholesterol-modified immunostimulatory molecules (Cho-CpG) leads to formation of sHDL nanodiscs co-loaded with Ag and CpG (sHDL-Ag/CpG). b, Upon administration, sHDL nanodiscs efficiently co-deliver Ag and CpG to draining lymph nodes, promote strong and durable Ag presentation by dendritic cells (DCs) (Signal 1), and induce DC maturation (Signal 2), resulting in elicitation of robust Ag-specific CD8α+ cytotoxic T lymphocyte (CTL) responses. Activated CTLs recognize and kill their target cancer cells in peripheral tissues and exert strong anti-tumor efficacy.

Experiments conducted during the course of developing embodiments for the present invention developed an alternative, simple strategy where preformed nanoparticles, with an established clinical manufacturing procedure and excellent safety profiles in humans, were mixed with Ag peptides and adjuvants to produce "personalized" cancer vaccines (FIG. 12). The strategy was based on synthetic high density lipoprotein (sHDL) nanodiscs, composed of phospholipids and apolipoprotein A1 (ApoA1)-mimetic peptides. Compared with other HDLs containing 243-amino acid ApoA1 purified from human plasma or produced recombinantly (see, e.g., Wolfrum, C. et al. Nat. Biotechnol. 25, 1149-1157 (2007); Diditchenko, S. et al. Arterioscler. Thromb. Vasc. Biol. 33, 2202-2211 (2013); Fischer, N. O. et al. J. Am. Chem. Soc. 135, 2044-2047 (2013); Tardy, C. et al. Atherosclerosis 232, 110-118 (2014); Duivenvoorden, R. et al. Nat. Commun. 5, 3065 (2014)), sHDL nanodiscs were synthesized with 22-mer peptides (22A), derived from the repeat a-helix domain of ApoA1 (see, e.g., U.S. Pat. Nos. 6,734,169; 8,378,068; Li, D., Gordon, S., Schwendeman, A. & Remaley, A. T. Apolipoprotein mimetic peptides for stimulating cholesterol efflux. in Apolipoprotein Mimetics in the Management of Human Disease (eds. Anantharamaiah, G. M. & Goldberg, D.) 29-42 (Springer, Switzerland, 2015)), with no sequence homology to endogenous ApoA1, thus averting potential trigger of autoimmunity. Importantly, sHDL has been previously manufactured for clinical testing and proven to be safe in humans with the maximum tolerated dose at ~2.2 g/m$^2$ (see, e.g., Khan, M., et al., Circulation 108 (Suppl IV), 563-564 (2003); Miles, J., et al. Proceedings of Arteriosclerosis Thrombosis and Vascular Biology 24, E19-E19 (2004), a value one- to two-orders of magnitude greater than most polymeric or inorganic nanoparticles in clinical trials (see, e.g., Alexis, F., et al., Mol. Pharm. 5, 505-515 (2008); Anselmo, A. C. & Mitragotri, S. A, AAPS J 17, 1041-1054 (2015).

Experiments conducted during the course of developing embodiments for the present invention developed a nanodisc-based platform for neo-antigen vaccination (FIG. 12). Exploiting the endogenous role of HDL as a nanoparticle for cholesterol, immunostimulatory agent CpG, a strong Toll-like receptor-9 agonist, was modified with cholesterol (Cho-CpG) to enhance its in vivo trafficking. It was shown that preformed sHDL nanodiscs can be simply mixed with cholesteryl-CpG and tumor Ag peptides, including neo-antigens identified via tumor DNA sequencing, to produce homogeneous, stable, and ultrasmall nanodiscs in <2 h at room temperature (RT). The nanodiscs efficiently promoted co-delivery of Ag/CpG to dLNs, prolonged Ag presentation on antigen-presenting cells (APCs), and elicited striking levels of CTL responses with anti-tumor efficacy. Owning to the facile production process, robust therapeutic efficacy, and clinical safety demonstrated previously (see, e.g., Khan, M., et al., Circulation 108 (Suppl IV), 563-564 (2003); Miles, J., et al. Proceedings of Arteriosclerosis Thrombosis and Vascular Biology 24, E19-E19 (2004)), this approach offers an attractive platform technology for patient-tailored cancer vaccines as well as other bioactive therapeutics.

Accordingly, in certain embodiments, nanoparticles (e.g., sHDL nanoparticles) conjugated with an antigen are used for inducing an immune response. In some embodiments, the nanoparticles are further complexed or admixed with an adjuvant (e.g., dendritic cell targeting molecule (DC)). In some embodiments, the nanoparticles are co-administered with an adjuvant.

Such embodiments are not limited to particular antigen. Indeed, antigens can be peptides, proteins, polysaccharides, saccharides, lipids, glycolipids, nucleic acids, or combinations thereof. The antigen can be derived from any source, including, but not limited to, a virus, bacterium, parasite, plant, protozoan, fungus, tissue or transformed cell such as a cancer or leukemic cell and can be a whole cell or immunogenic component thereof, e.g., cell wall components or molecular components thereof.

In some embodiments, the antigens are known in the art and are available from commercial government and scientific sources. In some embodiments, the antigens are whole inactivated or attenuated organisms. These organisms may be infectious organisms, such as viruses, parasites and bacteria. These organisms may also be tumor cells. The antigens may be purified or partially purified polypeptides derived from tumors or viral or bacterial sources. Criteria for identifying and selecting effective antigenic peptides (e.g., minimal peptide sequences capable of eliciting an immune response) can be found in the art. The antigens can be recombinant polypeptides produced by expressing DNA encoding the polypeptide antigen in a heterologous expression system. The antigens can be DNA encoding all or part of an antigenic protein. The DNA may be in the form of vector DNA such as plasmid DNA.

Antigens may be provided as single antigens or may be provided in combination. Antigens may also be provided as complex mixtures of polypeptides or nucleic acids.

In some embodiments, the antigen is a self antigen. As used herein, the term "self-antigen" refers to an immunogenic antigen or epitope which is native to a mammal and which may be involved in the pathogenesis of an autoimmune disease.

In some embodiments, the antigen is a viral antigen. Viral antigens can be isolated from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue D1NS3.

Viral antigens may be derived from a particular strain such as a papilloma virus, a herpes virus, i.e. herpes simplex 1 and 2; a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomeglavirus, Epstein-Barr, rotavirus, rhinovirus, adenovirus, coxsackieviruses, equine encephalitis, Japanese encephalitis, yellow fever, Rift Valley fever, and lymphocytic choriomeningitis.

In some embodiments, the antigen is a bacterial antigen. Bacterial antigens can originate from any bacteria including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium*, Cytophaga, Deinococcus, *Escherichia, Francisella, Halobacterium, Heliobacter, Haemophilus*, Hemophilus influenza type B (HIB), *Hyphomicrobium, Legionella, Leptspirosis, Listeria*, Meningococcus A, B and C, *Methanobacterium, Micrococcus, Myobacterium, Mycoplasma, Myxococcus, Neisseria, Nitrobacter*, Oscillatoria, Prochloron, *Proteus, Pseudomonas, Phodospirillum, Rickettsia, Salmonella, Shigella*, Spirillum, Spirochaeta, *Staphylococcus, Streptococcus, Streptomyces, Sulfolobus, Thermoplasma, Thiobacillus*, and *Treponema, Vibrio*, and *Yersinia*.

In some embodiments, the antigen is a parasite antigen. Parasite antigens can be obtained from parasites such as, but not limited to, an antigen derived from *Cryptococcus neoformans, Histoplasma capsulatum, Candida albicans, Candida tropicalis, Nocardia asteroides, Rickettsia rickettsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni*. These include Sporozoan antigens, Plasmodian antigens, such as all or part of a Circumsporozoite protein, a Sporozoite surface protein, a liver stage antigen, an apical membrane associated protein, or a Merozoite surface protein.

In some embodiments, the antigen is an allergen and environmental antigen, such as, but not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens. Important pollen allergens from trees, grasses and herbs originate from the taxonomic orders of Fagales, Oleales, Pinales and platanaceae including i.a. birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including i.e. grasses of the genera *Lolium, Phleum, Poa, Cynodon, Dactylis, Holcus, Phalaris, Secale*, and Sorghum, the orders of Asterales and Urticales including i.a. herbs of the genera Ambrosia, *Artemisia*, and *Parietaria*. Other allergen antigens that may be used include allergens from house dust mites of the genus *Dermatophagoides* and Euroglyphus, storage mite e.g Lepidoglyphys, Glycyphagus and Tyrophagus, those from cockroaches, midges and fleas e.g. Blatella, *Periplaneta*, Chironomus and Ctenocepphalides, those from mammals such as cat, dog and horse, birds, venom allergens including such originating from stinging or biting insects such as those from the taxonomic order of Hymenoptera including bees (superfamily Apidae), wasps (superfamily Vespidea), and ants (superfamily Formicoidae). Still other allergen antigens that may be used include inhalation allergens from fungi such as from the genera *Alternaria* and *Cladosporium*.

In some embodiments, the antigen is a tumor antigen. The antigen can be a tumor antigen, including a tumor-associated or tumor-specific antigen, such as, but not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triose-phosphate isomeras, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGS), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS.

One of the critical barriers to developing curative and tumor-specific immunotherapy is the identification and selection of highly specific and restricted tumor antigens to avoid autoimmunity. Tumor neo-antigens, which arise as a result of genetic change (e.g., inversions, translocations, deletions, missense mutations, splice site mutations, etc.) within malignant cells, represent the most tumor-specific class of antigens.

In some embodiments, the antigen is a neo-antigen. The term neoantigen is used herein to define any newly expressed antigenic determinant. Neoantigens may arise upon conformational change in a protein, as newly expressed determinants (especially on the surfaces of transformed or infected cells), as the result of complex formation of one or more molecules or as the result of cleavage of a molecule with a resultant display of new antigenic determinants. Thus, as used herein, the term neoantigen covers antigens expressed upon infection (e.g. viral infection, protozoal infection or bacterial infection), in prion-mediated diseases, an on cell transformation (cancer), in which latter case the neoantigen may be termed a tumour-associated antigen.

The present invention is not limited to a particular manner of identifying neo-antigens. In some embodiments, identification of neo-antigens involves identifying all, or nearly all, mutations in the neoplasia/tumor at the DNA level using whole genome sequencing, whole exome (e.g., only captured exons) sequencing, or RNA sequencing of tumor versus matched germline samples from each patient. In some embodiments, identification of neo-antigens involves analyzing the identified mutations with one or more peptide-MHC binding prediction algorithms to generate a plurality of candidate neo-antigen T cell epitopes that are expressed within the neoplasia/tumor and may bind patient HLA alleles. In some embodiments, identification of neo-antigens involves synthesizing the plurality of candidate neo-antigen peptides selected from the sets of all neo open reading frame peptides and predicted binding peptides for use in a cancer vaccine.

As such, the present invention is based, at least in part, on the ability to identify all, or nearly all, of the mutations within a neoplasia/tumor (e.g., translocations, inversions, large and small deletions and insertions, missense mutations, splice site mutations, etc.). In particular, these mutations are present in the genome of neoplasia/tumor cells of a subject, but not in normal tissue from the subject. Such mutations are of particular interest if they lead to changes that result in a protein with an altered amino acid sequence that is unique to the patient's neoplasia/tumor (e.g., a neo-antigen). For example, useful mutations may include: (1) non-synonymous mutations leading to different amino acids in the protein; (2) read-through mutations in which a stop codon is modified or deleted, leading to translation of a longer protein with a novel tumor-specific sequence at the C-terminus; (3) splice site mutations that lead to the inclusion of an intron in the mature mRNA and thus a unique tumor-specific protein sequence; (4) chromosomal rearrangements that give rise to a chimeric protein with tumor-specific sequences at the junction of 2 proteins (i.e., gene fusion); (5) frameshift mutations or deletions that lead to a new open reading frame with a novel tumor-specific protein sequence; and the like. Peptides with mutations or mutated polypeptides arising from, for example, splice-site, frameshift, read-through, or gene fusion mutations in tumor cells may be identified by sequencing DNA, RNA or protein in tumor versus normal cells.

Also within the scope of the present invention is personal neo-antigen peptides derived from common tumor driver genes and may further include previously identified tumor specific mutations.

Preferably, any suitable sequencing-by-synthesis platform can be used to identify mutations. Four major sequencing-by-synthesis platforms are currently available: the Genome Sequencers from Roche/454 Life Sciences, the HiSeq Analyzer from Illumina/Solexa, the SOLiD system from Applied BioSystems, and the Heliscope system from Helicos Biosciences. Sequencing-by-synthesis platforms have also been described by Pacific Biosciences and VisiGen Biotechnologies. Each of these platforms can be used in the methods of the invention. In some embodiments, a plurality of nucleic acid molecules being sequenced is bound to a support (e.g., solid support). To immobilize the nucleic acid on a support, a capture sequence/universal priming site can be added at the 3' and/or 5' end of the template. The nucleic acids may be bound to the support by hybridizing the capture sequence to a complementary sequence covalently attached to the support. The capture sequence (also referred to as a universal capture sequence) is a nucleic acid sequence complementary to a sequence attached to a support that may dually serve as a universal primer.

As an alternative to a capture sequence, a member of a coupling pair (such as, e.g., antibody/antigen, receptor/ligand, or the avidin-biotin pair as described in, e.g., U.S. Patent Application No. 2006/0252077) may be linked to each fragment to be captured on a surface coated with a respective second member of that coupling pair. Subsequent to the capture, the sequence may be analyzed, for example, by single molecule detection/sequencing, e.g., as described in the Examples and in U.S. Pat. No. 7,283,337, including template-dependent sequencing-by-synthesis. In sequencing-by-synthesis, the surface-bound molecule is exposed to a plurality of labeled nucleotide triphosphates in the presence of polymerase. The sequence of the template is determined by the order of labeled nucleotides incorporated into the 3' end of the growing chain. This can be done in real time or in a step-and-repeat mode. For real-time analysis, different optical labels to each nucleotide may be incorporated and multiple lasers may be utilized for stimulation of incorporated nucleotides.

Any cell type or tissue may be utilized to obtain nucleic acid samples for use in the sequencing methods described herein. In some embodiments, the DNA or RNA sample is obtained from a neoplasia/tumor or a bodily fluid, e.g., blood, obtained by known techniques (e.g. venipuncture) or saliva. Alternatively, nucleic acid tests can be performed on dry samples (e.g. hair or skin).

A variety of methods are available for detecting the presence of a particular mutation or allele in an individual's DNA or RNA. Advancements in this field have provided accurate, easy, and inexpensive large-scale SNP genotyping. Most recently, for example, several new techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods require amplification of the target genetic region, typically by PCR. Still other newly developed methods, based on the generation of small signal molecules by invasive cleavage followed by mass spectrometry or immobilized padlock probes and rolling-circle amplification, might eventually eliminate the need for PCR. Several of the methods known in the art for detecting specific single nucleotide polymorphisms are summarized below. The method of the present invention is understood to include all available methods.

PCR based detection means may include multiplex amplification of a plurality of markers simultaneously. For example, it is well known in the art to select PCR primers to generate PCR products that do not overlap in size and can be analyzed simultaneously.

Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

Several methods have been developed to facilitate analysis of single nucleotide polymorphisms in genomic DNA or cellular RNA. In one embodiment, the single base polymorphism can be detected by using a specialized exonuclease-resistant nucleotide, as disclosed, e.g., U.S. Pat. No. 4,656,127. According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site (see, e.g., French Patent No. 2,650,840; PCT Application No. WO1991/02087). As in the method of U.S. Pat. No. 4,656,127, a primer may be employed that is complementary to allelic sequences immediately 3' to a polymorphic site. The method determines the identity of the nucleotide of that site using labeled dideoxynucleotide derivatives, which, if complementary to the nucleotide of the polymorphic site, will become incorporated onto the terminus of the primer.

An alternative method, known as Genetic Bit Analysis or GBA® is described in PCT Application No. WO 1992/15712). GBA® uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Application No. WO1991/02087) the GBA® method is preferably a heterogeneous phase assay, in which the primer or the target molecule is immobilized to a solid phase. Recently, several primer-guided nucleotide incorporation procedures for assaying polymorphic sites in DNA have been described (see, e.g., Komher, J. S. et al., Nucl. Acids. Res. 17:7779-7784 (1989); Sokolov, B. P., Nucl. Acids Res. 18:3671 (1990); Syvanen, A.-C, et al., Genomics 8:684-692 (1990); Kuppuswamy, M. N. et al., Proc. Natl. Acad. Sci. (U.S.A.) 88: 1143-1147 (1991); Prezant, T. R. et al., Hum. Mutat. 1: 159-164 (1992); Ugozzoli, L. et al., GATA 9: 107-112 (1992); Nyren, P. et al., Anal. Biochem. 208: 171-175 (1993)). These methods differ from GBA® in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (see, e.g., Syvanen, A.-C, et al., Amer. J. Hum. Genet. 52:46-59 (1993)).

An alternative method for identifying tumor specific neo-antigens is direct protein sequencing. Protein sequencing of enzymatic digests using multidimensional MS techniques (MSn) including tandem mass spectrometry (MS/MS)) can also be used to identify neo-antigens of the invention. Such proteomic approaches permit rapid, highly automated analysis (see, e.g., K. Gevaert and J. Vandekerckhove, Electrophoresis 21: 1145-1154 (2000)). It is further contemplated within the scope of the invention that high-throughput methods for de novo sequencing of unknown proteins may be used to analyze the proteome of a patient's tumor to identify expressed neo-antigens. For example, meta shotgun protein sequencing may be used to identify expressed neo-antigens (see, e.g., Guthals et al. (2012) Shotgun Protein Sequencing with Meta-contig Assembly, Molecular and Cellular Proteomics 11(10): 1084-96).

Tumor specific neo-antigens may also be identified using MHC multimers to identify neo-antigen-specific T-cell responses. For example, high throughput analysis of neo-antigen-specific T-cell responses in patient samples may be performed using MHC tetramer-based screening techniques (see, e.g., Hombrink et al. (2011) High-Throughput Identification of Potential Minor Histocompatibility Antigens by MHC Tetramer-Based Screening: Feasibility and Limitations 6(8): 1-11; Hadrup et al. (2009) Parallel detection of antigen-specific T-cell responses by multidimensional encoding of MHC multimers, Nature Methods, 6(7):520-26; van Rooij et al. (2013) Tumor exome analysis reveals neoantigen-specific T-cell reactivity in an Ipilimumab-responsive melanoma, Journal of Clinical Oncology, 31: 1-4; and Heemskerk et al. (2013) The cancer antigenome, EMBO Journal, 32(2): 194-203). It is contemplated within the scope of the invention that such tetramer-based screening techniques may be used for the initial identification of tumor specific neo-antigens, or alternatively as a secondary screening protocol to assess what neo-antigens a patient may have already been exposed to, thereby facilitating the selection of candidate neo-antigens for the vaccines of the invention.

The invention further includes isolated peptides (e.g., neo-antigenic peptides containing the tumor specific mutations identified by the described methods, peptides that comprise known tumor specific mutations, and mutant polypeptides or fragments thereof identified by the described methods). These peptides and polypeptides are referred to herein as "neo-antigenic peptides" or "neo-antigenic polypeptides." The polypeptides or peptides can be of a variety of lengths and will minimally include the small region predicted to bind to the HLA molecule of the patient (the "epitope") as well as additional adjacent amino acids extending in both the N- and C-terminal directions. The polypeptides or peptides can be either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

In certain embodiments the size of the at least one neo-antigenic peptide molecule may comprise, but is not limited to, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, about 120 or greater amino molecule residues, and any range derivable therein. In specific embodiments the neo-antigenic peptide molecules are equal to or less than 50 amino acids. In a preferred embodiment, the neo-antigenic peptide molecules are equal to about 20 to about 30 amino acids.

As such, the present invention provides nanoparticles (e.g., sHDL nanoparticles) complexed with one or more neo-antigenic peptides. In some embodiments, the nanoparticle (e.g., sHDL nanoparticle) is complexed with one neo-antigenic peptide. In some embodiments, the nanoparticle (e.g., sHDL nanoparticle) is complexed with two neo-antigenic peptides. In some embodiments, the nanoparticle (e.g., sHDL nanoparticle) is complexed with at least 5 or more neo-antigenic peptides. In some embodiments, the nanoparticle (e.g., sHDL nanoparticle) is complexed with at least about 6, about 8, about 10, about 12, about 14, about 16, about 18, or about 20 distinct peptides. In some embodiments, the nanoparticle (e.g., sHDL nanoparticle) is complexed with at least 20 distinct peptides.

The neo-antigenic peptides, polypeptides, and analogs can be further modified to contain additional chemical moieties not normally part of the protein. Those derivatized moieties can improve the solubility, the biological half-life, absorption of the protein, or binding affinity. The moieties can also reduce or eliminate any desirable side effects of the proteins and the like. An overview for those moieties can be found in Remington's Pharmaceutical Sciences, 20$^{th}$ ed., Mack Publishing Co., Easton, Pa. (2000). For example, neo-antigenic peptides and polypeptides having the desired activity may be modified as necessary to provide certain desired attributes, e.g. improved pharmacological characteristics, while increasing or at least retaining substantially all of the biological activity of the unmodified peptide to bind the desired MHC molecule and activate the appropriate T cell. For instance, the neo-antigenic peptide and polypeptides may be subject to various changes, such as substitutions, either conservative or non-conservative, where such changes might provide for certain advantages in their use, such as improved MHC binding. Such conservative substitutions may encompass replacing an amino acid residue with another amino acid residue that is biologically and/or chemically similar, e.g., one hydrophobic residue for another, or one polar residue for another. The effect of single amino acid substitutions may also be probed using D-amino acids. Such modifications may be made using well known peptide synthesis procedures, as described in e.g., Merrifield, Science 232:341-347 (1986), Barany & Merrifield, The Peptides, Gross & Meienhofer, eds. (N.Y., Academic Press), pp. 1-284 (1979); and Stewart & Young, Solid Phase Peptide Synthesis, (Rockford, Ill., Pierce), 2d Ed. (1984).

In some embodiments, the neo-antigenic peptides and polypeptides may be modified with linking agents for purposes of facilitating complexing with the nanoparticle (e.g., sHDL nanoparticle). The invention is not limited to a particular type or kind of linking agent. In some embodiments, the linking agent is a cysteine-serine-serine (CSS) molecule.

In some embodiments wherein the nanoparticle is sHDL and the neo-antigenic peptide or polypeptide is modified with CSS, the sHDL is further modified with dioleoyl-sn-glycero-3-phosphoethanolamine-N-[3-(2-pyridyldithio) propionate] (DOPE-PDP) wherein upon mixing, the DOPE-PDP and CSS engage thereby resulting in a complexing (linking) of the CSS-Ag with the sHDL.

The neo-antigenic peptide and polypeptides may also be modified by extending or decreasing the compound's amino acid sequence, e.g., by the addition or deletion of amino acids. The neo-antigenic peptides, polypeptides, or analogs can also be modified by altering the order or composition of certain residues. It will be appreciated by the skilled artisan that certain amino acid residues essential for biological activity, e.g., those at critical contact sites or conserved residues, may generally not be altered without an adverse effect on biological activity. The non-critical amino acids need not be limited to those naturally occurring in proteins, such as L-α-amino acids, or their D-isomers, but may include non-natural amino acids as well, such as β-γ-δ-amino acids, as well as many derivatives of L-α-amino acids.

Typically, a neo-antigen polypeptide or peptide may be optimized by using a series of peptides with single amino acid substitutions to determine the effect of electrostatic charge, hydrophobicity, etc. on MHC binding. For instance, a series of positively charged (e.g., Lys or Arg) or negatively charged (e.g., Glu) amino acid substitutions may be made along the length of the peptide revealing different patterns of sensitivity towards various MHC molecules and T cell receptors. In addition, multiple substitutions using small, relatively neutral moieties such as Ala, Gly, Pro, or similar residues may be employed. The substitutions may be homo-oligomers or hetero-oligomers. The number and types of residues which are substituted or added depend on the spacing necessary between essential contact points and certain functional attributes which are sought (e.g., hydrophobicity versus hydrophilicity). Increased binding affinity for an MHC molecule or T cell receptor may also be achieved by such substitutions, compared to the affinity of the parent peptide. In any event, such substitutions should employ amino acid residues or other molecular fragments chosen to avoid, for example, steric and charge interference which might disrupt binding. Amino acid substitutions are typically of single residues. Substitutions, deletions, insertions or any combination thereof may be combined to arrive at a final peptide.

One of skill in the art will appreciate that there are a variety of ways in which to produce such tumor specific neo-antigens. In general, such tumor specific neo-antigens may be produced either in vitro or in vivo. Tumor specific neo-antigens may be produced in vitro as peptides or polypeptides, which may then be formulated into a personalized neoplasia vaccine and administered to a subject. Such in vitro production may occur by a variety of methods known to one of skill in the art such as, for example, peptide synthesis or expression of a peptide/polypeptide from a DNA or RNA molecule in any of a variety of bacterial, eukaryotic, or viral recombinant expression systems, followed by purification of the expressed peptide/polypeptide. Alternatively, tumor specific neo-antigens may be produced in vivo by introducing molecules (e.g., DNA, RNA, viral expression systems, and the like) that encode tumor specific neo-antigens into a subject, whereupon the encoded tumor specific neo-antigens are expressed.

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology Information's Genbank and GenPept databases located at the National Institutes of Health website. The coding regions for known genes may be amplified and/or expressed using the techniques disclosed herein or as would be known to those of ordinary skill in the art. Alternatively, various commercial preparations of proteins, polypeptides and peptides are known to those of skill in the art.

Peptides can be readily synthesized chemically utilizing reagents that are free of contaminating bacterial or animal substances (Merrifield RB: Solid phase peptide synthesis. I. The synthesis of a tetrapeptide. J. Am. Chem. Soc. 85:2149-54, 1963).

A further aspect of the invention provides a nucleic acid (e.g., a polynucleotide) encoding a neo-antigenic peptide of the invention, which may be used to produce the neo-antigenic peptide in vitro. The polynucleotide may be, e.g., DNA, cDNA, PNA, CNA, RNA, either single- and/or double-stranded, or native or stabilized forms of polynucleotides, such as e.g. polynucleotides with a phosphorothiate backbone, or combinations thereof and it may or may not contain introns so long as it codes for the peptide. A still further aspect of the invention provides an expression vector capable of expressing a polypeptide according to the invention. Expression vectors for different cell types are well known in the art and can be selected without undue experimentation. Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host (e.g., bacteria), although such controls are generally available in the expression vector. The vector is then introduced into the host bacteria for cloning using standard techniques (see, e.g., Sambrook et al. (1989) Molecular Cloning, A Laboratory Manual, Cold Spring Harbor Laboratory, Cold Spring Harbor, N.Y.).

The invention further embraces variants and equivalents which are substantially homologous to the identified tumor specific neo-antigens described herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid, or one neutral amino acid by another neutral amino acid. What is intended by a conservative amino acid substitution is well known in the art.

The invention also includes expression vectors comprising the isolated polynucleotides, as well as host cells containing the expression vectors. It is also contemplated within the scope of the invention that the neo-antigenic peptides may be provided in the form of RNA or cDNA molecules encoding the desired neo-antigenic peptides. The invention also provides that the one or more neo-antigenic peptides of the invention may be encoded by a single expression vector. The invention also provides that the one or more neo-antigenic peptides of the invention may be encoded and expressed in vivo using a viral based system (e.g., an adenovirus system).

The term "polynucleotide encoding a polypeptide" encompasses a polynucleotide which includes only coding sequences for the polypeptide as well as a polynucleotide which includes additional coding and/or non-coding sequences. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

In embodiments, the polynucleotides may comprise the coding sequence for the tumor specific neo-antigenic peptide fused in the same reading frame to a polynucleotide which aids, for example, in expression and/or secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide.

In some embodiments, the polynucleotides can comprise the coding sequence for the tumor specific neo-antigenic peptide fused in the same reading frame to a marker sequence that allows, for example, for purification of the encoded polypeptide, which may then be incorporated into the personalized neoplasia vaccine. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. Additional tags include, but are not limited to, Calmodulin tags, FLAG tags, Myc tags, S tags, SBP tags, Softag 1, Softag 3, V5 tag, Xpress tag, Isopeptag, SpyTag, Biotin Carboxyl Carrier Protein (BCCP) tags, GST tags, fluorescent protein tags (e.g., green fluorescent protein tags), maltose binding protein tags, Nus tags, Strep-tag, thioredoxin tag, TC tag, Ty tag, and the like. In embodiments, the polynucleotides may comprise the coding sequence for one or more of the tumor specific neo-antigenic peptides fused in the same reading frame to create a single concatamerized neo-antigenic peptide construct capable of producing multiple neo-antigenic peptides.

In embodiments, the present invention provides isolated nucleic acid molecules having a nucleotide sequence at least 60% identical, at least 65% identical, at least 70% identical, at least 75% identical, at least 80% identical, at least 85% identical, at least 90% identical, at least 95% identical, or at least 96%, 97%, 98% or 99% identical to a polynucleotide encoding a tumor specific neo-antigenic peptide of the present invention.

By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80% identical, at least 85% identical, at least 90% identical, and in some embodiments, at least 95%, 96%, 97%, 98%, or 99% identical to a reference sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482-489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

The isolated tumor specific neo-antigenic peptides described herein can be produced in vitro (e.g., in the laboratory) by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585.

In embodiments, a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (e.g., by synthesis, site-directed mutagenesis, or another method), the polynucleotide sequences encoding a particular isolated polypeptide of interest will be inserted into an expression vector and optionally operatively linked to an expression control sequence appropriate for expression of the protein in a desired host. Proper assembly can be confirmed by nucleotide sequencing, restriction mapping, and expression of a biologically active polypeptide in a suitable host. As well known in the art, in order to obtain high expression levels of a transfected gene in a host, the gene can be operatively linked to transcriptional and translational expression control sequences that are functional in the chosen expression host. Recombinant expression vectors may be used to amplify and express DNA encoding the tumor specific neo-antigenic peptides. Recombinant expression vectors are replicable DNA constructs which have synthetic or cDNA-derived DNA fragments encoding a tumor specific neo-antigenic peptide or a bioequivalent analog operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transforaiants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Generally, operatively linked means contiguous, and in the case of secretory leaders, means contiguous and in reading frame. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Escherichia coli*, including pCR 1, pBR322, pMB9 and their derivatives, wider host range plasmids, such as M13 and filamentous single-stranded DNA phages.

Suitable host cells for expression of a polypeptide include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin. Cell-free translation systems could also be employed. Appropriate cloning and expression vectors for use with bacterial, fungal, yeast, and mammalian cellular hosts are well known in the art (see Pouwels et al., Cloning Vectors: A Laboratory Manual, Elsevier, N.Y., 1985).

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (Cell 23: 175, 1981), and other cell lines capable of expressing an appropriate vector including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography, and the like), centrifugation, differential solubility, or by any other standard technique for protein purification. Affinity tags such as hexahistidine, maltose binding domain, influenza coat sequence, glutathione-S-transferase, and the like can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a cancer stem cell protein-Fc composition. Some or all of the foregoing purification steps, in various combinations, can also be employed to provide a homogeneous recombinant protein. Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

As such, in certain embodiments, the present invention relates to personalized strategies for the treatment of disorders (e.g., neoplasia), and more particularly tumors, by administering a therapeutically effective amount of a sHDL molecule complexed with one or more neoplasia/tumor specific neo-antigens to a subject (e.g., a mammal such as a human) (e.g., a vaccine composition capable of raising a specific T-cell response). Indeed, in certain embodiments, whole genome/exome sequencing may be used to identify all, or nearly all, mutated neo-antigens that are uniquely present in a neoplasia/tumor of an individual patient, and that this collection of mutated neo-antigens may be analyzed to identify a specific, optimized subset of neo-antigens for use as a personalized cancer vaccine for treatment of the patient's neoplasia/tumor. For example, in some embodiments, a population of neoplasia/tumor specific neo-antigens may be identified by sequencing the neoplasia/tumor and normal DNA of each patient to identify tumor-specific mutations, and determining the patient's HLA allotype. The population of neoplasia/tumor specific neo-antigens and their cognate native antigens may then be subject to bioinformatic analysis using validated algorithms to predict which tumor-specific mutations create epitopes that could bind to the patient's HLA allotype, and in particular which tumor-specific mutations create epitopes that could bind to the patient's HLA allotype more effectively than the cognate native antigen. Based on this analysis, one or more peptides corresponding to a subset of these mutations may be designed and synthesized for each patient, and pooled together for use as a cancer vaccine in immunizing the patient. The neo-antigens peptides may be combined another anti-neoplastic agent. In some embodiments, such neo-antigens are expected to bypass central thymic tolerance (thus allowing stronger antitumor T cell response), while reducing the potential for autoimmunity (e.g., by avoiding targeting of normal self-antigens).

The invention further provides a method of inducing a neoplasia/tumor specific immune response in a subject, vaccinating against a neoplasia/tumor, treating and or alleviating a symptom of cancer in a subject by administering the subject a neo-antigenic peptide or vaccine composition of the invention.

According to the invention, the above-described cancer vaccine may be used for a patient that has been diagnosed as having cancer, or at risk of developing cancer. In one embodiment, the patient may have a solid tumor such as breast, ovarian, prostate, lung, kidney, gastric, colon, testicular, head and neck, pancreas, brain, melanoma, and other tumors of tissue organs and hematological tumors, such as lymphomas and leukemias, including acute myelogenous leukemia, chronic myelogenous leukemia, chronic lymphocytic leukemia, T cell lymphocytic leukemia, and B cell lymphomas.

The peptide or composition of the invention is administered in an amount sufficient to induce a CTL response. The neo-antigenic peptide, polypeptide or vaccine composition of the invention can be administered alone or in combination with other therapeutic agents. The therapeutic agent is for example, a chemotherapeutic or biotherapeutic agent, radiation, or immunotherapy. Any suitable therapeutic treatment for a particular cancer may be administered. Examples of chemotherapeutic and biotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol®), pilocarpine, prochloroperazine, rituximab, tamoxifen, taxol, topotecan hydrochloride, trastuzumab, vinblastine, vincristine and vinorelbine tartrate. For prostate cancer treatment, a preferred chemotherapeutic agent with which anti-CTLA-4 can be combined is paclitaxel (Taxol®).

In addition, the subject may be further administered an anti-immunosuppressive or immuno stimulatory agent. For example, the subject is further administered an anti-CTLA antibody, anti-PD-1, anti-PD-L1, anti-TIM-3, anti-BTLA, anti-VISTA, anti-LAG3, anti-CD25, anti-CD27, anti-CD28, anti-CD137, anti-OX40, anti-GITR, anti-ICOS, anti-TIGIT, and inhibitors of IDO. Blockade of CTLA-4 or PD-1/PD-L1 by antibodies can enhance the immune response to cancerous cells in the patient. In particular, CTLA-4 blockade has been shown effective when following a vaccination protocol.

The optimum amount of each peptide to be included in the vaccine composition and the optimum dosing regimen can be determined by one skilled in the art without undue experimentation. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c, i.d., i.p., i.m., and i.v. Preferred methods of DNA injection include i.d., i.m., s.c, i.p. and i.v. For example, doses of between 1 and 500 mg 50 µg and 1.5 mg, preferably 10 µg to 500 µg, of peptide or DNA may be given and will depend from the respective peptide or DNA. Doses of this range were successfully used in previous trials (Brunsvig P F, et al., Cancer Immunol Immunother. 2006; 55(12): 1553-1564; M. Staehler, et al., ASCO meeting 2007; Abstract No 3017). Other methods of administration of the vaccine composition are known to those skilled in the art.

The inventive vaccine may be compiled so that the selection, number and/or amount of peptides present in the composition is/are tissue, cancer, and/or patient-specific. For instance, the exact selection of peptides can be guided by expression patterns of the parent proteins in a given tissue to avoid side effects. The selection may be dependent on the specific type of cancer, the status of the disease, earlier treatment regimens, the immune status of the patient, and, of course, the HLA-haplotype of the patient. Furthermore, the vaccine according to the invention can contain individualized components, according to personal needs of the particular patient. Examples include varying the amounts of peptides according to the expression of the related neoantigen in the particular patient, unwanted side-effects due to personal allergies or other treatments, and adjustments for secondary treatments following a first round or scheme of treatment.

Such vaccines may be administered to an individual already suffering from cancer. In therapeutic applications, such vaccines are administered to a patient in an amount sufficient to elicit an effective CTL response to the tumor antigen and to cure or at least partially arrest symptoms and/or complications. An amount adequate to accomplish this is defined as "therapeutically effective dose." Amounts effective for this use will depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 µg to about 50,000 µg of peptide for a 70 kg patient, followed by boosting dosages or from about 1.0 µg to about 10,000 µg of peptide pursuant to a boosting regimen over weeks to months depending upon the patient's response and condition and possibly by measuring specific CTL activity in the patient's blood. It should be kept in mind that the peptide and compositions of the present invention may generally be employed in serious disease states, that is, life-threatening or potentially life threatening situations, especially when the cancer has metastasized. For therapeutic use, administration should begin as soon as possible after the detection or surgical removal of tumors. This is followed by boosting doses until at least symptoms are substantially abated and for a period thereafter. The pharmaceutical compositions (e.g., vaccine compositions) for therapeutic treatment are intended for parenteral, topical, nasal, oral or local administration. Preferably, the pharmaceutical compositions are administered parenterally, e.g., intravenously, subcutaneously, intradermally, or intramuscularly. The compositions may be administered at the site of surgical excision to induce a local immune response to the tumor.

Such embodiments are not limited to a particular type of adjuvant. Generally, adjuvants are any substance whose admixture into the vaccine composition increases or otherwise modifies the immune response to the mutant peptide. Carriers are scaffold structures, for example a polypeptide or a polysaccharide, to which the antigenic peptide (e.g., neo-antigenic peptide) is capable of being associated. Optionally, adjuvants are conjugated covalently or non-covalently to the peptides or polypeptides of the invention.

The ability of an adjuvant to increase the immune response to an antigen is typically manifested by a significant increase in immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th2 response into a primarily cellular, or Th1 response.

Suitable adjuvants include, but are not limited to 1018 ISS, aluminum salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel® vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Several immunological adjuvants (e.g., MF59) specific for dendritic cells and their preparation have been described previously (Dupuis M, et al., Cell Immunol. 1998; 186(1): 18-27; Allison A C; Dev Biol Stand. 1998; 92:3-11). Also cytokines may be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, et al., J Immunother Emphasis Tumor Immunol. 1996 (6):414-418). Toll like receptors (TLRs) may also be used as adjuvants, and are important members of the family of pattern recognition receptors (PRRs) which recognize conserved motifs shared by many micro-organisms, termed "pathogen-associated molecular patterns" (PAMPS).

Recognition of these "danger signals" activates multiple elements of the innate and adaptive immune system. TLRs are expressed by cells of the innate and adaptive immune systems such as dendritic cells (DCs), macrophages, T and B cells, mast cells, and granulocytes and are localized in different cellular compartments, such as the plasma membrane, lysosomes, endosomes, and endolysosomes. Different TLRs recognize distinct PAMPS. For example, TLR4 is activated by LPS contained in bacterial cell walls, TLR9 is activated by unmethylated bacterial or viral CpG DNA, and TLR3 is activated by double stranded RNA. TLR ligand binding leads to the activation of one or more intracellular signaling pathways, ultimately resulting in the production of many key molecules associated with inflammation and immunity (particularly the transcription factor NF-κB and the Type-I interferons). TLR mediated DC activation leads to enhanced DC activation, phagocytosis, upregulation of activation and co-stimulation markers such as CD80, CD83, and CD86, expression of CCR7 allowing migration of DC to draining lymph nodes and facilitating antigen presentation to T cells, as well as increased secretion of cytokines such as type I interferons, IL-12, and IL-6. All of these downstream events are critical for the induction of an adaptive immune response.

Other receptors which may be targeted include the toll-like receptors (TLRs). TLRs recognize and bind to pathogen-associated molecular patterns (PAMPs). PAMPs target the TLR on the surface of the dendritic cell and signals internally, thereby potentially increasing DC antigen uptake, maturation and T-cell stimulatory capacity. PAMPs conjugated to the particle surface or co-encapsulated include unmethylated CpG DNA (bacterial), double-stranded RNA (viral), lipopolysacharride (bacterial), peptidoglycan (bacterial), lipoarabinomannin (bacterial), zymosan (yeast), mycoplasmal lipoproteins such as MALP-2 (bacterial), flagellin (bacterial) poly(inosinic-cytidylic) acid (bacterial), lipoteichoic acid (bacterial) or imidazoquinolines (synthetic).

Among the most promising cancer vaccine adjuvants currently in clinical development are the TLR9 agonist CpG and the synthetic double-stranded RNA (dsRNA) TLR3 ligand poly-ICLC. In preclinical studies poly-ICLC appears to be the most potent TLR adjuvant when compared to LPS and CpG due to its induction of pro-inflammatory cytokines and lack of stimulation of IL-10, as well as maintenance of high levels of co-stimulatory molecules in DCs. Furthermore, poly-ICLC was recently directly compared to CpG in non-human primates (rhesus macaques) as adjuvant for a protein vaccine consisting of human papillomavirus (HPV) 16 capsomers (Stahl-Hennig C, Eisenblatter M, Jasny E, et al. Synthetic double-stranded RNAs are adjuvants for the induction of T helper 1 and humoral immune responses to human papillomavirus in rhesus macaques. PLoS pathogens. April 2009; 5(4)).

In some embodiments, the adjuvant is a dendritic cell targeting molecule (DC). DC is potent and is responsible for initiating antigen-specific immune responses. One biological feature of DCs is their ability to sense conditions under which antigen is encountered, initiating a process of "DC maturation". Using receptors for various microbial and inflammatory products, DCs respond to antigen exposure in different ways depending on the nature of the pathogen (virus, bacteria, protozoan) encountered. This information is transmitted to T cells by altered patterns of cytokine release at the time of antigen presentation in lymph nodes, altering the type of T cell response elicited. Thus, targeting DCs provides the opportunity not only to quantitatively enhance the delivery of antigen and antigen responses in general, but to qualitatively control the nature of the immune response depending on the desired vaccination outcome.

Dendritic cells express a number of cell surface receptors that can mediate the endocytosis of bound antigen. Targeting exogenous antigens to internalizing surface molecules on systemically-distributed antigen presenting cells facilitates uptake of antigens and thus overcomes a major rate-limiting step in immunization and thus in vaccination.

Dendritic cell targeting molecules include monoclonal or polyclonal antibodies or fragments thereof that recognize and bind to epitopes displayed on the surface of dendritic cells. Dendritic cell targeting molecules also include ligands which bind to a cell surface receptor on dendritic cells. One such receptor, the lectin DEC-205, has been used in vitro and in mice to boost both humoral (antibody-based) and cellular (CD8 T cell) responses by 2-4 orders of magnitude (see, e.g., Hawiger, et al., J. Exp. Med., 194(6):769-79 (2001); Bonifaz, et al., J. Exp. Med., 196(12):1627-38 (2002); Bonifaz, et al., J. Exp. Med., 199(6):815-24 (2004)).

A variety of other endocytic receptors, including a mannose-specific lectin (mannose receptor) and IgG Fc receptors, have also been targeted in this way with similar enhancement of antigen presentation efficiency. Other suitable receptors which may be targeted include, but are not limited to, DC-SIGN, 33D1, SIGLEC-H, DCIR, CD11c, heat shock protein receptors and scavenger receptors.

In some embodiments, the adjuvant is CpG. CpG immuno stimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly, it enhances dendritic cell maturation and differentiation, resulting in enhanced activation of Th1 cells and strong cytotoxic T-lymphocyte (CTL) generation, even in the absence of CD4 T-cell help. The Th1 bias induced by TLR9 stimulation is maintained even in the presence of vaccine adjuvants such as alum or incomplete Freund's adjuvant (IFA) that normally promote a Th2 bias. CpG oligonucleotides show even greater adjuvant activity when formulated or co-administered with other adjuvants or in formulations such as microparticles, nano particles, lipid emulsions or similar formulations, which are especially necessary for inducing a strong response when the antigen is relatively weak. They also accelerate the immune response and enabled the antigen doses to be reduced by approximately two orders of magnitude, with comparable antibody responses to the full-dose vaccine without CpG in some experiments (Arthur M. Krieg, Nature Reviews, Drug Discovery, 5, Jun. 2006, 471-484). U.S. Pat. No. 6,406,705 B1 describes the combined use of CpG oligonucleotides, non-nucleic acid adjuvants and an antigen to induce an antigen-specific immune response. A commercially available CpG TLR9 antagonist is dSLIM (double Stem Loop Immunomodulator) by Mologen (Berlin, GERMANY), which is a preferred component of the pharmaceutical composition of the present invention. Other TLR binding molecules such as RNA binding TLR 7, TLR 8 and/or TLR 9 may also be used.

Xanthenone derivatives such as, for example, Vadimezan or AsA404 (also known as 5,6-dimethylxanthenone-4-acetic acid (DMXAA)), may also be used as adjuvants according to embodiments of the invention. Alternatively, such derivatives may also be administered in parallel to the vaccine of the invention, for example via systemic or intratumoral delivery, to stimulate immunity at the tumor site. Without being bound by theory, it is believed that such xanthenone derivatives act by stimulating interferon (IFN) production via the stimulator of IFN gene ISTING) receptor (see e.g., Conlon et al. (2013) Mouse, but not Human STING, Binds and Signals in Response to the Vascular Disrupting Agent 5, 6-Dimethylxanthenone-4-Acetic Acid, Journal of Immunology, 190:5216-25 and Kim et al. (2013) Anticancer Flavonoids are Mouse-Selective STING Agonists, 8: 1396-1401). Other examples of useful adjuvants include, but are not limited to, chemically modified CpGs (e.g. CpR, Idera), Poly(I:C)(e.g. polyi:Cl2U), non-CpG bacterial DNA or RNA as well as immunoactive small molecules and antibodies such as cyclophosphamide, sunitinib, bevacizumab, celebrex, NCX-4016, sildenafil, tadalafil, vardenafil, sorafinib, XL-999, CP-547632, pazopanib, ZD2171, AZD2171, ipilimumab, tremelimumab, and SC58175, which may act therapeutically and/or as an adjuvant. The amounts and concentrations of adjuvants and additives useful in the context of the present invention can readily be determined by the skilled artisan without undue experimentation. Additional adjuvants include colony-stimulating factors, such as Granulocyte Macrophage Colony Stimulating Factor (GM-CSF, sargramostim).

Poly-ICLC is a synthetically prepared double-stranded RNA consisting of polyI and polyC strands of average length of about 5000 nucleotides, which has been stabilized to thermal denaturation and hydrolysis by serum nucleases by the addition of polylysine and carboxymethylcellulose. The compound activates TLR3 and the RNA helicase-domain of MDA5, both members of the PAMP family, leading to DC and natural killer (NK) cell activation and production of a "natural mix" of type I interferons, cytokines, and chemokines. Furthermore, poly-ICLC exerts a more direct, broad host-targeted anti-infectious and possibly antitumor effect mediated by the two IFN-inducible nuclear enzyme systems, the 2' 5'-OAS and the PI/eIF2a kinase, also known as the PKR (4-6), as well as RIG-I helicase and MDA5.

Such methods are not limited to generating sHDL nanoparticles conjugated with an antigen and an adjuvant (e.g., dendritic cell targeting molecule). In some embodiments, the antigen and adjust are conjugated to outer surface of the sHDL nanoparticle.

In some embodiments, the sHDL nanoparticle is synthesized with thiol-reactive phospholipids that permit reduction-sensitive linkage of the antigen and/or adjuvant. In some embodiments, loading of the DC within the sHDL nanoparticle is facilitated through cholesterol modification of the DC molecule. In some embodiments, lyophilization methods are used for the preparation of homogenous sHDL. In some embodiments, phospholipids and ApoA mimetic peptides are dissolved in glacial acetic acid and lyophilized. In some embodiments, antigen peptides are incubated with sHDL in a buffer (e.g., a sodium phosphate buffer (pH 7.4)) (e.g., at room temperature for 3 hours) to allow for the conjugation of antigen peptides. In some embodiments, the unconjugated antigen peptides are removed using a desalting column (MWCO=7000 Da). In some embodiments, incorporation of the cholesterol modified DC (Cho-DC) to sHDL involves incubation with sHDL at room temperature for approximately 30 min.

Such embodiments are not limited to a particular manner of characterizing the sHDL conjugated with antigen and DC. In some embodiments, the morphology of sHDL is observed by TEM. In some embodiments, the size distribution of sHDL is analyzed by dynamic light scattering (DLS) using a Malven Nanosizer instrument and GPC assay.

The sHDL nanoparticles configured to activate an immune response (e.g., sHDL-αGalCer) (e.g., Ag/DC-sHDL) are useful for activating T cells in subjects for prophylactic and therapeutic applications. Activation of T cells by nanoparticle vaccine compositions increases their proliferation, cytokine production, differentiation, effector functions and/or survival. Methods for measuring these are well known to those in the art. The T cells activated by the nanoparticle vaccine compositions can be any cell which express the T cell receptor, including α/β and γ/δ T cell receptors. T-cells include all cells which express CD3, including T-cell subsets which also express CD4 and CD8. T-cells include both naive and memory cells and effector cells such as CTL. T-cells also include regulatory cells such as Th1, Tc1, Th2, Tc2, Th3, Treg, and Tr1 cells. T-cells also include NKT-cells and similar unique classes of the T-cell lineage. In some embodiments, the T cells that are activated are $CD8^+$ T cells.

In general, compositions comprising the sHDL nanoparticles configured to activate an immune response (e.g., sHDL-αGalCer) (e.g., Ag/DC-sHDL) are useful for treating a subject having or being predisposed to any disease or disorder to which the subject's immune system mounts an immune response. The compositions are useful as prophylactic vaccines, which confer resistance in a subject to subsequent exposure to infectious agents. The compositions are also useful as therapeutic vaccines, which can be used to initiate or enhance a subject's immune response to a pre-existing antigen, such as a tumor antigen in a subject with cancer, or a viral antigen in a subject infected with a virus. The compositions are also useful as desensitizing vaccines, which function to "tolerize" an individual to an environmental antigen, such as an allergen.

The ability to target these compositions to professional antigen-presenting cells such as dendritic cells, and the ability of these compositions to elicit T-cell mediated immune responses by causing cross-presentation of antigens makes these compositions especially useful for eliciting a cell-mediated response to a disease-related antigen in order to attack the disease. Thus, in some embodiments, the type of disease to be treated or prevented is a malignant tumor or a chronic infectious disease caused by a bacterium, virus, protozoan, helminth, or other microbial pathogen that enters intracellularly and is attacked, i.e., by the cytotoxic T lymphocytes.

The desired outcome of a prophylactic, therapeutic or de-sensitized immune response may vary according to the disease, according to principles well known in the art. For example, an immune response against an infectious agent may completely prevent colonization and replication of an infectious agent, affecting "sterile immunity" and the absence of any disease symptoms. However, a vaccine against infectious agents may be considered effective if it reduces the number, severity or duration of symptoms; if it reduces the number of individuals in a population with symptoms; or reduces the transmission of an infectious agent. Similarly, immune responses against cancer, allergens or infectious agents may completely treat a disease, may alleviate symptoms, or may be one facet in an overall therapeutic intervention against a disease. For example, the stimulation of an immune response against a cancer may be coupled with surgical, chemotherapeutic, radiologic, hormonal and other immunologic approaches in order to affect treatment.

Subjects with or exposed to infectious agents can be treated therapeutically or prophylactically the sHDL nanoparticles configured to activate an immune response (e.g., sHDL-αGalCer) (e.g., Ag/DC-sHDL) as disclosed herein. Infectious agents include bacteria, viruses and parasites. In some instances, the subject can be treated prophylactically, such as when there may be a risk of developing disease from an infectious agent. An individual traveling to or living in an area of endemic infectious disease may be considered to be at risk and a candidate for prophylactic vaccination against the particular infectious agent. Preventative treatment can be applied to any number of diseases where there is a known relationship between the particular disease and a particular risk factor, such as geographical location or work environment.

Subjects with or at risk for developing malignant tumors can be treated therapeutically or prophylactically the sHDL nanoparticles configured to activate an immune response (e.g., sHDL-αGalCer) (e.g., Ag/DC-sHDL) as disclosed herein. In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer refers specifically to a malignant tumor. In addition to uncontrolled growth, malignant tumors exhibit metastasis. In this process, small clusters of cancerous cells dislodge from a tumor, invade the blood or lymphatic vessels, and are carried to other tissues, where they continue to proliferate. In this way a primary tumor at one site can give rise to a secondary tumor at another site. The sHDL nanoparticles configured to activate an immune response (e.g., sHDL-αGalCer) (e.g., Ag/DC-sHDL) as disclosed herein are useful for treating subjects having malignant tumors.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. A melanoma is a type of carcinoma of the skin for which this invention is particularly useful. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated in with the provided sHDL nanoparticles configured to activate an immune response (e.g., sHDL-αGalCer) (e.g., Ag/DC-sHDL) include, but are not limited to, the following: bladder, brain, breast, cervical, colo-rectal, esophageal, kidney, liver, lung, nasopharangeal, pancreatic, prostate, skin, stomach, uterine, and the like. Administration is not limited to the treatment of an existing tumor or infectious disease but can also be used to prevent or lower the risk of developing such diseases in an individual, i.e., for prophylactic use. Potential candidates for prophylactic vaccination include individuals with a high risk of developing cancer, i.e., with a personal or familial history of certain types of cancer.

Subjects with or at risk for exposure to allergens can be treated therapeutically or prophylactically the sHDL nanoparticles configured to activate an immune response (e.g., sHDL-αGalCer) (e.g., Ag/DC-sHDL) as disclosed herein. Such sHDL nanoparticles may be administered to subjects for the purpose of preventing and/or attenuating allergic reactions, such as allergic reactions which lead to anaphylaxis. Allergic reactions may be characterized by the $T_H2$ responses against an antigen leading to the presence of IgE antibodies. Stimulation of $T_H1$ immune responses and the production of IgG antibodies may alleviate allergic disease. Thus, the sHDL nanoparticles configured to activate an immune response (e.g., sHDL-αGalCer) (e.g., Ag/DC-sHDL) as disclosed herein are useful for producing antibodies that prevent and/or attenuate allergic reactions in subjects exposed to allergens.

Subjects with or at risk for immunosuppressed conditions can be treated therapeutically or prophylactically the sHDL nanoparticles configured to activate an immune response (e.g., sHDL-αGalCer) (e.g., Ag/DC-sHDL) as disclosed herein. The sHDL nanoparticle vaccines disclosed herein can be used for treatment of disease conditions characterized by immunosuppression, including, but not limited to, AIDS or AIDS-related complex, idiopathic immuno suppression, drug induced immunosuppression, other virally or environmentally-induced conditions, and certain congenital immune deficiencies. Such sHDL nanoparticle vaccine compositions can also be employed to increase immune function that has been impaired by the use of radiotherapy of immunosuppressive drugs (e.g., certain chemotherapeutic agents), and therefore can be particularly useful when used in conjunction with such drugs or radiotherapy.

Subjects with or at risk for coronary heart disease and/or elevated LDL-C levels can be treated therapeutically or prophylactically the sHDL nanoparticles configured to activate an immune response as disclosed herein. While effectiveness of mAb therapy against PCSK9 has established (see, e.g., Banerjee, Y.; et al., New England Journal of Medicine 2012, 366 (25), 2425-2426; Stein, E. A.; et al., Circulation 2013, 128 (19), 2113-2120), development of more durable PCSK9 vaccines are needed. In addition, one of the challenges for PCSK9 vaccines is that self antigens, such as PCSK9 peptides, are not immunogenic, unless they are coupled to vaccine/adjuvant systems that can efficiently co-deliver antigens and immunostimulatory molecules to immune cells (see, e.g., Krishnamachari, Y.; et al., Advanced Drug Delivery Reviews 2009, 61 (3), 205-217; Hamdy, S.; et al., Advanced Drug Delivery Reviews 2011, 63 (10-11), 943-955).

Embodiments of the present invention wherein sHDL nanoparticles are conjugated with a PCSK9-antigen and a CpG-adjuvant (PCSK9-Ag/CpG-sHDL) address such needs. Indeed, vaccination against PCSK9 with PCSK9-Ag/CpG-sHDL embodiments effectively inhibits interaction between PCSK9 and LDLR, while avoiding the need for repeated injections of expensive mAb (see, e.g., Fattori, E.; et al., Journal of Lipid Research 2012, 53 (8), 1654-1661; Gergana Galabova, et al., PLOS ONE 2014, 9 (12)). Moreover, such PCSK9-Ag/CpG-sHDL nanoparticles have a sufficiently small size (e.g., 10-45 nm) permitting efficient drainage to the lymph nodes compared to larger particles (see, e.g., Bachmann, M. F.; et al., Nature Reviews Immunology 2010, 10 (11), 787-796).

In general, methods of administering vaccines as disclosed herein (e.g., sHDL nanoparticles configured to activate an immune response (e.g., sHDL-αGalCer) (e.g., Ag/DC-sHDL)) are well known in the art. Any acceptable method known to one of ordinary skill in the art may be used to administer a formulation to the subject. The administration may be localized (i.e., to a particular region, physiological system, tissue, organ, or cell type) or systemic. Vaccines can be administered by a number of routes including, but not limited to: oral, inhalation (nasal or pulmonary), intravenous, intraperitoneal, intramuscular, transdermal, subcutaneous, topical, sublingual, or rectal means. Injections can be e.g., intravenous, intradermal, subcutaneous, intramuscular, or intraperitoneal. In some embodiments, the injections can be given at multiple locations.

Administration of the formulations may be accomplished by any acceptable method which allows an effective amount of the vaccine to reach its target. The particular mode selected will depend upon factors such as the particular formulation, the severity of the state of the subject being treated, and the dosage required to induce an effective immune response. As generally used herein, an "effective amount" is that amount which is able to induce an immune response in the treated subject. The actual effective amounts of vaccine can vary according to the specific antigen or combination thereof being utilized, the particular composition formulated, the mode of administration, and the age, weight, condition of the individual being vaccinated, as well as the route of administration and the disease or disorder.

In certain embodiments, glycolipids encapsulated within sHDL nanoparticles are used as stimulators of natural killer T cell-mediated immune responses.

Natural killer T (NKT) cells are a heterogeneous group of T cells that share properties of both T cells and natural killer cells. Many of these cells recognize the non-polymorphic CD1d molecule, an antigen-presenting molecule that binds self and foreign lipids and glycolipids. NKT cells constitute only approximately 0.1% of all peripheral blood T cells. NKT cells are a subset of T cells that coexpress an αβ T-cell receptor, but also express a variety of molecular markers that are typically associated with NK cells, such as NK1.1. The best-known NKT cells differ from conventional αβ T cells in that their T-cell receptors are far more limited in diversity ('invariant' or 'type 1' NKT). They and other CD1d-restricted T cells ('type 2' NKT) recognize lipids and glycolipids presented by CD1d molecules, a member of the CD1 family of antigen-presenting molecules, rather than peptide-major histocompatibility complexes (MI-ICs). NKT cells include both NK1.1$^+$ and NK1.1$^-$, as well as CD4$^+$, CD4$^-$, CD8$^+$ and CD8$^-$ cells.

In some embodiments the glycolipid is the synthetic glycolipid alpha-galactosylceramide (αGalCer). Dendritic cells presenting antigens in the context of CD1d can lead to rapid innate and prolonged production of cytokines such as interferon and IL-4 by natural killer T cells (NKT cells). CD1d is a major histocompatibility complex class I-like molecule that presents glycolipid antigens to a subset of NKT cells. Advantageously, αGalCer is not toxic to humans and has been shown to act as an adjuvant, priming both antigen-specific CD4+ and CD8+ T cell responses. For example, it has been shown that αGalCer in conjunction with a malaria vaccine can lead to cytotoxic responses against infected cells, which is an ideal scenario for vaccines against infectious diseases. In addition to αGalCer, other glycolipids that function as adjuvants to activate NKT cell-mediated immune responses can be used.

The present invention is not limited to particular methods for generating sHDL nanoparticles having encapsulated αGalCer. For example, in some embodiments, lyophilization methods are used for the preparation of homogenous sHDL. In some embodiments, phospholipids and ApoA mimetic peptides are dissolved in glacial acetic acid and lyophilized. In some embodiments, loading of αGalCer into the sHDL nanoparticle is facilitated through hydrophobic interactions between the αGalCer and the sHDL. In some embodiments, the lyophilized phospholipids and ApoA mimetic peptides are hydrated (e.g., hydrated in PBS (pH 7.4)) and thermocycled above and below the transition temperature (Tm) of phospholipids to form blank sHDL, which are next incubated with αGalCer at room temperature for an optimal amount of time (e.g., 5, 10, 20, 25, 30, 35, 50, 80, 120, 360 minutes) to form sHDL comprising encapsulated αGalCer.

Such embodiments are not limited to a particular manner of characterizing the sHDL comprising encapsulated αGalCer. In some embodiments, the morphology of sHDL-αGalCer is observed by TEM. In some embodiments, the size distribution of sHDL-αGalCer is analyzed by dynamic light scattering (DLS) using a Malven Nanosizer instrument and GPC assay.

Such embodiments are not limited to a particular manner of assessing the delivery profile of the αGalCer in vitro and in vivo. In some embodiments, labelling the molecules with an imaging agent (e.g., fluorescent dye Cy3) permits visualization of the biodistribution of αGalCer molecules at the organ level and also the intracellular delivery profile.

In certain embodiments, the present invention provides methods for inducing a natural killer T cell-mediated immune response in a cell comprising exposing the cell to a composition comprising an αGalCer glycolipid encapsulated within a sHDL nanoparticle, wherein such exposure results in the induction of a natural killer T cell-mediated immune response. In some embodiments, the cells are in vivo cells. In some embodiments, the cells are in vitro cells. In some embodiments, the cells are ex vivo cells.

In certain embodiments, the present invention provides methods for inducing a natural killer T cell-mediated immune response in a subject (e.g., a human patient) comprising administering to the patient a pharmaceutical composition comprising an αGalCer glycolipid encapsulated within a sHDL nanoparticle, wherein such administration results in the induction of a natural killer T cell-mediated immune response.

Additional Embodiments

In certain embodiments, the sHDL nanoparticles as described herein (e.g., configured for RNA Interference) (e.g., configured for activating an immune response) encapsulate one or more therapeutic agents. Such embodiments are not limited to particular type or kind of therapeutic agent.

In some embodiments, the therapeutic agent configured for treating and/or preventing cancer. Examples of such therapeutic agents include, but are not limited to, chemotherapeutic agents, anti-oncogenic agents, anti-angiogenic agents, tumor suppressor agents, anti-microbial agents, etc.

In some embodiments, the therapeutic agent is configured for treating and/or preventing autoimmune disorders and/or inflammatory disorders. Examples of such therapeutic agents include, but are not limited to, disease-modifying antirheumatic drugs (e.g., leflunomide, methotrexate, sulfasalazine, hydroxychloroquine), biologic agents (e.g., rituximab, infliximab, etanercept, adalimumab, golimumab), nonsteroidal anti-inflammatory drugs (e.g., ibuprofen, celecoxib, ketoprofen, naproxen, piroxicam, diclofenac), analgesics (e.g., acetaminophen, tramadol), immunomodulators (e.g., anakinra, abatacept), glucocorticoids (e.g., prednisone, methylprednisone), TNF-α inhibitors (e.g., adalimumab, certolizumab pegol, etanercept, golimumab, infliximab), IL-1 inhibitors, and metalloprotease inhibitors. In some embodiments, the therapeutic agents include, but are not limited to, infliximab, adalimumab, etanercept, parenteral gold or oral gold.

In some embodiments, the therapeutic agent is configured for treating and/or preventing cardiovascular related disorders (e.g., atherosclerosis, heart failure, arrhythmia, atrial fibrillation, hypertension, coronary artery disease, angina pectoris, etc.). Examples of therapeutic agents known to be useful in treating and/or preventing cardiovascular related disorders include, angiotensin-converting enzyme (ACE) inhibitors (e.g., benazepril, enalapril, Lisinopril, perindopril, Ramipril), adenosine, alpha blockers (alpha adrenergic antagonist medications) (e.g., clonidine, guanabenz, labetalol, phenoxybenzamine, terazosin, doxazosin, guanfacine, methyldopa, prazosin), angtiotensin II receptor blockers (ARBs) (e.g., candesartan, irbesartan, olmesartan medoxomil, telmisartan, eprosartan, losartan, tasosartan, valsartan), anticoagulants (e.g., heparin fondaparinux, warfarin, ardeparin, enoxaparin, reviparin, dalteparin, nadroparin, tinzaparin), antiplatelet agents (e.g., abciximab, clopidogrel, eptifibatide, ticlopidine, cilostazol, dipyridamole, sulfinpyrazone, tirofiban), beta blockers (e.g., acebutolol, betaxolol, carteolol, metoprolol, penbutolol, propranolol, atenolol, bisoprolol, esmolol, nadolol, pindolol, timolol), calcium channel blockers (e.g., amlopidine, felodipine, isradipine, nifedipine, verapamil, diltiazem, nicardipine, nimodipine, nisoldipine), diuretics, aldosterone blockers, loop diuretics (e.g., bumetanide, furosemide, ethacrynic acid, torsemide), potassium-sparing diuretics, thiazide diuretics (e.g., chlorothiazide, chlorthalidone, hydrochlorothiazide, hydroflumethiazide, methyclothiazide, metolazone, polythiazide, quinethazone, trichlormethiazide), inoptropics, bile acid sequestrants (e.g., cholestyramine, coletipol, colesevelam), fibrates (e.g., clofibrate, gemfibrozil, fenofibrate), statins (e.g., atorvastatinm, lovastatin, simvastatin, fluvastatin, pravastatin), selective cholesterol absorption inhibitors (e.g., ezetimibe), potassium channel blockers (e.g., amidarone, ibutilide, dofetilide), sodium channel blockers (e.g., disopyramide, mexiletine, procainamide, quinidine, flecainide, moricizine, propafenone), thrombolytic agents (e.g., alteplase, reteplase, tenecteplase, anistreplase, streptokinase, urokinase), vasoconstrictors, vasodilators (e.g., hydralazine, minoxidil, mecamylamine, isorbide dintrate, isorbide mononitrate, nitroglycerin).

Generally, the sHDL nanoparticles so formed are spherical and have a diameter of from about 5 nm to about 20 nm (e.g., 4-75 nm, 4-60 nm, 4-50 nm, 4-22 nm, 6-18 nm, 8-15 nm, 8-10 nm, etc.). In some embodiments, the sHDL nanoparticles are subjected to size exclusion chromatography to yield a more homogeneous preparation.

In some embodiments, the sHDL nanoparticles further encapsulate agents useful for determining the location of administered particles. Agents useful for this purpose include fluorescent tags, radionuclides and contrast agents.

Suitable imaging agents include, but are not limited to, fluorescent molecules such as those described by Molecular Probes (Handbook of fluorescent probes and research products), such as Rhodamine, fluorescein, Texas red, Acridine Orange, Alexa Fluor (various), Allophycocyanin, 7-aminoactinomycin D, BOBO-1, BODIPY (various), Calcien, Calcium Crimson, Calcium green, Calcium Orange, 6-carboxyrhodamine 6G, Cascade blue, Cascade yellow, DAPI, DiA, DID, Dil, DiO, DiR, ELF 97, Eosin, ER Tracker Blue-White, EthD-1, Ethidium bromide, Fluo-3, Fluo4, FM1-43, FM4-64, Fura-2, Fura Red, Hoechst 33258, Hoechst 33342, 7-hydroxy-4-methylcoumarin, Indo-1, JC-1, JC-9, JOE dye, Lissamine rhodamine B, *Lucifer* Yellow CH, LysoSensor Blue DND-167, LysoSensor Green, LysoSensor Yellow/Blu, Lysotracker Green FM, Magnesium Green, Marina Blue, Mitotracker Green FM, Mitotracker Orange CMTMRos, MitoTracker Red CMXRos, Monobromobimane, NBD amines, NeruoTrace 500/525 green, Nile red, Oregon Green, Pacific Blue. POP-1, Propidium iodide, Rhodamine 110, Rhodamine Red, R-Phycoerythrin, Resorfin, RH414, Rhod-2, Rhodamine Green, Rhodamine 123, ROX dye, Sodium Green, SYTO blue (various), SYTO green (Various), SYTO orange (various), SYTOX blue, SYTOX green, SYTOX orange, Tetramethylrhodamine B, TOT-1, TOT-3, X-rhod-1, YOYO-1, YOYO-3. In some embodiments, ceramides are provided as imaging agents. In some embodiments, SW agonists are provided as imaging agents.

Additionally radionuclides can be used as imaging agents. Suitable radionuclides include, but are not limited to radioactive species of Fe(III), Fe(II), Cu(II), Mg(II), Ca(II), and Zn(1l) Indium, Gallium and Technetium. Other suitable contrast agents include metal ions generally used for chelation in paramagnetic T1-type MIR contrast agents, and include di- and tri-valent cations such as copper, chromium, iron, gadolinium, manganese, erbium, europium, dysprosium and holmium. Metal ions that can be chelated and used for radionuclide imaging, include, but are not limited to metals such as gallium, germanium, cobalt, calcium, indium, iridium, rubidium, yttrium, ruthenium, yttrium, technetium, rhenium, platinum, thallium and samarium. Additionally metal ions known to be useful in neutron-capture radiation therapy include boron and other metals with large nuclear cross-sections. Also suitable are metal ions useful in ultrasound contrast, and X-ray contrast compositions.

Examples of other suitable contrast agents include gases or gas emitting compounds, which are radioopaque.

In some embodiments, the sHDL nanoparticles further encapsulate a targeting agent. In some embodiments, targeting agents are used to assist in delivery of the sHDL-TA nanoparticles to desired body regions (e.g., bodily regions affected by a cardiovascular related disorder). Examples of targeting agents include, but are not limited to, an antibody, receptor ligand, hormone, vitamin, and antigen, however, the present invention is not limited by the nature of the targeting agent. In some embodiments, the antibody is specific for a disease-specific antigen. In some embodiments, the receptor ligand includes, but is not limited to, a ligand for CFTR, EGFR, estrogen receptor, FGR2, folate receptor, IL-2 receptor, glycoprotein, and VEGFR. In some embodiments, the receptor ligand is folic acid.

In some embodiments, the sHDL nanoparticles of the present invention may be delivered to local sites in a patient by a medical device. Medical devices that are suitable for use in the present invention include known devices for the localized delivery of therapeutic agents. Such devices include, but are not limited to, catheters such as injection catheters, balloon catheters, double balloon catheters, microporous balloon catheters, channel balloon catheters, infusion catheters, perfusion catheters, etc., which are, for example, coated with the therapeutic agents or through which the agents are administered; needle injection devices such as hypodermic needles and needle injection catheters; needleless injection devices such as jet injectors; coated stents, bifurcated stents, vascular grafts, stent grafts, etc.; and coated vaso-occlusive devices such as wire coils.

Exemplary devices are described in U.S. Pat. Nos. 5,935,114; 5,908,413; 5,792,105; 5,693,014; 5,674,192; 5,876,445; 5,913,894; 5,868,719; 5,851,228; 5,843,089; 5,800,519; 5,800,508; 5,800,391; 5,354,308; 5,755,722; 5,733,303; 5,866,561; 5,857,998; 5,843,003; and 5,933,145; the entire contents of which are incorporated herein by reference. Exemplary stents that are commercially available and may be used in the present application include the RADIUS (SCIMED LIFE SYSTEMS, Inc.), the SYMPHONY (Boston Scientific Corporation), the Wallstent (Schneider Inc.), the PRECEDENT II (Boston Scientific Corporation) and the NIR (Medinol Inc.). Such devices are delivered to and/or implanted at target locations within the body by known techniques.

In some embodiments, the present invention also provides kits comprising sHDL nanoparticles as described herein. In some embodiments, the kits comprise one or more of the reagents and tools necessary to generate sHDL nanoparticles, and methods of using such sHDL nanoparticles.

The sHDL nanoparticles of the present invention may be characterized for size and uniformity by any suitable analytical techniques. These include, but are not limited to, atomic force microscopy (AFM), electrospray-ionization mass spectroscopy, MALDI-TOF mass spectroscopy, $^{13}C$ nuclear magnetic resonance spectroscopy, high performance liquid chromatography (HPLC) size exclusion chromatography (SEC) (equipped with multi-angle laser light scattering, dual UV and refractive index detectors), capillary electrophoresis and get electrophoresis. These analytical methods assure the uniformity of the sHDL nanoparticle population and are important in the production quality control for eventual use in in vivo applications.

In some embodiments, gel permeation chromatography (GPC), which can separate sHDL nanoparticles from liposomes and free ApoA-I mimetic peptide, is used to analyze the sHDL-TA nanoparticles. In some embodiments, the size distribution and zeta-potential is determined by dynamic light scattering (DLS) using, for example, a Malven Nanosizer instrument.

Where clinical applications are contemplated, in some embodiments of the present invention, the sHDL nanoparticles are prepared as part of a pharmaceutical composition in a form appropriate for the intended application. Generally, this entails preparing compositions that are essentially free of pyrogens, as well as other impurities that could be harmful to humans or animals. However, in some embodiments of the present invention, a straight sHDL nanoparticle formulation may be administered using one or more of the routes described herein.

In preferred embodiments, the sHDL nanoparticles are used in conjunction with appropriate salts and buffers to render delivery of the compositions in a stable manner to allow for uptake by target cells. Buffers also are employed when the sHDL nanoparticles are introduced into a patient. Aqueous compositions comprise an effective amount of the sHDL nanoparticles to cells dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. Except insofar as any conventional media or agent is incompatible with the vectors or cells of the present invention, its use in therapeutic compositions is contemplated. Supplementary active ingredients may also be incorporated into the compositions.

In some embodiments of the present invention, the active compositions include classic pharmaceutical preparations. Administration of these compositions according to the present invention is via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection.

The active sHDL nanoparticles may also be administered parenterally or intraperitoneally or intratumorally. Solutions of the active compounds as free base or pharmacologically acceptable salts are prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it may be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active sHDL nanoparticles in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, sHDL nanoparticles are administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution is suitably buffered, if necessary, and the liquid diluent first rendered isotonic with sufficient saline or glucose. These particular aqueous solutions are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). In some embodiments of the present invention, the active particles or agents are formulated within a therapeutic mixture to comprise about 0.0001 to 1.0 milligrams, or about 0.001 to 0.1 milligrams, or about 0.1 to 1.0 or even about 10 milligrams per dose or so. Multiple doses may be administered.

Additional formulations that are suitable for other modes of administration include vaginal suppositories and pessaries. A rectal pessary or suppository may also be used. Suppositories are solid dosage forms of various weights and shapes, usually medicated, for insertion into the rectum, vagina or the urethra. After insertion, suppositories soften, melt or dissolve in the cavity fluids. In general, for suppositories, traditional binders and carriers may include, for example, polyalkylene glycols or triglycerides; such suppositories may be formed from mixtures containing the active ingredient in the range of 0.5% to 10%, preferably 1%-2%. Vaginal suppositories or pessaries are usually globular or oviform and weighing about 5 g each. Vaginal medications are available in a variety of physical forms, e.g., creams, gels or liquids, which depart from the classical concept of suppositories. The sHDL nanoparticles also may be formulated as inhalants.

The present invention also includes methods involving co-administration of the sHDL nanoparticles as described herein with one or more additional active agents. Indeed, it is a further aspect of this invention to provide methods for enhancing prior art therapies and/or pharmaceutical compositions by co-administering the sHDL nanoparticles of this invention. In co-administration procedures, the agents may be administered concurrently or sequentially. In some embodiments, the sHDL nanoparticles described herein are administered prior to the other active agent(s). The agent or agents to be co-administered depends on the type of condition being treated.

The present disclosure further provides kits comprising compositions comprising sHDL nanoparticles as described herein or the ingredients necessary to synthesize the sHDL nanoparticles as described herein. In some embodiments, the kit includes all of the components necessary, sufficient or useful for administering such sHDL nanoparticles.

EXPERIMENTAL

The following examples are provided in order to demonstrate and further illustrate certain preferred embodiments and aspects of the present invention and are not to be construed as limiting the scope thereof.

Example 1

This example describes the materials and methods for synthesis of a sHDL loaded with biomacromolecules
Materials 1,2-dimyristoyl-sn-glycero-3-phosphocholine (DMPC), 1,2-dioleoyl-sn-glycero-3-phosphoethanolamine (DOPE), and rhodamine (Rhod)-labeled DOPE (DOPE-Rhod) were all purchased form Avanti Polar Lipids (Alabaster, Ala.). Dioleoyl-sn-glycero-3-phosphoethanolamine-N-[3-(2-pyridyldithio) propionate] (DOPE-PDP) was additionally synthesized. All peptides including HDL mimicking peptide (22A; SEQ ID NO: 4), SIINFEKL (SEQ ID NO: 341), CSSSIINFEKL (SEQ ID NO: 342), and FITC labeled CSSSIINFEK(FITC)L used were customized from GenScript. The oligodeoxynucleotide TLR 9 ligand CpG 1826 (5'-tccatgacgttcctgacgtt-3', lower case letters represent phosphorothioate backbone) (SEQ ID NO: 343) and cholesterol modified CpG 1826 (5'-tccatgacgttcctgacgtt-3'-TEG-cholesterol) were ordered from Integrated DNA Technologies. HPLC grade solvents such as methanol and acetonitrile were purchased from fisher scientific. Fetal bovine serum (FBS), penicillin-streptomycin, β-mercaptoethanol and ACK lysing buffer were purchased from Life Technologies (Grand Island, N.Y.). Granulocyte macrophage colony stimulating factor (GM-CSF) was the product of PeproTech (Rocky Hill, N.J.). Rat anti-mouse CD16/32, CD86-PE, CD40-APC, SIINFEKL H-2K$^b$-PE and MHC Class II-FITC were from eBioscience (San Diego, Calif.). Rat anti-mouse CD8-APC, hamster anti-mouse CD11c-PE and streptavidin-Cy7 were from BD Bioscience (San Jose, Calif.). iTAg tetramer/PE-H-2 Kb OVA (SIINFEKL) was purchased from Beckman Coulter (Brea, Calif.).
Preparation of sHDL Nanoparticles Loaded with Peptides, Nucleic Acids, or Glycolipids.

DMPC and DOPE-PDP (weight ratio=4:0.25) were dissolved in chloroform. The mixture was dried with nitrogen flow for 5 min and then put in a vacuum oven for 1 h. The obtained lipid film was hydrated in 10 mM sodium phosphate buffer (0.3117 g/L NaH$_2$PO$_4$·H$_2$O and 2.0747 g/L Na$_2$HPO$_4$·7H$_2$O) and sonicated with a bath sonicator for 10 min, followed by probe sonication for another 2.5 min. 22A peptide dissolved in endotoxin free water was added to the above mixture (22A:lipids=1:2, weight ratio), which was then subjected to heating (50° C.) for 3 min and cooling (ice water) for 3 min, with 3 cycles in total, to obtain sHDL.

To load tumor antigen peptides to sHDL, cysteine terminated tumor antigen peptides dissolved in endotoxin free water were added to the above sHDL (antigen peptides: DOPE-PDP=2.5:1, molar ratio) and incubated at room temperature with gentle shaking on an orbital shaker for 3 h. Unreacted tumor antigen peptides were removed by using Zeba Spin Desalting columns with a MWCO=7000 Da cutoff (Pierce) following the manufacturer's instructions. The conjugation efficiency of tumor antigen peptides was calculated based on the decrease of DOPE-PDP determined by the HPLC. Briefly, 200 µl sHDL formulations were freeze-dried and reconstituted in 300 µl methanol. The mixture was filtered by a 220 nm PTFE filter before 20 µl was injected to a Shimadzu HPLC system equipped with a Vydac 219TP Diphenyl column (4.6 mm×250 mm ID). The two solvents used for the HPLC analysis consisted of water:trifluoroacetic acid=100:0.5 (mobile phase A) and methanol:acetonitrile:trifluoroacetic acid=50:50:0.05 (mobile phase B). Gradient programming of the solvent system was: 25% mobile phase B was linearly increased to 100% B over 75 min, linearly decreased to 25% B at 80 min, and maintained at 25% during 80-90 min for equilibration before the next analysis. The flow rate was 1 mL/min and the detection wavelength was 220 nm. The loading efficiency of tumor antigen peptides was also determined by using FITC-labeled peptides and measuring the fluorescence intensity of sHDL formulations at Ex=490 nm and Em=520 nm after dissolving the formulations with 1% Triton X-100 containing PBS.

To load CpG to sHDL, different concentrations of cholesterol modified CpG (Cho-CpG) were incubated with sHDL at room temperature with gentle shaking on an orbital shaker for 30 min. The amount of CpG incorporated into sHDL and free CpG were analyzed by the gel permeation chromatography (GPC). Briefly, the sHDL formulations were diluted by PBS to a concentration of 0.5 mg/mL 22A peptide. The formulations were filtered through a 220 nm filter before 40 µl samples were injected to a Shimadzu HPLC system equipped with a TSKgel G2000SW×l column (7.8 mm ID×30 cm, Tosoh Bioscience LLC). The flow rate of mobile phase PBS (pH 7.4) was set at 0.7 mL/min and detection wavelength was set at 260 nm for CpG.

To load alpha-galactosylceramide (aGC) to sHDL, a lyophilization-based method of producing sHDL was developed. Briefly, phospholipids, aGC and ApoA mimetic peptides were dissolved in glacial acetic acid and lyophilized. The obtained powder was hydrated in PBS (pH 7.4) and cycled above and below the transition temperature (Tm) of phospholipids to form aGC-sHDL. Similar protocol was utilized for loading siRNA into sHDL. Cholesterol-modified PCSK9 siRNA was incubated with blank sHDL at room temperature for 30 min to form PCSK9 siRNA-sHDL.

Morphology and Size Measurement of sHDL

The sHDL formulations were diluted to 0.5 mg/mL 22A with PBS and the sizes were measured by dynamic light scattering (DLS, Zetasizer Nano ZSP, Malvern, UK). The morphology of sHDL was observed by transmission electron microscopy (TEM) after proper dilution of the original samples.

Preparation of Bone Marrow-Derived Dendritic Cells (BMDCs)

BMDCs were prepared. Briefly, femur and tibia of a mouse were harvested, washed and grinded in BMDC culture media (RPMI 1640 supplemented with 10% FBS, 1% penicillin-streptomycin, 50 µM β-mercaptoethanol, and 20 ng/ml GM-CSF). Cells were collected by passing the cell suspension through a cell strainer (mesh size=40 µm), followed by centrifugation. Cells were seeded into non-tissue culture treated petri-dish at a density of $2\times10^5$ cells/ml, cultured at 37° C. with 5% $CO_2$. Culture media were refreshed on days 3, 6 and 8, and BMDCs were used during day 8-12.

Up-Regulation of Activation Markers on BMDCs

Immature BMDCs were plated at $1\times10^6$ cells/well in 12-well plates 24 h prior to use. The old media were aspirated and BMDCs were washed once with PBS before incubated with 0.5 µg/mL different CpG-containing formulations or 0.5 µg/mL LPS (positive control) for 24 h at 37° C. BMDCs were harvested, washed once with FACS buffer (1% BSA in PBS), incubated with anti-CD16/32 at room temperature for 10 min, and then stained with fluorescent probe-labeled antibodies against CD11c, CD40, CD80, CD86, and MHC class II at room temperature for 30 min. Finally, cells were washed twice by FACS buffer and resuspended in 2 µg/ml DAPI solution and analyzed by flow cytometry (Cyan 5, Beckman Coulter, USA).

Antigen Presentation by BMDCs

Immature BMDCs were plated at $1\times10^6$ cells/well in 12-well plates 24 h prior to use. The old media were aspirated and BMDCs were washed once with PBS before incubated with 0.5 µg/mL CpG and/or 0.5 µg/mL antigen peptide-containing formulations in complete media for different lengths of time (2, 6, 24, and 48 h) at 37° C. BMDCs were harvested, washed once with FACS buffer, incubated with anti-CD16/32 at room temperature for 10 min, and then stained with PE-tagged anti mouse SIINFEKL H-2K$^b$ monoclonal antibody 25-D1.16 at room temperature for 30 min. Finally, cells were washed twice with FACS buffer and resuspended in 2 µg/ml DAPI solution and analyzed by flow cytometry (Cyan 5, Beckman Coulter, USA).

Imaging the Intracellular Delivery of sHDL-Based Peptide Vaccine with CLSM $1\times10^6$ cells JAWSII cells in 2 mL complete media were seeded in 35 mm petri dishes (MatTek) that have been pre-equilibrated with the same culture media and allowed to settle overnight. To learn the intracellular delivery profile of sHDL itself, DOPE-Rhod was used to label the lipid of sHDL, and 22A peptide of sHDL was labeled by incubating sHDL with Texas Red®-X, Succinimidyl Ester (Life Technologies), followed by passing through the desalting column to remove the unreacted dye. These labeled sHDL were incubated with JAWSII cells at 37° C. for 24 h. After incubation, cells were washed 3 times with PBS and the incubated with phenol and serum free media containing 500 nM LysoTracker® Green DND-26 (Life Technologies) and 2 ug/mL Hoechst for 30 min at 37° C. to stain the lysosomes and nuclei, respectively, before imaging using a confocal microscope (Nikon A1). To learn the intracellular delivery profile of the antigen peptides, free CSSSIINFEK(FITC)L+CpG or sHDL-CSSSIINFEK(FITC)L/CpG were incubated with JAWSII cells for different lengths of time (6, 24, and 48h). After incubation, cells were washed 3 times with PBS and the incubated with phenol and serum free media containing 50 nM LysoTracker® Red DND-99 (Life Technologies) and 2 ug/mL Hoechst for 30 min at 37° C. to stain the lysosomes and nuclei, respectively, before imaging using a confocal microscope (Nikon A1).

B3Z T Cell Activation In Vitro

BMDCs were plated at $5\times10^4$ cells/well in a U-bottom 96-well plate and allowed to grow overnight. The old media were aspirated and BMDCs were washed once with PBS before incubated with different concentrations (0.02, 0.1, and 0.5 µg/mL) of SIINFEKL and CpG containing formulations for 24 h or 48 h at 37° C. After incubation, cells were carefully washed 3 times with PBS, and $10\times10^4$B3Z T cells/well were added and cocultured for another 24 h in RPMI 1640 supplemented with 10% FBS, 2 mM L-glutamine, 55 µM β-mercaptoethanol, 1 mM pyruvate and 100 U/mL penicillin and 100 µg/mL streptomycin. Cells were then pelleted via centrifugation (1500 rcf, 7 min). The media were carefully aspirated, and 150 µL CPRG/lysis buffer (0.15 mM chlorophenol red-β-D-galactopyranoside (CPRG), 0.1% Triton-X 100, 9 mM MgCl2, 100 uM mercaptoethanol in PBS) was added. The plates were incubated at 37° C. in the dark for 90 min, after which the absorbance of released chlorophenol red was measured at 570 nm using a plate reader.

Lymph Nodes Draining of Antigen Peptides sHDL-CSSSIINFEK(FITC)L was prepared as described above. Female C57BL/6 mice of age 6-8 weeks were purchased from Harlan Laboratories. C57BL/6 mice were subcutaneously injected with free CSSSIINFEK(FITC)L or sHDL-CSSSIINFEK(FITC)L. 24 hours after injection, mice were euthanized by carbon dioxide inhalation and axillary lymph nodes and inguinal lymph nodes were harvested and imaged with IVIS optical imaging system (Caliper Lifesciences).

In Vivo Vaccination and Analysis of Cytotoxic T Cell Responses in Prophylactic and Therapeutic Settings of Melanoma Tumor Growth C57BL/6 mice were immunized with different formulations containing SIINFEKL (15 µg/mouse) and CpG (15 µg/mouse) by subcutaneous injection at the tail base following the predetermined schedule. The percent of tumor antigen specific CD8+ T cells were determined 7 days after each vaccination by the tetramer staining assay. In brief, 100 µl of blood will be drawn from each mouse and the blood samples were lysed with ACK lysing buffer, followed by centrifugation to collect pellets, which were then washed once by FACS buffer and blocked by CD16/32 blocking antibody and incubated with PE labeled SIINFEKL tetramer for 30 min at room temperature. Samples were then incubated with anti-CD8-APC for 20 min on ice. Cells were washed twice with FACS buffer and resuspended in 2 µg/ml DAPI solution for analysis by flow cytometry (Cyan 5, Beckman Coulter, USA). To examine the effect of T cell responses against tumor growth, one day after the last tetramer staining, the mice were challenged by subcutaneous injection of 0.2 million B16.OVA/mouse on the right flank. The tumor development was monitored every other day and the tumor volume was calculated by the following equation: tumor volume=length×width$^2$×0.52. In order to examine the effect of sHDL vaccination against established tumor, C57BL/6 mice were inoculated with 0.2 million B16.OVA/mouse on the right flank by subcutaneous injection on day 0. On day 4 and 11, the mice were immunized with different formulations containing tumor antigen peptides (15 µg/mouse) and CpG (15 µg/mouse). The percent of tumor antigen specific CD8+ T cells were determined on day 10 and 17 by the tetramer staining assay as described above. The tumor volume was monitored every other day.

aGC-CD1d Presentation Assay

JAWSII cells were seeded at a density of 0.2 million/well to 12-well plates. After 48 h, media were replaced with fresh media containing 2000 ng/mL of different formulations of aGC. After 20-24 h incubation with formulations, cells were harvested into FACS tubes by trypsination, washed twice by FACS buffer and then incubated with CD16/32 blocking reagent for 10 min at R. T. Cells were then incubated with anti-mouse aGC-CD1d-PE for 30 min at R. T, washed twice by FACS buffer, and suspended in 0.3 mL FACS buffer containing DAPI for flow cytometry.

Characterization of PCSK9 siRNA-Loaded sHDL

To quantify the amount of PCSK9 siRNA molecules that are loaded into sHDL, various concentrations of PCSK9 siRNA was incubated with sHDL, and the concentration of PCSK9 siRNA associated with sHDL versus free form will be measured at 260 nm using the gel permeation chromatography (GPC) assay.

PCSK9 Knockdown in HepG2 Cells

Different formulations of PCSK9 siRNA were incubated with HepG2 cells for 48 h. After incubation, cells were washed twice with PBS and the cell lysate was prepared. The PCSK9 protein level was analyzed by the western blot assay.

Biodistribution of sHDL

To study the biodistribution of sHDL, DiD-loaded sHDL was intravenously injected to the C57BL/6 mice. 24 h post injection, the mice were euthanized and the distribution of sHDL in major organs (heart, liver, spleen, lung and kidney) was analyzed using the IVIS optical imaging system.

Example II

Figure 1B:
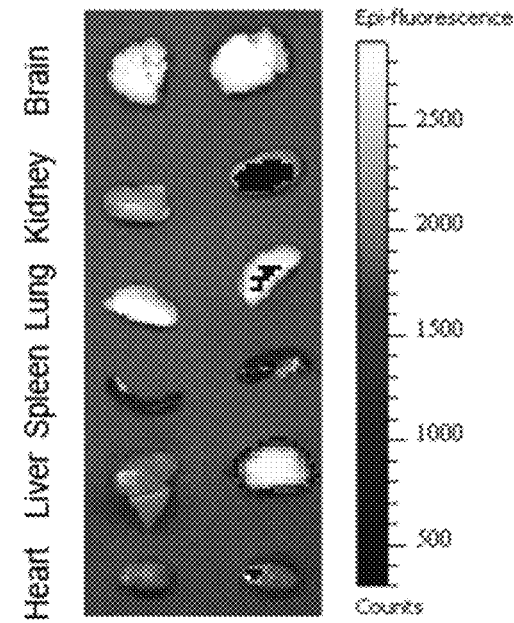
FIG. 1: (A) TEM picture and size distribution of sHDL; (B) Biodistribution of DiR-labeled sHDL in mice; (C) Cellular uptake of DiO-sHDL by SR-BI negative or positive cells without or with excess blank sHDL; (D) schematic of HDL-siRNA; (E) GPC assay of sHDL loaded with different concentrations of PCSK9 siRNA; (F) The western blot showed that PCSK9 siRNA-sHDL was better able to knockdown PCSK9 than the free PCSK9 Cho-siRNA in HepG2 cells.
Figure 1A:
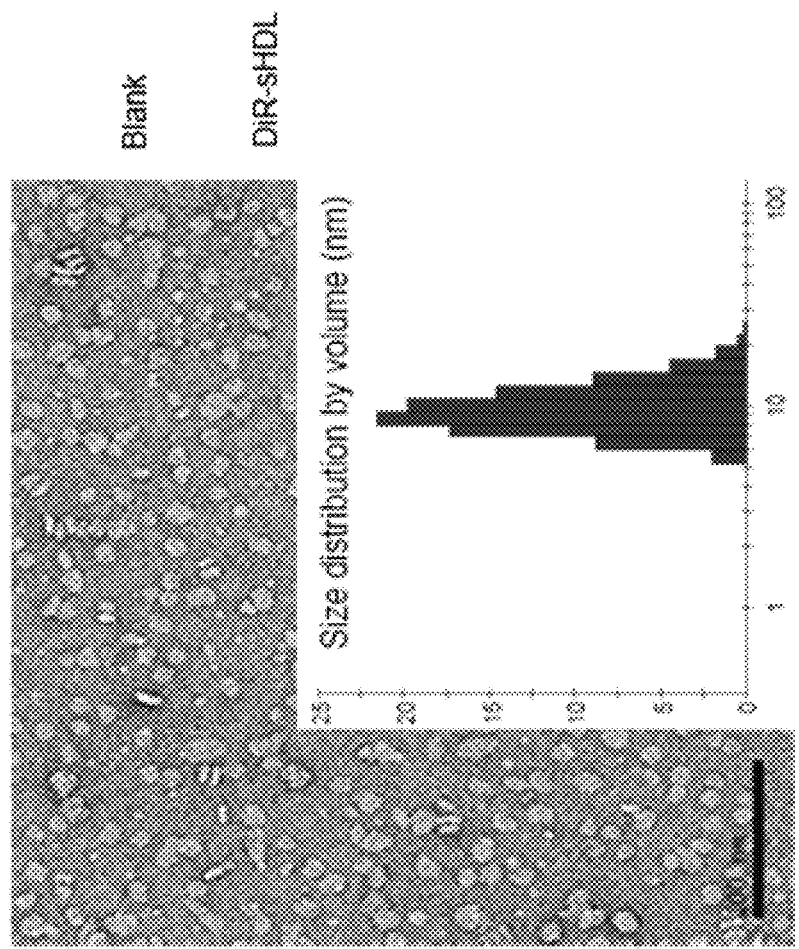
Figure 1C:
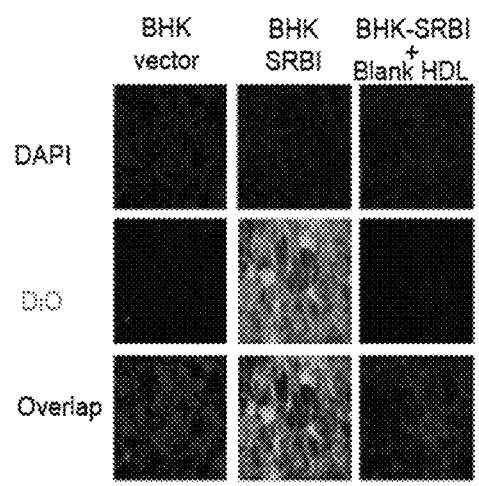
Figure 1D:
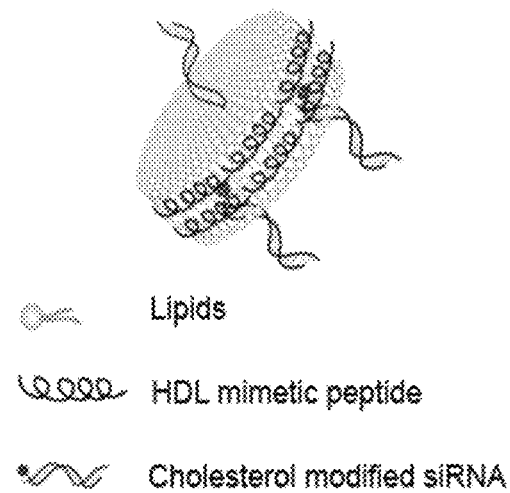
Figure 1E:
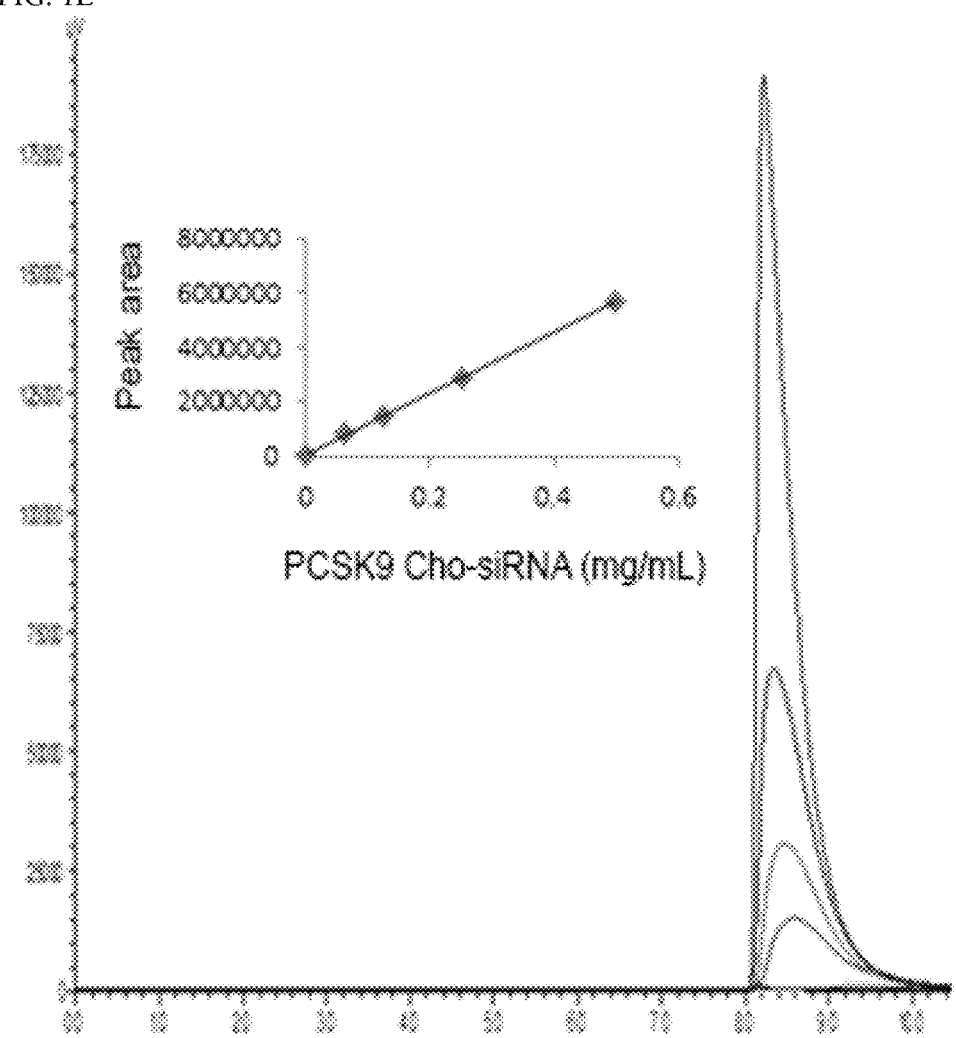

This example demonstrates that PCSK9 siRNA incorporated into sHDL can efficiently accumulate in the liver, deliver its cargo into SR-BI positive cells, and knockdown PCSK9 in HepG2 cells. Rapid and cheap lyophilization methods for the preparation of homogeneous sHDL nanoparticles were implemented. The homogeneity of the sHDL was confirmed by transmission electron microscopy (TEM), dynamic laser scattering (DLS), and gel permeation chromatography (GPC) (FIG. 1A). When sHDL was labeled by the fluorescent dye DiR and intravenously injected to mice, the majority of DiR signal was detected in the liver, with little or no signal in other organs (FIG. 1B). sHDL also efficiently delivered the fluorescent dye DiO into SR-BI positive cells (BHK-SR-BI), but not SR-BI negative cells (BHK-vector), and the uptake by SR-BI positive cells was blocked by the excess blank sHDL (FIG. 1C). Moreover, the preliminary data showed that the cholesterol modified PCSK9 siRNA (PCSK9 Cho-siRNA) could be quantitatively incorporated into sHDL. Although free PCSK9 Cho-siRNA can knockdown PCSK9 in HepG2 cells due to the increased uptake of siRNA induced by cholesterol conjugation, PCSK9 siRNA-sHDL is still better able to knockdown PCSK9 protein in HepG2 cells in vitro (FIG. 1D-F).

Example III

This example demonstrates that co-localized delivery of antigen and adjuvant by sHDL leads to potent immune response. FIG. 4A presents a schematic of antigens and adjuvants-loaded sHDL. When a MHC class I antigen peptide (CD8+ T cell epitope peptide SIINFEKL derived from ovalbumin) was incubated with functional lipids-containing sHDL, the antigen peptide was quantitatively conjugated to functional lipids of sHDL, as can be seen by the disappearance of functional lipids and appearance of lipid-peptide conjugates (FIG. 2B). The cholesterol modified CpG (Cho-CpG) was also shown to be quantitatively incorporated into sHDL (FIG. 2C). After 1 primary dose and two booster doses, the antigen and CpG-loaded sHDL (sHDL-Ag/CpG) elicited more potent immune responses than the mixture of antigens and CpG in Montanide (CpG+Montanide is one of the most potent experimental adjuvant currently undergoing clinical evaluations) (FIG. 2D).

Figure 3:
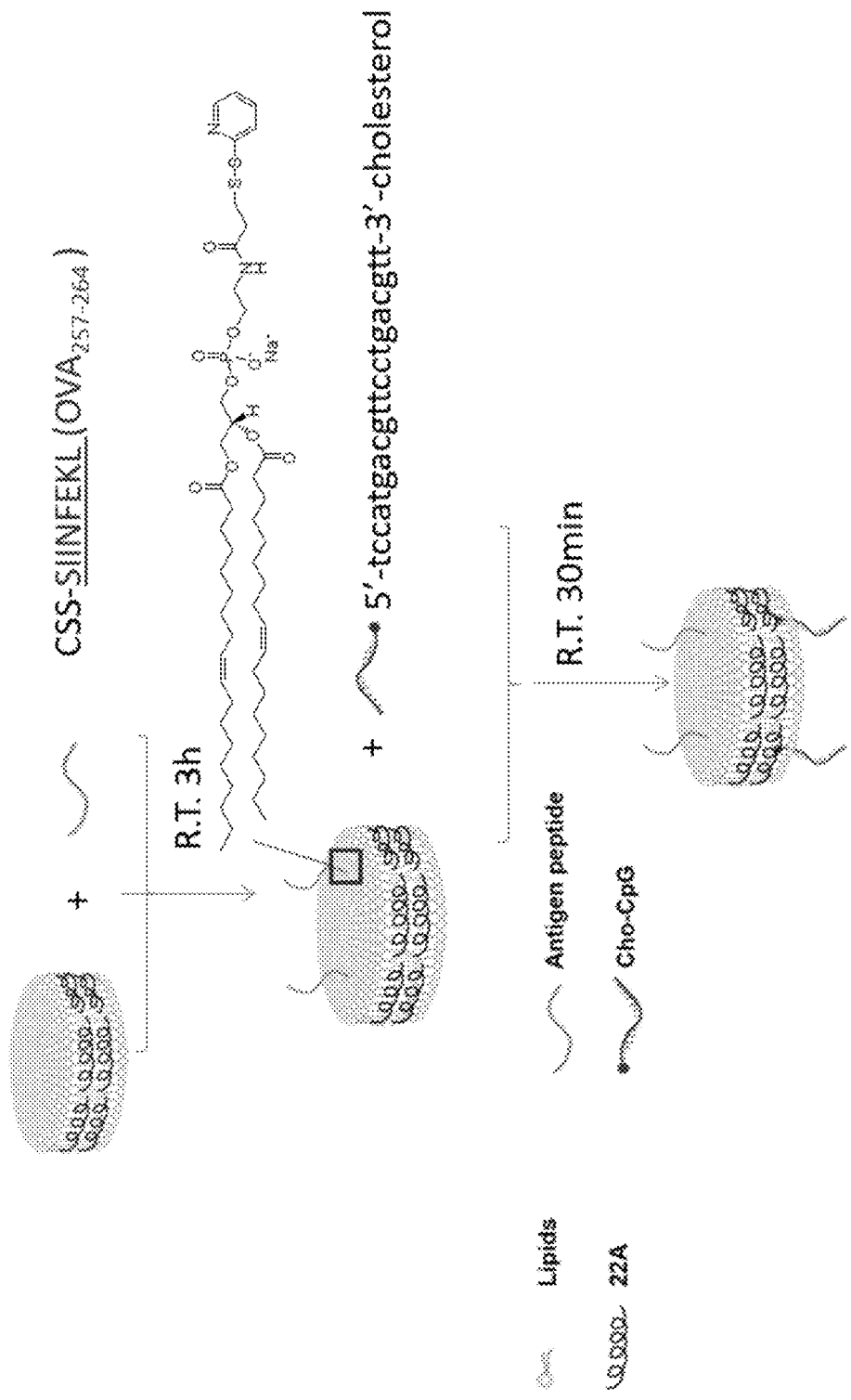
FIG. 3 shows a schematic of the synthesis of sHDL-CSSSIINFEK(FITC)L/CpG.

FIG. 3 shows a schematic of the synthesis of sHDL-CSSSIINFEK(FITC)L/CpG.

FIG. 4 shows homogenous particle size of sHDL-Ag/CpG as analyzed by cryoEM and dynamic light scattering.

Figure 5A:
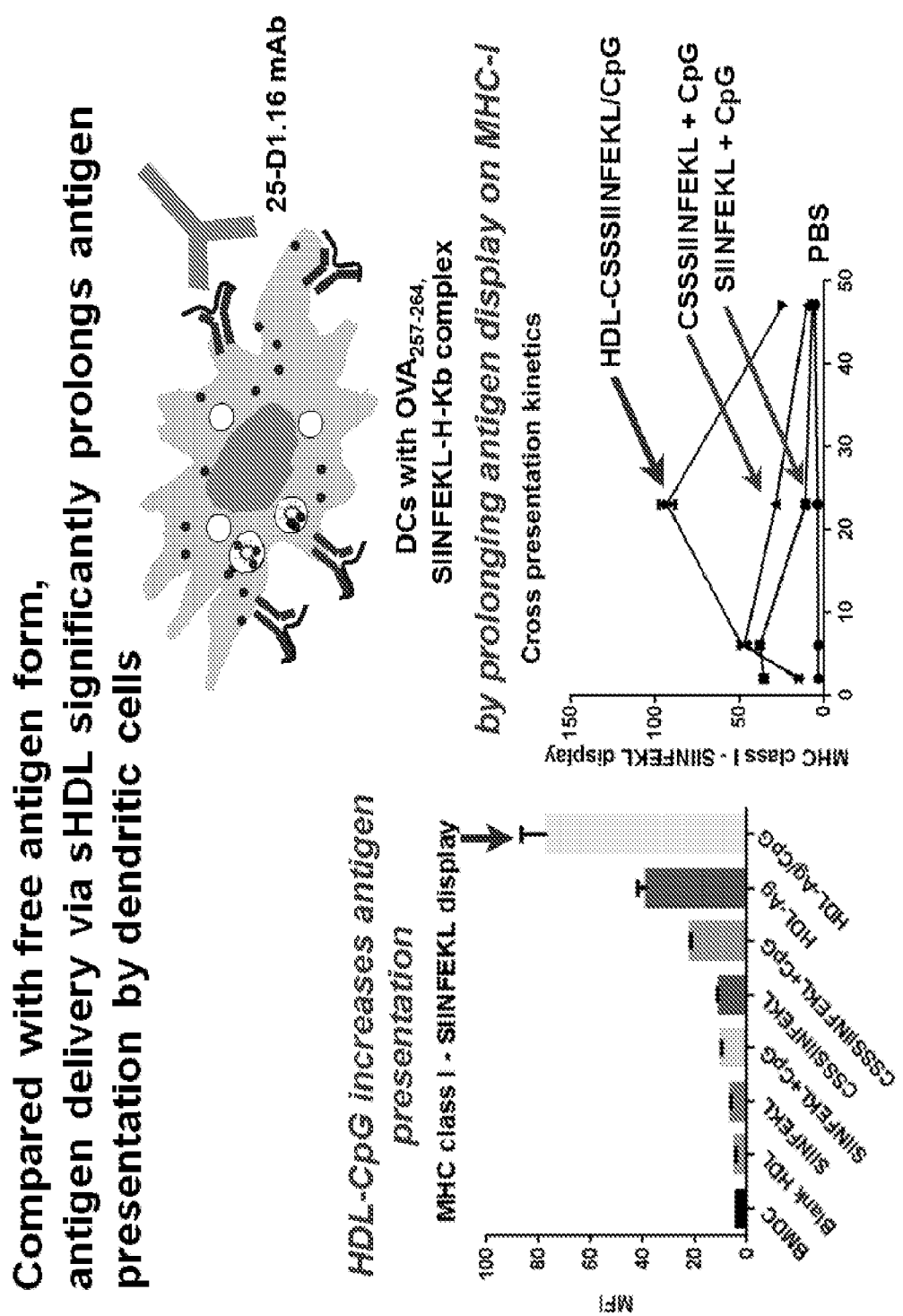
FIGS. 5A and 5B show that compared with free antigen form, antigen delivery via sHDL significantly prolongs antigen presentation by dendritic cells.
Figure 5B:
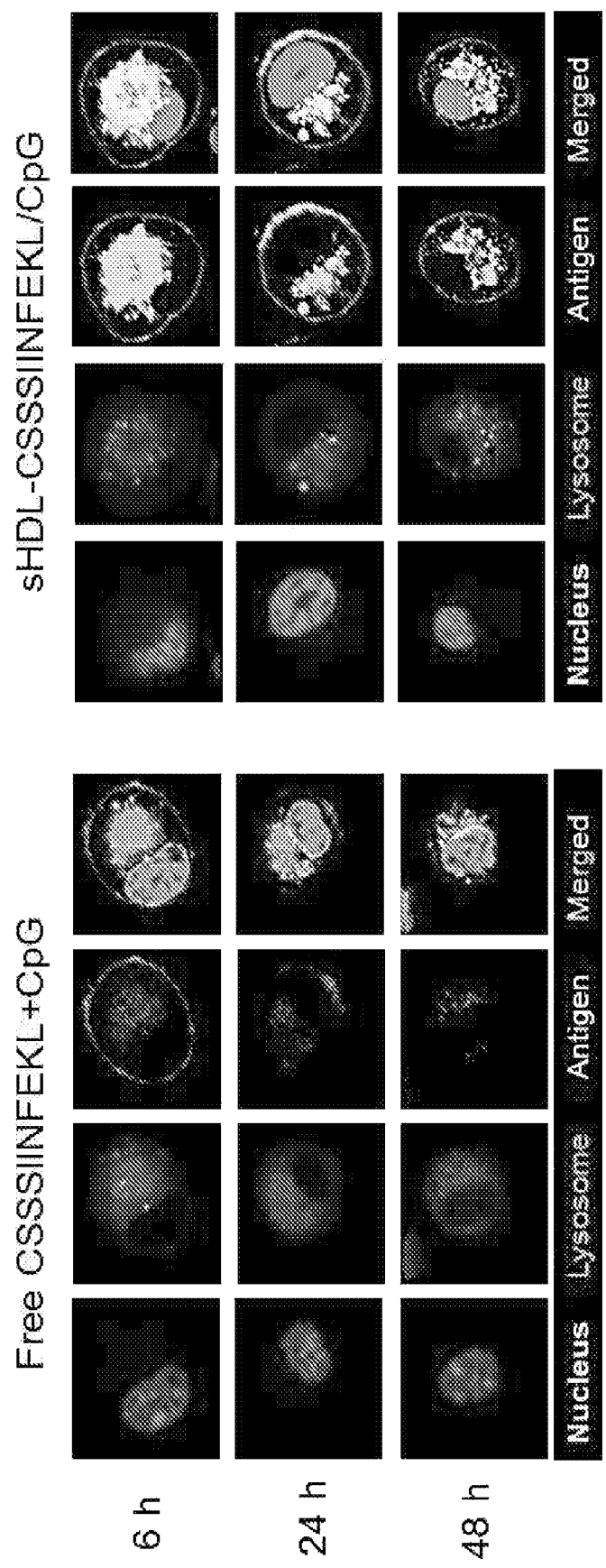

FIGS. 5A and 5B show that compared with free antigen form, antigen delivery via sHDL significantly prolongs antigen presentation by dendritic cells.

Figure 6:
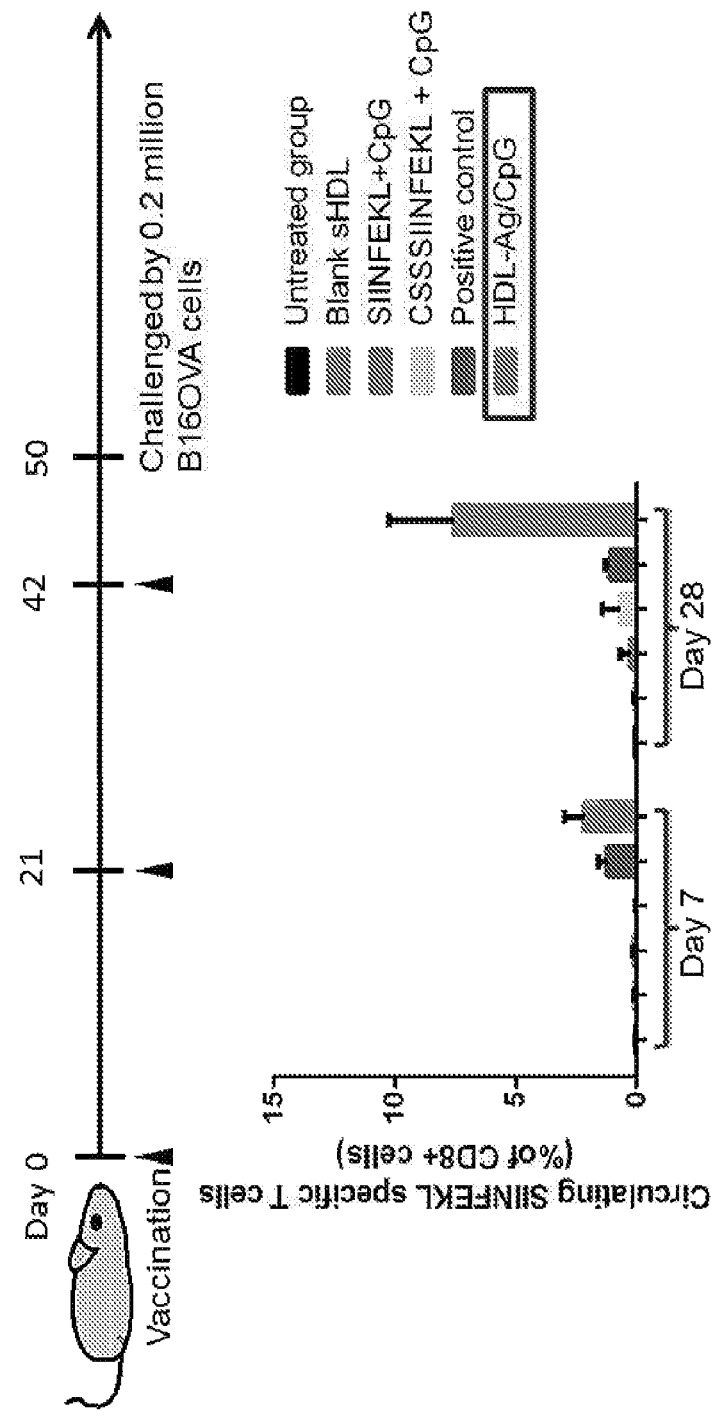
FIG. 6 shows that sHDL-Ag/CpG significantly enhances elicitation of antigen-specific CD8+ T cells, compared with vaccination with free antigen mixed with conventional adjuvants.

FIG. 6 shows that sHDL-Ag/CpG significantly enhances elicitation of antigen-specific CD8+ T cells, compared with vaccination with free antigen mixed with conventional adjuvants.

Figure 7:
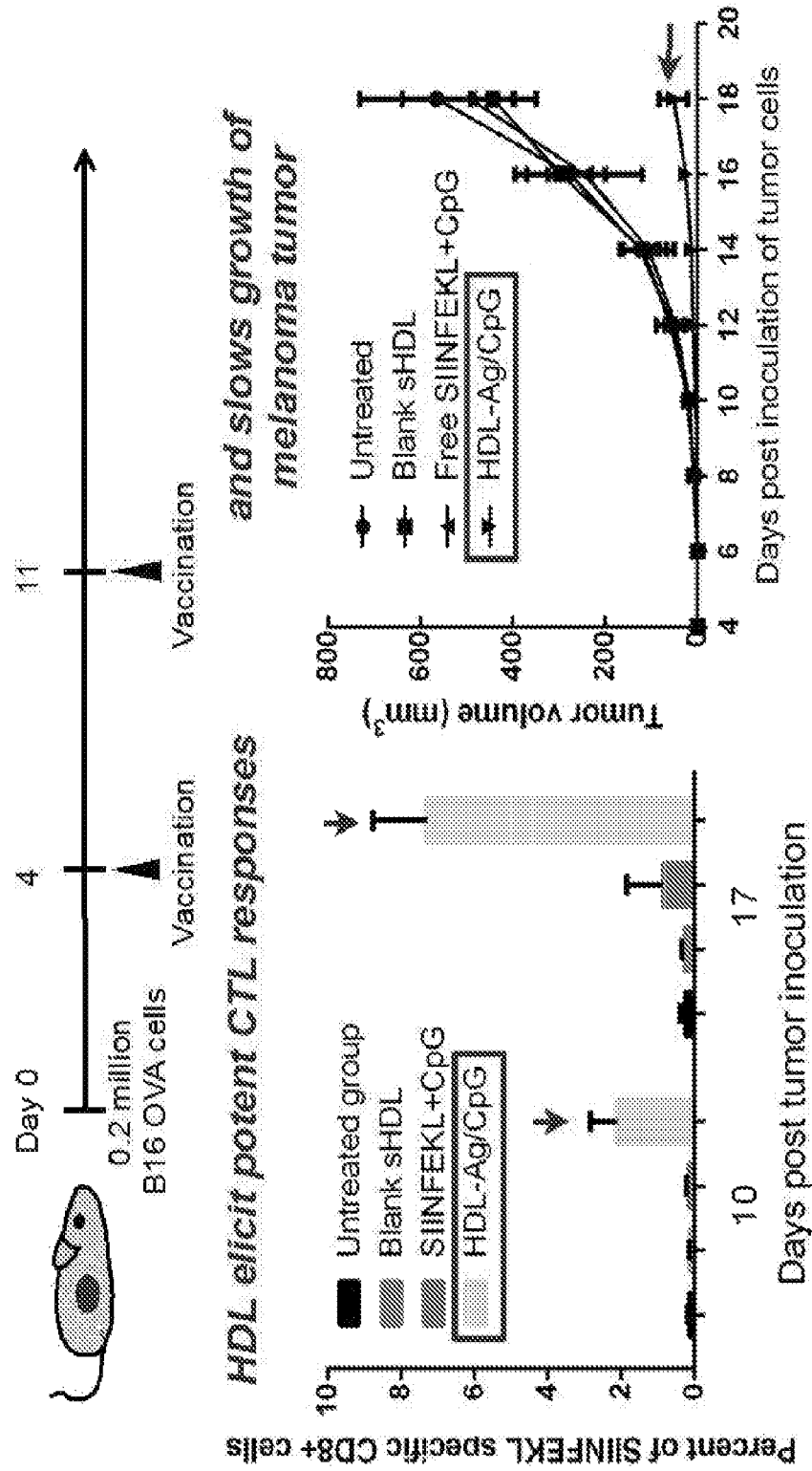
FIG. 7 shows sHDL-Ag/CpG vaccination elicits strong CD8+ T cell responses in tumor-bearing mice and reduces tumor growth.

FIG. 7 shows sHDL-Ag/CpG vaccination elicits strong CD8+ T cell responses in tumor-bearing mice and reduces tumor growth.

Example IV

This example demonstrates that sHDL delivering alpha-galactosylceramide, a glycolipid ligand for CD1-d to activate induction of natural killer T cells.

Figure 8:
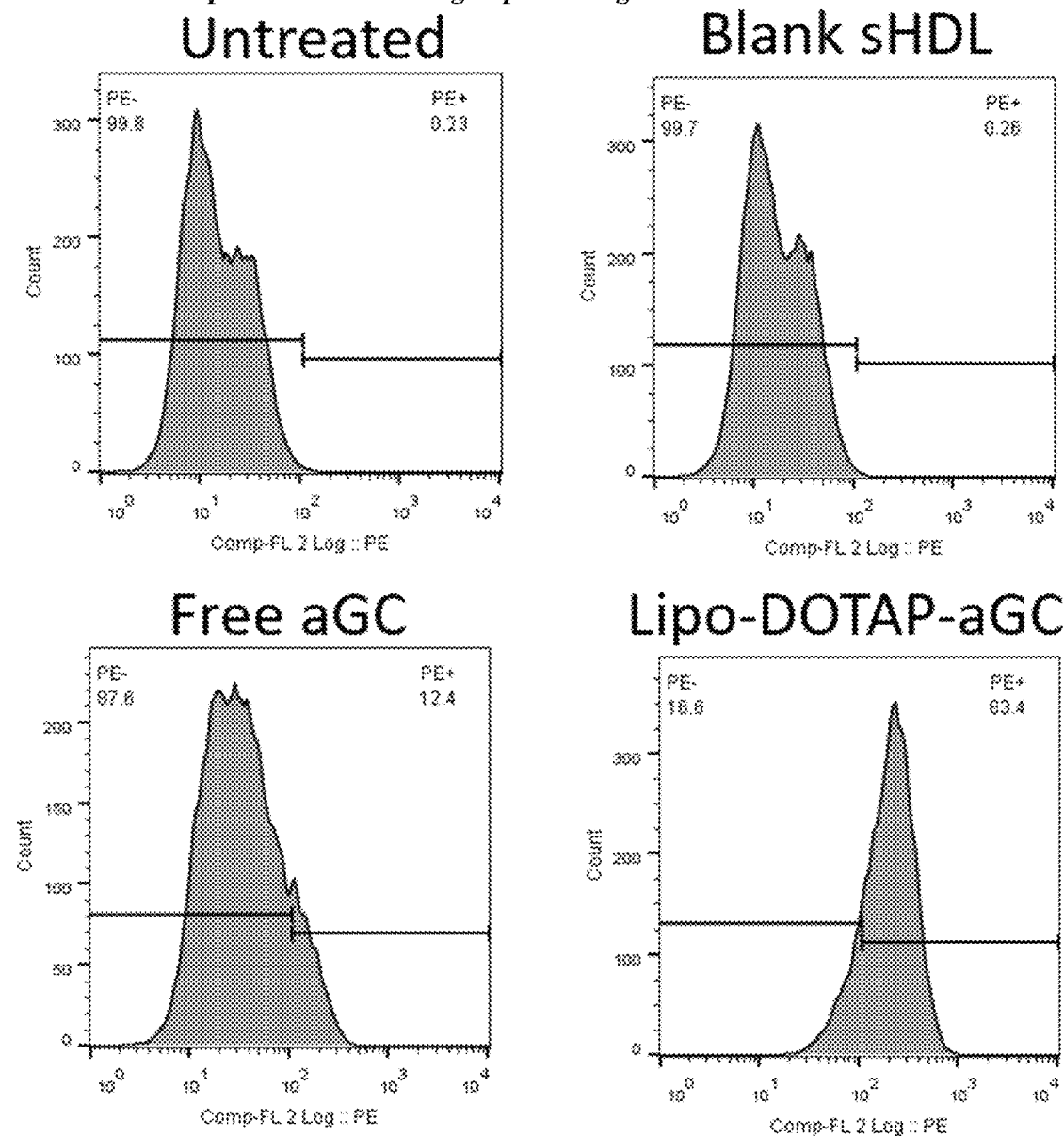
FIG. 8 shows that compared with free soluble form, alpha-GalCer delivered via sHDL significantly enhanced CD1d presentation of antigen-presenting cells.
Figure 8:
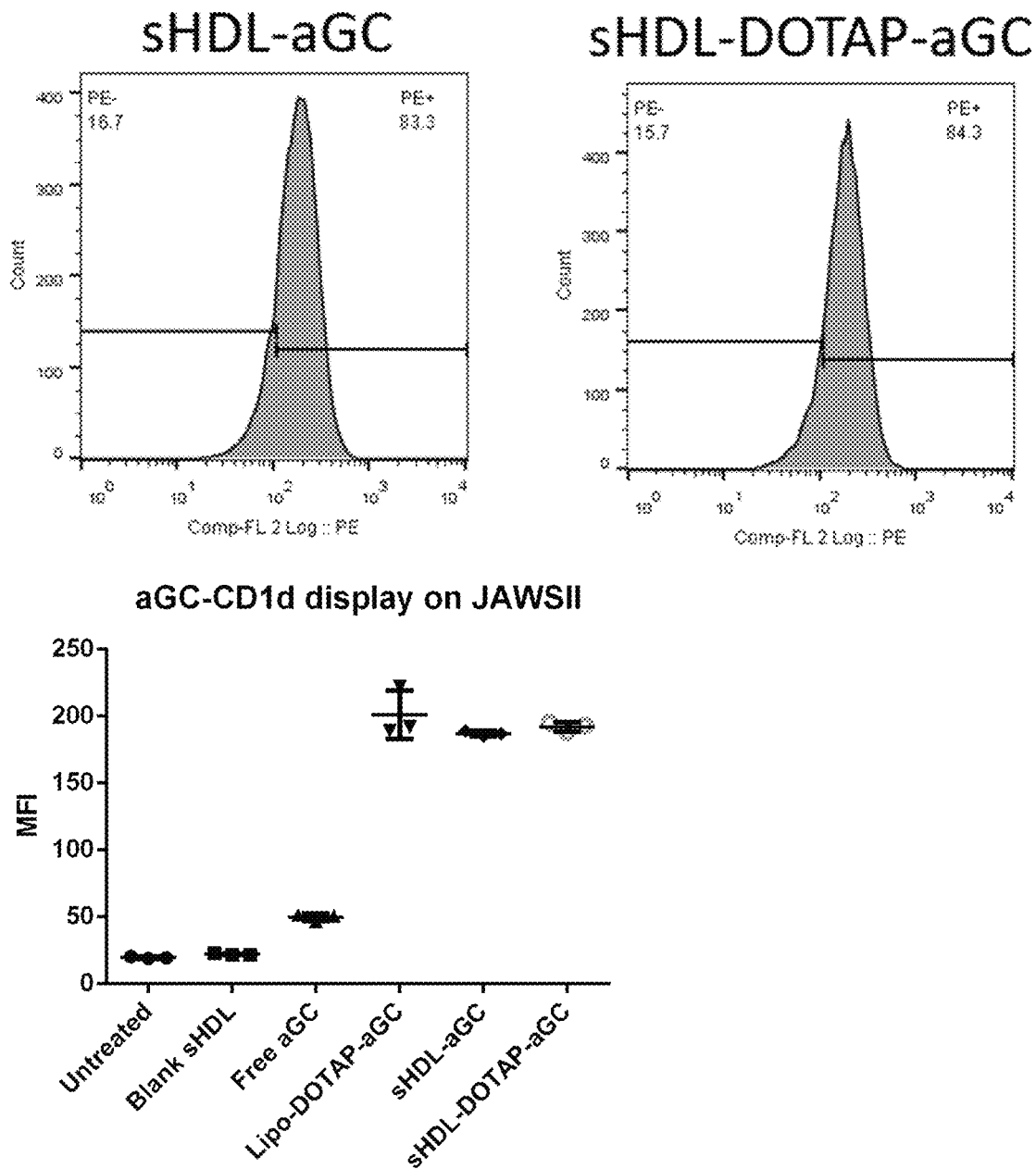

FIG. 8 shows that compared with free soluble form, alpha-GalCer delivered via sHDL significantly enhanced CD1d presentation of antigen-presenting cells.

Figure 9:
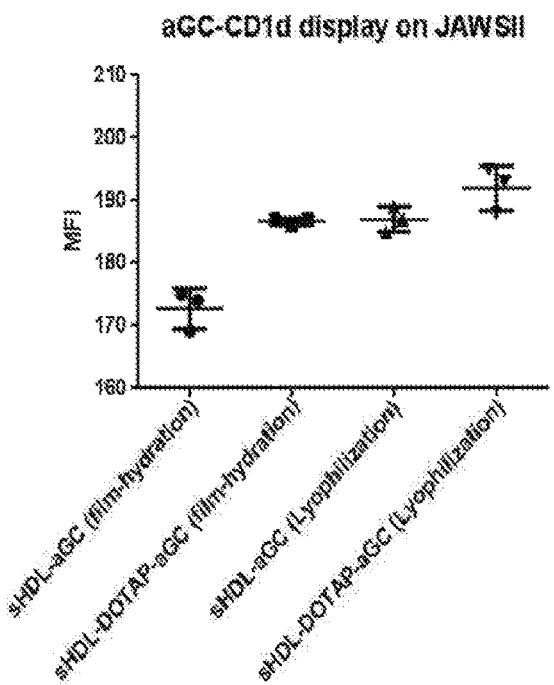
FIG. 9 shows that lyophilization offers a convenient method of large-scale synthesis of sHDL loaded with alpha-GalCer.

FIG. 9 shows that lyophilization offers a convenient method of large-scale synthesis of sHDL loaded with alpha-GalCer.

Example V

This example demonstrates that preformed high density lipoprotein-mimicking nanodiscs can be readily coupled with antigen (Ag) peptides and adjuvants, producing stable, ultrasmall nanoparticles that markedly improve Ag/adjuvant co-delivery to lymphoid organs and achieve sustained Ag presentation on dendritic cells.

Lipids and peptides conducive to nanodisc formation were first identified. DMPC lipid films were hydrated and added with a series of ApoA1-mimetic peptides, followed by thermal cycling between 50° C. and 4° C. A subset of peptides, including 22A and D-amino acids of 22A, were identified that produced clear sHDL suspensions, stable for one month when stored at 4° C. (FIG. 13a). In addition, use of phospholipids with transition temperature (Tm) below RT (e.g. POPC and DOPC with Tm=−2° C. and −17° C., respectively) produced murky liposomal suspension, whereas lipids with high Tm (e.g. DPPC and DMPC with Tm=41° C. and 24° C., respectively) formed clear sHDL suspensions in the presence of 22A (FIG. 13b), showing flexibility in the materials design. Based on their size, homogeneity, and long-term stability, 22A and DMPC as the key components of nanodisc vaccines were chosen for further investigation.

Figure 14:
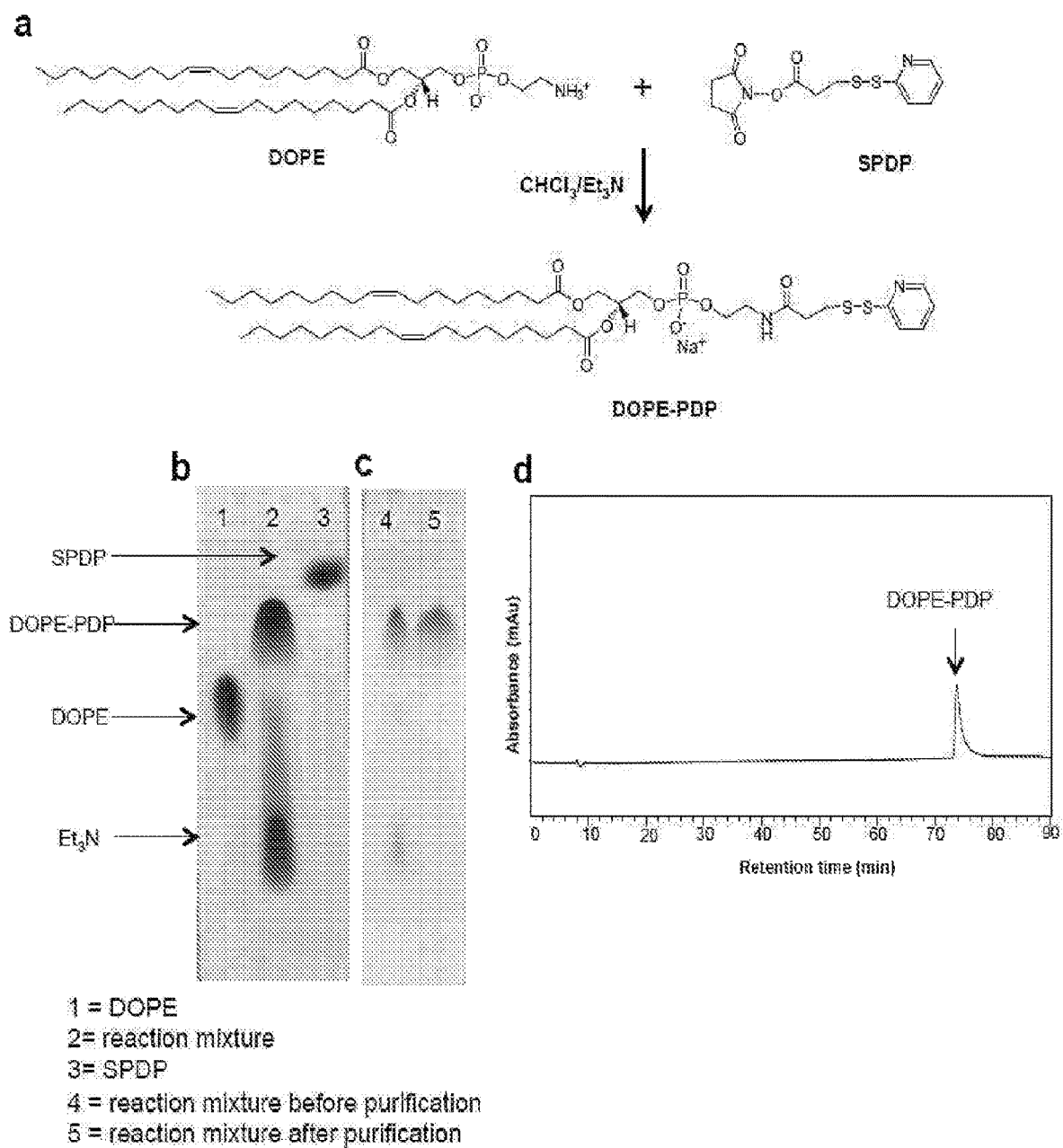
FIG. 14: Synthesis of functional lipid DOPE-PDP. a, DOPE, SPDP (succinimidyl 3-(2-pyridyldithio) propionate) and triethylamine (1:1:1.5 molar ratio) were dissolved in chloroform and allowed to react in dark with stirring for 5 h. b, The reaction progress was monitored by thin layer chromatography (TLC), using the following mixture as the developing solvent:chloroform/methanol/water=65/25/4 (volume ratio). c-d, The reaction mixture was purified using a silica gel column, and the purity was assessed by c, TLC and d, HPLC using the condition described in Example VI.
Figure 15:
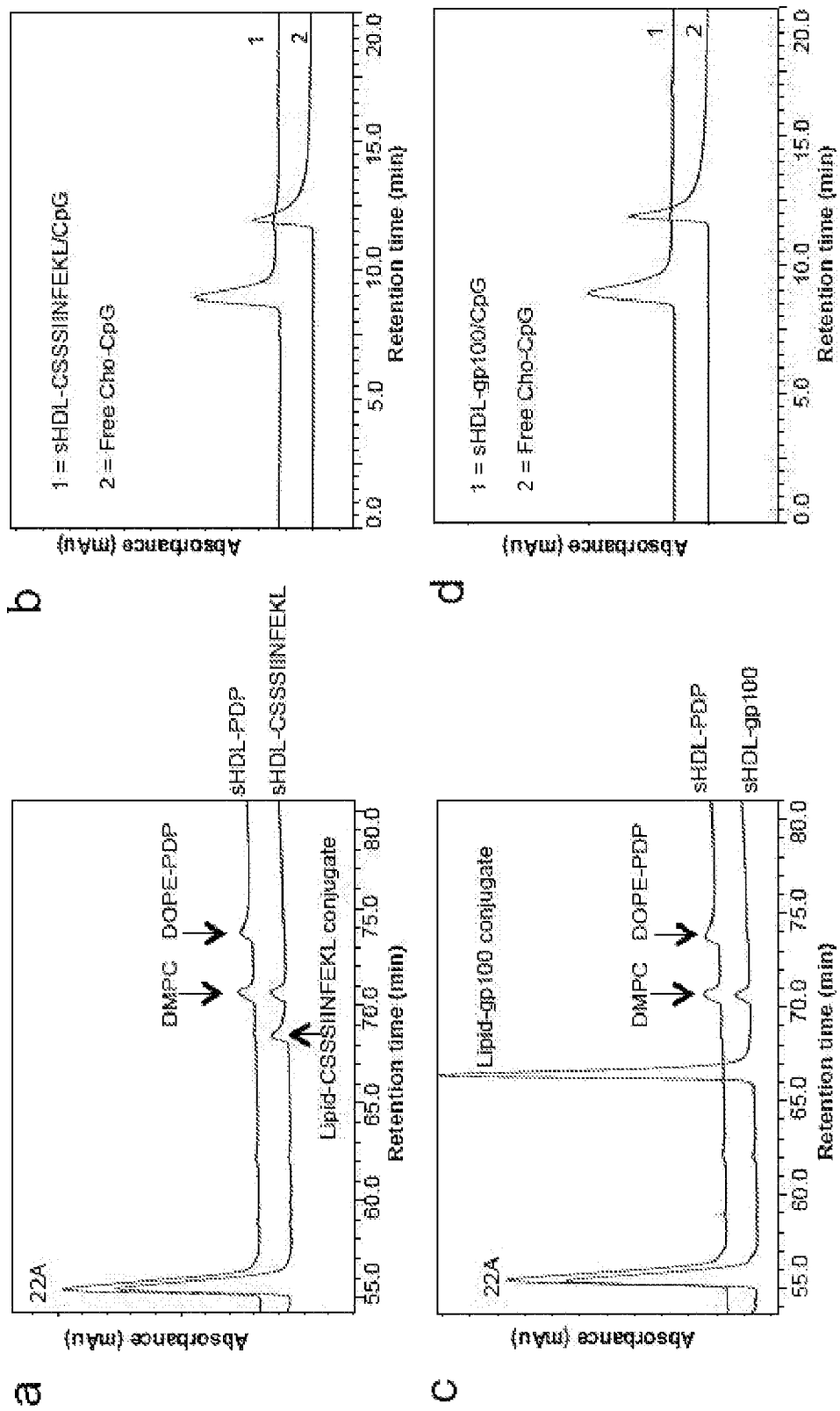
FIG. 15: Preparation and characterization of sHDL-CSSSIINFEKL/CpG, sHDL-gp100/CpG, and sHDL-Adpgk/CpG. CSSSIINFEKL, CSS-gp 100 or CSS-Adpgk were incubated with sHDL-PDP, followed by insertion of Cho-CpG to sHDL-CSSSIINFEKL, sHDLgp100 or sHDL-Adpgk. Shown are HPLC chromatograms confirming the conjugation of a, CSSSIINFEKL, c, gp 100, or e, Adpgk to sHDL-PDP. GPC of b, sHDL-CSSSIINFEKL/CpG, d, sHDL-gp100/CpG, and f, sHDL-Adpgk/CpG showed homogeneity of all formulations and efficient loading of Cho-CpG in sHDL nanodiscs.
Figure 15:
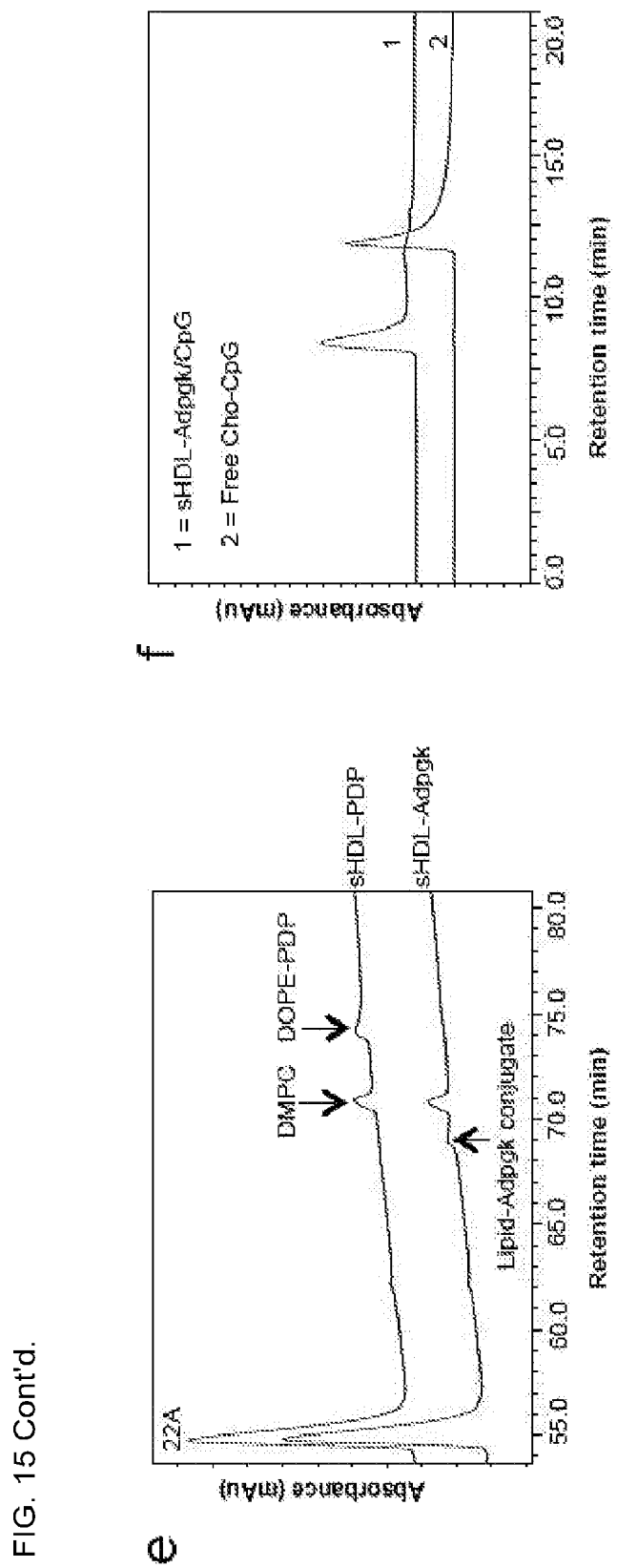
Figure 16:
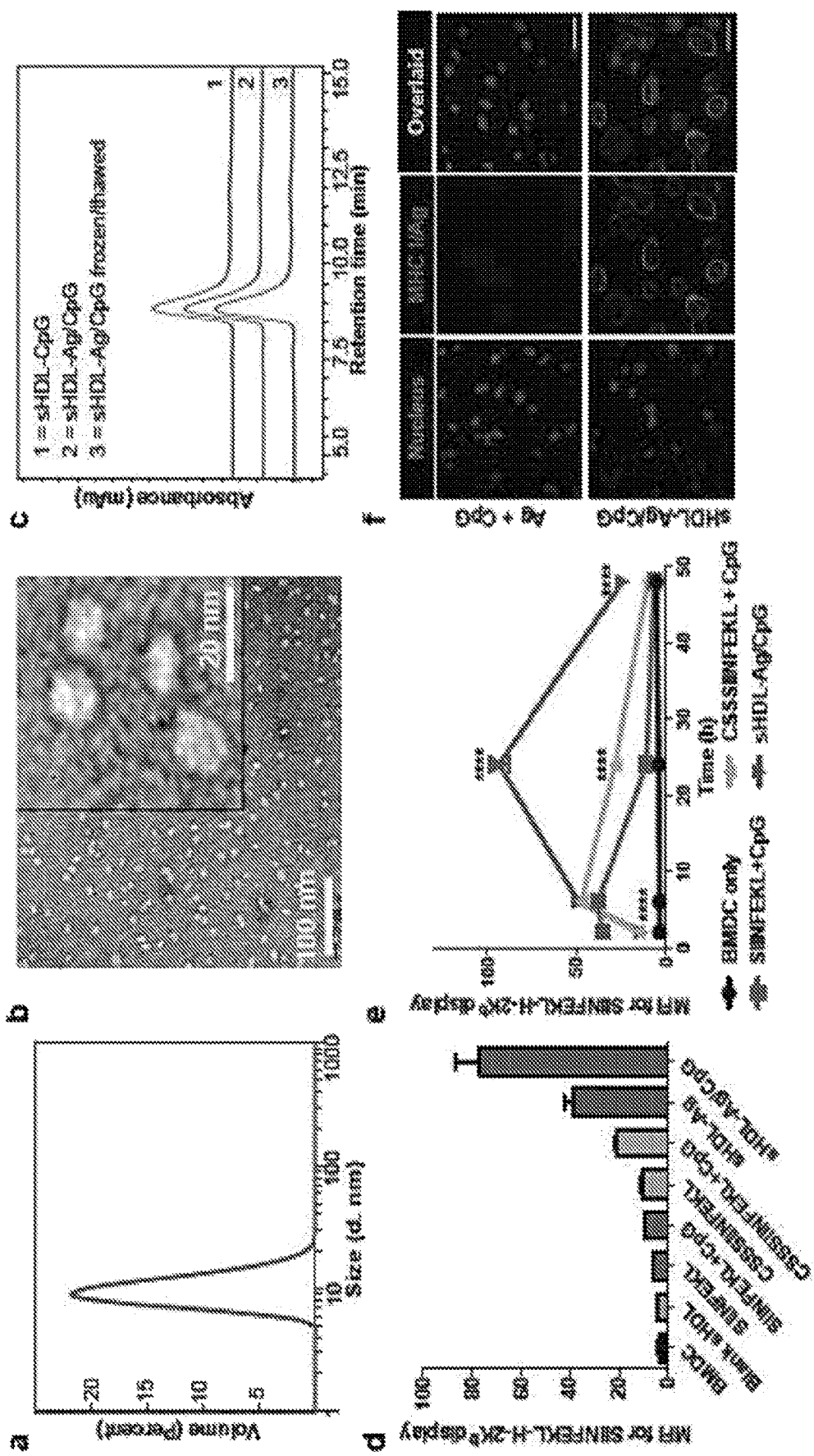
FIG. 16: Strong and durable Ag presentation mediated by sHDL nanodiscs. a, Dynamic light scattering analysis and b, transmission electron microscopy imaging showed uniform sHDL-Ag/CpG (10.5 nm±0.5 average diameter) with nanodisc-like morphology. c, Homogeneity of nanodiscs was maintained after sterile-filtration (0.22 μm), and long-term storage (8 weeks) at −20° C., followed by thawing at 37° C. d-e, BMDCs were incubated with vaccine formulations for d, 24 h or e, indicated lengths of time, and Ag presentation was quantified by flow-cytometry analysis of DCs stained with 25-D1.16 mAb that recognizes SIINFEKL-H-2K$^b$ complex. f-g, Confocal microscopy images of JAWSII cells (immature DCs). f, JAWSII cells were incubated with free Ag+CpG or sHDL-Ag/CpG for 24 h and stained with 25-D1.16 mAb. Scale bars=20 μm. g, JAWSII cells were incubated with free CSSSIINFEK$_{(FITC)}$L+CpG or sHDL- CSSSIINFEK$_{(FITC)}$L/CpG for 6, 24, or 48 h, followed by staining with Hochest and Lysotracker. Scale bars=10 µm. h, BMDCs were incubated with different concentrations of indicated formulations: low dose=20 nM SIINFEKL and 3 nM CpG; medium dose=100 nM SIINFEKL and 15 nM CpG; and high dose=500 nM SIINFEKL and 75 nM CpG. After incubation for 24 h or 48 h, BMDCs were co-cultured with SIINFEKL-specific B3Z T-cell hybridoma for another 24 h, followed by assessment of T cell activation. The data show mean±SD from a representative experiment (n=3) from 2-4 independent experiments. **** $p<0.0001$, analyzed by two-way ANOVA with Tukey's HSD post-test.
Figure 16:
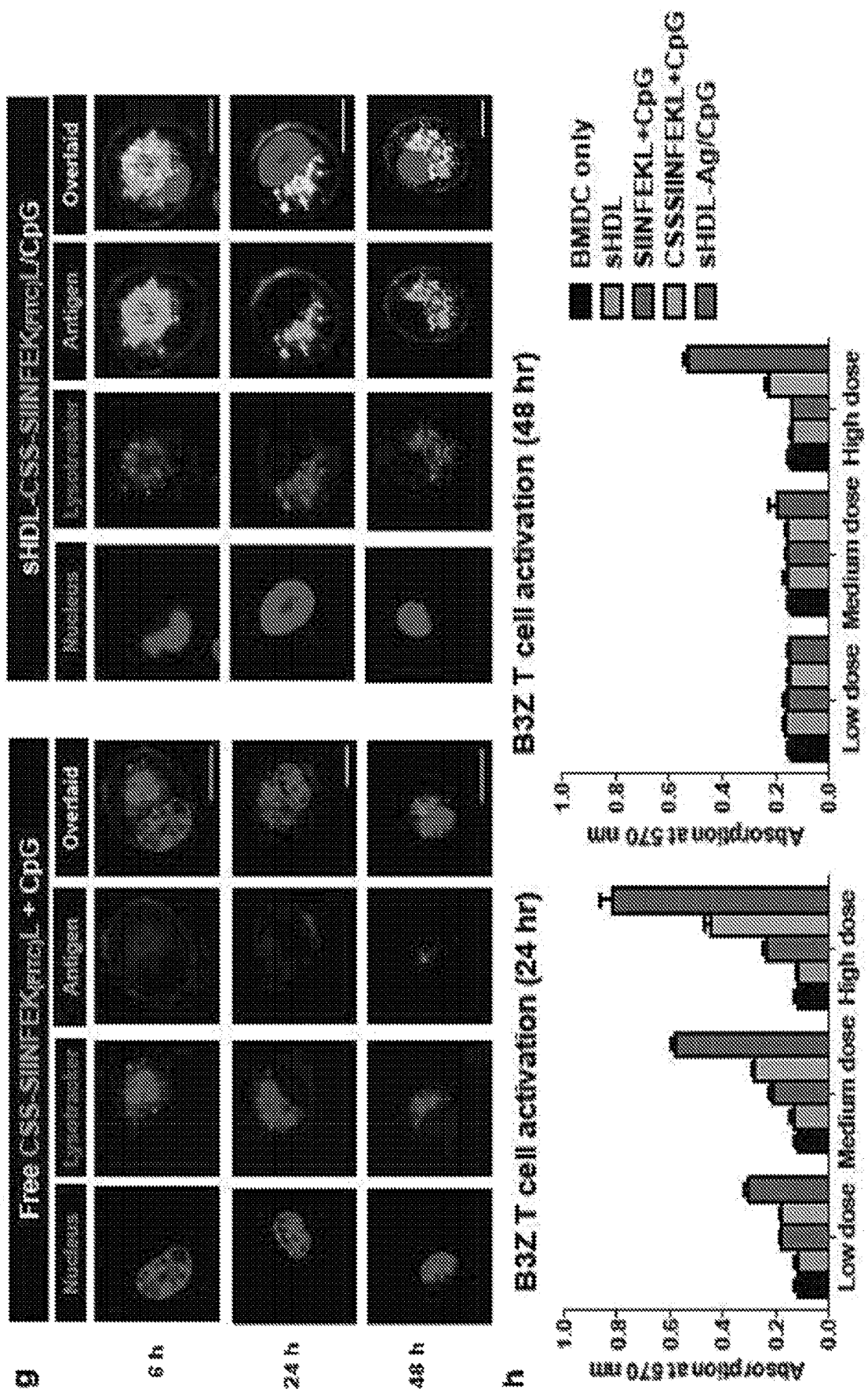

To achieve intracellular release of Ag within APCs via reduction-sensitive conjugation of Ag on sHDL, we synthesized dioleoyl-sn-glycero-3-phosphoethanolamine-N-[3-(2-pyridyldithio) propionate] (PDP, FIG. 14) and incorporated PDP into sHDL (4 mol %). When incubated for 30 min at RT with Ag peptides modified with a cysteine-serine-serine (CSS) linker (see, e.g., Hirosue, S., et al., Vaccine 28, 7897-7906 (2010)), sHDL nanodiscs were efficiently surface-decorated with various Ag peptides (e.g., $OVA_{257-264}$, a model CD8α+ T-cell epitope Ag from ovalbumin; $gp100_{25-33}$, melanoma-associated Ag; and Adgpk, neo-antigen in MC-38), and subsequent incubation with Cho-CpG for 30 min at RT led to almost complete (~98%) insertion of CpG into sHDL, producing nanodiscs co-loaded with Ag and CpG (termed sHDL-Ag/CpG, with ~6.5 Ag peptides and ~1 CpG molecule per nanodisc, FIG. 15; Table 3). sHDL-Ag/CpG exhibited uniform disc-like morphology with an average diameter of 10.5±0.5 nm and polydispersity index of 0.20±0.02 (FIG. 16a and 16b). Importantly, sHDL-Ag/CpG could be readily sterile-filtered and stored frozen at −20° C. for at least 8 weeks before thawing at 37° C., without negatively affecting its homogeneity (FIG. 16c).

TABLE 3

| Formulations | % of PDP-lipid converted to Ag-lipid | % of Cho-CpG inserted into sHDL | Size (d · nm) | PDI |
|---|---|---|---|---|
| sHDL-CSSSIINFEKL/CpG | 92.0 ± 3.5% | 98.5 ± 1.1% | 10.5 ± 0.5 | 0.20 ± 0.02 |
| sHDL-gp100/CpG | 91.6 ± 2.7% | 98.2 ± 1.5% | 10.3 ± 0.5 | 0.23 ± 0.03 |
| sHDL-Adpgk/CpG | 91.1 ± 3.1% | 98.5 ± 1.8% | 10.8 ± 0.3 | 0.22 ± 0.02 |

Figure 17:
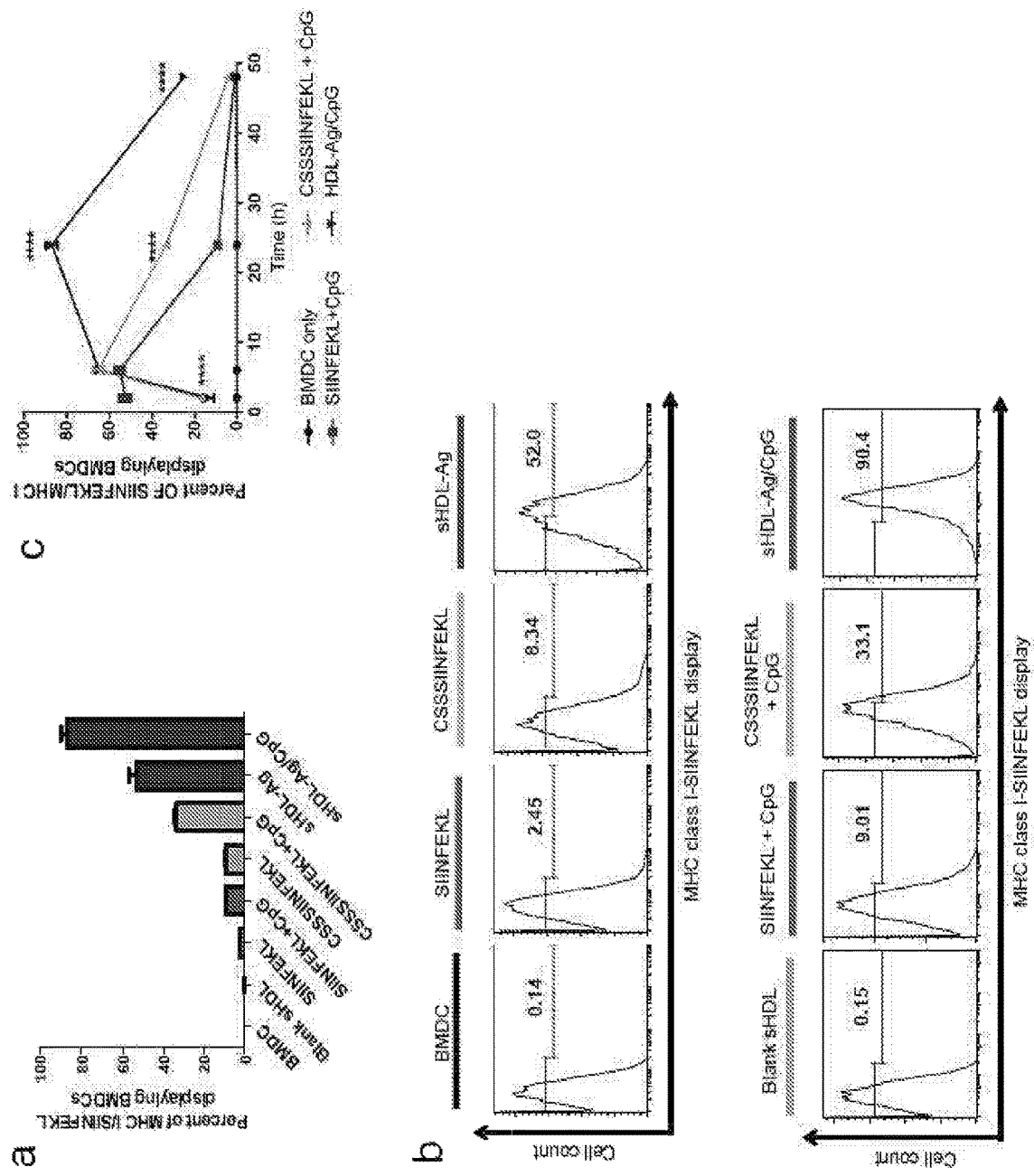
FIG. 17: Strong and durable Ag presentation mediated by sHDL-Ag/CpG. BMDCs were incubated with vaccine formulations for a-b, 24 h, or c, indicated lengths of time, and Ag presentation was quantified by flow-cytometry analysis of DCs stained with 25-D1.16 mAb that recognizes SIINFEKL-H-2Kb complex. Shown are a, the percent of antigen presenting BMDCs at the 24 h time point, b, representative histograms, and c, the percent of antigen presenting BMDCs over 48 h. The data show mean±SD from a representative experiment (n=3) from 2-4 independent experiments. **** $p<0.0001$, analyzed by two-way ANOVA with Tukey's HSD post-test.

The impact of nanodiscs on Ag presentation was next examined. Bone marrow derived dendritic cells (BMDCs) pulsed for 24 h with sHDL-CSSSIINFEKL/CpG presented $OVA_{257-264}$ SIINFEKL with a greater efficiency than BMDCs treated with free Ag peptides admixed with CpG or sHDL-CSSSIINFEKL, as determined by staining DCs with the 25-D1.16 mAb directed against SIINFEKL-H-2$K^b$ complexes (FIGS. 16d; 17a and 17b). Interestingly, DCs pulsed with free SIINFEKL+CpG efficiently presented Ag for the first 6 h of incubation, but Ag presentation decreased precipitously past 6 h (FIGS. 16e and 16f; FIG. 17c), suggesting initial direct Ag binding to MHC-I molecules, followed by rapid Ag degradation or disassociation. In contrast, Ag presentation with sHDL-Ag/CpG gradually increased over time, achieving~9-fold greater levels at 24 h and maintaining~4-fold higher levels even at 48 h, compared with free SIINFEKL+CpG.

Figure 18:
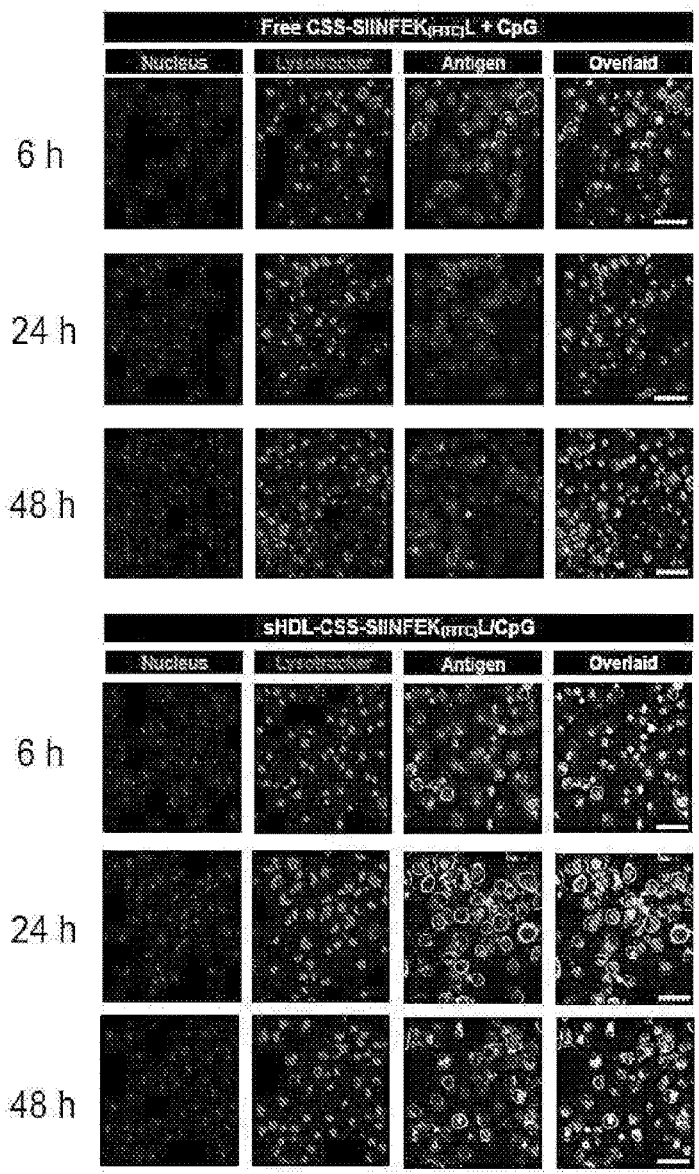
FIG. 18: Ag delivery and presentation mediated by sHDL-Ag/CpG (broader view). JAWSII cells were incubated with free CSSSIINFEK(FITC)L+CpG or sHDL-CSSSIINFEK(FITC)L/CpG for 6, 24, or 48 h, and stained with Hochest and Lysotracker. Scale bar=50 µm.
Figure 19:
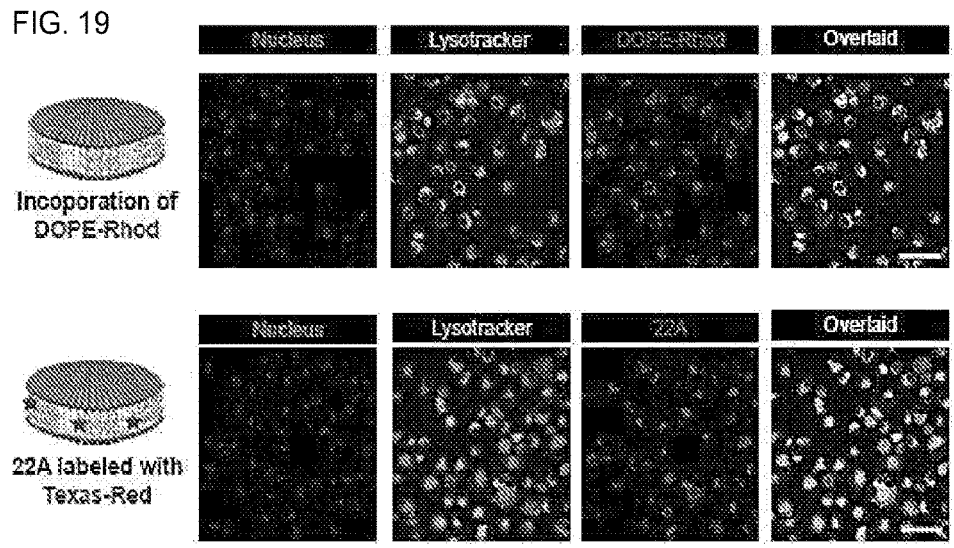
FIG. 19: Intracellular delivery of sHDL (broader view). JAWSII cells were incubated for 24 h with sHDL containing either Rhodamine-labeled DOPE (DOPE-Rhod) or Texas Red-labeled 22A and stained with Hochest and Lysotracker. Scale bar=50 µm.
Figure 20:
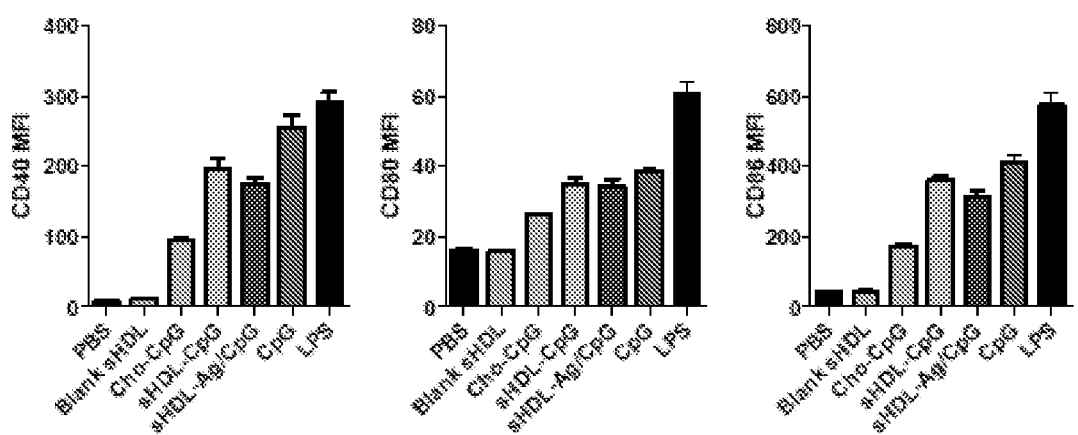
FIG. 20: Stimulation of bone marrow-derived dendritic cells (BMDCs) by CpG-containing formulations. BMDCs were incubated with blank sHDL or 75 nM CpG formulations for 24 h. The expression levels of CD40, CD80, and CD86 were measured by flow cytometry after staining with corresponding fluorophore-labeled antibodies. The data show mean±SD from a representative experiment (n=3) from 3 independent experiments.

Intrigued by prolonged Ag presentation, the process of nanodisc uptake and Ag localization using CSS-SIINFEK$_{(FITC)}$L was investigated; SIINFEKL modified with FITC at ε-amino group in the lysine residue is known to retain its binding capacity to H-2$K^b$ molecules (see, e.g., Saini, S. K. et al. Proc. Natl. Acad. Sci. U.S.A. 110, 15383-15388 (2013). JAWSII cells (immortalized immature DCs) incubated with free Ag(FITC)+CpG displayed weak fluorescence signal on the plasma membrane at 6 h, and only dim fluorescence was observed by 24 h (FIG. 16g; FIG. 18). In stark contrast, sHDL-Ag(FITC)/CpG treatment led to strong FITC signal co-localized with endosomes/lysosomes by 6 h, and robust Ag(FITC) signal was detected on cell membranes by 24 h and sustained up to 48 h. In addition, nanodiscs containing Rh-PE or Texas Red-labeled-22A were predominantly found within endosomes/lysosomes, indicating cellular uptake of intact whole nanodiscs (FIG. 19). To assess the impact of prolonged Ag presentation on T-cell cross-priming, BMDCs were treated with free Ag peptides+CpG or sHDL-Ag/CpG for 24 or 48 h, and then added SIINFEKL-specific, H-2$K^b$-restricted B3Z T-cell hybridomas. BMDCs pulsed with sHDL-Ag/CpG promoted strong B3Z T-cell activation even after 48 h incubation, whereas free Ag peptides+CpG induced minimal B3Z T-cell activation beyond the 24 h period (FIG. 16h). Moreover, sHDL-Ag/CpG potently stimulated DC maturation (FIG. 20). Altogether, whereas free Ag peptide was rapidly loaded and dissociated from MHC-I molecules on cell membranes, nanodiscs facilitated intracellular delivery of Ag/CpG and mediated their sustained release within endosomes/lysosomes, thereby promoting durable Ag presentation, APC maturation, and cross-priming CD8α+ T-cells in vitro.

Figure 22:
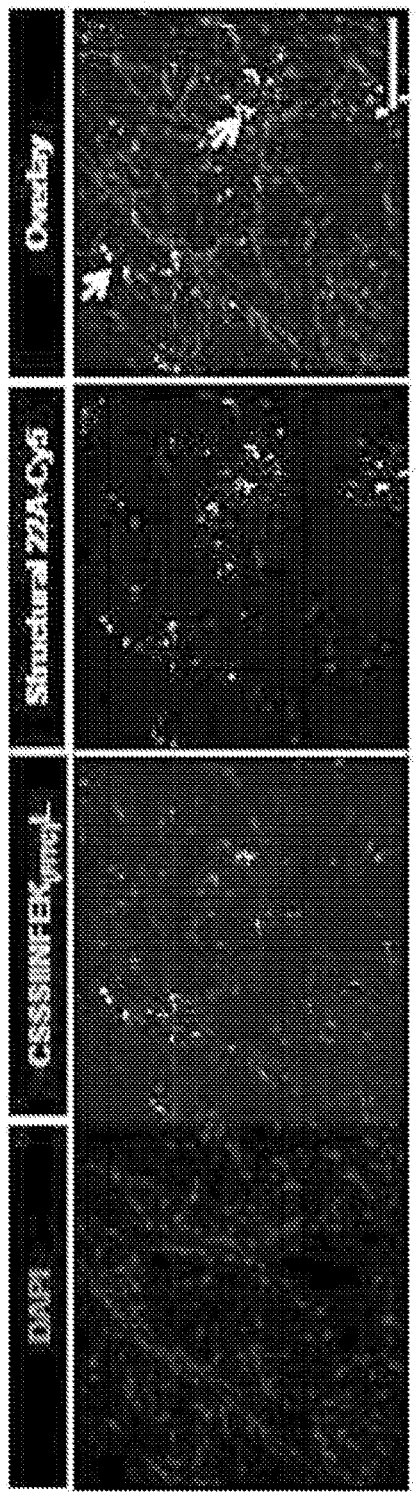
FIG. 22: Colocalization of antigen peptides and sHDL in dLNs after subcutaneous administration. sHDL-CSSSIINFEK(FITC)L nanodiscs incorporated with Cy5-labeled 22A were injected subcutaneously (31 nmol antigen peptides/mouse) at the tail base of C57BL/6 mice. After 24 h, draining inguinal lymph nodes were harvested and frozen sections were prepared for confocal microscopy. The confocal images showed antigen peptides and 22A were colocalized in the lymph nodes (indicated by white arrows). Scale bar=50 µm.

The impact of nanodiscs on lymphatic delivery of Ag/CpG and induction of CTL responses in vivo (see, e.g., Reddy, S. T. et al. Nat. Biotechnol. 25, 1159-1164 (2007)) was next investigated. C57BL/6 mice injected subcutaously at tail base with 31 nmol free CSS-SIINFEK$_{(FITC)}$L had minimal FITC signal in inguinal dLNs after 1 day (see, e.g., FIG. 21a), potentially due to systemic dissemination of small MW Ag peptide or direct Ag binding on non-APCs at the injection site (see, e.g., Melief, C. J. & van der Burg, S. H. Nat. Rev. Cancer 8, 351-360 (2008). In contrast, sHDL-Ag group exhibited markedly increased FITC signal in dLNs (p<0.01, FIG. 21a), with Ag(FITC) and Cy5-tagged 22A co-localized within dLNs (FIG. 22). Similarly, injection of 2.3 nmol Cy5-tagged Cho-CpG in sHDL increased its LN accumulation, compared with injection in free soluble form (p<0.01, FIG. 21b). These results showed that sHDL nanodisc promoted co-delivery of Ag and CpG to dLNs. C57BL/6 mice were next immunized with 15.5 nmol Ag and 2.3 nmol CpG (non-fluorophore tagged), and peripheral blood mononuclear cells (PBMCs) were analyzed for the frequency of SIINFEKL-MHC-I tetramer+CD8α+ T-cells. The mixture of free Ag peptides (SIINFEKL or CSS-SIINFEKL) and CpG induced 1-3% Ag-specific CTLs after the third immunization (FIGS. 21c and 21d). As the benchmark, animals with the equivalent doses of Ag and CpG emulsified in water-in-oil Montanide were also vaccinated (see, e.g., Speiser, D. E. et al. J. Clin. Invest. 115, 739-746 (2005); Fourcade, J. et al. J. Immunother. 31, 781-791 (2008)). Ag+CpG+Montanide elicited~2% Ag-specific CTLs after priming; however, no further T-cell expansion was observed even after the third immunization, consistent with a recent study reporting dysfunction and deletion of high-avidity T-cells after repeated immunizations with a depot-forming water-in-oil adjuvant (see, e.g., Rezvani, K. et al. Haematologica 96, 432-440 (2011); Hailemichael, Y. et al. Nat. Med. 19, 465-472 (2013)). In striking contrast, sHDL-Ag/CpG group elicited a peak frequency of ~21% Ag-specific CD8α+ T-cells after the third vaccination (29-fold greater than soluble SIINFEKL+CpG and 9-fold greater than Ag+CpG+Montanide, p<0.0001, FIGS. 21c and 21d). When challenged with 2×10$^5$ B16OVA cells, mice immunized with sHDL-Ag/CpG had no detectable tumor masses up to 28 days, with 40% of animals surviving for more than 200 days, whereas mice immunized with free Ag peptides+ CpG or Ag+CpG+Montanide all succumbed to tumors with marginal survival benefits (FIGS. 21e and 20. Importantly, throughout such experiments, no signs of toxicity or autoimmunity in animals immunized multiple times with sHDL-Ag/CpG were observed.

Figure 23:
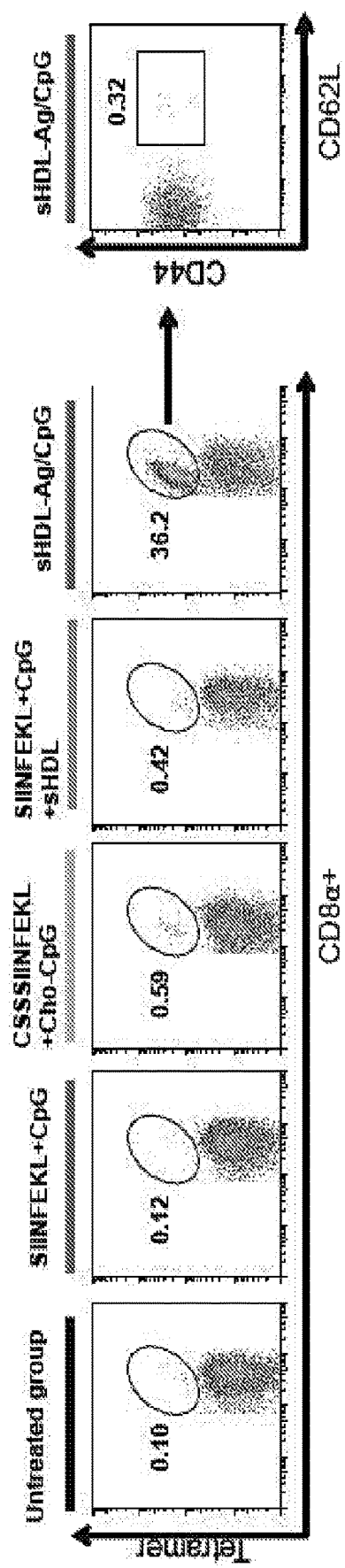
FIG. 23: Elicitation of CTL responses with sHDL-Ag/CpG vaccination. C57BL/6 mice were immunized with the indicated formulations in a biweekly interval. Shown are representative scatter plots for SIINFEKL-specific CD8+ T-cells among PBMCs on day 35 and their effector CD8+ T-cell phenotype as analyzed by CD44 and CD62L staining.

Experiments were conducted to rule out the possibility that CSS-modified peptides or Cho-CpG dissociated from sHDL-Ag/CpG in vivo were responsible for the strong CTL responses. Introducing the CSS linker to SIINFEKL and replacing free CpG with Cho-CpG in free soluble form resulted in minimal T-cell responses, and the physical mixture of Ag, CpG, and sHDL also elicited weak CTL responses (FIG. 21g). In contrast, sHDL-Ag/CpG nanodiscs drastically improved CTL responses, eliciting remarkable 41-fold greater frequency of Ag-specific CD8α+ T-cells than CSSSINFEKL+Cho-CpG group (day 35, p<0.0001, FIG. 21g), with CTLs primarily exhibiting CD44$^{high}$CD62L$^{low}$ effector phenotype and robust IFN-γ$^+$ ELISPOT responses (FIG. 21h; FIG. 23).

Figure 24:
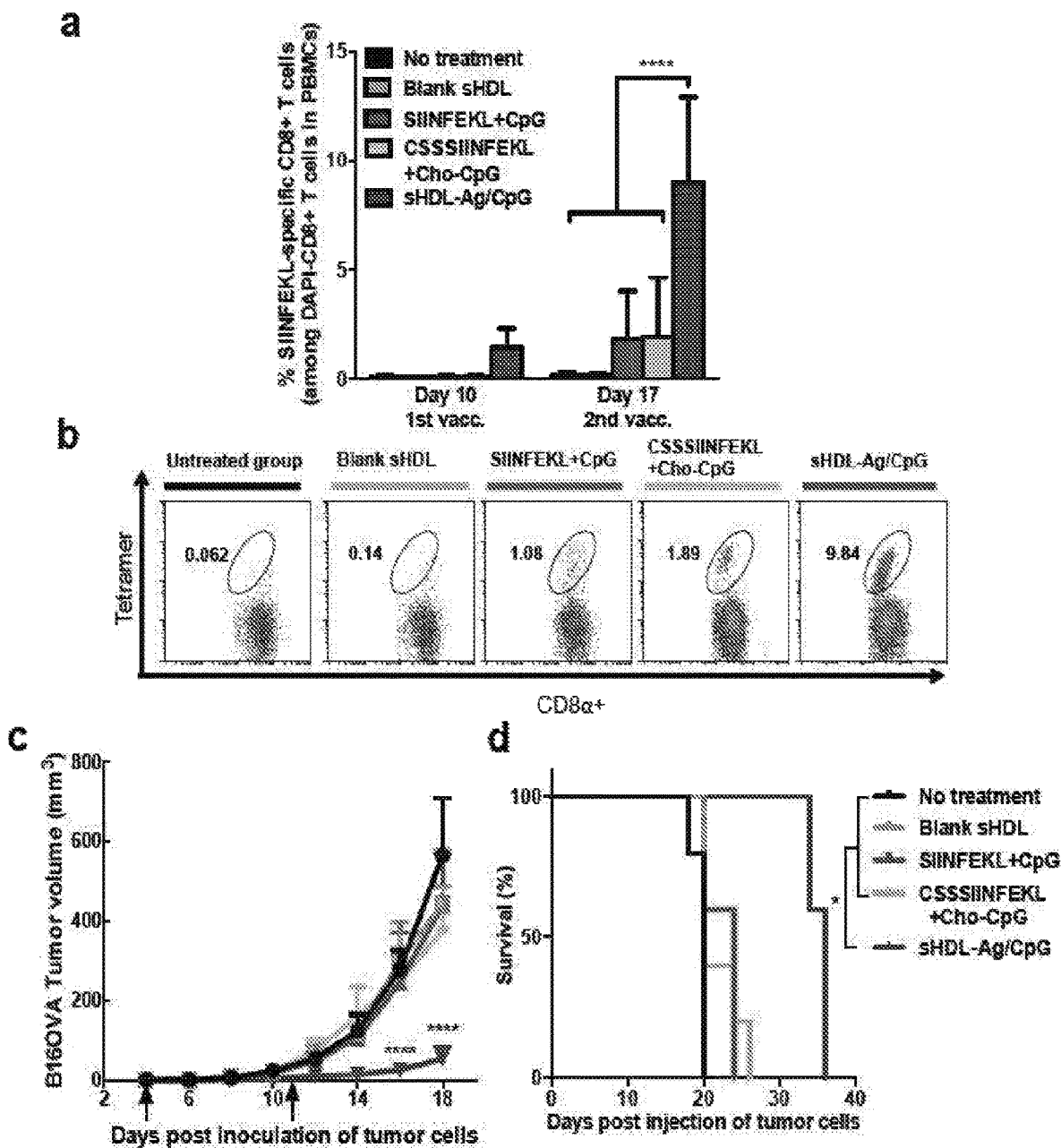
FIG. 24: Therapeutic vaccination against melanoma with sHDL-Ag/CpG. C57BL/6 mice (n=5) were inoculated subcutaneously with 2×10$^5$ B16OVA cells and vaccinated on days 4 and 11 with the indicted formulations (equivalent to 15.5 nmol Ag peptide and 2.3 nmol CpG). a, Shown are the frequency of SIINFEKL-specific CD8α+ T-cells among PBMCs as measured by tetramer staining; b, their representative scatter plots on day 17; c, B16OVA tumor growth; and d, animal survival. The data show mean±SD from a representative experiment (n=5) from 2-3 independent experiments. * $p<0.05$, and **** $p<0.0001$, analyzed by (a, c) two-way ANOVA with Tukey's HSD post-test or (d) log-rank (Mantel-Cox) test. Asterisks in panels c indicate statistically significant differences between sHDL-Ag/CpG and all other groups.
Figure 25:
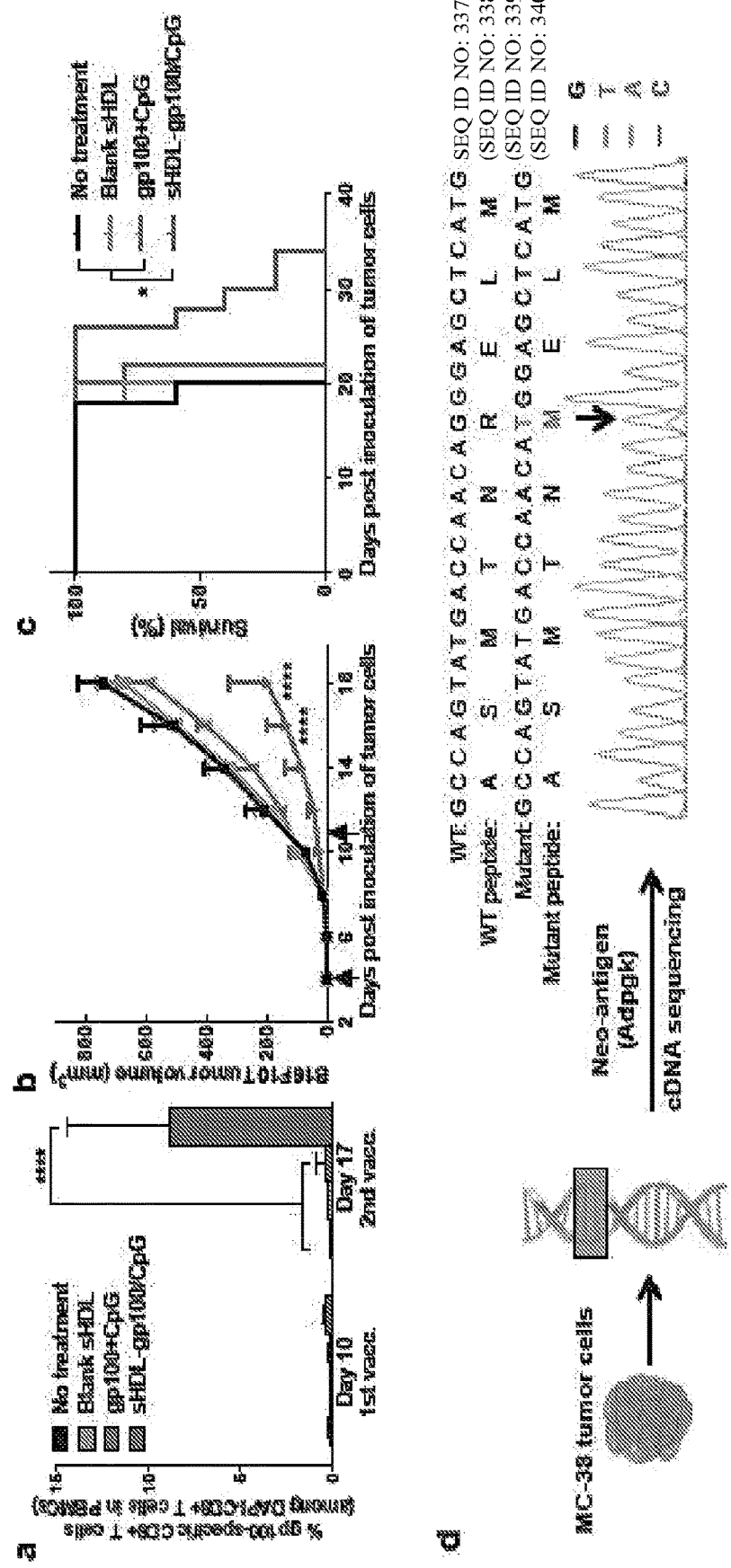
FIG. 25: Nanodisc vaccination with tumor-associated antigens and tumor-specific neo-antigens for treatment of melanoma and colon adenocarcinoma. a-c, C57BL/6 mice were inoculated subcutaneously with 2×10$^5$ non-immunogenic B16F10 melanoma cells and vaccinated on days 4 and 11 with the indicted formulations (equivalent to 15.5 nmol Ag peptide and 2.3 nmol CpG). a, Shown are the frequency of gp100-specific CD8α+ T-cells among PBMCs; b, B16F10 tumor growth; and c, animal survival. d, Mutation of Adpgk in MC-38 murine colon adenocarcinoma cells was confirmed by sequencing cDNA of Adpgk. e-h, C57BL/6 mice were inoculated subcutaneously with 10$^5$ MC-38 tumor cells and vaccinated with the indicated formulations (equivalent to 15.5 nmol mutated Adpgk peptide and 2.3 nmol CpG) on days 10, 17, and 24. Shown are e, the frequencies of Adpgk-specific CD8α+ T-cells among PBMCs and representative scatter plots of Adpgk-tetramer+CD8α+ T-cells on day 23; f, the percentages of intracellular IFN-γ$^+$, TNF-α$^+$, and IFN-γ$^+$TNF-α$^+$CD8α+ T-cells among PBMCs on day 30 after ex vivo restimulation with the mutated Adpgk Ag and their representative scatter plots; g, growth of MC-38 tumor masses; and h, animal survival. The data show mean±SD from a representative experiment (n=5-8) from 2-3 independent experiments. * $p<0.05$,  $p<0.01$, * $p<0.001$, and **** $p<0.0001$, analyzed by (a, b, e, g) two-way or (f) one-way ANOVA with Tukey's HSD post-test or (c, h) log-rank (Mantel-Cox) test. Asterisks in (b, g) indicate statistically significant differences between sHDL-Ag/CpG and all other groups.
Figure 25:
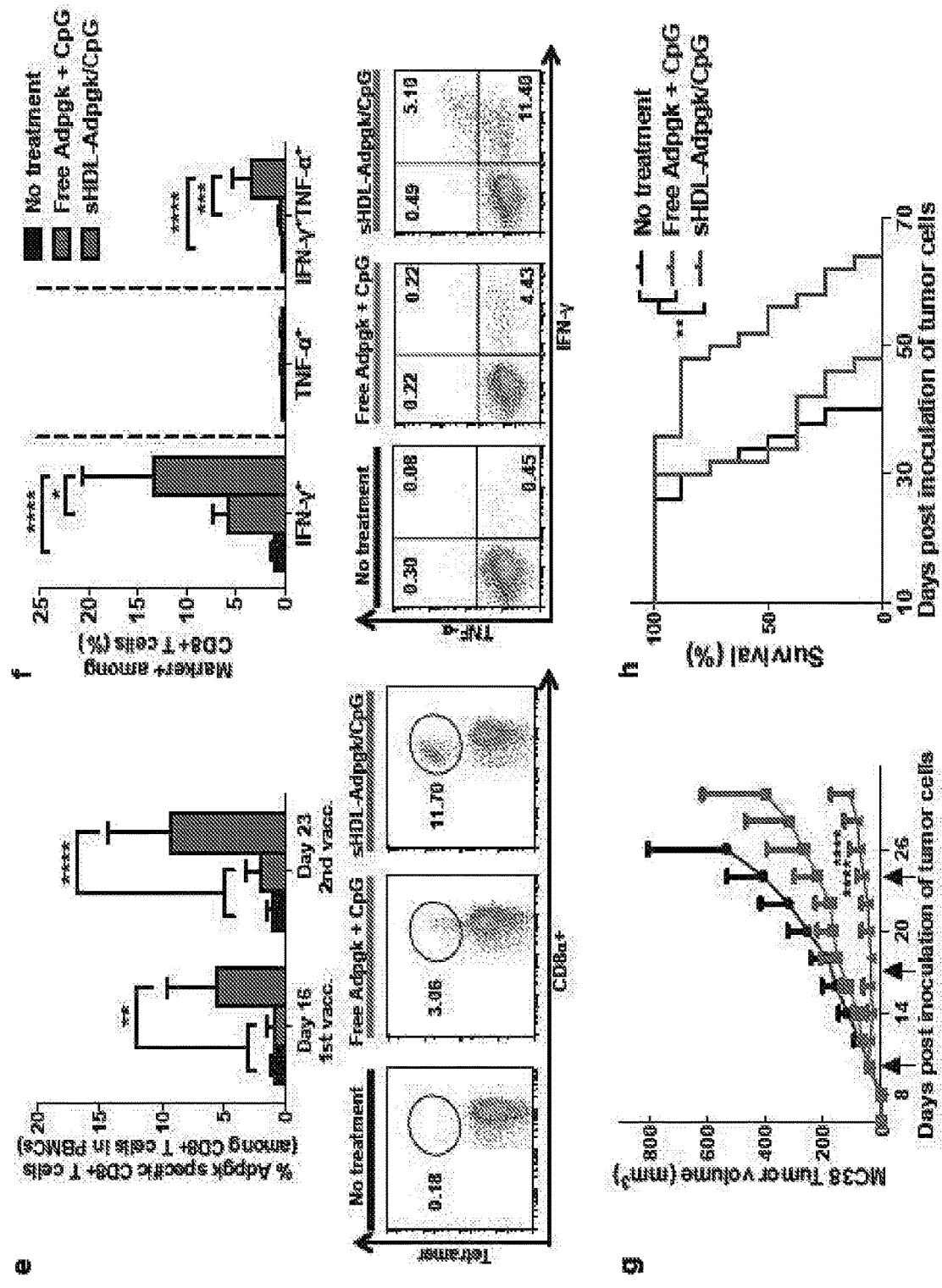
Figure 26:
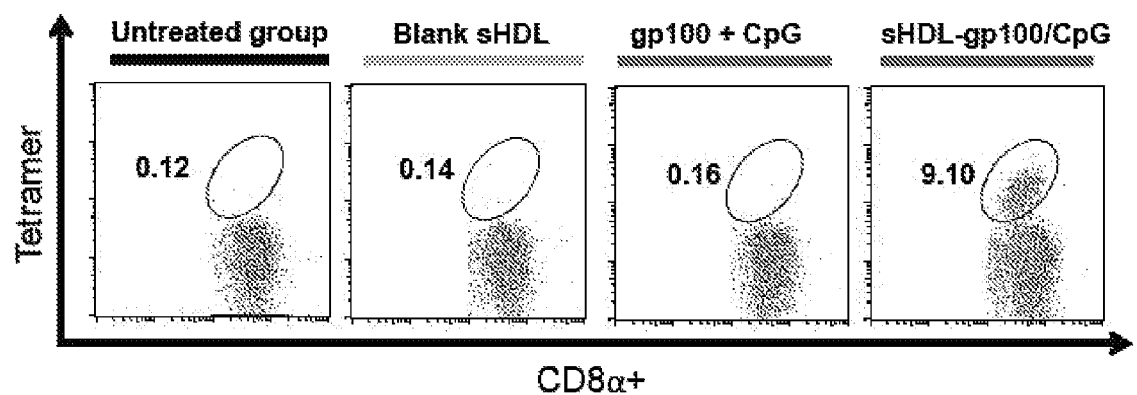
FIG. 26: Therapeutic vaccination against melanoma with sHDLAg/CpG. C57BL/6 mice were inoculated subcutaneously with 2×10$^5$ B16F10 cells and vaccinated on days 4 and 11 with the indicted formulations (equivalent to 15.5 nmol Ag peptide and 2.3 nmol CpG). Shown are the representative scatter plots for gp100-specific CD8α+ T-cells among PBMCs in B16F10 tumor-bearing mice on day 17.

The anti-tumor efficacy of sHDL in tumor-bearing mice was evaluated. Therapeutic sHDL vaccination in mice bearing B16OVA melanoma led to strong Ag-specific CTL responses with significantly slowed tumor growth and extended animal survival (FIG. 24). Nanodisc vaccines were next tested using non-immunogenic B16F10 melanoma as a more clinically relevant model. After confirming incorporation of gp100$_{25-33}$ together with Cho-CpG into nanodiscs (FIG. 15; Table 3), mice were treated with 15.5 nmol Ag and 2.3 nmol CpG on days 4 and 11 post subcutaneous inoculation of B16F10 cells. Vaccinations with sHDL-gp100/CpG elicited robust CTL responses, generating 22-fold higher frequency of gp100-specific CTLs than free gp100+CpG (day 17, p<0.0001, FIG. 25a; FIG. 26), leading to significantly delayed tumor growth and prolonged animal survival, compared with the free gp100+CpG group that had no effects (FIGS. 25b and 25c).

Finally, to demonstrate the utility of the platform technology for vaccination against neo-antigens, the murine MC-38 colon carcinoma model recently reported to harbor a single-epitope mutation within Adpgk protein (ASMTN RELM→ASMTNMELM) was employed, with the neo-epitope presented in MHC-I H-2D$^b$ molecules (see, e.g., Yadav, M. et al. Nature 515, 572-576 (2014)). The Adpgk neo-antigen mutation in MC-38 cells was confirmed by cDNA sequencing (FIG. 25d; FIG. 27) and synthesized sHDL-Adpgk/CpG by mixing nanodiscs with the neo-epitope modified with the CSS-linker and Cho-CpG. C57BL/6 mice were inoculated subcutaneously with 10$^5$ MC-38 cells and treated with 15.5 nmol Adpgk mutated peptide and 2.3 nmol CpG. Mice treated with free Adpgk Ag+CpG had similar levels of Adpgk-specific CD8α+ T-cells as non-immunized, MC-38-bearing mice, whereas sHDL-Adpgk/CpG markedly enhanced CTL responses (day 23, p<0.001, FIG. 25e). In addition, sHDL-Adpgk/CpG induced polyfunctional IFN-γ$^+$ and IFN-γ$^+$TNF-α$^+$ Adpgk-specific CD8α+ T-cells (2.5-fold and 7-fold greater than the free Adpgk+CpG group, p<0.05 and p<0.001, respectively, FIG. 25f). Importantly, therapeutic treatments with sHDL-Adpgk/CpG substantially slowed MC-38 tumor growth and extended animal survival, in contrast to the traditional soluble Adpgk+CpG vaccine with no statistically significant effects on tumor growth or survival (median survival: 54 d versus 33 d, respectively, p<0.01, FIG. 25g and FIG. 25h).

Example VI

This example pertains to the materials and methods for Example V.
Materials 1,2-dimyristoyl-sn-glycero-3-phosphocholine (DMPC), 1,2-dioleoyl-sn-glycero-3-phosphoethanolamine (DOPE), and rhodamine (Rhod)-labeled DOPE (DOPE-Rhod) were purchased from Avanti Polar Lipids (Alabaster, Ala.). ApoA1 mimetic peptide (22A), OVA$_{257-264}$ SIINFEKL, CSSSIINFEKL, CSSSIINFEK(FITC)L, hgp100$_{25-33}$ KVPRNQDWL, CSSSKVPRNQDWL, and Adpgk mutant peptide ASMTNMELM were synthesized by GenScript Corp. (Piscataway, N. J.). CSSASMENMELM was synthesized by AnaSpec (Fremont, Calif.). The oligodeoxynucleotide TLR9 ligand CpG 1826 (5'-tccatgacgttcctgacgtt-3', lower case letters represent phosphorothioate backbone), CpG 1826 modified with cholesterol at the 3' end (Cho-CpG), and Cy5 modified Cho-CpG were synthesized by Integrated DNA Technologies (Coralville, Iowa). HPLC grade methanol and acetonitrile were purchased from Fisher Scientific (Pittsburgh, Pa.). Fetal bovine serum (FBS), penicillin-streptomycin, β-mercaptoethanol and ACK lysis buffer were purchased from Life Technologies (Grand Island, N.Y.). Granulocyte macrophage colony stimulating factor (GM-CSF) was from GenScript Corp. (Piscataway, N. J.). Anti-mouse CD16/32, CD86-PE, CD40-APC, CD62L-PECy7, and 25-D1.16 mAb-PE against SIINFEKL/H-2K$^b$ were from eBioscience (San Diego, Calif.). Anti-mouse CD8α-APC, CD44-FITC, TNF-α-FITC, IFN-γ-PE, and CD11c-PECy7 were from BD Bioscience (San Jose, Calif.). Tetramer H-2K$^b$-SIINFEKL-PE and Tetramer H-2D$^b$-KVPRNQDWL-PE was purchased from Beckman Coulter (Brea, Calif.). Tetramer/H-2D$^b$-ASMTNMELM-PE was kindly provided by the NIH Tetramer Core Facility (Atlanta, Ga.). We obtained B3Z CD8α+ T cell hybridoma from Dr. N. Shastri (University of California, Berkeley); B16OVA from Dr. Kenneth Rock (University of Massachusetts, Amherst, Mass.); and MC-38 cells from Dr. Weiping Zou (University of Michigan, Ann Arbor, Mich.).

Methods

Synthesis and Characterization of DOPE-PDP

Dioleoyl-sn-glycero-3-phosphoethanolamine-N-[3-(2-pyridyldithio) propionate] (DOPE-PDP) was synthesized as reported previously with slight modifications (see, e.g., Kuai, R., et al. Mol. Pharm. 7, 1816-1826 (2010)). Briefly, DOPE, SPDP (succinimidyl 3-(2-pyridyldithio) propionate) and triethylamine (1:1:1.5 molar ratio) were dissolved in chloroform. The mixture was reacted in the dark for 5 h. The reaction progress was monitored by thin layer chromatography (TLC), using the following mixture as the developing solvent: chloroform/methanol/water=65/25/4 (volume ratio). After TLC indicated disappearance of the starting materials and appearance of a faster-running spot, the reaction mixture was dried by rotary evaporation and purified on a silica gel column.

Synthesis of sHDL Co-Loaded with Antigen Peptides and CpG

DMPC and DOPE-PDP (molar ratio=96:4) were dissolved in chloroform. The mixture was dried with nitrogen flow and place under vacuum for at least 1 h. The resulting lipid film was hydrated in 10 mM sodium phosphate buffer (0.3117 g/L NaH$_2$PO$_4$.H$_2$O and 2.0747 g/L Na$_2$HPO$_4$.7H$_2$O, pH 7.4) and sonicated in a bath sonicator for 10 min, followed by probe sonication for another 2.5 min. ApoA1 mimetic peptide 22A dissolved in endotoxin free water was added to the above mixture (22A:lipids=1:7.5 molar ratio), which was then subjected to heating (50° C.) for 3 min and cooling (ice water) for 3 min, with 3 cycles in total, to obtain sHDL.

To conjugate tumor antigen peptides to sHDL, cysteine terminated tumor antigen peptides dissolved in endotoxin free water were added to the above sHDL (antigen peptides: DOPE-PDP=2.5:1, molar ratio) and incubated at room temperature with gentle shaking on an orbital shaker. Unreacted tumor antigen peptides were removed by using Zeba Spin Desalting columns (Pierce) following the manufacturer's instructions. The conjugation efficiency of tumor antigen peptides was calculated based on the decrease of absorbance signal associated with DOPE-PDP as determined by HPLC. Briefly, 200 μl sHDL formulations were freeze-dried and reconstituted in 300 μl methanol. The mixture was filtered by a 0.22 μm PTFE filter and analyzed with a Shimadzu HPLC system using a Vydac 219TP Diphenyl column (4.6 mm×250 mm ID). The two solvents used for the HPLC analysis consisted of water:trifluoroacetic acid=100:0.5 (mobile phase A) and methanol:acetonitrile:trifluoroacetic acid=50:50:0.05 (mobile phase B) (0-75 min, 15-100%). The flow rate was 0.4 mL/min and the detection wavelength was 220 nm. The loading efficiency of tumor antigen peptides in sHDL was confirmed by using FITC-labeled peptides and measuring the fluorescence intensity of sHDL formulations at Ex=490 nm and Em=520 nm after dissolving the formulations in PBS containing 1% Triton X-100.

To load CpG in sHDL, different concentrations (0-200 μg/mL) of cholesterol modified CpG (Cho-CpG) were incubated with sHDL at room temperature with gentle shaking on an orbital shaker. The amount of CpG incorporated into sHDL and free CpG was analyzed by gel permeation chromatography (GPC). Briefly, the sHDL formulations were diluted in PBS to a concentration of 0.5 mg/mL 22A peptide. The formulations were filtered through a 0.22 μm filter and analyzed with a Shimadzu HPLC system equipped with a TSKgel G2000SW×1 column (7.8 mm ID×30 cm, Tosoh Bioscience LLC). The flow rate of mobile phase PBS (pH 7.4) was set at 0.7 mL/min, and the detection wavelength was set at 260 nm for CpG.

Characterization of Peptide/CpG-Loaded sHDL Formulations

The sHDL formulations were diluted to 0.5 mg/mL 22A with PBS, and the particle sizes were measured by dynamic light scattering (DLS, Zetasizer Nano ZSP, Malvern, UK). The morphology of sHDL was observed by transmission electron microscopy (TEM) after proper dilution of the original samples. Briefly, 3 μL of the sample solution was deposited on a carbon film-coated 400 mesh copper grid (Electron Microscopy Sciences) and dried for 1 minute. The samples were then negatively-stained with 5 droplets of 1% uranyl acetate solution, excessive solutions on the grid were blotted, and the grid was dried before TEM observation. All images were acquired on JEM 1200EX electron microscope (JEOL USA, Peabody, Mass.) equipped with an AMT XR-60 digital camera (Advanced Microscopy Techniques Corp. Woburn, Mass.).

Preparation of BMDCs

BMDCs were prepared as described previously (see, e.g., Lutz, M. B., et al. J. Immunol. Methods 223, 77-92 (1999)). Briefly, femur and tibia were harvested aseptically from C57BL/6 mice, and the bone marrow was flushed into a petri dish using a 5 mL syringe (26 G needle) loaded with BMDC culture media (RPMI 1640 supplemented with 10% FBS, 100 U/mL penicillin, 100 μg/ml streptomycin, 50 μM β-mercaptoethanol, and 20 ng/ml GM-CSF). Cells were collected by passing the cell suspension through a cell strainer (mesh size=40 μm), followed by centrifugation. Cells were seeded into non-tissue culture treated petri-dish at a density of 2×10$^5$ cells/ml, cultured at 37° C. with 5% CO$_2$. Culture media were refreshed on days 3, 6, 8, and 10, and BMDCs were used for the following assays on days 8-12.

Activation of BMDCs

Immature BMDCs were plated at 1×10$^6$ cells/well in 12-well plates. After 24 h, BMDCs were washed once with PBS and incubated with 75 nM of CpG in different formulations or 0.5 μg/mL LPS (positive control) for 24 h at 37° C. with 5% CO$_2$. BMDCs were harvested, washed with FACS buffer (1% BSA in PBS), incubated with anti-CD16/32 at room temperature for at least 10 min, and then stained with fluorophore-labeled antibodies against CD11c, CD40, CD80, and CD86 at room temperature for 30 min. Finally, cells were washed twice by FACS buffer, resuspended in 2 μg/ml DAPI solution, and analyzed by flow cytometry (Cyan 5, Beckman Coulter, USA).

Antigen Presentation on BMDCs

Immature BMDCs were plated at 1×10$^6$ cells/well in 12-well plates 24 h prior to use. BMDCs were washed with PBS and incubated with 75 nM CpG and/or 500 nM antigen peptide in various formulations in complete media for different lengths of time (2, 6, 24, and 48 h). BMDCs were then harvested, washed with FACS buffer, incubated with anti-CD16/32 at room temperature for at least 10 min, and stained with PE-conjugated anti-mouse SIINFEKL/H-2K$^b$ mAb 25-D1.16 at room temperature for 30 min. Cells were then washed, resuspended in 2 µg/ml DAPI solution, and analyzed by flow cytometry (Cyan 5, Beckman Coulter, USA).

Confocal Microscopy Imaging of the Intracellular Trafficking of sHDL

JAWSII cells (ATCC, Manassas, Va.) were seeded at $1\times10^6$ cells on 35 mm petri dishes (MatTek Corp., Ashland, Mass.) that have been pre-equilibrated with the complete cell culture media and cultured overnight. To investigate the intracellular delivery profiles of antigen peptides, JAWSII cells were incubated with the physical mixture of free CSSSIINFEK(FITC)L and CpG, or sHDL-CSSSIINFEK (FITC)L/CpG for different lengths of time (6, 24, and 48 h). Cells were then washed 3 times with PBS and incubated for 30 min at 37° C. with 50 nM LysoTracker® Red DND-99 (Invitrogen) and 2 µg/mL Hoechst in phenol/serum-free media to stain lysosomes and nuclei, respectively. In parallel, to study the intracellular delivery profiles of structural components of sHDL, the lipid layers of sHDL were incorporated with DOPE-Rhod by adding 0.5 mol % DOPE-Rhod in the initial lipid film, while 22A peptide of sHDL was labeled by incubating pre-formed sHDL with Texas Red®-X succinimidyl ester (Life Technologies) and passing Texas Red-labeled sHDL through a desalting column to remove the unreacted dye. The resulting fluorophore-tagged sHDL formulations were incubated with JAWSII cells at 37° C. with 5% $CO_2$. After 24 h incubation, cells were washed 3 times with PBS and then incubated for 30 min at 37° C. with 500 nM LysoTracker® Green DND-26 (Invitrogen) and 2 µg/mL Hoechst in phenol/serum-free media to stain lysosomes and nuclei, respectively. JAWSII cells were then imaged using a confocal microscope (Nikon A1).

Activation of B3Z CD8+T Hybridoma Cells with sHDL

BMDCs were plated at $5\times10^4$ cells/well in a U-bottom 96-well plate. After overnight culture, BMDCs were washed with PBS and incubated with different formulations of SIINFEKL (20, 100 and 500 nM) and CpG (3, 15, and 75 nM) for 24 h or 48 h at 37° C. Cells were then carefully washed 3 times with PBS, and $10^5$ B3Z CD8+T hybridoma cells/well were added in RPMI 1640 supplemented with 10% FBS, 2 mM L-glutamine, 55 µM β-mercaptoethanol, 1 mM pyruvate and 100 U/mL penicillin and 100 µg/mL streptomycin. After 24 h of incubation, cells were pelleted via centrifugation (1500 rcf, 7 min), the media were carefully aspirated, and 150 µL CPRG/lysis buffer (0.15 mM chlorophenol red-β-D-galactopyranoside (CPRG), 0.1% Triton-X 100, 9 mM MgCl2, 100 µM mercaptoethanol in PBS) was added. The plates were incubated at 37° C. in the dark for 90 min, after which the absorbance of released chlorophenol red was measured at 570 nm using a microplate reader.

In Vivo Immunization Studies

Animals were cared for following federal, state, and local guidelines. All work performed on animals was in accordance with and approved by University Committee on Use and Care of Animals (UCUCA) at University of Michigan, Ann Arbor. Female C57BL/6 mice of age 6-8 weeks (Harlan Laboratories) were immunized with different formulations containing antigen peptides (15.5 nmol/mouse) and CpG (2.3 nmol/mouse) in 100 µl volume by subcutaneous injection at the tail base on indicated time points. In some studies, antigen peptide and CpG emulsified in Montanide served as a positive control (see, e.g., Speiser, D. E., et al. J. Clin. Invest. 115, 739-746 (2005); Fourcade, J., et al. J. Immunother. 31, 781-791 (2008); Karbach, J., et al. Int. J. Cancer 126, 909-918 (2010)). Briefly, antigen peptide (155 nmol) and CpG (23 nmol) in 0.5 mL PBS were thoroughly emulsified in 0.5 mL Montanide until the mixture was homogeneous.

For lymph node draining studies, C57BL/6 mice were injected with free CSSSIINFEK(FITC)L, sHDL-CSSSIINFEK(FITC)L, free Cho-CpG(Cy5), or sHDL-Cho-CpG (Cy5). After 24 h, inguinal lymph nodes were harvested, and FITC or Cy5 fluorescence signal was measured with IVIS optical imaging system (Caliper Life Sciences).

For prophylactic tumor challenge studies, vaccinated animals were challenged on day 8 after last immunization by subcutaneous injection of $2\times10^5$ B16OVA cells/mouse on the right flank. Tumor growth was monitored every other day, and the tumor volume throughout this study was calculated by the following equation (see, e.g., Gorrin-Rivas, M. J., et al. Clin. Cancer Res. 6, 1647-1654 (2000)): tumor volume=length×width×0.52. Animals were euthanized when the tumor masses reached 1.5 cm in diameter or when animals became moribund with severe weight loss or ulceration.

For therapeutic tumor vaccination studies, C57BL/6 mice were inoculated with tumor cells ($2\times10^5$ B16OVA cells, $2\times10^5$ B16F10 cells, or $1\times10^5$ MC38 cells per mouse) on the right flank by subcutaneous injection on day 0. For B16OVA and B16F10 studies, mice were vaccinated on days 4 and 11 with different formulations containing 15.5 nmol of tumor antigen peptides (SIINFEKL and hgp100, respectively) and 2.3 nmol of CpG. For MC-38 studies, mice were vaccinated on days 10, 17, and 24 with 15.5 nmol of ASMTNMELM and 2.3 nmol of CpG in either sHDL or free soluble form. Tumor growth was monitored as indicated above.

Peptide-MHC Tetramer Assay

Immunized mice were analyzed for the percentages of tumor antigen-specific CD8α+ T cells among peripheral blood mononuclear cells (PBMCs) using the tetramer staining assay, as described previously (see, e.g., Ochyl, L. J. & Moon, J. J. J. Vis. Exp. e52771 (2015)). In brief, 100 µl of blood was drawn from each mouse on indicated time points by submandibular bleeding, and red blood cells were lysed with ACK lysis buffer. PBMCs were then washed with FACS buffer and blocked by anti-CD16/32 antibody and incubated with peptide-MHC tetramer tagged with PE (e.g. $H-2K^b$-restricted SIINFEKL, $H-2D^b$-restricted KVPRNQDWL, or $H-2D^b$-restricted ASMTNMELM) for 30 min at room temperature. Samples were then incubated with anti-CD8α-APC for 20 min on ice. Cells were washed twice with FACS buffer and resuspended in 2 µg/ml DAPI solution for analysis by flow cytometry (Cyan 5, Beckman Coulter, USA).

ELISPOT and Intracellular Cytokine Staining Assays

For ELISPOT assay, spleens from immunized mice were harvested aseptically, processed into single cell suspensions for each mouse, and seeded at $3\times10^5$ splenocytes per well in 96-well PVDF plates (EMD Millipore) pre-incubated overnight with IFN-γ coating Ab (R&D Systems). Splenocytes were co-incubated with antigen peptides (2.5 µg/ml) or controls for 24 hours. Assays were completed using sequential incubations with biotinylated-secondary Ab, streptavidin-alkaline phosphatase (Sigma Chemical), and NBT/BCIP substrate (Surmodics). Developed spots were enumerated using an AID iSpot Reader (Autoimmun Diagnostika GmbH, Germany). For intracellular cytokine staining (ICS) assay, 100-150 µL peripheral blood collected from vaccinated mice was lysed with ACK lysis buffer, washed with PBS, and were plated at ~10 million cells/mL in 50 µL T cell media (RPMI 1640 supplemented with 10% FBS, 2 mM L-glutamine, 55 µM β-mercaptoethanol, 1 mM pyruvate and 100 U/mL penicillin and 100 μg/mL streptomycin, HEPES, and non-essential amino acids) in 96-well U bottom plates. Cells were pulsed with 10 μg/mL antigen peptides for 6 hours with protein transport inhibitor, brefeldin A (BD Biosciences), added during the last 4 h of incubation. Cells were then washed twice with ice-cold FACS buffer (1% BSA in PBS), followed by incubation with anti-CD16/32 for at least 10 minutes and anti-CD8α for 20 min on ice. Cells were then fix/permeabilized for 20 min on ice and then stained with anti-IFN-γ-PE and anti-TNF-α-FITC for 30 min on ice. After extensive washing, cells were analyzed by flow cytometry.

cDNA Sequencing of Neo-Epitope (Adpgk) in MC-38 Cells

Total RNA was extracted from MC-38 cells by the RNeasy® mini Kit (QIAGEN) following the manufacturer's instructions. The first-strand cDNA was synthesized using 1 μg of total RNA with the SuperScript™ III First-Strand Synthesis SuperMix Kit (Invitrogen). Adpgk cDNA with lengths of 250 bp and 485 bp were selectively amplified by using the following two sets of sequence specific primers. Primer 1: TGCCAACCGCTTCATCTTCT (forward primer) and GGTAGACCAGCGTGTGGAAA (reverse primer); Primer 2: CTCCAACGGGGCCATGAATA (forward primer) and CGTGGGAAAGACCTGCTGAT (reverse primer). The amplification was performed using the SuperScript One Step RT-PCR System (Invitrogen). The final cDNA products were visualized in 1.5% agarose gels with ethidium bromide, and the Adpgk cDNA bands were cut and purified using the PureLink® Quick Gel Extraction and PCR Purification Combo Kit (Invitrogen). The purified cDNA was sequenced by the Sanger sequencing method (see, e.g., Sanger, F., Nicklen, S. & Coulson, A. R. DNA sequencing with chain-terminating inhibitors. Proc. Natl. Acad. Sci. U.S.A. 74, 5463-5467 (1977)) at the University of Michigan DNA Sequencing Core.

Example VII

This example describes neo-antigen vaccination using other nanoparticles, including sHDL, liposomes, and gold nanoparticles (FIG. 29), and the generation of multivalent neo-antigen vaccination using multiple neo-antigen peptides (FIG. 28).

Preparation of sHDL Loaded with Multivalent Neo-Antigens

To prepare nanodisc-based multivalent peptide vaccine, multiple neo-antigen peptides (M30 and M27) modified with CSS linker at N-terminus were conjugated to DOPE-PDP in dimethylformamide at room temperature for 3 hours, followed by dilution with 10× water and lyophilization to obtain lipid-peptide conjugates. The conjugate was mixed with DMPC and 22A in acetic acid and lyophilized. The resulting powder was then subjected to heating (50° C.) for 3 min and cooling (ice water) for 3 min, with 3 cycles in total, to obtain sHDL loaded with different neo-antigens (sHDL-M30/M27). Alternatively, the conjugate was dissolved in DMSO and incubated with preformed sHDL to obtain sHDL loaded with different neo-antigens (sHDL-M30/M27). Any unincorporated neo-antigen peptides were removed by passing through a desalting column. The loading efficiency was analyzed by HPLC. Cholesterol-CpG was incubated with the above sHDL at room temperature for 30 min to obtain the nanodisc-based multivalent peptide vaccine (sHDL-M30/M27/CpG).

Preparation of Liposomes Loaded with Neo-Antigens

To prepare liposome-based neo-antigen vaccines, DMPC and DOPE-PDP (molar ratio=92:8) were dissolved in chloroform. The mixture was dried with nitrogen flow and placed under vacuum for at least 1 h. The resulting lipid film was hydrated in 10 mM sodium phosphate buffer (0.3117 g/L NaH2PO4. H2O and 2.0747 g/L Na2HPO4.7H2O, pH 7.4) and sonicated in a bath sonicator for 10 min, followed by probe sonication for another 2.5 min to obtain liposomes. The neo-antigen peptide Adpgk was conjugated to liposomes after incubation of CSS-modified Adpgk peptides with PDP-displaying liposomes, followed by desalting column-based separation of unconjugated peptides. The conjugation efficiency was analyzed by HPLC. Cholesterol-CpG was incubated with the above liposomes at room temperature for 30 min to obtain the liposome-based neo-antigen peptide vaccine (lip-Adpgk/CpG).

Preparation of Spiky Gold Nanoparticle-Based Neo-Antigen Peptide Vaccine

To obtain spiky gold nanoparticles (AuNPs), citrate gold nanoparticles were first prepared by boiling HAuCl4 aqueous solution with sodium citrate. They were sequentially added with HAuCl4, HCl, AgNO3, and ascorbic acid at room temperature under vigorous stirring to form AuNPs via seed-mediated growth method. As-synthesized AuNPs were purified and concentrated by centrifugation with 0.01% SDS. AuNP-based peptide vaccine was prepared by thiol-mediated surface decoration of neo-antigen peptides on AuNPs followed by polyIC and CpG layer loading through electrostatic complexation. Briefly, peptide vaccine was surface-conjugated to AuNPs by overnight incubation of AuNPs with CSS-modified neo-antigen peptide, CSS-ASMTNMELM. Any unreacted peptide was removed from AuNP conjugates by centrifugation. To load polyIC and CpG via electrostatic interaction, polyethylene glycol (average Mn 6,000)-modified polyethyleneimine (branched, average Mw~25,000) (PEG-PEI) was employed. The peptide-conjugated AuNPs were mixed with PEG-PEI for 10 min, purified from excessive PEG-PEG by centrifugation, and added to polyIC and CpG mixture solution in 10 mM NaCl. After 5 min, the mixture was transferred to PEG-PEI solution in 10 mM NaCl, and the salt concentration was stepwise increased to 150 mM NaCl by the increment of 50 mM every 5 min. Finally, the crude mixture solution was centrifuged with 0.01% tween20 to remove any unbound polyIC and CpG.

Intracellular Cytokine Staining

C57BL/6 mice were vaccinated with nanodisc-based multivalent neo-antigen peptide vaccine (sHDL-M30/M27/CpG) on day 0, 7, and 14. Seven days after the last vaccination, 100-150 μL peripheral blood collected from vaccinated mice was lysed with ACK lysis buffer, washed with PBS, and were plated at ~10 million cells/mL in 50 μL T cell media (RPMI 1640 supplemented with 10% FBS, 2 mM L-glutamine, 55 μM β-mercaptoethanol, 1 mM pyruvate and 100 U/mL penicillin and 100 μg/mL streptomycin, HEPES, and non-essential amino acids) in 96-well U bottom plates. Cells were co-cultured with 50000 BMDCs/well and pulsed with 20 μg/mL of M30 or M27 peptide for 6 hours with protein transport inhibitor, brefeldin A (BD Biosciences), added during the last 4 h of incubation. Cells were then washed twice with ice-cold FACS buffer (1% BSA in PBS), followed by incubation with anti-CD16/32 for at least 10 minutes and anti-CD8α and anti-CD4 for 20 min on ice. Cells were then fix/permeabilized for 20 min on ice and stained with anti-IFN-γ-PE for 30 min on ice. After extensive washing, cells were analyzed by flow cytometry. The results shown in FIG. 28 indicate that sHDL-M30/M27/CpG generated high frequencies of CD4+ T-cells against neo-antigen M30 (FIG. 28A) and CD8+ T-cells against neo-antigen M27 (FIG. 28B).

Therapeutic Study

For therapeutic tumor vaccination studies, C57BL/6 mice were inoculated with tumor cells (1×10$^5$ MC38 cells per mouse) on the right flank by subcutaneous injection on day 0. Mice were vaccinated on days 10 and 17 with 15.5 nmol of ASMTNMELM and 2.3 nmol of CpG (or 15 μg polyIC/mouse) formulated in either liposomes or soluble forms. For the group of mice immunized with AuNPs, intratumoral administration of AuNPs modified with Adpgk and adjuvants was performed on days 10 (both w/and w/o laser groups) and 16 (only w/o laser group) with 12 nmol of ASMTNMELM, 5.2 nmol of CpG, and 83 μg polyIC per mouse. Laser was directly irradiated to tumor tissues at 1.2 W/cm$^2$ for 5 min using 808 nm CW diode laser.

On indicated time points, PBMCs were collected and stained for Adpgk-specific CD8+ T cells among PBMCs via tetramer staining, followed by cytometric analysis. The tetramer staining of PBMCs indicated that Adpgk-containing liposomes and AuNPs all generated stronger neo-antigen-specific CD8+ T cell responses, compared with vaccination with soluble peptide plus adjuvants (FIG. 29A). In addition, tumor growth was monitored every other day, and the tumor volume throughout this study was calculated by the following equation: tumor volume=length×width$^2$×0.52. Animals were euthanized when the tumor masses reached 1.5 cm in diameter or when animals became moribund with severe weight loss or ulceration. The results indicated that Adpgk-containing nanoparticles, including liposomes and AuNPs, slowed tumor progression, compared with vaccination with soluble peptide and CpG (FIG. 29B).

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A composition comprising an sHDL nanoparticle, wherein the sHDL nanoparticle comprises (i) a phospholipid selected from 1,2-dimyristoyl-sn-glycero-3-phosphocholine (DMPC) and dipalmitoylphosphatidylcholine (DPPC), (ii) dioleoyl-sn-glycero-3-phosphoethanolamine-N-[3-(2-pyridyldithio) propionate] (DOPE-PDP), (iii) an apolipoprotein mimetic having the sequence PVLDLFRELLNELL-EALKQKLK (SEQ ID NO: 4), and (iv) one or more antigenic peptides, wherein each of the one or more antigenic peptides is complexed to DOPE-PDP on the outer surface of the sHDL nanoparticle.

2. The composition of claim 1, wherein the one or more antigenic peptides are one or more specific neo-antigenic peptides for an analyzed and identified neo-antigenic mutation predicted to encode neo-antigenic peptides.

3. The composition of claim 2, wherein the one or more antigenic peptides range from about 5 to about 50 amino acids in length.

4. The composition of claim 1, further comprising an adjuvant.

5. The composition of claim 4, wherein the adjuvant is selected from the group consisting of a CpG immunostimulatory oligonucleotide, polyIC, poly-ICLC, imiquimod, resiquimod, gardiquimod, a imidazoquinoline, and telratolimod.

6. The composition of claim 1, wherein the phospholipid is DMPC.

7. The composition of claim 1, wherein the phospholipid is DPPC.

* * * * *

SEQUENCE LISTING

```
<160> NUMBER OF SEQ ID NOS: 341

<210> SEQ ID NO 1
<211> LENGTH: 22
<212> TYPE: PRT
<213> ORGANISM: Artificial sequence
<220> FEATURE:
<223> OTHER INFORMATION: synthetic

<400> SEQUENCE: 1

Pro Val Leu Asp Leu Phe Arg Glu Leu Leu Asn Glu Leu Leu Glu Glx
1               5                   10                  15

Leu Lys Gln Lys Leu Lys
            20

<210> SEQ ID NO 2
<211> LENGTH: 23
<212> TYPE: PRT
<213> ORGANISM: Artificial sequence
<220> FEATURE:
<223> OTHER INFORMATION: synthetic

<400> SEQUENCE: 2

Gly Val Leu Asp Leu Phe Arg Glu Leu Leu Asn Glu Leu Leu Glu Ala
1               5                   10                  15

Leu Lys Gln Lys Leu Lys Lys
            20

<210> SEQ ID NO 3
<211> LENGTH: 22
<212> TYPE: PRT
<213> ORGANISM: Artificial sequence
<220> FEATURE:
<223> OTHER INFORMATION: synthetic

<400> SEQUENCE: 3

Pro Val Leu Asp Leu Phe Arg Glu Leu Leu Asn Glu Leu Leu Glu Trp
1               5                   10                  15
```

```
Leu Lys Gln Lys Leu Lys
            20

<210> SEQ ID NO 4
<211> LENGTH: 22
<212> TYPE: PRT
<213> ORGANISM: Artificial sequence
<220> FEATURE:
<223> OTHER INFORMATION: synthetic

<400> SEQUENCE: 4

Pro Val Leu Asp Leu Phe Arg Glu Leu Leu Asn Glu Leu Leu Glu Ala
1               5                   10                  15

Leu Lys Gln Lys Leu Lys
            20

<210> SEQ ID NO 5
<211> LENGTH: 23
<212> TYPE: PRT
<213> ORGANISM: Artificial sequence
<220> FEATURE:
<223> OTHER INFORMATION: synthetic

<400> SEQUENCE: 5

Pro Val Leu Asp Leu Phe Arg Glu Leu Leu Asn Glu Leu Leu Glu Ala
1               5                   10                  15

Leu Lys Gln Lys Leu Lys Lys
            20

<210> SEQ ID NO 6
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 6

Pro Val Leu Asp Leu Phe Arg Glu Leu Leu Asn Glu Xaa Leu Glu Ala
1               5                   10                  15

Leu Lys Gln Lys Leu Lys
            20

<210> SEQ ID NO 7
<211> LENGTH: 22
<212> TYPE: PRT
<213> ORGANISM: Artificial sequence
<220> FEATURE:
<223> OTHER INFORMATION: synthetic

<400> SEQUENCE: 7

Pro Val Leu Asp Leu Phe Lys Glu Leu Leu Asn Glu Leu Leu Glu Ala
1               5                   10                  15

Leu Lys Gln Lys Leu Lys
            20

<210> SEQ ID NO 8
<211> LENGTH: 22
<212> TYPE: PRT
```

```
<213> ORGANISM: Artificial sequence
<220> FEATURE:
<223> OTHER INFORMATION: synthetic

<400> SEQUENCE: 8

Pro Val Leu Asp Leu Phe Arg Glu Leu Leu Asn Glu Gly Leu Glu Ala
1               5                   10                  15

Leu Lys Gln Lys Leu Lys
            20

<210> SEQ ID NO 9
<211> LENGTH: 22
<212> TYPE: PRT
<213> ORGANISM: Artificial sequence
<220> FEATURE:
<223> OTHER INFORMATION: synthetic

<400> SEQUENCE: 9

Pro Val Leu Asp Leu Phe Arg Glu Leu Gly Asn Glu Leu Leu Glu Ala
1               5                   10                  15

Leu Lys Gln Lys Leu Lys
            20

<210> SEQ ID NO 10
<211> LENGTH: 22
<212> TYPE: PRT
<213> ORGANISM: Artificial sequence
<220> FEATURE:
<223> OTHER INFORMATION: synthetic

<400> SEQUENCE: 10

Pro Val Leu Asp Leu Phe Arg Glu Leu Leu Asn Glu Leu Leu Glu Ala
1               5                   10                  15

Glx Lys Gln Lys Leu Lys
            20

<210> SEQ ID NO 11
<211> LENGTH: 22
<212> TYPE: PRT
<213> ORGANISM: Artificial sequence
<220> FEATURE:
<223> OTHER INFORMATION: synthetic

<400> SEQUENCE: 11

Pro Val Leu Asp Leu Phe Lys Glu Leu Leu Gln Glu Leu Leu Glu Ala
1               5                   10                  15

Leu Lys Gln Lys Leu Lys
            20

<210> SEQ ID NO 12
<211> LENGTH: 22
<212> TYPE: PRT
<213> ORGANISM: Artificial sequence
<220> FEATURE:
<223> OTHER INFORMATION: synthetic

<400> SEQUENCE: 12

Pro Val Leu Asp Leu Phe Arg Glu Leu Leu Asn Glu Leu Leu Glu Ala
1               5                   10                  15

Gly Lys Gln Lys Leu Lys
            20

<210> SEQ ID NO 13
<211> LENGTH: 22
```

```
<212> TYPE: PRT
<213> ORGANISM: Artificial sequence
<220> FEATURE:
<223> OTHER INFORMATION: synthetic

<400> SEQUENCE: 13

Gly Val Leu Asp Leu Phe Arg Glu Leu Leu Asn Glu Gly Leu Glu Ala
1               5                   10                  15

Leu Lys Gln Lys Leu Lys
            20

<210> SEQ ID NO 14
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Orn
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 14

Pro Val Leu Asp Leu Phe Arg Glu Leu Leu Asn Glu Leu Leu Glu Ala
1               5                   10                  15

Leu Xaa Gln Xaa Leu Xaa
            20

<210> SEQ ID NO 15
<211> LENGTH: 22
<212> TYPE: PRT
<213> ORGANISM: Artificial sequence
<220> FEATURE:
<223> OTHER INFORMATION: synthetic

<400> SEQUENCE: 15

Pro Val Leu Asp Leu Phe Arg Glu Leu Trp Asn Glu Leu Leu Glu Ala
1               5                   10                  15

Leu Lys Gln Lys Leu Lys
            20

<210> SEQ ID NO 16
<211> LENGTH: 22
<212> TYPE: PRT
<213> ORGANISM: Artificial sequence
<220> FEATURE:
<223> OTHER INFORMATION: synthetic

<400> SEQUENCE: 16

Pro Val Leu Asp Leu Leu Arg Glu Leu Leu Asn Glu Leu Leu Glu Ala
1               5                   10                  15

Leu Lys Gln Lys Leu Lys
            20

<210> SEQ ID NO 17
<211> LENGTH: 22
```

```
<212> TYPE: PRT
<213> ORGANISM: Artificial sequence
<220> FEATURE:
<223> OTHER INFORMATION: synthetic

<400> SEQUENCE: 17

Pro Val Leu Glu Leu Phe Lys Glu Leu Leu Gln Glu Leu Leu Glu Ala
1               5                   10                  15

Leu Lys Gln Lys Leu Lys
            20

<210> SEQ ID NO 18
<211> LENGTH: 22
<212> TYPE: PRT
<213> ORGANISM: Artificial sequence
<220> FEATURE:
<223> OTHER INFORMATION: synthetic

<400> SEQUENCE: 18

Gly Val Leu Asp Leu Phe Arg Glu Leu Leu Asn Glu Leu Leu Glu Ala
1               5                   10                  15

Leu Lys Gln Lys Leu Lys
            20

<210> SEQ ID NO 19
<211> LENGTH: 22
<212> TYPE: PRT
<213> ORGANISM: Artificial sequence
<220> FEATURE:
<223> OTHER INFORMATION: synthetic

<400> SEQUENCE: 19

Pro Val Leu Asp Leu Phe Arg Glu Leu Leu Asn Glu Gly Leu Glu Ala
1               5                   10                  15

Leu Lys Gln Lys Leu Lys
            20

<210> SEQ ID NO 20
<211> LENGTH: 22
<212> TYPE: PRT
<213> ORGANISM: Artificial sequence
<220> FEATURE:
<223> OTHER INFORMATION: synthetic

<400> SEQUENCE: 20

Pro Val Leu Asp Leu Phe Arg Glu Gly Leu Asn Glu Leu Leu Glu Ala
1               5                   10                  15

Leu Lys Gln Lys Leu Lys
            20

<210> SEQ ID NO 21
<211> LENGTH: 22
<212> TYPE: PRT
<213> ORGANISM: Artificial sequence
<220> FEATURE:
<223> OTHER INFORMATION: synthetic

<400> SEQUENCE: 21

Pro Val Leu Asp Leu Phe Arg Glu Leu Leu Asn Glu Leu Leu Glu Ala
1               5                   10                  15

Leu Lys Gln Lys Leu Lys
            20

<210> SEQ ID NO 22
```

```
<211> LENGTH: 22
<212> TYPE: PRT
<213> ORGANISM: Artificial sequence
<220> FEATURE:
<223> OTHER INFORMATION: synthetic

<400> SEQUENCE: 22

Pro Val Leu Asp Leu Phe Arg Glu Leu Leu Asn Glu Leu Leu Glu Gly
1               5                   10                  15

Leu Lys Gln Lys Leu Lys
            20

<210> SEQ ID NO 23
<211> LENGTH: 22
<212> TYPE: PRT
<213> ORGANISM: Artificial sequence
<220> FEATURE:
<223> OTHER INFORMATION: synthetic

<400> SEQUENCE: 23

Pro Leu Leu Glu Leu Phe Lys Glu Leu Leu Gln Glu Leu Leu Glu Ala
1               5                   10                  15

Leu Lys Gln Lys Leu Lys
            20

<210> SEQ ID NO 24
<211> LENGTH: 22
<212> TYPE: PRT
<213> ORGANISM: Artificial sequence
<220> FEATURE:
<223> OTHER INFORMATION: synthetic

<400> SEQUENCE: 24

Pro Val Leu Asp Leu Phe Arg Glu Leu Leu Asn Glu Leu Leu Glu Ala
1               5                   10                  15

Leu Gln Lys Lys Leu Lys
            20

<210> SEQ ID NO 25
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 25

Pro Val Leu Asp Phe Phe Arg Glu Leu Leu Asn Glu Xaa Leu Glu Ala
1               5                   10                  15

Leu Lys Gln Lys Leu Lys
            20

<210> SEQ ID NO 26
<211> LENGTH: 22
<212> TYPE: PRT
<213> ORGANISM: Artificial sequence
<220> FEATURE:
<223> OTHER INFORMATION: synthetic

<400> SEQUENCE: 26
```

```
Pro Val Leu Asp Leu Phe Arg Glu Leu Leu Asn Glu Leu Leu Glu Leu
1               5                   10                  15

Leu Lys Gln Lys Leu Lys
            20

<210> SEQ ID NO 27
<211> LENGTH: 22
<212> TYPE: PRT
<213> ORGANISM: Artificial sequence
<220> FEATURE:
<223> OTHER INFORMATION: synthetic

<400> SEQUENCE: 27

Pro Val Leu Asp Leu Phe Arg Glu Leu Leu Asn Glu Leu Glx Glu Ala
1               5                   10                  15

Leu Lys Gln Lys Leu Lys
            20

<210> SEQ ID NO 28
<211> LENGTH: 22
<212> TYPE: PRT
<213> ORGANISM: Artificial sequence
<220> FEATURE:
<223> OTHER INFORMATION: synthetic

<400> SEQUENCE: 28

Pro Val Leu Asp Leu Phe Arg Glu Leu Leu Asn Glu Leu Trp Glu Ala
1               5                   10                  15

Leu Lys Gln Lys Leu Lys
            20

<210> SEQ ID NO 29
<211> LENGTH: 22
<212> TYPE: PRT
<213> ORGANISM: Artificial sequence
<220> FEATURE:
<223> OTHER INFORMATION: synthetic

<400> SEQUENCE: 29

Ala Val Leu Asp Leu Phe Arg Glu Leu Leu Asn Glu Leu Leu Glu Ala
1               5                   10                  15

Leu Lys Gln Lys Leu Lys
            20

<210> SEQ ID NO 30
<211> LENGTH: 22
<212> TYPE: PRT
<213> ORGANISM: Artificial sequence
<220> FEATURE:
<223> OTHER INFORMATION: synthetic

<400> SEQUENCE: 30

Pro Val Leu Asp Leu Pro Arg Glu Leu Leu Asn Glu Leu Leu Glu Ala
1               5                   10                  15

Leu Lys Gln Lys Leu Lys
            20

<210> SEQ ID NO 31
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
```

```
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 31

Pro Val Leu Asp Leu Phe Leu Glu Leu Leu Asn Glu Xaa Leu Glu Ala
1               5                   10                  15

Leu Lys Gln Lys Leu Lys
            20

<210> SEQ ID NO 32
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (1)..(1)
<223> OTHER INFORMATION: Xaa can be any naturally occurring amino acid

<400> SEQUENCE: 32

Xaa Val Leu Asp Leu Phe Arg Glu Leu Leu Asn Glu Leu Leu Glu Ala
1               5                   10                  15

Leu Lys Gln Lys Leu Lys
            20

<210> SEQ ID NO 33
<211> LENGTH: 22
<212> TYPE: PRT
<213> ORGANISM: Artificial sequence
<220> FEATURE:
<223> OTHER INFORMATION: synthetic

<400> SEQUENCE: 33

Pro Val Leu Asp Leu Phe Arg Glu Lys Leu Asn Glu Leu Leu Glu Ala
1               5                   10                  15

Leu Lys Gln Lys Leu Lys
            20

<210> SEQ ID NO 34
<211> LENGTH: 22
<212> TYPE: PRT
<213> ORGANISM: Artificial sequence
<220> FEATURE:
<223> OTHER INFORMATION: synthetic

<400> SEQUENCE: 34

Pro Val Leu Asp Glx Phe Arg Glu Leu Leu Asn Glu Leu Leu Glu Ala
1               5                   10                  15

Leu Lys Gln Lys Leu Lys
            20

<210> SEQ ID NO 35
<211> LENGTH: 22
<212> TYPE: PRT
<213> ORGANISM: Artificial sequence
<220> FEATURE:
<223> OTHER INFORMATION: synthetic

<400> SEQUENCE: 35
```

```
Pro Val Leu Asp Trp Phe Arg Glu Leu Leu Asn Glu Leu Leu Glu Ala
1               5                   10                  15

Leu Lys Gln Lys Leu Lys
            20
```

<210> SEQ ID NO 36
<211> LENGTH: 22
<212> TYPE: PRT
<213> ORGANISM: Artificial sequence
<220> FEATURE:
<223> OTHER INFORMATION: synthetic

<400> SEQUENCE: 36

```
Pro Leu Leu Glu Leu Leu Lys Glu Leu Leu Gln Glu Leu Leu Glu Ala
1               5                   10                  15

Leu Lys Gln Lys Leu Lys
            20
```

<210> SEQ ID NO 37
<211> LENGTH: 22
<212> TYPE: PRT
<213> ORGANISM: Artificial sequence
<220> FEATURE:
<223> OTHER INFORMATION: synthetic

<400> SEQUENCE: 37

```
Pro Val Leu Asp Leu Phe Arg Glu Trp Leu Asn Glu Leu Leu Glu Ala
1               5                   10                  15

Leu Lys Gln Lys Leu Lys
            20
```

<210> SEQ ID NO 38
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 38

```
Pro Val Leu Asp Leu Phe Arg Glu Leu Leu Asn Glu Xaa Leu Glu Ala
1               5                   10                  15

Trp Lys Gln Lys Leu Lys
            20
```

<210> SEQ ID NO 39
<211> LENGTH: 22
<212> TYPE: PRT
<213> ORGANISM: Artificial sequence
<220> FEATURE:
<223> OTHER INFORMATION: synthetic

<400> SEQUENCE: 39

```
Pro Val Leu Asp Leu Phe Arg Glu Leu Leu Glu Glu Leu Leu Lys Ala
1               5                   10                  15

Leu Lys Lys Lys Leu Lys
            20
```

<210> SEQ ID NO 40

```
<211> LENGTH: 22
<212> TYPE: PRT
<213> ORGANISM: Artificial sequence
<220> FEATURE:
<223> OTHER INFORMATION: synthetic

<400> SEQUENCE: 40

Pro Val Leu Asp Leu Phe Asn Glu Leu Leu Arg Glu Leu Leu Glu Ala
1               5                   10                  15

Leu Gln Lys Lys Leu Lys
            20

<210> SEQ ID NO 41
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 41

Pro Val Leu Asp Leu Trp Arg Glu Leu Leu Asn Glu Xaa Leu Glu Ala
1               5                   10                  15

Leu Lys Gln Lys Leu Lys
            20

<210> SEQ ID NO 42
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 42

Pro Val Leu Asp Glu Phe Arg Glu Lys Leu Asn Glu Xaa Trp Glu Ala
1               5                   10                  15

Leu Lys Gln Lys Leu Lys
            20

<210> SEQ ID NO 43
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 43

Pro Val Leu Asp Glu Phe Arg Glu Lys Leu Trp Glu Xaa Leu Glu Ala
1               5                   10                  15
```

```
Leu Lys Gln Lys Leu Lys
            20

<210> SEQ ID NO 44
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 44

Pro Val Leu Asp Glu Phe Arg Glu Lys Leu Asn Glu Xaa Leu Glu Ala
1               5                   10                  15

Leu Lys Gln Lys Leu Lys
            20

<210> SEQ ID NO 45
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 45

Pro Val Leu Asp Glu Phe Arg Glu Lys Leu Asn Glu Xaa Leu Glu Ala
1               5                   10                  15

Leu Lys Gln Lys Leu Lys
            20

<210> SEQ ID NO 46
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 46

Pro Val Leu Asp Leu Phe Arg Glu Lys Leu Asn Glu Xaa Leu Glu Ala
1               5                   10                  15

Leu Lys Gln Lys Leu Lys
            20

<210> SEQ ID NO 47
<211> LENGTH: 21
<212> TYPE: PRT
<213> ORGANISM: Artificial sequence
<220> FEATURE:
```

<223> OTHER INFORMATION: synthetic

<400> SEQUENCE: 47

Val Leu Asp Leu Phe Arg Glu Leu Leu Asn Glu Gly Leu Glu Ala Leu
1               5                   10                  15

Lys Gln Lys Leu Lys
            20

<210> SEQ ID NO 48
<211> LENGTH: 22
<212> TYPE: PRT
<213> ORGANISM: Artificial sequence
<220> FEATURE:
<223> OTHER INFORMATION: synthetic

<400> SEQUENCE: 48

Pro Val Leu Asp Leu Phe Arg Glu Leu Leu Asn Glu Leu Leu Glu Ala
1               5                   10                  15

Leu Lys Gln Lys Leu Lys
            20

<210> SEQ ID NO 49
<211> LENGTH: 22
<212> TYPE: PRT
<213> ORGANISM: Artificial sequence
<220> FEATURE:
<223> OTHER INFORMATION: synthetic

<400> SEQUENCE: 49

Pro Val Leu Asp Leu Phe Arg Asn Leu Leu Glu Lys Leu Leu Glu Ala
1               5                   10                  15

Leu Glu Gln Lys Leu Lys
            20

<210> SEQ ID NO 50
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 50

Pro Val Leu Asp Leu Phe Arg Glu Leu Leu Trp Glu Xaa Leu Glu Ala
1               5                   10                  15

Leu Lys Gln Lys Leu Lys
            20

<210> SEQ ID NO 51
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 51

Pro Val Leu Asp Leu Phe Trp Glu Leu Leu Asn Glu Xaa Leu Glu Ala
1               5                   10                  15

Leu Lys Gln Lys Leu Lys
            20

<210> SEQ ID NO 52
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 52

Pro Val Trp Asp Glu Phe Arg Glu Lys Leu Asn Glu Xaa Leu Glu Ala
1               5                   10                  15

Leu Lys Gln Lys Leu Lys
            20

<210> SEQ ID NO 53
<211> LENGTH: 22
<212> TYPE: PRT
<213> ORGANISM: Artificial sequence
<220> FEATURE:
<223> OTHER INFORMATION: synthetic

<400> SEQUENCE: 53

Val Val Leu Asp Leu Phe Arg Glu Leu Leu Asn Glu Leu Leu Glu Ala
1               5                   10                  15

Leu Lys Gln Lys Leu Lys
            20

<210> SEQ ID NO 54
<211> LENGTH: 22
<212> TYPE: PRT
<213> ORGANISM: Artificial sequence
<220> FEATURE:
<223> OTHER INFORMATION: synthetic

<400> SEQUENCE: 54

Pro Val Leu Asp Leu Phe Arg Glu Leu Leu Asn Glu Trp Leu Glu Ala
1               5                   10                  15

Leu Lys Gln Lys Leu Lys
            20

<210> SEQ ID NO 55
<211> LENGTH: 19
<212> TYPE: PRT
<213> ORGANISM: Artificial sequence
<220> FEATURE:
<223> OTHER INFORMATION: synthetic

<400> SEQUENCE: 55

Pro Leu Phe Arg Glu Leu Leu Asn Glu Leu Leu Glu Ala Leu Lys Gln
1               5                   10                  15

Lys Leu Lys

<210> SEQ ID NO 56
<211> LENGTH: 22
<212> TYPE: PRT
<213> ORGANISM: Artificial sequence
<220> FEATURE:
<223> OTHER INFORMATION: synthetic

<400> SEQUENCE: 56

Pro Val Leu Asp Leu Phe Arg Glu Leu Leu Asn Glu Leu Leu Glu Ala
1               5                   10                  15

Leu Lys Gln Lys Lys Lys
            20

<210> SEQ ID NO 57
<211> LENGTH: 22
<212> TYPE: PRT
<213> ORGANISM: Artificial sequence
<220> FEATURE:
<223> OTHER INFORMATION: synthetic

<400> SEQUENCE: 57

Pro Val Leu Asp Leu Phe Arg Asn Leu Leu Glu Glu Leu Leu Lys Ala
1               5                   10                  15

Leu Glu Gln Lys Leu Lys
            20

<210> SEQ ID NO 58
<211> LENGTH: 21
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 58

Pro Val Leu Asp Glu Phe Arg Glu Lys Leu Asn Glu Xaa Leu Glu Ala
1               5                   10                  15

Leu Lys Gln Lys Leu
            20

<210> SEQ ID NO 59
<211> LENGTH: 22
<212> TYPE: PRT
<213> ORGANISM: Artificial sequence
<220> FEATURE:
<223> OTHER INFORMATION: synthetic

<400> SEQUENCE: 59

Leu Val Leu Asp Leu Phe Arg Glu Leu Leu Asn Glu Leu Leu Glu Ala
1               5                   10                  15

Leu Lys Gln Lys Leu Lys
            20

<210> SEQ ID NO 60
<211> LENGTH: 19
<212> TYPE: PRT
<213> ORGANISM: Artificial sequence
<220> FEATURE:
<223> OTHER INFORMATION: synthetic

<400> SEQUENCE: 60

Pro Val Leu Asp Leu Phe Arg Glu Leu Leu Asn Glu Leu Leu Glu Ala
1               5                   10                  15

Leu Lys Gln

<210> SEQ ID NO 61
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 61

Pro Val Leu Asp Glu Phe Arg Trp Lys Leu Asn Glu Xaa Leu Glu Ala
1               5                   10                  15

Leu Lys Gln Lys Leu Lys
            20

<210> SEQ ID NO 62
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 62

Pro Val Leu Asp Glu Trp Arg Glu Lys Leu Asn Glu Xaa Leu Glu Ala
1               5                   10                  15

Leu Lys Gln Lys Leu Lys
            20

<210> SEQ ID NO 63
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 63

Pro Val Leu Asp Phe Phe Arg Glu Lys Leu Asn Glu Xaa Leu Glu Ala
1               5                   10                  15

Leu Lys Gln Lys Leu Lys
            20

<210> SEQ ID NO 64
<211> LENGTH: 22

```
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 64

Pro Trp Leu Asp Glu Phe Arg Glu Lys Leu Asn Glu Xaa Leu Glu Ala
1               5                   10                  15

Leu Lys Gln Lys Leu Lys
            20

<210> SEQ ID NO 65
<211> LENGTH: 21
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (12)..(12)
<223> OTHER INFORMATION: Xaa can be any naturally occurring amino acid

<400> SEQUENCE: 65

Val Leu Asp Glu Phe Arg Glu Lys Leu Asn Glu Xaa Leu Glu Ala Leu
1               5                   10                  15

Lys Gln Lys Leu Lys
            20

<210> SEQ ID NO 66
<211> LENGTH: 22
<212> TYPE: PRT
<213> ORGANISM: Artificial sequence
<220> FEATURE:
<223> OTHER INFORMATION: synthetic

<400> SEQUENCE: 66

Pro Val Leu Asp Leu Phe Arg Asn Leu Leu Glu Glu Leu Leu Glu Ala
1               5                   10                  15

Leu Gln Lys Lys Leu Lys
            20

<210> SEQ ID NO 67
<211> LENGTH: 21
<212> TYPE: PRT
<213> ORGANISM: Artificial sequence
<220> FEATURE:
<223> OTHER INFORMATION: synthetic

<400> SEQUENCE: 67

Val Leu Asp Leu Phe Arg Glu Leu Leu Asn Glu Leu Leu Glu Ala Leu
1               5                   10                  15

Lys Gln Lys Leu Lys
            20

<210> SEQ ID NO 68
<211> LENGTH: 22
<212> TYPE: PRT
```

<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 68

Pro Val Leu Asp Glu Phe Arg Glu Leu Leu Lys Glu Xaa Leu Glu Ala
1               5                   10                  15

Leu Lys Gln Lys Leu Lys
            20

<210> SEQ ID NO 69
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 69

Pro Val Leu Asp Glu Phe Arg Lys Lys Leu Asn Glu Xaa Leu Glu Ala
1               5                   10                  15

Leu Lys Gln Lys Leu Lys
            20

<210> SEQ ID NO 70
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 70

Pro Val Leu Asp Glu Phe Arg Glu Leu Leu Tyr Glu Xaa Leu Glu Ala
1               5                   10                  15

Leu Lys Gln Lys Leu Lys
            20

<210> SEQ ID NO 71
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (14)..(14)
<223> OTHER INFORMATION: Xaa can be any naturally occurring amino acid

<400> SEQUENCE: 71

Pro Val Leu Asp Glu Phe Arg Glu Lys Leu Asn Glu Leu Xaa Glu Ala
1               5                   10                  15

Leu Lys Gln Lys Leu Lys
            20

<210> SEQ ID NO 72
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 72

Pro Val Leu Asp Leu Phe Arg Glu Leu Leu Asn Glu Xaa Leu Trp Ala
1               5                   10                  15

Leu Lys Gln Lys Leu Lys
            20

<210> SEQ ID NO 73
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 73

Pro Val Leu Asp Glu Phe Trp Glu Lys Leu Asn Glu Xaa Leu Glu Ala
1               5                   10                  15

Leu Lys Gln Lys Leu Lys
            20

<210> SEQ ID NO 74
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 74

Pro Val Leu Asp Lys Phe Arg Glu Lys Leu Asn Glu Xaa Leu Glu Ala
1               5                   10                  15

Leu Lys Gln Lys Leu Lys
            20

```
<210> SEQ ID NO 75
<211> LENGTH: 22
<212> TYPE: PRT
<213> ORGANISM: Artificial sequence
<220> FEATURE:
<223> OTHER INFORMATION: synthetic

<400> SEQUENCE: 75

Pro Val Leu Asp Glu Phe Arg Glu Lys Leu Asn Glu Glu Leu Glu Ala
1               5                   10                  15

Leu Lys Gln Lys Leu Lys
            20

<210> SEQ ID NO 76
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 76

Pro Val Leu Asp Glu Phe Arg Glu Leu Leu Phe Glu Xaa Leu Glu Ala
1               5                   10                  15

Leu Lys Gln Lys Leu Lys
            20

<210> SEQ ID NO 77
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 77

Pro Val Leu Asp Glu Phe Arg Glu Lys Leu Asn Lys Xaa Leu Glu Ala
1               5                   10                  15

Leu Lys Gln Lys Leu Lys
            20

<210> SEQ ID NO 78
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<222> LOCATION: (13)..(13)
<223> OTHER INFORMATION: Xaa can be any naturally occurring amino acid

<400> SEQUENCE: 78

Pro Val Leu Asp Glu Phe Arg Asp Lys Leu Asn Glu Xaa Leu Glu Ala
1               5                   10                  15

Leu Lys Gln Lys Leu Lys
```

20

```
<210> SEQ ID NO 79
<211> LENGTH: 22
<212> TYPE: PRT
<213> ORGANISM: Artificial sequence
<220> FEATURE:
<223> OTHER INFORMATION: synthetic

<400> SEQUENCE: 79

Pro Val Leu Asp Glu Phe Arg Glu Leu Leu Asn Glu Leu Leu Glu Ala
1               5                   10                  15

Leu Lys Gln Lys Leu Lys
            20

<210> SEQ ID NO 80
<211> LENGTH: 22
<212> TYPE: PRT
<213> ORGANISM: Artificial sequence
<220> FEATURE:
<223> OTHER INFORMATION: synthetic

<400> SEQUENCE: 80

Pro Val Leu Asp Leu Phe Glu Arg Leu Leu Asn Glu Leu Leu Glu Ala
1               5                   10                  15

Leu Gln Lys Lys Leu Lys
            20

<210> SEQ ID NO 81
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 81

Pro Val Leu Asp Glu Phe Arg Glu Lys Leu Asn Trp Xaa Leu Glu Ala
1               5                   10                  15

Leu Lys Gln Lys Leu Lys
            20

<210> SEQ ID NO 82
<211> LENGTH: 20
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (11)..(11)
<223> OTHER INFORMATION: Xaa can be any naturally occurring amino acid

<400> SEQUENCE: 82

Leu Asp Glu Phe Arg Glu Lys Leu Asn Glu Xaa Leu Glu Ala Leu Lys
1               5                   10                  15

Gln Lys Leu Lys
            20
```

```
<210> SEQ ID NO 83
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 83

Pro Val Leu Asp Glu Phe Arg Glu Lys Leu Asn Glu Xaa Leu Glu Ala
1               5                   10                  15

Leu Trp Gln Lys Leu Lys
            20

<210> SEQ ID NO 84
<211> LENGTH: 22
<212> TYPE: PRT
<213> ORGANISM: Artificial sequence
<220> FEATURE:
<223> OTHER INFORMATION: synthetic

<400> SEQUENCE: 84

Pro Val Leu Asp Glu Phe Arg Glu Lys Leu Asn Glu Leu Leu Glu Ala
1               5                   10                  15

Leu Lys Gln Lys Leu Lys
            20

<210> SEQ ID NO 85
<211> LENGTH: 21
<212> TYPE: PRT
<213> ORGANISM: Artificial sequence
<220> FEATURE:
<223> OTHER INFORMATION: synthetic

<400> SEQUENCE: 85

Pro Leu Asp Leu Phe Arg Glu Leu Leu Asn Glu Leu Leu Glu Ala Leu
1               5                   10                  15

Lys Gln Lys Leu Lys
            20

<210> SEQ ID NO 86
<211> LENGTH: 22
<212> TYPE: PRT
<213> ORGANISM: Artificial sequence
<220> FEATURE:
<223> OTHER INFORMATION: synthetic

<400> SEQUENCE: 86

Pro Val Leu Glu Leu Phe Glu Arg Leu Leu Asp Glu Leu Leu Asn Ala
1               5                   10                  15

Leu Gln Lys Lys Leu Lys
            20

<210> SEQ ID NO 87
<211> LENGTH: 22
<212> TYPE: PRT
<213> ORGANISM: Artificial sequence
<220> FEATURE:
<223> OTHER INFORMATION: synthetic
```

<400> SEQUENCE: 87

Pro Leu Leu Glu Leu Leu Lys Glu Leu Leu Gln Glu Leu Leu Glu Ala
1               5                   10                  15

Leu Lys Gln Lys Leu Lys
            20

<210> SEQ ID NO 88
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 88

Pro Val Leu Asp Lys Phe Arg Glu Leu Leu Asn Glu Xaa Leu Glu Ala
1               5                   10                  15

Leu Lys Gln Lys Leu Lys
            20

<210> SEQ ID NO 89
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 89

Pro Val Leu Asp Glu Phe Arg Glu Lys Leu Asn Glu Xaa Leu Trp Ala
1               5                   10                  15

Leu Lys Gln Lys Leu Lys
            20

<210> SEQ ID NO 90
<211> LENGTH: 19
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (10)..(10)
<223> OTHER INFORMATION: Xaa can be any naturally occurring amino acid

<400> SEQUENCE: 90

Asp Glu Phe Arg Glu Lys Leu Asn Glu Xaa Leu Glu Ala Leu Lys Gln
1               5                   10                  15

Lys Leu Lys

<210> SEQ ID NO 91

```
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 91

Pro Val Leu Asp Glu Phe Arg Glu Leu Leu Asn Glu Xaa Leu Glu Ala
1               5                   10                  15

Leu Lys Gln Lys Leu Lys
            20

<210> SEQ ID NO 92
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 92

Pro Val Leu Asp Glu Phe Arg Glu Leu Tyr Asn Glu Xaa Leu Glu Ala
1               5                   10                  15

Leu Lys Gln Lys Leu Lys
            20

<210> SEQ ID NO 93
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 93

Pro Val Leu Asp Glu Phe Arg Glu Lys Leu Asn Glu Xaa Leu Lys Ala
1               5                   10                  15

Leu Lys Gln Lys Leu Lys
            20

<210> SEQ ID NO 94
<211> LENGTH: 22
<212> TYPE: PRT
<213> ORGANISM: Artificial sequence
<220> FEATURE:
<223> OTHER INFORMATION: synthetic

<400> SEQUENCE: 94

Pro Val Leu Asp Glu Phe Arg Glu Lys Leu Asn Glu Ala Leu Glu Ala
1               5                   10                  15
```

Leu Lys Gln Lys Leu Lys
            20

<210> SEQ ID NO 95
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 95

Pro Val Leu Asp Leu Phe Arg Glu Leu Leu Asn Leu Xaa Leu Glu Ala
1               5                   10                  15

Leu Lys Gln Lys Leu Lys
            20

<210> SEQ ID NO 96
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 96

Pro Val Leu Asp Leu Phe Arg Glu Leu Leu Asn Glu Xaa Leu Glu Ala
1               5                   10                  15

Leu Lys Gln Lys Leu Lys
            20

<210> SEQ ID NO 97
<211> LENGTH: 15
<212> TYPE: PRT
<213> ORGANISM: Artificial sequence
<220> FEATURE:
<223> OTHER INFORMATION: synthetic

<400> SEQUENCE: 97

Pro Val Leu Asp Leu Phe Arg Glu Leu Leu Asn Glu Leu Leu Glu
1               5                   10                  15

<210> SEQ ID NO 98
<211> LENGTH: 22
<212> TYPE: PRT
<213> ORGANISM: Artificial sequence
<220> FEATURE:
<223> OTHER INFORMATION: synthetic

<400> SEQUENCE: 98

Pro Val Leu Asp Leu Phe Arg Glu Leu Leu Asn Glu Glu Leu Glu Ala
1               5                   10                  15

Leu Lys Gln Lys Leu Lys
            20

```
<210> SEQ ID NO 99
<211> LENGTH: 22
<212> TYPE: PRT
<213> ORGANISM: Artificial sequence
<220> FEATURE:
<223> OTHER INFORMATION: synthetic

<400> SEQUENCE: 99

Lys Leu Lys Gln Lys Leu Ala Glu Leu Leu Glu Asn Leu Leu Glu Arg
1               5                   10                  15

Phe Leu Asp Leu Val Pro
            20

<210> SEQ ID NO 100
<211> LENGTH: 22
<212> TYPE: PRT
<213> ORGANISM: Artificial sequence
<220> FEATURE:
<223> OTHER INFORMATION: synthetic

<400> SEQUENCE: 100

Pro Val Leu Asp Leu Phe Arg Glu Leu Leu Asn Glu Leu Leu Glu Ala
1               5                   10                  15

Leu Lys Gln Lys Leu Lys
            20

<210> SEQ ID NO 101
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 101

Pro Val Leu Asp Leu Phe Arg Glu Leu Leu Asn Trp Xaa Leu Glu Ala
1               5                   10                  15

Leu Lys Gln Lys Leu Lys
            20

<210> SEQ ID NO 102
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 102

Pro Val Leu Asp Leu Phe Arg Glu Leu Leu Asn Leu Xaa Leu Glu Ala
1               5                   10                  15

Leu Lys Glu Lys Leu Lys
            20
```

```
<210> SEQ ID NO 103
<211> LENGTH: 22
<212> TYPE: PRT
<213> ORGANISM: Artificial sequence
<220> FEATURE:
<223> OTHER INFORMATION: synthetic

<400> SEQUENCE: 103

Pro Val Leu Asp Glu Phe Arg Glu Leu Leu Asn Glu Glu Leu Glu Ala
1               5                   10                  15

Leu Lys Gln Lys Leu Lys
            20

<210> SEQ ID NO 104
<211> LENGTH: 15
<212> TYPE: PRT
<213> ORGANISM: Artificial sequence
<220> FEATURE:
<223> OTHER INFORMATION: synthetic

<400> SEQUENCE: 104

Pro Leu Leu Asn Glu Leu Leu Glu Ala Leu Lys Gln Lys Leu Lys
1               5                   10                  15

<210> SEQ ID NO 105
<211> LENGTH: 22
<212> TYPE: PRT
<213> ORGANISM: Artificial sequence
<220> FEATURE:
<223> OTHER INFORMATION: synthetic

<400> SEQUENCE: 105

Pro Ala Ala Asp Ala Phe Arg Glu Ala Ala Asn Glu Ala Ala Glu Ala
1               5                   10                  15

Ala Lys Gln Lys Ala Lys
            20

<210> SEQ ID NO 106
<211> LENGTH: 22
<212> TYPE: PRT
<213> ORGANISM: Artificial sequence
<220> FEATURE:
<223> OTHER INFORMATION: synthetic

<400> SEQUENCE: 106

Pro Val Leu Asp Leu Phe Arg Glu Lys Leu Asn Glu Glu Leu Glu Ala
1               5                   10                  15

Leu Lys Gln Lys Leu Lys
            20

<210> SEQ ID NO 107
<211> LENGTH: 22
<212> TYPE: PRT
<213> ORGANISM: Artificial sequence
<220> FEATURE:
<223> OTHER INFORMATION: synthetic

<400> SEQUENCE: 107

Lys Leu Lys Gln Lys Leu Ala Glu Leu Leu Glu Asn Leu Leu Glu Arg
1               5                   10                  15

Phe Leu Asp Leu Val Pro
            20

<210> SEQ ID NO 108
<211> LENGTH: 22
```

```
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 108

Pro Val Leu Asp Leu Phe Arg Trp Leu Leu Asn Glu Xaa Leu Glu Ala
1               5                   10                  15

Leu Lys Gln Lys Leu Lys
            20

<210> SEQ ID NO 109
<211> LENGTH: 22
<212> TYPE: PRT
<213> ORGANISM: Artificial sequence
<220> FEATURE:
<223> OTHER INFORMATION: synthetic

<400> SEQUENCE: 109

Pro Val Leu Asp Glu Phe Arg Glu Lys Leu Asn Glu Arg Leu Glu Ala
1               5                   10                  15

Leu Lys Gln Lys Leu Lys
            20

<210> SEQ ID NO 110
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(14)
<223> OTHER INFORMATION: Xaa can be any naturally occurring amino acid

<400> SEQUENCE: 110

Pro Val Leu Asp Glu Phe Arg Glu Lys Leu Asn Glu Xaa Xaa Glu Ala
1               5                   10                  15

Leu Lys Gln Lys Leu Lys
            20

<210> SEQ ID NO 111
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 111

Pro Val Leu Asp Glu Phe Arg Glu Lys Leu Trp Glu Xaa Trp Glu Ala
1               5                   10                  15
```

Leu Lys Gln Lys Leu Lys
            20

<210> SEQ ID NO 112
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 112

Pro Val Leu Asp Glu Phe Arg Glu Lys Leu Asn Glu Xaa Ser Glu Ala
1               5                   10                  15

Leu Lys Gln Lys Leu Lys
            20

<210> SEQ ID NO 113
<211> LENGTH: 22
<212> TYPE: PRT
<213> ORGANISM: Artificial sequence
<220> FEATURE:
<223> OTHER INFORMATION: synthetic

<400> SEQUENCE: 113

Pro Val Leu Asp Glu Phe Arg Glu Lys Leu Asn Glu Pro Leu Glu Ala
1               5                   10                  15

Leu Lys Gln Lys Leu Lys
            20

<210> SEQ ID NO 114
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 114

Pro Val Leu Asp Glu Phe Arg Glu Lys Leu Asn Glu Xaa Met Glu Ala
1               5                   10                  15

Leu Lys Gln Lys Leu Lys
            20

<210> SEQ ID NO 115
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

```
<400> SEQUENCE: 115

Pro Lys Leu Asp Glu Phe Arg Glu Lys Leu Asn Glu Xaa Leu Glu Ala
1               5                   10                  15

Leu Lys Gln Lys Leu Lys
            20

<210> SEQ ID NO 116
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 116

Pro His Leu Asp Glu Phe Arg Glu Lys Leu Asn Glu Xaa Leu Glu Ala
1               5                   10                  15

Leu Lys Gln Lys Leu Lys
            20

<210> SEQ ID NO 117
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 117

Pro Glu Leu Asp Glu Phe Arg Glu Lys Leu Asn Glu Xaa Leu Glu Ala
1               5                   10                  15

Leu Lys Gln Lys Leu Lys
            20

<210> SEQ ID NO 118
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (13)..(13)
<223> OTHER INFORMATION: Xaa can be any naturally occurring amino acid

<400> SEQUENCE: 118

Pro Val Leu Asp Glu Phe Arg Glu Lys Leu Asn Glu Xaa Leu Glu Ala
1               5                   10                  15

Leu Glu Gln Lys Leu Lys
            20
```

```
<210> SEQ ID NO 119
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (17)..(17)
<223> OTHER INFORMATION: Xaa can be any naturally occurring amino acid

<400> SEQUENCE: 119

Pro Val Leu Asp Glu Phe Arg Glu Lys Leu Asn Glu Glu Leu Glu Ala
1               5                   10                  15

Xaa Lys Gln Lys Leu Lys
            20

<210> SEQ ID NO 120
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Aib
<220> FEATURE:
<221> NAME/KEY: misc_feature
<222> LOCATION: (16)..(16)
<223> OTHER INFORMATION: Xaa can be any naturally occurring amino acid

<400> SEQUENCE: 120

Pro Val Leu Asp Glu Phe Arg Glu Lys Leu Asn Glu Glu Leu Glu Xaa
1               5                   10                  15

Leu Lys Gln Lys Leu Lys
            20

<210> SEQ ID NO 121
<211> LENGTH: 22
<212> TYPE: PRT
<213> ORGANISM: Artificial sequence
<220> FEATURE:
<223> OTHER INFORMATION: synthetic

<400> SEQUENCE: 121

Pro Val Leu Asp Glu Phe Arg Glu Lys Leu Asn Glu Glu Leu Glu Ala
1               5                   10                  15

Leu Trp Gln Lys Leu Lys
            20

<210> SEQ ID NO 122
<211> LENGTH: 22
<212> TYPE: PRT
<213> ORGANISM: Artificial sequence
<220> FEATURE:
<223> OTHER INFORMATION: synthetic

<400> SEQUENCE: 122

Pro Val Leu Asp Glu Phe Arg Glu Lys Leu Asn Glu Glu Leu Glu Trp
1               5                   10                  15

Leu Lys Gln Lys Leu Lys
            20

<210> SEQ ID NO 123
```

-continued

```
<211> LENGTH: 22
<212> TYPE: PRT
<213> ORGANISM: Artificial sequence
<220> FEATURE:
<223> OTHER INFORMATION: synthetic

<400> SEQUENCE: 123

Gln Val Leu Asp Leu Phe Arg Glu Leu Leu Asn Glu Leu Leu Glu Ala
1               5                   10                  15

Leu Lys Gln Lys Leu Lys
            20

<210> SEQ ID NO 124
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Orn
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 124

Pro Val Leu Asp Leu Phe Xaa Glu Leu Leu Asn Glu Leu Leu Glu Ala
1               5                   10                  15

Leu Xaa Gln Xaa Leu Xaa
            20

<210> SEQ ID NO 125
<211> LENGTH: 22
<212> TYPE: PRT
<213> ORGANISM: Artificial sequence
<220> FEATURE:
<223> OTHER INFORMATION: synthetic

<400> SEQUENCE: 125

Asn Val Leu Asp Leu Phe Arg Glu Leu Leu Asn Glu Leu Leu Glu Ala
1               5                   10                  15

Leu Lys Gln Lys Leu Lys
            20

<210> SEQ ID NO 126
<211> LENGTH: 22
<212> TYPE: PRT
<213> ORGANISM: Artificial sequence
<220> FEATURE:
<223> OTHER INFORMATION: synthetic

<400> SEQUENCE: 126

Pro Val Leu Asp Leu Phe Arg Glu Leu Leu Asn Glu Leu Gly Glu Ala
1               5                   10                  15

Leu Lys Gln Lys Leu Lys
```

20

<210> SEQ ID NO 127
<211> LENGTH: 22
<212> TYPE: PRT
<213> ORGANISM: Artificial sequence
<220> FEATURE:
<223> OTHER INFORMATION: synthetic

<400> SEQUENCE: 127

Pro Val Leu Asp Leu Phe Arg Glu Leu Leu Asn Glu Leu Leu Glu Leu
1               5                   10                  15

Leu Lys Gln Lys Leu Lys
            20

<210> SEQ ID NO 128
<211> LENGTH: 22
<212> TYPE: PRT
<213> ORGANISM: Artificial sequence
<220> FEATURE:
<223> OTHER INFORMATION: synthetic

<400> SEQUENCE: 128

Pro Val Leu Asp Leu Phe Arg Glu Leu Leu Asn Glu Leu Leu Glu Phe
1               5                   10                  15

Leu Lys Gln Lys Leu Lys
            20

<210> SEQ ID NO 129
<211> LENGTH: 22
<212> TYPE: PRT
<213> ORGANISM: Artificial sequence
<220> FEATURE:
<223> OTHER INFORMATION: synthetic

<400> SEQUENCE: 129

Pro Val Leu Glu Leu Phe Asn Asp Leu Leu Arg Glu Leu Leu Glu Ala
1               5                   10                  15

Leu Gln Lys Lys Leu Lys
            20

<210> SEQ ID NO 130
<211> LENGTH: 22
<212> TYPE: PRT
<213> ORGANISM: Artificial sequence
<220> FEATURE:
<223> OTHER INFORMATION: synthetic

<400> SEQUENCE: 130

Pro Val Leu Glu Leu Phe Asn Asp Leu Leu Arg Glu Leu Leu Glu Ala
1               5                   10                  15

Leu Lys Gln Lys Leu Lys
            20

<210> SEQ ID NO 131
<211> LENGTH: 22
<212> TYPE: PRT
<213> ORGANISM: Artificial sequence
<220> FEATURE:
<223> OTHER INFORMATION: synthetic

<400> SEQUENCE: 131

Pro Val Leu Glu Leu Phe Lys Glu Leu Leu Asn Glu Leu Leu Asp Ala
1               5                   10                  15

Leu Arg Gln Lys Leu Lys
            20

<210> SEQ ID NO 132
<211> LENGTH: 22
<212> TYPE: PRT
<213> ORGANISM: Artificial sequence
<220> FEATURE:
<223> OTHER INFORMATION: synthetic

<400> SEQUENCE: 132

Pro Val Leu Asp Leu Phe Arg Glu Leu Leu Glu Asn Leu Leu Glu Ala
1               5                   10                  15

Leu Gln Lys Lys Leu Lys
            20

<210> SEQ ID NO 133
<211> LENGTH: 22
<212> TYPE: PRT
<213> ORGANISM: Artificial sequence
<220> FEATURE:
<223> OTHER INFORMATION: synthetic

<400> SEQUENCE: 133

Pro Val Leu Glu Leu Phe Glu Arg Leu Leu Glu Asp Leu Leu Gln Ala
1               5                   10                  15

Leu Asn Lys Lys Leu Lys
            20

<210> SEQ ID NO 134
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Orn
<220> FEATURE:
<221> NAME/KEY: misc_feature
<222> LOCATION: (19)..(19)
<223> OTHER INFORMATION: Xaa can be any naturally occurring amino acid

<400> SEQUENCE: 134

Pro Val Leu Glu Leu Phe Glu Arg Leu Leu Glu Asp Leu Leu Lys Ala
1               5                   10                  15

Leu Asn Xaa Lys Leu Lys
            20

<210> SEQ ID NO 135
<211> LENGTH: 22
<212> TYPE: PRT
<213> ORGANISM: Artificial sequence
<220> FEATURE:
<223> OTHER INFORMATION: synthetic

<400> SEQUENCE: 135

Asp Val Leu Asp Leu Phe Arg Glu Leu Leu Asn Glu Leu Leu Glu Ala
1               5                   10                  15

Leu Lys Gln Lys Leu Lys
            20

<210> SEQ ID NO 136
<211> LENGTH: 22
<212> TYPE: PRT
<213> ORGANISM: Artificial sequence
<220> FEATURE:
<223> OTHER INFORMATION: synthetic

<400> SEQUENCE: 136

Pro Ala Leu Glu Leu Phe Lys Asp Leu Leu Gln Glu Leu Leu Glu Ala
1               5                   10                  15

Leu Lys Gln Lys Leu Lys
            20

<210> SEQ ID NO 137
<211> LENGTH: 22
<212> TYPE: PRT
<213> ORGANISM: Artificial sequence
<220> FEATURE:
<223> OTHER INFORMATION: synthetic

<400> SEQUENCE: 137

Pro Val Leu Asp Leu Phe Arg Glu Leu Leu Asn Glu Gly Leu Glu Ala
1               5                   10                  15

Glx Lys Gln Lys Leu Lys
            20

<210> SEQ ID NO 138
<211> LENGTH: 22
<212> TYPE: PRT
<213> ORGANISM: Artificial sequence
<220> FEATURE:
<223> OTHER INFORMATION: synthetic

<400> SEQUENCE: 138

Pro Val Leu Asp Leu Phe Arg Glu Leu Leu Asn Glu Gly Leu Glu Trp
1               5                   10                  15

Leu Lys Gln Lys Leu Lys
            20

<210> SEQ ID NO 139
<211> LENGTH: 22
<212> TYPE: PRT
<213> ORGANISM: Artificial sequence
<220> FEATURE:
<223> OTHER INFORMATION: synthetic

<400> SEQUENCE: 139

Pro Val Leu Asp Leu Phe Arg Glu Leu Trp Asn Glu Gly Leu Glu Ala
1               5                   10                  15

Leu Lys Gln Lys Leu Lys
            20

<210> SEQ ID NO 140
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Orn
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 140

Pro Val Leu Asp Leu Phe Arg Glu Leu Leu Asn Glu Gly Leu Glu Ala
1               5                   10                  15

Leu Xaa Gln Xaa Leu Xaa
            20

<210> SEQ ID NO 141
<211> LENGTH: 22
<212> TYPE: PRT
<213> ORGANISM: Artificial sequence
<220> FEATURE:
<223> OTHER INFORMATION: synthetic

<400> SEQUENCE: 141

Pro Val Leu Asp Phe Phe Arg Glu Leu Leu Asn Glu Gly Leu Glu Ala
1               5                   10                  15

Leu Lys Gln Lys Leu Lys
            20

<210> SEQ ID NO 142
<211> LENGTH: 22
<212> TYPE: PRT
<213> ORGANISM: Artificial sequence
<220> FEATURE:
<223> OTHER INFORMATION: synthetic

<400> SEQUENCE: 142

Pro Val Leu Glu Leu Phe Arg Glu Leu Leu Asn Glu Gly Leu Glu Ala
1               5                   10                  15

Leu Lys Gln Lys Leu Lys
            20

<210> SEQ ID NO 143
<211> LENGTH: 22
<212> TYPE: PRT
<213> ORGANISM: Artificial sequence
<220> FEATURE:
<223> OTHER INFORMATION: synthetic

<400> SEQUENCE: 143

Pro Val Leu Asp Leu Phe Arg Glu Leu Leu Asn Glu Gly Leu Glu Ala
1               5                   10                  15

Leu Lys Gln Lys Leu Lys
            20

<210> SEQ ID NO 144
<211> LENGTH: 22
<212> TYPE: PRT
<213> ORGANISM: Artificial sequence
<220> FEATURE:
<223> OTHER INFORMATION: synthetic

<400> SEQUENCE: 144

Pro Val Leu Glu Leu Phe Glu Asn Leu Leu Glu Arg Leu Leu Asp Ala
1               5                   10                  15

Leu Gln Lys Lys Leu Lys
            20

<210> SEQ ID NO 145
<211> LENGTH: 22
<212> TYPE: PRT

```
<213> ORGANISM: Artificial sequence
<220> FEATURE:
<223> OTHER INFORMATION: synthetic

<400> SEQUENCE: 145

Gly Val Leu Glu Leu Phe Glu Asn Leu Glu Arg Leu Leu Asp Ala
1               5                   10                  15

Leu Gln Lys Lys Leu Lys
            20

<210> SEQ ID NO 146
<211> LENGTH: 22
<212> TYPE: PRT
<213> ORGANISM: Artificial sequence
<220> FEATURE:
<223> OTHER INFORMATION: synthetic

<400> SEQUENCE: 146

Pro Val Leu Glu Leu Phe Glu Asn Leu Glu Arg Leu Leu Asp Ala
1               5                   10                  15

Leu Gln Lys Lys Leu Lys
            20

<210> SEQ ID NO 147
<211> LENGTH: 22
<212> TYPE: PRT
<213> ORGANISM: Artificial sequence
<220> FEATURE:
<223> OTHER INFORMATION: synthetic

<400> SEQUENCE: 147

Pro Val Leu Glu Leu Phe Glu Asn Leu Glu Arg Leu Phe Asp Ala
1               5                   10                  15

Leu Gln Lys Lys Leu Lys
            20

<210> SEQ ID NO 148
<211> LENGTH: 22
<212> TYPE: PRT
<213> ORGANISM: Artificial sequence
<220> FEATURE:
<223> OTHER INFORMATION: synthetic

<400> SEQUENCE: 148

Pro Val Leu Glu Leu Phe Glu Asn Leu Glu Arg Leu Gly Asp Ala
1               5                   10                  15

Leu Gln Lys Lys Leu Lys
            20

<210> SEQ ID NO 149
<211> LENGTH: 22
<212> TYPE: PRT
<213> ORGANISM: Artificial sequence
<220> FEATURE:
<223> OTHER INFORMATION: synthetic

<400> SEQUENCE: 149

Pro Val Leu Glu Leu Phe Glu Asn Leu Trp Glu Arg Leu Leu Asp Ala
1               5                   10                  15

Leu Gln Lys Lys Leu Lys
            20

<210> SEQ ID NO 150
<211> LENGTH: 22
```

```
<212> TYPE: PRT
<213> ORGANISM: Artificial sequence
<220> FEATURE:
<223> OTHER INFORMATION: synthetic

<400> SEQUENCE: 150

Pro Leu Leu Glu Leu Phe Glu Asn Leu Leu Glu Arg Leu Leu Asp Ala
1               5                   10                  15

Leu Gln Lys Lys Leu Lys
            20

<210> SEQ ID NO 151
<211> LENGTH: 22
<212> TYPE: PRT
<213> ORGANISM: Artificial sequence
<220> FEATURE:
<223> OTHER INFORMATION: synthetic

<400> SEQUENCE: 151

Pro Val Leu Glu Leu Phe Glu Asn Leu Gly Glu Arg Leu Leu Asp Ala
1               5                   10                  15

Leu Gln Lys Lys Leu Lys
            20

<210> SEQ ID NO 152
<211> LENGTH: 22
<212> TYPE: PRT
<213> ORGANISM: Artificial sequence
<220> FEATURE:
<223> OTHER INFORMATION: synthetic

<400> SEQUENCE: 152

Pro Val Phe Glu Leu Phe Glu Asn Leu Leu Glu Arg Leu Leu Asp Ala
1               5                   10                  15

Leu Gln Lys Lys Leu Lys
            20

<210> SEQ ID NO 153
<211> LENGTH: 22
<212> TYPE: PRT
<213> ORGANISM: Artificial sequence
<220> FEATURE:
<223> OTHER INFORMATION: synthetic

<400> SEQUENCE: 153

Ala Val Leu Glu Leu Phe Glu Asn Leu Leu Glu Arg Leu Leu Asp Ala
1               5                   10                  15

Leu Gln Lys Lys Leu Lys
            20

<210> SEQ ID NO 154
<211> LENGTH: 22
<212> TYPE: PRT
<213> ORGANISM: Artificial sequence
<220> FEATURE:
<223> OTHER INFORMATION: synthetic

<400> SEQUENCE: 154

Pro Val Leu Glu Leu Phe Glu Asn Leu Leu Glu Arg Gly Leu Asp Ala
1               5                   10                  15

Leu Gln Lys Lys Leu Lys
            20

<210> SEQ ID NO 155
```

```
<211> LENGTH: 22
<212> TYPE: PRT
<213> ORGANISM: Artificial sequence
<220> FEATURE:
<223> OTHER INFORMATION: synthetic

<400> SEQUENCE: 155

Pro Val Leu Glu Leu Phe Leu Asn Leu Trp Glu Arg Leu Leu Asp Ala
1               5                   10                  15

Leu Gln Lys Lys Leu Lys
            20

<210> SEQ ID NO 156
<211> LENGTH: 22
<212> TYPE: PRT
<213> ORGANISM: Artificial sequence
<220> FEATURE:
<223> OTHER INFORMATION: synthetic

<400> SEQUENCE: 156

Pro Val Leu Glu Leu Phe Leu Asn Leu Leu Glu Arg Leu Leu Asp Ala
1               5                   10                  15

Leu Gln Lys Lys Leu Lys
            20

<210> SEQ ID NO 157
<211> LENGTH: 22
<212> TYPE: PRT
<213> ORGANISM: Artificial sequence
<220> FEATURE:
<223> OTHER INFORMATION: synthetic

<400> SEQUENCE: 157

Pro Val Leu Glu Phe Phe Glu Asn Leu Leu Glu Arg Leu Leu Asp Ala
1               5                   10                  15

Leu Gln Lys Lys Leu Lys
            20

<210> SEQ ID NO 158
<211> LENGTH: 22
<212> TYPE: PRT
<213> ORGANISM: Artificial sequence
<220> FEATURE:
<223> OTHER INFORMATION: synthetic

<400> SEQUENCE: 158

Pro Val Leu Glu Leu Phe Leu Asn Leu Leu Glu Arg Leu Leu Asp Trp
1               5                   10                  15

Leu Gln Lys Lys Leu Lys
            20

<210> SEQ ID NO 159
<211> LENGTH: 22
<212> TYPE: PRT
<213> ORGANISM: Artificial sequence
<220> FEATURE:
<223> OTHER INFORMATION: synthetic

<400> SEQUENCE: 159

Pro Val Leu Asp Leu Phe Glu Asn Leu Leu Glu Arg Leu Leu Asp Ala
1               5                   10                  15

Leu Gln Lys Lys Leu Lys
            20
```

<210> SEQ ID NO 160
<211> LENGTH: 22
<212> TYPE: PRT
<213> ORGANISM: Artificial sequence
<220> FEATURE:
<223> OTHER INFORMATION: synthetic

<400> SEQUENCE: 160

Pro Val Leu Glu Leu Phe Glu Asn Leu Leu Glu Arg Leu Leu Asp Trp
1               5                   10                  15

Leu Gln Lys Lys Leu Lys
            20

<210> SEQ ID NO 161
<211> LENGTH: 22
<212> TYPE: PRT
<213> ORGANISM: Artificial sequence
<220> FEATURE:
<223> OTHER INFORMATION: synthetic

<400> SEQUENCE: 161

Pro Val Leu Glu Leu Phe Glu Asn Leu Leu Glu Arg Leu Leu Glu Ala
1               5                   10                  15

Leu Gln Lys Lys Leu Lys
            20

<210> SEQ ID NO 162
<211> LENGTH: 22
<212> TYPE: PRT
<213> ORGANISM: Artificial sequence
<220> FEATURE:
<223> OTHER INFORMATION: synthetic

<400> SEQUENCE: 162

Pro Val Leu Glu Leu Phe Glu Asn Trp Leu Glu Arg Leu Leu Asp Ala
1               5                   10                  15

Leu Gln Lys Lys Leu Lys
            20

<210> SEQ ID NO 163
<211> LENGTH: 22
<212> TYPE: PRT
<213> ORGANISM: Artificial sequence
<220> FEATURE:
<223> OTHER INFORMATION: synthetic

<400> SEQUENCE: 163

Pro Val Leu Glu Leu Phe Glu Asn Leu Leu Glu Arg Leu Trp Asp Ala
1               5                   10                  15

Leu Gln Lys Lys Leu Lys
            20

<210> SEQ ID NO 164
<211> LENGTH: 22
<212> TYPE: PRT
<213> ORGANISM: Artificial sequence
<220> FEATURE:
<223> OTHER INFORMATION: synthetic

<400> SEQUENCE: 164

Pro Val Leu Glu Leu Phe Glu Asn Leu Leu Glu Arg Leu Leu Asp Ala
1               5                   10                  15

Trp Gln Lys Lys Leu Lys
            20

<210> SEQ ID NO 165
<211> LENGTH: 22
<212> TYPE: PRT
<213> ORGANISM: Artificial sequence
<220> FEATURE:
<223> OTHER INFORMATION: synthetic

<400> SEQUENCE: 165

Pro Val Leu Glu Leu Phe Glu Asn Leu Leu Glu Arg Leu Leu Asp Leu
1               5                   10                  15

Leu Gln Lys Lys Leu Lys
            20

<210> SEQ ID NO 166
<211> LENGTH: 22
<212> TYPE: PRT
<213> ORGANISM: Artificial sequence
<220> FEATURE:
<223> OTHER INFORMATION: synthetic

<400> SEQUENCE: 166

Pro Val Leu Glu Leu Phe Leu Asn Leu Leu Glu Lys Leu Leu Asp Ala
1               5                   10                  15

Leu Gln Lys Lys Leu Lys
            20

<210> SEQ ID NO 167
<211> LENGTH: 22
<212> TYPE: PRT
<213> ORGANISM: Artificial sequence
<220> FEATURE:
<223> OTHER INFORMATION: synthetic

<400> SEQUENCE: 167

Pro Val Leu Glu Leu Phe Glu Asn Gly Leu Glu Arg Leu Leu Asp Ala
1               5                   10                  15

Leu Gln Lys Lys Leu Lys
            20

<210> SEQ ID NO 168
<211> LENGTH: 22
<212> TYPE: PRT
<213> ORGANISM: Artificial sequence
<220> FEATURE:
<223> OTHER INFORMATION: synthetic

<400> SEQUENCE: 168

Pro Val Leu Glu Leu Phe Glu Gln Leu Leu Glu Lys Leu Leu Asp Ala
1               5                   10                  15

Leu Gln Lys Lys Leu Lys
            20

<210> SEQ ID NO 169
<211> LENGTH: 22
<212> TYPE: PRT
<213> ORGANISM: Artificial sequence
<220> FEATURE:
<223> OTHER INFORMATION: synthetic

<400> SEQUENCE: 169

Pro Val Leu Glu Leu Phe Glu Asn Leu Leu Glu Lys Leu Leu Asp Ala
1               5                   10                  15

Leu Gln Lys Lys Leu Lys
            20

```
<210> SEQ ID NO 170
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Orn
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 170

Pro Val Leu Glu Leu Phe Glu Asn Leu Leu Glu Xaa Leu Leu Asp Ala
1               5                   10                  15

Leu Gln Xaa Xaa Leu Xaa
            20

<210> SEQ ID NO 171
<211> LENGTH: 22
<212> TYPE: PRT
<213> ORGANISM: Artificial sequence
<220> FEATURE:
<223> OTHER INFORMATION: synthetic

<400> SEQUENCE: 171

Pro Val Leu Glu Leu Phe Glu Asn Leu Leu Glu Lys Leu Leu Asp Leu
1               5                   10                  15

Leu Gln Lys Lys Leu Lys
            20

<210> SEQ ID NO 172
<211> LENGTH: 22
<212> TYPE: PRT
<213> ORGANISM: Artificial sequence
<220> FEATURE:
<223> OTHER INFORMATION: synthetic

<400> SEQUENCE: 172

Pro Val Leu Glu Leu Phe Leu Asn Leu Leu Glu Arg Leu Gly Asp Ala
1               5                   10                  15

Leu Gln Lys Lys Leu Lys
            20

<210> SEQ ID NO 173
<211> LENGTH: 22
<212> TYPE: PRT
<213> ORGANISM: Artificial sequence
<220> FEATURE:
<223> OTHER INFORMATION: synthetic

<400> SEQUENCE: 173

Pro Val Leu Asp Leu Phe Asp Asn Leu Leu Asp Arg Leu Leu Asp Leu
1               5                   10                  15

Leu Asn Lys Lys Leu Lys
            20
```

```
<210> SEQ ID NO 174
<211> LENGTH: 22
<212> TYPE: PRT
<213> ORGANISM: Artificial sequence
<220> FEATURE:
<223> OTHER INFORMATION: synthetic

<400> SEQUENCE: 174

Pro Val Leu Glu Leu Phe Glu Asn Leu Leu Glu Arg Leu Leu Asp Ala
1               5                   10                  15

Leu Gln Lys Lys Leu Lys
            20

<210> SEQ ID NO 175
<211> LENGTH: 22
<212> TYPE: PRT
<213> ORGANISM: Artificial sequence
<220> FEATURE:
<223> OTHER INFORMATION: synthetic

<400> SEQUENCE: 175

Pro Val Leu Glu Leu Phe Glu Asn Leu Leu Glu Arg Leu Leu Glu Leu
1               5                   10                  15

Leu Asn Lys Lys Leu Lys
            20

<210> SEQ ID NO 176
<211> LENGTH: 22
<212> TYPE: PRT
<213> ORGANISM: Artificial sequence
<220> FEATURE:
<223> OTHER INFORMATION: synthetic

<400> SEQUENCE: 176

Pro Val Leu Glu Leu Trp Glu Asn Leu Leu Glu Arg Leu Leu Asp Ala
1               5                   10                  15

Leu Gln Lys Lys Leu Lys
            20

<210> SEQ ID NO 177
<211> LENGTH: 22
<212> TYPE: PRT
<213> ORGANISM: Artificial sequence
<220> FEATURE:
<223> OTHER INFORMATION: synthetic

<400> SEQUENCE: 177

Gly Val Leu Glu Leu Phe Leu Asn Leu Leu Glu Arg Leu Leu Asp Ala
1               5                   10                  15

Leu Gln Lys Lys Leu Lys
            20

<210> SEQ ID NO 178
<211> LENGTH: 22
<212> TYPE: PRT
<213> ORGANISM: Artificial sequence
<220> FEATURE:
<223> OTHER INFORMATION: synthetic

<400> SEQUENCE: 178

Pro Val Leu Glu Leu Phe Asp Asn Leu Leu Glu Lys Leu Leu Glu Ala
1               5                   10                  15

Leu Gln Lys Lys Leu Arg
```

```
20

<210> SEQ ID NO 179
<211> LENGTH: 22
<212> TYPE: PRT
<213> ORGANISM: Artificial sequence
<220> FEATURE:
<223> OTHER INFORMATION: synthetic

<400> SEQUENCE: 179

Pro Val Leu Glu Leu Phe Asp Asn Leu Leu Glu Arg Leu Leu Asp Ala
1               5                   10                  15

Leu Gln Lys Lys Leu Lys
            20

<210> SEQ ID NO 180
<211> LENGTH: 22
<212> TYPE: PRT
<213> ORGANISM: Artificial sequence
<220> FEATURE:
<223> OTHER INFORMATION: synthetic

<400> SEQUENCE: 180

Pro Val Leu Glu Leu Phe Asp Asn Leu Leu Asp Lys Leu Leu Asp Ala
1               5                   10                  15

Leu Gln Lys Lys Leu Arg
            20

<210> SEQ ID NO 181
<211> LENGTH: 22
<212> TYPE: PRT
<213> ORGANISM: Artificial sequence
<220> FEATURE:
<223> OTHER INFORMATION: synthetic

<400> SEQUENCE: 181

Pro Val Leu Glu Leu Phe Glu Asn Leu Leu Glu Arg Trp Leu Asp Ala
1               5                   10                  15

Leu Gln Lys Lys Leu Lys
            20

<210> SEQ ID NO 182
<211> LENGTH: 22
<212> TYPE: PRT
<213> ORGANISM: Artificial sequence
<220> FEATURE:
<223> OTHER INFORMATION: synthetic

<400> SEQUENCE: 182

Pro Val Leu Glu Leu Phe Glu Asn Leu Leu Glu Lys Leu Leu Glu Ala
1               5                   10                  15

Leu Gln Lys Lys Leu Lys
            20

<210> SEQ ID NO 183
<211> LENGTH: 22
<212> TYPE: PRT
<213> ORGANISM: Artificial sequence
<220> FEATURE:
<223> OTHER INFORMATION: synthetic

<400> SEQUENCE: 183

Pro Leu Leu Glu Leu Phe Glu Asn Leu Leu Glu Lys Leu Leu Asp Ala
1               5                   10                  15
```

-continued

Leu Gln Lys Lys Leu Lys
            20

<210> SEQ ID NO 184
<211> LENGTH: 22
<212> TYPE: PRT
<213> ORGANISM: Artificial sequence
<220> FEATURE:
<223> OTHER INFORMATION: synthetic

<400> SEQUENCE: 184

Pro Val Leu Glu Leu Phe Leu Asn Leu Leu Glu Arg Leu Leu Asp Ala
1               5                   10                  15

Trp Gln Lys Lys Leu Lys
            20

<210> SEQ ID NO 185
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Orn
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 185

Pro Val Leu Glu Leu Phe Glu Asn Leu Leu Glu Arg Leu Leu Asp Ala
1               5                   10                  15

Leu Gln Xaa Xaa Leu Xaa
            20

<210> SEQ ID NO 186
<211> LENGTH: 22
<212> TYPE: PRT
<213> ORGANISM: Artificial sequence
<220> FEATURE:
<223> OTHER INFORMATION: synthetic

<400> SEQUENCE: 186

Pro Val Leu Glu Leu Phe Glu Gln Leu Leu Glu Arg Leu Leu Asp Ala
1               5                   10                  15

Leu Gln Lys Lys Leu Lys
            20

<210> SEQ ID NO 187
<211> LENGTH: 22
<212> TYPE: PRT
<213> ORGANISM: Artificial sequence
<220> FEATURE:
<223> OTHER INFORMATION: synthetic

<400> SEQUENCE: 187

Pro Val Leu Glu Leu Phe Glu Asn Leu Leu Glu Arg Leu Leu Asp Ala
1               5                   10                  15

Leu Asn Lys Lys Leu Lys
            20

```
<210> SEQ ID NO 188
<211> LENGTH: 22
<212> TYPE: PRT
<213> ORGANISM: Artificial sequence
<220> FEATURE:
<223> OTHER INFORMATION: synthetic

<400> SEQUENCE: 188

Pro Val Leu Glu Leu Phe Glu Asn Leu Leu Asp Arg Leu Leu Asp Ala
1               5                   10                  15

Leu Gln Lys Lys Leu Lys
            20

<210> SEQ ID NO 189
<211> LENGTH: 22
<212> TYPE: PRT
<213> ORGANISM: Artificial sequence
<220> FEATURE:
<223> OTHER INFORMATION: synthetic

<400> SEQUENCE: 189

Asp Val Leu Glu Leu Phe Glu Asn Leu Leu Glu Arg Leu Leu Asp Ala
1               5                   10                  15

Leu Gln Lys Lys Leu Lys
            20

<210> SEQ ID NO 190
<211> LENGTH: 22
<212> TYPE: PRT
<213> ORGANISM: Artificial sequence
<220> FEATURE:
<223> OTHER INFORMATION: synthetic

<400> SEQUENCE: 190

Pro Val Leu Glu Phe Trp Asp Asn Leu Leu Asp Lys Leu Leu Asp Ala
1               5                   10                  15

Leu Gln Lys Lys Leu Arg
            20

<210> SEQ ID NO 191
<211> LENGTH: 18
<212> TYPE: PRT
<213> ORGANISM: Artificial sequence
<220> FEATURE:
<223> OTHER INFORMATION: synthetic

<400> SEQUENCE: 191

Pro Val Leu Asp Leu Leu Arg Glu Leu Leu Glu Glu Leu Lys Gln Lys
1               5                   10                  15

Leu Lys

<210> SEQ ID NO 192
<211> LENGTH: 18
<212> TYPE: PRT
<213> ORGANISM: Artificial sequence
<220> FEATURE:
<223> OTHER INFORMATION: synthetic

<400> SEQUENCE: 192

Pro Val Leu Asp Leu Phe Lys Glu Leu Leu Glu Glu Leu Lys Gln Lys
1               5                   10                  15

Leu Lys

<210> SEQ ID NO 193
```

```
<211> LENGTH: 18
<212> TYPE: PRT
<213> ORGANISM: Artificial sequence
<220> FEATURE:
<223> OTHER INFORMATION: synthetic

<400> SEQUENCE: 193

Pro Val Leu Asp Leu Phe Arg Glu Leu Leu Glu Glu Leu Lys Gln Lys
1               5                   10                  15

Leu Lys

<210> SEQ ID NO 194
<211> LENGTH: 18
<212> TYPE: PRT
<213> ORGANISM: Artificial sequence
<220> FEATURE:
<223> OTHER INFORMATION: synthetic

<400> SEQUENCE: 194

Pro Val Leu Glu Leu Phe Arg Glu Leu Leu Glu Glu Leu Lys Gln Lys
1               5                   10                  15

Leu Lys

<210> SEQ ID NO 195
<211> LENGTH: 18
<212> TYPE: PRT
<213> ORGANISM: Artificial sequence
<220> FEATURE:
<223> OTHER INFORMATION: synthetic

<400> SEQUENCE: 195

Pro Val Leu Glu Leu Phe Lys Glu Leu Leu Glu Glu Leu Lys Gln Lys
1               5                   10                  15

Leu Lys

<210> SEQ ID NO 196
<211> LENGTH: 18
<212> TYPE: PRT
<213> ORGANISM: Artificial sequence
<220> FEATURE:
<223> OTHER INFORMATION: synthetic

<400> SEQUENCE: 196

Pro Val Leu Asp Leu Phe Arg Glu Leu Leu Glu Glu Leu Lys Asn Lys
1               5                   10                  15

Leu Lys

<210> SEQ ID NO 197
<211> LENGTH: 18
<212> TYPE: PRT
<213> ORGANISM: Artificial sequence
<220> FEATURE:
<223> OTHER INFORMATION: synthetic

<400> SEQUENCE: 197

Pro Leu Leu Asp Leu Phe Arg Glu Leu Leu Glu Glu Leu Lys Gln Lys
1               5                   10                  15

Leu Lys

<210> SEQ ID NO 198
<211> LENGTH: 18
<212> TYPE: PRT
<213> ORGANISM: Artificial sequence
<220> FEATURE:
```

<223> OTHER INFORMATION: synthetic

<400> SEQUENCE: 198

Gly Val Leu Asp Leu Phe Arg Glu Leu Leu Glu Glu Leu Lys Gln Lys
1               5                   10                  15

Leu Lys

<210> SEQ ID NO 199
<211> LENGTH: 18
<212> TYPE: PRT
<213> ORGANISM: Artificial sequence
<220> FEATURE:
<223> OTHER INFORMATION: synthetic

<400> SEQUENCE: 199

Pro Val Leu Asp Leu Phe Arg Glu Leu Trp Glu Glu Leu Lys Gln Lys
1               5                   10                  15

Leu Lys

<210> SEQ ID NO 200
<211> LENGTH: 18
<212> TYPE: PRT
<213> ORGANISM: Artificial sequence
<220> FEATURE:
<223> OTHER INFORMATION: synthetic

<400> SEQUENCE: 200

Asn Val Leu Asp Leu Phe Arg Glu Leu Leu Glu Glu Leu Lys Gln Lys
1               5                   10                  15

Leu Lys

<210> SEQ ID NO 201
<211> LENGTH: 18
<212> TYPE: PRT
<213> ORGANISM: Artificial sequence
<220> FEATURE:
<223> OTHER INFORMATION: synthetic

<400> SEQUENCE: 201

Pro Leu Leu Asp Leu Phe Lys Glu Leu Leu Glu Glu Leu Lys Gln Lys
1               5                   10                  15

Leu Lys

<210> SEQ ID NO 202
<211> LENGTH: 18
<212> TYPE: PRT
<213> ORGANISM: Artificial sequence
<220> FEATURE:
<223> OTHER INFORMATION: synthetic

<400> SEQUENCE: 202

Pro Ala Leu Glu Leu Phe Lys Asp Leu Leu Glu Glu Leu Arg Gln Lys
1               5                   10                  15

Leu Arg

<210> SEQ ID NO 203
<211> LENGTH: 18
<212> TYPE: PRT
<213> ORGANISM: Artificial sequence
<220> FEATURE:
<223> OTHER INFORMATION: synthetic

<400> SEQUENCE: 203

Ala Val Leu Asp Leu Phe Arg Glu Leu Leu Glu Glu Leu Lys Gln Lys
1               5                   10                  15

Leu Lys

<210> SEQ ID NO 204
<211> LENGTH: 18
<212> TYPE: PRT
<213> ORGANISM: Artificial sequence
<220> FEATURE:
<223> OTHER INFORMATION: synthetic

<400> SEQUENCE: 204

Pro Val Leu Asp Phe Phe Arg Glu Leu Leu Glu Glu Leu Lys Gln Lys
1               5                   10                  15

Leu Lys

<210> SEQ ID NO 205
<211> LENGTH: 18
<212> TYPE: PRT
<213> ORGANISM: Artificial sequence
<220> FEATURE:
<223> OTHER INFORMATION: synthetic

<400> SEQUENCE: 205

Pro Val Leu Asp Leu Phe Arg Glu Trp Leu Glu Glu Leu Lys Gln Lys
1               5                   10                  15

Leu Lys

<210> SEQ ID NO 206
<211> LENGTH: 18
<212> TYPE: PRT
<213> ORGANISM: Artificial sequence
<220> FEATURE:
<223> OTHER INFORMATION: synthetic

<400> SEQUENCE: 206

Pro Leu Leu Glu Leu Leu Lys Glu Leu Leu Glu Glu Leu Lys Gln Lys
1               5                   10                  15

Leu Lys

<210> SEQ ID NO 207
<211> LENGTH: 18
<212> TYPE: PRT
<213> ORGANISM: Artificial sequence
<220> FEATURE:
<223> OTHER INFORMATION: synthetic

<400> SEQUENCE: 207

Pro Val Leu Glu Leu Leu Lys Glu Leu Leu Glu Glu Leu Lys Gln Lys
1               5                   10                  15

Leu Lys

<210> SEQ ID NO 208
<211> LENGTH: 18
<212> TYPE: PRT
<213> ORGANISM: Artificial sequence
<220> FEATURE:
<223> OTHER INFORMATION: synthetic

<400> SEQUENCE: 208

Pro Ala Leu Glu Leu Phe Lys Asp Leu Leu Glu Glu Leu Arg Gln Arg
1               5                   10                  15

Leu Lys

```
<210> SEQ ID NO 209
<211> LENGTH: 18
<212> TYPE: PRT
<213> ORGANISM: Artificial sequence
<220> FEATURE:
<223> OTHER INFORMATION: synthetic

<400> SEQUENCE: 209

Pro Val Leu Asp Leu Phe Arg Glu Leu Leu Asn Glu Leu Leu Gln Lys
1               5                   10                  15

Leu Lys

<210> SEQ ID NO 210
<211> LENGTH: 18
<212> TYPE: PRT
<213> ORGANISM: Artificial sequence
<220> FEATURE:
<223> OTHER INFORMATION: synthetic

<400> SEQUENCE: 210

Pro Val Leu Asp Leu Phe Arg Glu Leu Leu Glu Glu Leu Lys Gln Lys
1               5                   10                  15

Leu Lys

<210> SEQ ID NO 211
<211> LENGTH: 18
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Orn
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 211

Pro Val Leu Asp Leu Phe Arg Glu Leu Leu Glu Glu Leu Xaa Gln Xaa
1               5                   10                  15

Leu Xaa

<210> SEQ ID NO 212
<211> LENGTH: 18
<212> TYPE: PRT
<213> ORGANISM: Artificial sequence
<220> FEATURE:
<223> OTHER INFORMATION: synthetic
<220> FEATURE:
<221> NAME/KEY: misc_feature
<223> OTHER INFORMATION: Xaa = Orn
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
```

```
<220> FEATURE:
<221> NAME/KEY: misc_feature
<222> LOCATION: (16)..(16)
<223> OTHER INFORMATION: Xaa can be any naturally occurring amino acid

<400> SEQUENCE: 212

Pro Val Leu Asp Leu Phe Xaa Glu Leu Leu Glu Glu Leu Xaa Gln Xaa
1               5                   10                  15

Leu Lys

<210> SEQ ID NO 213
<211> LENGTH: 18
<212> TYPE: PRT
<213> ORGANISM: Artificial sequence
<220> FEATURE:
<223> OTHER INFORMATION: synthetic

<400> SEQUENCE: 213

Pro Ala Leu Glu Leu Phe Lys Asp Leu Leu Glu Glu Phe Arg Gln Arg
1               5                   10                  15

Leu Lys

<210> SEQ ID NO 214
<211> LENGTH: 18
<212> TYPE: PRT
<213> ORGANISM: Artificial sequence
<220> FEATURE:
<223> OTHER INFORMATION: synthetic

<400> SEQUENCE: 214

Pro Val Leu Asp Leu Phe Arg Glu Leu Leu Glu Glu Leu Lys Gln Lys
1               5                   10                  15

Leu Lys

<210> SEQ ID NO 215
<211> LENGTH: 18
<212> TYPE: PRT
<213> ORGANISM: Artificial sequence
<220> FEATURE:
<223> OTHER INFORMATION: synthetic

<400> SEQUENCE: 215

Pro Val Leu Asp Leu Phe Arg Glu Leu Leu Glu Glu Trp Lys Gln Lys
1               5                   10                  15

Leu Lys

<210> SEQ ID NO 216
<211> LENGTH: 18
<212> TYPE: PRT
<213> ORGANISM: Artificial sequence
<220> FEATURE:
<223> OTHER INFORMATION: synthetic

<400> SEQUENCE: 216

Pro Val Leu Glu Leu Phe Lys Glu Leu Leu Glu Glu Leu Lys Gln Lys
1               5                   10                  15

Leu Lys

<210> SEQ ID NO 217
<211> LENGTH: 18
<212> TYPE: PRT
<213> ORGANISM: Artificial sequence
<220> FEATURE:
<223> OTHER INFORMATION: synthetic
```

<400> SEQUENCE: 217

Pro Val Leu Asp Leu Phe Arg Glu Leu Leu Glu Leu Leu Lys Gln Lys
1               5                   10                  15

Leu Lys

<210> SEQ ID NO 218
<211> LENGTH: 18
<212> TYPE: PRT
<213> ORGANISM: Artificial sequence
<220> FEATURE:
<223> OTHER INFORMATION: synthetic

<400> SEQUENCE: 218

Pro Val Leu Asp Leu Phe Arg Glu Leu Leu Asn Glu Leu Leu Gln Lys
1               5                   10                  15

Leu Lys

<210> SEQ ID NO 219
<211> LENGTH: 18
<212> TYPE: PRT
<213> ORGANISM: Artificial sequence
<220> FEATURE:
<223> OTHER INFORMATION: synthetic

<400> SEQUENCE: 219

Pro Val Leu Asp Leu Phe Arg Glu Leu Leu Asn Glu Leu Trp Gln Lys
1               5                   10                  15

Leu Lys

<210> SEQ ID NO 220
<211> LENGTH: 18
<212> TYPE: PRT
<213> ORGANISM: Artificial sequence
<220> FEATURE:
<223> OTHER INFORMATION: synthetic

<400> SEQUENCE: 220

Pro Val Leu Asp Leu Phe Arg Glu Leu Leu Glu Glu Leu Gln Lys Lys
1               5                   10                  15

Leu Lys

<210> SEQ ID NO 221
<211> LENGTH: 18
<212> TYPE: PRT
<213> ORGANISM: Artificial sequence
<220> FEATURE:
<223> OTHER INFORMATION: synthetic

<400> SEQUENCE: 221

Asp Val Leu Asp Leu Phe Arg Glu Leu Leu Glu Glu Leu Lys Gln Lys
1               5                   10                  15

Leu Lys

<210> SEQ ID NO 222
<211> LENGTH: 18
<212> TYPE: PRT
<213> ORGANISM: Artificial sequence
<220> FEATURE:
<223> OTHER INFORMATION: synthetic

<400> SEQUENCE: 222

Pro Val Leu Asp Ala Phe Arg Glu Leu Leu Glu Ala Leu Leu Gln Leu

```
1               5                   10                  15

Lys Lys

<210> SEQ ID NO 223
<211> LENGTH: 18
<212> TYPE: PRT
<213> ORGANISM: Artificial sequence
<220> FEATURE:
<223> OTHER INFORMATION: synthetic

<400> SEQUENCE: 223

Pro Val Leu Asp Ala Phe Arg Glu Leu Leu Glu Ala Leu Ala Gln Leu
1               5                   10                  15

Lys Lys

<210> SEQ ID NO 224
<211> LENGTH: 18
<212> TYPE: PRT
<213> ORGANISM: Artificial sequence
<220> FEATURE:
<223> OTHER INFORMATION: synthetic

<400> SEQUENCE: 224

Pro Val Leu Asp Leu Phe Arg Glu Gly Trp Glu Glu Leu Lys Gln Lys
1               5                   10                  15

Leu Lys

<210> SEQ ID NO 225
<211> LENGTH: 18
<212> TYPE: PRT
<213> ORGANISM: Artificial sequence
<220> FEATURE:
<223> OTHER INFORMATION: synthetic

<400> SEQUENCE: 225

Pro Val Leu Asp Ala Phe Arg Glu Leu Ala Glu Ala Leu Ala Gln Leu
1               5                   10                  15

Lys Lys

<210> SEQ ID NO 226
<211> LENGTH: 18
<212> TYPE: PRT
<213> ORGANISM: Artificial sequence
<220> FEATURE:
<223> OTHER INFORMATION: synthetic

<400> SEQUENCE: 226

Pro Val Leu Asp Ala Phe Arg Glu Leu Gly Glu Ala Leu Leu Gln Leu
1               5                   10                  15

Lys Lys

<210> SEQ ID NO 227
<211> LENGTH: 18
<212> TYPE: PRT
<213> ORGANISM: Artificial sequence
<220> FEATURE:
<223> OTHER INFORMATION: synthetic

<400> SEQUENCE: 227

Pro Val Leu Asp Leu Phe Arg Glu Leu Gly Glu Glu Leu Lys Gln Lys
1               5                   10                  15

Leu Lys
```

```
<210> SEQ ID NO 228
<211> LENGTH: 18
<212> TYPE: PRT
<213> ORGANISM: Artificial sequence
<220> FEATURE:
<223> OTHER INFORMATION: synthetic

<400> SEQUENCE: 228

Pro Val Leu Asp Leu Phe Arg Glu Gly Leu Glu Glu Leu Lys Gln Lys
1               5                  10                  15

Leu Lys

<210> SEQ ID NO 229
<211> LENGTH: 18
<212> TYPE: PRT
<213> ORGANISM: Artificial sequence
<220> FEATURE:
<223> OTHER INFORMATION: synthetic

<400> SEQUENCE: 229

Pro Val Leu Asp Leu Phe Arg Glu Leu Leu Glu Glu Gly Lys Gln Lys
1               5                  10                  15

Leu Lys

<210> SEQ ID NO 230
<211> LENGTH: 18
<212> TYPE: PRT
<213> ORGANISM: Artificial sequence
<220> FEATURE:
<223> OTHER INFORMATION: synthetic

<400> SEQUENCE: 230

Pro Val Leu Glu Leu Phe Glu Arg Leu Leu Glu Asp Leu Gln Lys Lys
1               5                  10                  15

Leu Lys

<210> SEQ ID NO 231
<211> LENGTH: 18
<212> TYPE: PRT
<213> ORGANISM: Artificial sequence
<220> FEATURE:
<223> OTHER INFORMATION: synthetic

<400> SEQUENCE: 231

Pro Val Leu Asp Leu Phe Arg Glu Leu Leu Glu Lys Leu Glu Gln Lys
1               5                  10                  15

Leu Lys

<210> SEQ ID NO 232
<211> LENGTH: 18
<212> TYPE: PRT
<213> ORGANISM: Artificial sequence
<220> FEATURE:
<223> OTHER INFORMATION: synthetic

<400> SEQUENCE: 232

Pro Leu Leu Glu Leu Phe Lys Glu Leu Leu Glu Glu Leu Lys Gln Lys
1               5                  10                  15

Leu Lys

<210> SEQ ID NO 233
<211> LENGTH: 18
<212> TYPE: PRT
```

```
<213> ORGANISM: Artificial sequence
<220> FEATURE:
<223> OTHER INFORMATION: synthetic

<400> SEQUENCE: 233

Leu Asp Asp Leu Leu Gln Lys Trp Ala Glu Ala Phe Asn Gln Leu Leu
1               5                   10                  15

Lys Lys

<210> SEQ ID NO 234
<211> LENGTH: 18
<212> TYPE: PRT
<213> ORGANISM: Artificial sequence
<220> FEATURE:
<223> OTHER INFORMATION: synthetic

<400> SEQUENCE: 234

Glu Trp Leu Lys Ala Phe Tyr Glu Lys Val Leu Glu Lys Leu Lys Glu
1               5                   10                  15

Leu Phe

<210> SEQ ID NO 235
<211> LENGTH: 18
<212> TYPE: PRT
<213> ORGANISM: Artificial sequence
<220> FEATURE:
<223> OTHER INFORMATION: synthetic

<400> SEQUENCE: 235

Glu Trp Leu Glu Ala Phe Tyr Lys Lys Val Leu Glu Lys Leu Lys Glu
1               5                   10                  15

Leu Phe

<210> SEQ ID NO 236
<211> LENGTH: 18
<212> TYPE: PRT
<213> ORGANISM: Artificial sequence
<220> FEATURE:
<223> OTHER INFORMATION: synthetic

<400> SEQUENCE: 236

Asp Trp Leu Lys Ala Phe Tyr Asp Lys Val Ala Glu Lys Leu Lys Glu
1               5                   10                  15

Ala Phe

<210> SEQ ID NO 237
<211> LENGTH: 18
<212> TYPE: PRT
<213> ORGANISM: Artificial sequence
<220> FEATURE:
<223> OTHER INFORMATION: synthetic

<400> SEQUENCE: 237

Asp Trp Phe Lys Ala Phe Tyr Asp Lys Val Phe Glu Lys Phe Lys Glu
1               5                   10                  15

Phe Phe

<210> SEQ ID NO 238
<211> LENGTH: 18
<212> TYPE: PRT
<213> ORGANISM: Artificial sequence
<220> FEATURE:
<223> OTHER INFORMATION: synthetic
```

```
<400> SEQUENCE: 238

Gly Ile Lys Lys Phe Leu Gly Ser Ile Trp Lys Phe Ile Lys Ala Phe
1               5                   10                  15

Val Gly

<210> SEQ ID NO 239
<211> LENGTH: 18
<212> TYPE: PRT
<213> ORGANISM: Artificial sequence
<220> FEATURE:
<223> OTHER INFORMATION: synthetic

<400> SEQUENCE: 239

Asp Trp Phe Lys Ala Phe Tyr Asp Lys Val Ala Glu Lys Phe Lys Glu
1               5                   10                  15

Ala Phe

<210> SEQ ID NO 240
<211> LENGTH: 18
<212> TYPE: PRT
<213> ORGANISM: Artificial sequence
<220> FEATURE:
<223> OTHER INFORMATION: synthetic

<400> SEQUENCE: 240

Asp Trp Leu Lys Ala Phe Tyr Asp Lys Val Ala Glu Lys Leu Lys Glu
1               5                   10                  15

Ala Phe

<210> SEQ ID NO 241
<211> LENGTH: 18
<212> TYPE: PRT
<213> ORGANISM: Artificial sequence
<220> FEATURE:
<223> OTHER INFORMATION: synthetic

<400> SEQUENCE: 241

Asp Trp Leu Lys Ala Phe Tyr Asp Lys Val Phe Glu Lys Phe Lys Glu
1               5                   10                  15

Phe Phe

<210> SEQ ID NO 242
<211> LENGTH: 18
<212> TYPE: PRT
<213> ORGANISM: Artificial sequence
<220> FEATURE:
<223> OTHER INFORMATION: synthetic

<400> SEQUENCE: 242

Glu Trp Leu Glu Ala Phe Tyr Lys Lys Val Leu Glu Lys Leu Lys Glu
1               5                   10                  15

Leu Pro

<210> SEQ ID NO 243
<211> LENGTH: 18
<212> TYPE: PRT
<213> ORGANISM: Artificial sequence
<220> FEATURE:
<223> OTHER INFORMATION: synthetic

<400> SEQUENCE: 243

Asp Trp Phe Lys Ala Phe Tyr Asp Lys Phe Phe Glu Lys Phe Lys Glu
1               5                   10                  15
```

Phe Phe

<210> SEQ ID NO 244
<211> LENGTH: 18
<212> TYPE: PRT
<213> ORGANISM: Artificial sequence
<220> FEATURE:
<223> OTHER INFORMATION: synthetic

<400> SEQUENCE: 244

Glu Trp Leu Lys Ala Phe Tyr Glu Lys Val Leu Glu Lys Leu Lys Glu
1               5                   10                  15

Leu Phe

<210> SEQ ID NO 245
<211> LENGTH: 18
<212> TYPE: PRT
<213> ORGANISM: Artificial sequence
<220> FEATURE:
<223> OTHER INFORMATION: synthetic

<400> SEQUENCE: 245

Glu Trp Leu Lys Ala Glu Tyr Glu Lys Val Glu Glu Lys Leu Lys Glu
1               5                   10                  15

Leu Phe

<210> SEQ ID NO 246
<211> LENGTH: 18
<212> TYPE: PRT
<213> ORGANISM: Artificial sequence
<220> FEATURE:
<223> OTHER INFORMATION: synthetic

<400> SEQUENCE: 246

Glu Trp Leu Lys Ala Glu Tyr Glu Lys Val Leu Glu Lys Leu Lys Glu
1               5                   10                  15

Leu Phe

<210> SEQ ID NO 247
<211> LENGTH: 18
<212> TYPE: PRT
<213> ORGANISM: Artificial sequence
<220> FEATURE:
<223> OTHER INFORMATION: synthetic

<400> SEQUENCE: 247

Glu Trp Leu Lys Ala Phe Tyr Lys Lys Val Leu Glu Lys Leu Lys Glu
1               5                   10                  15

Leu Phe

<210> SEQ ID NO 248
<211> LENGTH: 15
<212> TYPE: PRT
<213> ORGANISM: Artificial sequence
<220> FEATURE:
<223> OTHER INFORMATION: synthetic

<400> SEQUENCE: 248

Pro Val Leu Asp Leu Phe Arg Glu Leu Leu Glu Gln Lys Leu Lys
1               5                   10                  15

<210> SEQ ID NO 249
<211> LENGTH: 16

```
<212> TYPE: PRT
<213> ORGANISM: Artificial sequence
<220> FEATURE:
<223> OTHER INFORMATION: synthetic

<400> SEQUENCE: 249

Pro Val Leu Asp Leu Phe Arg Glu Leu Leu Glu Glu Leu Lys Gln Lys
1               5                   10                  15

<210> SEQ ID NO 250
<211> LENGTH: 16
<212> TYPE: PRT
<213> ORGANISM: Artificial sequence
<220> FEATURE:
<223> OTHER INFORMATION: synthetic

<400> SEQUENCE: 250

Pro Val Leu Asp Leu Phe Arg Glu Leu Leu Glu Lys Leu Lys Gln Lys
1               5                   10                  15

<210> SEQ ID NO 251
<211> LENGTH: 15
<212> TYPE: PRT
<213> ORGANISM: Artificial sequence
<220> FEATURE:
<223> OTHER INFORMATION: synthetic

<400> SEQUENCE: 251

Pro Val Leu Asp Leu Phe Arg Glu Leu Leu Glu Lys Leu Gln Lys
1               5                   10                  15

<210> SEQ ID NO 252
<211> LENGTH: 16
<212> TYPE: PRT
<213> ORGANISM: Artificial sequence
<220> FEATURE:
<223> OTHER INFORMATION: synthetic

<400> SEQUENCE: 252

Pro Val Leu Asp Leu Phe Arg Glu Leu Leu Glu Ala Leu Lys Gln Lys
1               5                   10                  15

<210> SEQ ID NO 253
<211> LENGTH: 16
<212> TYPE: PRT
<213> ORGANISM: Artificial sequence
<220> FEATURE:
<223> OTHER INFORMATION: synthetic

<400> SEQUENCE: 253

Pro Val Leu Asp Leu Phe Glu Asn Leu Leu Glu Arg Leu Lys Gln Lys
1               5                   10                  15

<210> SEQ ID NO 254
<211> LENGTH: 16
<212> TYPE: PRT
<213> ORGANISM: Artificial sequence
<220> FEATURE:
<223> OTHER INFORMATION: synthetic

<400> SEQUENCE: 254

Pro Val Leu Asp Leu Phe Arg Glu Leu Leu Asn Glu Leu Lys Gln Lys
1               5                   10                  15

<210> SEQ ID NO 255
<211> LENGTH: 18
<212> TYPE: PRT
```

```
<213> ORGANISM: Artificial sequence
<220> FEATURE:
<223> OTHER INFORMATION: synthetic

<400> SEQUENCE: 255

Asp Trp Leu Lys Ala Phe Tyr Asp Lys Val Ala Glu Lys Leu Lys Glu
1               5                   10                  15

Ala Phe

<210> SEQ ID NO 256
<211> LENGTH: 18
<212> TYPE: PRT
<213> ORGANISM: Artificial sequence
<220> FEATURE:
<223> OTHER INFORMATION: synthetic

<400> SEQUENCE: 256

Asp Trp Leu Lys Ala Phe Tyr Asp Lys Val Ala Glu Lys Leu Lys Glu
1               5                   10                  15

Ala Phe

<210> SEQ ID NO 257
<211> LENGTH: 18
<212> TYPE: PRT
<213> ORGANISM: Artificial sequence
<220> FEATURE:
<223> OTHER INFORMATION: synthetic

<400> SEQUENCE: 257

Asp Trp Leu Lys Ala Phe Tyr Asp Lys Val Ala Glu Lys Leu Lys Glu
1               5                   10                  15

Ala Phe

<210> SEQ ID NO 258
<211> LENGTH: 18
<212> TYPE: PRT
<213> ORGANISM: Artificial sequence
<220> FEATURE:
<223> OTHER INFORMATION: synthetic

<400> SEQUENCE: 258

Asp Trp Phe Lys Ala Phe Tyr Asp Lys Val Ala Glu Lys Leu Lys Glu
1               5                   10                  15

Ala Phe

<210> SEQ ID NO 259
<211> LENGTH: 18
<212> TYPE: PRT
<213> ORGANISM: Artificial sequence
<220> FEATURE:
<223> OTHER INFORMATION: synthetic

<400> SEQUENCE: 259

Asp Trp Leu Lys Ala Phe Tyr Asp Lys Val Ala Glu Lys Phe Lys Glu
1               5                   10                  15

Ala Phe

<210> SEQ ID NO 260
<211> LENGTH: 18
<212> TYPE: PRT
<213> ORGANISM: Artificial sequence
<220> FEATURE:
<223> OTHER INFORMATION: synthetic
```

```
<400> SEQUENCE: 260

Asp Trp Phe Lys Ala Phe Tyr Asp Lys Val Ala Glu Lys Phe Lys Glu
1               5                   10                  15

Ala Phe

<210> SEQ ID NO 261
<211> LENGTH: 18
<212> TYPE: PRT
<213> ORGANISM: Artificial sequence
<220> FEATURE:
<223> OTHER INFORMATION: synthetic

<400> SEQUENCE: 261

Asp Trp Leu Lys Ala Phe Tyr Asp Lys Val Phe Glu Lys Phe Lys Glu
1               5                   10                  15

Phe Phe

<210> SEQ ID NO 262
<211> LENGTH: 18
<212> TYPE: PRT
<213> ORGANISM: Artificial sequence
<220> FEATURE:
<223> OTHER INFORMATION: synthetic

<400> SEQUENCE: 262

Asp Trp Leu Lys Ala Phe Tyr Asp Lys Phe Phe Glu Lys Phe Lys Glu
1               5                   10                  15

Phe Phe

<210> SEQ ID NO 263
<211> LENGTH: 18
<212> TYPE: PRT
<213> ORGANISM: Artificial sequence
<220> FEATURE:
<223> OTHER INFORMATION: synthetic

<400> SEQUENCE: 263

Asp Trp Phe Lys Ala Phe Tyr Asp Lys Phe Phe Glu Lys Phe Lys Glu
1               5                   10                  15

Phe Phe

<210> SEQ ID NO 264
<211> LENGTH: 18
<212> TYPE: PRT
<213> ORGANISM: Artificial sequence
<220> FEATURE:
<223> OTHER INFORMATION: synthetic

<400> SEQUENCE: 264

Asp Trp Leu Lys Ala Phe Tyr Asp Lys Val Ala Glu Lys Leu Lys Glu
1               5                   10                  15

Phe Phe

<210> SEQ ID NO 265
<211> LENGTH: 18
<212> TYPE: PRT
<213> ORGANISM: Artificial sequence
<220> FEATURE:
<223> OTHER INFORMATION: synthetic

<400> SEQUENCE: 265

Asp Trp Leu Lys Ala Phe Tyr Asp Lys Val Phe Glu Lys Phe Lys Glu
1               5                   10                  15
```

Ala Phe

<210> SEQ ID NO 266
<211> LENGTH: 18
<212> TYPE: PRT
<213> ORGANISM: Artificial sequence
<220> FEATURE:
<223> OTHER INFORMATION: synthetic

<400> SEQUENCE: 266

Asp Trp Leu Lys Ala Phe Tyr Asp Lys Val Phe Glu Lys Leu Lys Glu
1               5                   10                  15

Phe Phe

<210> SEQ ID NO 267
<211> LENGTH: 18
<212> TYPE: PRT
<213> ORGANISM: Artificial sequence
<220> FEATURE:
<223> OTHER INFORMATION: synthetic

<400> SEQUENCE: 267

Asp Trp Leu Lys Ala Phe Tyr Asp Lys Val Ala Glu Lys Phe Lys Glu
1               5                   10                  15

Phe Phe

<210> SEQ ID NO 268
<211> LENGTH: 18
<212> TYPE: PRT
<213> ORGANISM: Artificial sequence
<220> FEATURE:
<223> OTHER INFORMATION: synthetic

<400> SEQUENCE: 268

Asp Trp Leu Lys Ala Phe Tyr Asp Lys Val Phe Glu Lys Phe Lys Glu
1               5                   10                  15

Phe Phe

<210> SEQ ID NO 269
<211> LENGTH: 18
<212> TYPE: PRT
<213> ORGANISM: Artificial sequence
<220> FEATURE:
<223> OTHER INFORMATION: synthetic

<400> SEQUENCE: 269

Glu Trp Leu Lys Leu Phe Tyr Glu Lys Val Leu Glu Lys Phe Lys Glu
1               5                   10                  15

Ala Phe

<210> SEQ ID NO 270
<211> LENGTH: 18
<212> TYPE: PRT
<213> ORGANISM: Artificial sequence
<220> FEATURE:
<223> OTHER INFORMATION: synthetic

<400> SEQUENCE: 270

Glu Trp Leu Lys Ala Phe Tyr Asp Lys Val Ala Glu Lys Phe Lys Glu
1               5                   10                  15

Ala Phe

```
<210> SEQ ID NO 271
<211> LENGTH: 18
<212> TYPE: PRT
<213> ORGANISM: Artificial sequence
<220> FEATURE:
<223> OTHER INFORMATION: synthetic

<400> SEQUENCE: 271

Glu Trp Leu Lys Ala Phe Tyr Asp Lys Val Ala Glu Lys Leu Lys Glu
1               5                   10                  15

Phe Phe

<210> SEQ ID NO 272
<211> LENGTH: 18
<212> TYPE: PRT
<213> ORGANISM: Artificial sequence
<220> FEATURE:
<223> OTHER INFORMATION: synthetic

<400> SEQUENCE: 272

Glu Trp Leu Lys Ala Phe Tyr Asp Lys Val Phe Glu Lys Phe Lys Glu
1               5                   10                  15

Ala Phe

<210> SEQ ID NO 273
<211> LENGTH: 18
<212> TYPE: PRT
<213> ORGANISM: Artificial sequence
<220> FEATURE:
<223> OTHER INFORMATION: synthetic

<400> SEQUENCE: 273

Glu Trp Leu Lys Ala Phe Tyr Asp Lys Val Phe Glu Lys Leu Lys Glu
1               5                   10                  15

Phe Phe

<210> SEQ ID NO 274
<211> LENGTH: 18
<212> TYPE: PRT
<213> ORGANISM: Artificial sequence
<220> FEATURE:
<223> OTHER INFORMATION: synthetic

<400> SEQUENCE: 274

Glu Trp Leu Lys Ala Phe Tyr Asp Lys Val Ala Glu Lys Phe Lys Glu
1               5                   10                  15

Phe Phe

<210> SEQ ID NO 275
<211> LENGTH: 18
<212> TYPE: PRT
<213> ORGANISM: Artificial sequence
<220> FEATURE:
<223> OTHER INFORMATION: synthetic

<400> SEQUENCE: 275

Glu Trp Leu Lys Ala Phe Tyr Asp Lys Val Phe Glu Lys Phe Lys Glu
1               5                   10                  15

Phe Phe

<210> SEQ ID NO 276
<211> LENGTH: 14
<212> TYPE: PRT
<213> ORGANISM: Artificial sequence
```

```
<220> FEATURE:
<223> OTHER INFORMATION: synthetic

<400> SEQUENCE: 276

Ala Phe Tyr Asp Lys Val Ala Glu Lys Leu Lys Glu Ala Phe
1               5                   10

<210> SEQ ID NO 277
<211> LENGTH: 14
<212> TYPE: PRT
<213> ORGANISM: Artificial sequence
<220> FEATURE:
<223> OTHER INFORMATION: synthetic

<400> SEQUENCE: 277

Ala Phe Tyr Asp Lys Val Ala Glu Lys Phe Lys Glu Ala Phe
1               5                   10

<210> SEQ ID NO 278
<211> LENGTH: 14
<212> TYPE: PRT
<213> ORGANISM: Artificial sequence
<220> FEATURE:
<223> OTHER INFORMATION: synthetic

<400> SEQUENCE: 278

Ala Phe Tyr Asp Lys Val Ala Glu Lys Phe Lys Glu Ala Phe
1               5                   10

<210> SEQ ID NO 279
<211> LENGTH: 14
<212> TYPE: PRT
<213> ORGANISM: Artificial sequence
<220> FEATURE:
<223> OTHER INFORMATION: synthetic

<400> SEQUENCE: 279

Ala Phe Tyr Asp Lys Phe Phe Glu Lys Phe Lys Glu Phe Phe
1               5                   10

<210> SEQ ID NO 280
<211> LENGTH: 14
<212> TYPE: PRT
<213> ORGANISM: Artificial sequence
<220> FEATURE:
<223> OTHER INFORMATION: synthetic

<400> SEQUENCE: 280

Ala Phe Tyr Asp Lys Phe Phe Glu Lys Phe Lys Glu Phe Phe
1               5                   10

<210> SEQ ID NO 281
<211> LENGTH: 14
<212> TYPE: PRT
<213> ORGANISM: Artificial sequence
<220> FEATURE:
<223> OTHER INFORMATION: synthetic

<400> SEQUENCE: 281

Ala Phe Tyr Asp Lys Val Ala Glu Lys Phe Lys Glu Ala Phe
1               5                   10

<210> SEQ ID NO 282
<211> LENGTH: 14
<212> TYPE: PRT
<213> ORGANISM: Artificial sequence
<220> FEATURE:
```

```
<223> OTHER INFORMATION: synthetic

<400> SEQUENCE: 282

Ala Phe Tyr Asp Lys Val Ala Glu Lys Leu Lys Glu Phe Phe
1               5                   10

<210> SEQ ID NO 283
<211> LENGTH: 14
<212> TYPE: PRT
<213> ORGANISM: Artificial sequence
<220> FEATURE:
<223> OTHER INFORMATION: synthetic

<400> SEQUENCE: 283

Ala Phe Tyr Asp Lys Val Phe Glu Lys Phe Lys Glu Ala Phe
1               5                   10

<210> SEQ ID NO 284
<211> LENGTH: 14
<212> TYPE: PRT
<213> ORGANISM: Artificial sequence
<220> FEATURE:
<223> OTHER INFORMATION: synthetic

<400> SEQUENCE: 284

Ala Phe Tyr Asp Lys Val Phe Glu Lys Leu Lys Glu Phe Phe
1               5                   10

<210> SEQ ID NO 285
<211> LENGTH: 14
<212> TYPE: PRT
<213> ORGANISM: Artificial sequence
<220> FEATURE:
<223> OTHER INFORMATION: synthetic

<400> SEQUENCE: 285

Ala Phe Tyr Asp Lys Val Ala Glu Lys Phe Lys Glu Phe Phe
1               5                   10

<210> SEQ ID NO 286
<211> LENGTH: 14
<212> TYPE: PRT
<213> ORGANISM: Artificial sequence
<220> FEATURE:
<223> OTHER INFORMATION: synthetic

<400> SEQUENCE: 286

Lys Ala Phe Tyr Asp Lys Val Phe Glu Lys Phe Lys Glu Phe
1               5                   10

<210> SEQ ID NO 287
<211> LENGTH: 14
<212> TYPE: PRT
<213> ORGANISM: Artificial sequence
<220> FEATURE:
<223> OTHER INFORMATION: synthetic

<400> SEQUENCE: 287

Leu Phe Tyr Glu Lys Val Leu Glu Lys Phe Lys Glu Ala Phe
1               5                   10

<210> SEQ ID NO 288
<211> LENGTH: 14
<212> TYPE: PRT
<213> ORGANISM: Artificial sequence
<220> FEATURE:
<223> OTHER INFORMATION: synthetic
```

<400> SEQUENCE: 288

Ala Phe Tyr Asp Lys Val Ala Glu Lys Phe Lys Glu Ala Phe
1               5                   10

<210> SEQ ID NO 289
<211> LENGTH: 14
<212> TYPE: PRT
<213> ORGANISM: Artificial sequence
<220> FEATURE:
<223> OTHER INFORMATION: synthetic

<400> SEQUENCE: 289

Ala Phe Tyr Asp Lys Val Ala Glu Lys Leu Lys Glu Phe Phe
1               5                   10

<210> SEQ ID NO 290
<211> LENGTH: 14
<212> TYPE: PRT
<213> ORGANISM: Artificial sequence
<220> FEATURE:
<223> OTHER INFORMATION: synthetic

<400> SEQUENCE: 290

Ala Phe Tyr Asp Lys Val Phe Glu Lys Phe Lys Glu Ala Phe
1               5                   10

<210> SEQ ID NO 291
<211> LENGTH: 14
<212> TYPE: PRT
<213> ORGANISM: Artificial sequence
<220> FEATURE:
<223> OTHER INFORMATION: synthetic

<400> SEQUENCE: 291

Ala Phe Tyr Asp Lys Val Phe Glu Lys Leu Lys Glu Phe Phe
1               5                   10

<210> SEQ ID NO 292
<211> LENGTH: 14
<212> TYPE: PRT
<213> ORGANISM: Artificial sequence
<220> FEATURE:
<223> OTHER INFORMATION: synthetic

<400> SEQUENCE: 292

Ala Phe Tyr Asp Lys Val Ala Glu Lys Phe Lys Glu Phe Phe
1               5                   10

<210> SEQ ID NO 293
<211> LENGTH: 14
<212> TYPE: PRT
<213> ORGANISM: Artificial sequence
<220> FEATURE:
<223> OTHER INFORMATION: synthetic

<400> SEQUENCE: 293

Ala Phe Tyr Asp Lys Val Phe Glu Lys Phe Lys Glu Phe Phe
1               5                   10

<210> SEQ ID NO 294
<211> LENGTH: 18
<212> TYPE: PRT
<213> ORGANISM: Artificial sequence
<220> FEATURE:
<223> OTHER INFORMATION: synthetic

```
<400> SEQUENCE: 294

Asp Trp Leu Lys Ala Leu Tyr Asp Lys Val Ala Glu Lys Leu Lys Glu
1               5                   10                  15

Ala Leu

<210> SEQ ID NO 295
<211> LENGTH: 18
<212> TYPE: PRT
<213> ORGANISM: Artificial sequence
<220> FEATURE:
<223> OTHER INFORMATION: synthetic

<400> SEQUENCE: 295

Asp Trp Phe Lys Ala Phe Tyr Glu Lys Val Ala Glu Lys Leu Lys Glu
1               5                   10                  15

Phe Phe

<210> SEQ ID NO 296
<211> LENGTH: 18
<212> TYPE: PRT
<213> ORGANISM: Artificial sequence
<220> FEATURE:
<223> OTHER INFORMATION: synthetic

<400> SEQUENCE: 296

Asp Trp Phe Lys Ala Phe Tyr Glu Lys Phe Phe Glu Lys Phe Lys Glu
1               5                   10                  15

Phe Phe

<210> SEQ ID NO 297
<211> LENGTH: 18
<212> TYPE: PRT
<213> ORGANISM: Artificial sequence
<220> FEATURE:
<223> OTHER INFORMATION: synthetic

<400> SEQUENCE: 297

Glu Trp Leu Lys Ala Leu Tyr Glu Lys Val Ala Glu Lys Leu Lys Glu
1               5                   10                  15

Ala Leu

<210> SEQ ID NO 298
<211> LENGTH: 18
<212> TYPE: PRT
<213> ORGANISM: Artificial sequence
<220> FEATURE:
<223> OTHER INFORMATION: synthetic

<400> SEQUENCE: 298

Glu Trp Leu Lys Ala Phe Tyr Glu Lys Val Ala Glu Lys Leu Lys Glu
1               5                   10                  15

Ala Phe

<210> SEQ ID NO 299
<211> LENGTH: 18
<212> TYPE: PRT
<213> ORGANISM: Artificial sequence
<220> FEATURE:
<223> OTHER INFORMATION: synthetic

<400> SEQUENCE: 299

Glu Trp Phe Lys Ala Phe Tyr Glu Lys Val Ala Glu Lys Leu Lys Glu
1               5                   10                  15
```

Phe Phe

<210> SEQ ID NO 300
<211> LENGTH: 18
<212> TYPE: PRT
<213> ORGANISM: Artificial sequence
<220> FEATURE:
<223> OTHER INFORMATION: synthetic

<400> SEQUENCE: 300

Glu Trp Leu Lys Ala Phe Tyr Glu Lys Val Phe Glu Lys Phe Lys Glu
1               5                   10                  15

Phe Phe

<210> SEQ ID NO 301
<211> LENGTH: 18
<212> TYPE: PRT
<213> ORGANISM: Artificial sequence
<220> FEATURE:
<223> OTHER INFORMATION: synthetic

<400> SEQUENCE: 301

Glu Trp Leu Lys Ala Phe Tyr Glu Lys Phe Phe Glu Lys Phe Lys Glu
1               5                   10                  15

Phe Phe

<210> SEQ ID NO 302
<211> LENGTH: 18
<212> TYPE: PRT
<213> ORGANISM: Artificial sequence
<220> FEATURE:
<223> OTHER INFORMATION: synthetic

<400> SEQUENCE: 302

Glu Trp Phe Lys Ala Phe Tyr Glu Lys Phe Phe Glu Lys Phe Lys Glu
1               5                   10                  15

Phe Phe

<210> SEQ ID NO 303
<211> LENGTH: 18
<212> TYPE: PRT
<213> ORGANISM: Artificial sequence
<220> FEATURE:
<223> OTHER INFORMATION: synthetic

<400> SEQUENCE: 303

Asp Phe Leu Lys Ala Trp Tyr Asp Lys Val Ala Glu Lys Leu Lys Glu
1               5                   10                  15

Ala Trp

<210> SEQ ID NO 304
<211> LENGTH: 18
<212> TYPE: PRT
<213> ORGANISM: Artificial sequence
<220> FEATURE:
<223> OTHER INFORMATION: synthetic

<400> SEQUENCE: 304

Glu Phe Leu Lys Ala Trp Tyr Glu Lys Val Ala Glu Lys Leu Lys Glu
1               5                   10                  15

Ala Trp

```
<210> SEQ ID NO 305
<211> LENGTH: 18
<212> TYPE: PRT
<213> ORGANISM: Artificial sequence
<220> FEATURE:
<223> OTHER INFORMATION: synthetic

<400> SEQUENCE: 305

Asp Phe Trp Lys Ala Trp Tyr Asp Lys Val Ala Glu Lys Leu Lys Glu
1               5                   10                  15

Trp Trp

<210> SEQ ID NO 306
<211> LENGTH: 18
<212> TYPE: PRT
<213> ORGANISM: Artificial sequence
<220> FEATURE:
<223> OTHER INFORMATION: synthetic

<400> SEQUENCE: 306

Glu Phe Trp Lys Ala Trp Tyr Glu Lys Val Ala Glu Lys Leu Lys Glu
1               5                   10                  15

Trp Trp

<210> SEQ ID NO 307
<211> LENGTH: 18
<212> TYPE: PRT
<213> ORGANISM: Artificial sequence
<220> FEATURE:
<223> OTHER INFORMATION: synthetic

<400> SEQUENCE: 307

Asp Lys Leu Lys Ala Phe Tyr Asp Lys Val Phe Glu Trp Ala Lys Glu
1               5                   10                  15

Ala Phe

<210> SEQ ID NO 308
<211> LENGTH: 18
<212> TYPE: PRT
<213> ORGANISM: Artificial sequence
<220> FEATURE:
<223> OTHER INFORMATION: synthetic

<400> SEQUENCE: 308

Asp Lys Trp Lys Ala Val Tyr Asp Lys Phe Ala Glu Ala Phe Lys Glu
1               5                   10                  15

Phe Leu

<210> SEQ ID NO 309
<211> LENGTH: 18
<212> TYPE: PRT
<213> ORGANISM: Artificial sequence
<220> FEATURE:
<223> OTHER INFORMATION: synthetic

<400> SEQUENCE: 309

Glu Lys Leu Lys Ala Phe Tyr Glu Lys Val Phe Glu Trp Ala Lys Glu
1               5                   10                  15

Ala Phe

<210> SEQ ID NO 310
<211> LENGTH: 18
<212> TYPE: PRT
<213> ORGANISM: Artificial sequence
```

```
<220> FEATURE:
<223> OTHER INFORMATION: synthetic

<400> SEQUENCE: 310

Glu Lys Trp Lys Ala Val Tyr Glu Lys Phe Ala Glu Ala Phe Lys Glu
1               5                   10                  15

Phe Leu

<210> SEQ ID NO 311
<211> LENGTH: 18
<212> TYPE: PRT
<213> ORGANISM: Artificial sequence
<220> FEATURE:
<223> OTHER INFORMATION: synthetic

<400> SEQUENCE: 311

Asp Trp Leu Lys Ala Phe Val Asp Lys Phe Ala Glu Lys Phe Lys Glu
1               5                   10                  15

Ala Tyr

<210> SEQ ID NO 312
<211> LENGTH: 18
<212> TYPE: PRT
<213> ORGANISM: Artificial sequence
<220> FEATURE:
<223> OTHER INFORMATION: synthetic

<400> SEQUENCE: 312

Glu Lys Trp Lys Ala Val Tyr Glu Lys Phe Ala Glu Ala Phe Lys Glu
1               5                   10                  15

Phe Leu

<210> SEQ ID NO 313
<211> LENGTH: 18
<212> TYPE: PRT
<213> ORGANISM: Artificial sequence
<220> FEATURE:
<223> OTHER INFORMATION: synthetic

<400> SEQUENCE: 313

Asp Trp Leu Lys Ala Phe Val Tyr Asp Lys Val Phe Lys Leu Lys Glu
1               5                   10                  15

Phe Phe

<210> SEQ ID NO 314
<211> LENGTH: 18
<212> TYPE: PRT
<213> ORGANISM: Artificial sequence
<220> FEATURE:
<223> OTHER INFORMATION: synthetic

<400> SEQUENCE: 314

Glu Trp Leu Lys Ala Phe Val Tyr Glu Lys Val Phe Lys Leu Lys Glu
1               5                   10                  15

Phe Phe

<210> SEQ ID NO 315
<211> LENGTH: 18
<212> TYPE: PRT
<213> ORGANISM: Artificial sequence
<220> FEATURE:
<223> OTHER INFORMATION: synthetic

<400> SEQUENCE: 315
```

Asp Trp Leu Arg Ala Phe Tyr Asp Lys Val Ala Glu Lys Leu Lys Glu
1               5                   10                  15

Ala Phe

<210> SEQ ID NO 316
<211> LENGTH: 18
<212> TYPE: PRT
<213> ORGANISM: Artificial sequence
<220> FEATURE:
<223> OTHER INFORMATION: synthetic

<400> SEQUENCE: 316

Glu Trp Leu Arg Ala Phe Tyr Glu Lys Val Ala Glu Lys Leu Lys Glu
1               5                   10                  15

Ala Phe

<210> SEQ ID NO 317
<211> LENGTH: 18
<212> TYPE: PRT
<213> ORGANISM: Artificial sequence
<220> FEATURE:
<223> OTHER INFORMATION: synthetic

<400> SEQUENCE: 317

Asp Trp Leu Lys Ala Phe Tyr Asp Arg Val Ala Glu Lys Leu Lys Glu
1               5                   10                  15

Ala Phe

<210> SEQ ID NO 318
<211> LENGTH: 18
<212> TYPE: PRT
<213> ORGANISM: Artificial sequence
<220> FEATURE:
<223> OTHER INFORMATION: synthetic

<400> SEQUENCE: 318

Glu Trp Leu Lys Ala Phe Tyr Glu Arg Val Ala Glu Lys Leu Lys Glu
1               5                   10                  15

Ala Phe

<210> SEQ ID NO 319
<211> LENGTH: 18
<212> TYPE: PRT
<213> ORGANISM: Artificial sequence
<220> FEATURE:
<223> OTHER INFORMATION: synthetic

<400> SEQUENCE: 319

Asp Trp Leu Lys Ala Phe Tyr Asp Lys Val Ala Glu Arg Leu Lys Glu
1               5                   10                  15

Ala Phe

<210> SEQ ID NO 320
<211> LENGTH: 18
<212> TYPE: PRT
<213> ORGANISM: Artificial sequence
<220> FEATURE:
<223> OTHER INFORMATION: synthetic

<400> SEQUENCE: 320

Glu Trp Leu Lys Ala Phe Tyr Glu Lys Val Ala Glu Arg Leu Lys Glu
1               5                   10                  15

Ala Phe

<210> SEQ ID NO 321
<211> LENGTH: 18
<212> TYPE: PRT
<213> ORGANISM: Artificial sequence
<220> FEATURE:
<223> OTHER INFORMATION: synthetic

<400> SEQUENCE: 321

Asp Trp Leu Lys Ala Phe Tyr Asp Lys Val Ala Glu Lys Leu Arg Glu
1               5                   10                  15

Ala Phe

<210> SEQ ID NO 322
<211> LENGTH: 18
<212> TYPE: PRT
<213> ORGANISM: Artificial sequence
<220> FEATURE:
<223> OTHER INFORMATION: synthetic

<400> SEQUENCE: 322

Glu Trp Leu Lys Ala Phe Tyr Glu Lys Val Ala Glu Lys Leu Arg Glu
1               5                   10                  15

Ala Phe

<210> SEQ ID NO 323
<211> LENGTH: 18
<212> TYPE: PRT
<213> ORGANISM: Artificial sequence
<220> FEATURE:
<223> OTHER INFORMATION: synthetic

<400> SEQUENCE: 323

Asp Trp Leu Lys Ala Phe Tyr Asp Arg Val Ala Glu Arg Leu Lys Glu
1               5                   10                  15

Ala Phe

<210> SEQ ID NO 324
<211> LENGTH: 18
<212> TYPE: PRT
<213> ORGANISM: Artificial sequence
<220> FEATURE:
<223> OTHER INFORMATION: synthetic

<400> SEQUENCE: 324

Glu Trp Leu Lys Ala Phe Tyr Glu Arg Val Ala Glu Arg Leu Lys Glu
1               5                   10                  15

Ala Phe

<210> SEQ ID NO 325
<211> LENGTH: 18
<212> TYPE: PRT
<213> ORGANISM: Artificial sequence
<220> FEATURE:
<223> OTHER INFORMATION: synthetic

<400> SEQUENCE: 325

Asp Trp Leu Arg Ala Phe Tyr Asp Lys Val Ala Glu Lys Leu Arg Glu
1               5                   10                  15

Ala Phe

<210> SEQ ID NO 326

```
<211> LENGTH: 18
<212> TYPE: PRT
<213> ORGANISM: Artificial sequence
<220> FEATURE:
<223> OTHER INFORMATION: synthetic

<400> SEQUENCE: 326

Glu Trp Leu Arg Ala Phe Tyr Glu Lys Val Ala Glu Lys Leu Arg Glu
1               5                   10                  15

Ala Phe

<210> SEQ ID NO 327
<211> LENGTH: 18
<212> TYPE: PRT
<213> ORGANISM: Artificial sequence
<220> FEATURE:
<223> OTHER INFORMATION: synthetic

<400> SEQUENCE: 327

Asp Trp Leu Arg Ala Phe Tyr Asp Arg Val Ala Glu Lys Leu Lys Glu
1               5                   10                  15

Ala Phe

<210> SEQ ID NO 328
<211> LENGTH: 18
<212> TYPE: PRT
<213> ORGANISM: Artificial sequence
<220> FEATURE:
<223> OTHER INFORMATION: synthetic

<400> SEQUENCE: 328

Glu Trp Leu Arg Ala Phe Tyr Glu Arg Val Ala Glu Lys Leu Lys Glu
1               5                   10                  15

Ala Phe

<210> SEQ ID NO 329
<211> LENGTH: 18
<212> TYPE: PRT
<213> ORGANISM: Artificial sequence
<220> FEATURE:
<223> OTHER INFORMATION: synthetic

<400> SEQUENCE: 329

Asp Trp Leu Lys Ala Phe Tyr Asp Lys Val Ala Glu Arg Leu Arg Glu
1               5                   10                  15

Ala Phe

<210> SEQ ID NO 330
<211> LENGTH: 18
<212> TYPE: PRT
<213> ORGANISM: Artificial sequence
<220> FEATURE:
<223> OTHER INFORMATION: synthetic

<400> SEQUENCE: 330

Glu Trp Leu Lys Ala Phe Tyr Glu Lys Val Ala Glu Arg Leu Arg Glu
1               5                   10                  15

Ala Phe

<210> SEQ ID NO 331
<211> LENGTH: 18
<212> TYPE: PRT
<213> ORGANISM: Artificial sequence
<220> FEATURE:
```

<223> OTHER INFORMATION: synthetic

<400> SEQUENCE: 331

Asp Trp Leu Arg Ala Phe Tyr Asp Lys Val Ala Glu Arg Leu Lys Glu
1               5                   10                  15

Ala Phe

<210> SEQ ID NO 332
<211> LENGTH: 18
<212> TYPE: PRT
<213> ORGANISM: Artificial sequence
<220> FEATURE:
<223> OTHER INFORMATION: synthetic

<400> SEQUENCE: 332

Glu Trp Leu Arg Ala Phe Tyr Glu Lys Val Ala Glu Arg Leu Lys Glu
1               5                   10                  15

Ala Phe

<210> SEQ ID NO 333
<211> LENGTH: 18
<212> TYPE: PRT
<213> ORGANISM: Artificial sequence
<220> FEATURE:
<223> OTHER INFORMATION: synthetic

<400> SEQUENCE: 333

Phe Ala Glu Lys Phe Lys Glu Ala Val Lys Asp Tyr Phe Ala Lys Phe
1               5                   10                  15

Trp Asp

<210> SEQ ID NO 334
<211> LENGTH: 18
<212> TYPE: PRT
<213> ORGANISM: Artificial sequence
<220> FEATURE:
<223> OTHER INFORMATION: synthetic

<400> SEQUENCE: 334

Asp Trp Phe Lys Ala Phe Tyr Asp Lys Val Ala Glu Lys Phe Lys Glu
1               5                   10                  15

Ala Phe

<210> SEQ ID NO 335
<211> LENGTH: 18
<212> TYPE: PRT
<213> ORGANISM: Artificial sequence
<220> FEATURE:
<223> OTHER INFORMATION: synthetic

<400> SEQUENCE: 335

Asp Trp Leu Lys Ala Phe Tyr Asp Lys Val Ala Glu Lys Leu Lys Glu
1               5                   10                  15

Ala Phe

<210> SEQ ID NO 336
<211> LENGTH: 34
<212> TYPE: PRT
<213> ORGANISM: Artificial sequence
<220> FEATURE:
<223> OTHER INFORMATION: synthetic

<400> SEQUENCE: 336

Pro Ala Leu Glu Asp Leu Arg Gln Gly Leu Leu Pro Val Leu Glu Ser
1               5                   10                  15

Phe Lys Val Phe Leu Ser Ala Leu Glu Glu Tyr Thr Lys Lys Leu Asn
            20                  25                  30

Thr Gln

<210> SEQ ID NO 337
<211> LENGTH: 23
<212> TYPE: DNA
<213> ORGANISM: Artificial sequence
<220> FEATURE:
<223> OTHER INFORMATION: synthetic

<400> SEQUENCE: 337
gccagtatgc aagggagctc atg                                           23

<210> SEQ ID NO 338
<211> LENGTH: 25
<212> TYPE: PRT
<213> ORGANISM: Artificial sequence
<220> FEATURE:
<223> OTHER INFORMATION: synthetic

<400> SEQUENCE: 338

Gly Ala Ser Thr Ala Met Gly Ala Thr Cys Ala Asn Cys Ala Arg Gly
1               5                   10                  15

Gly Glu Gly Cys Leu Cys Ala Met Gly
            20                  25

<210> SEQ ID NO 339
<211> LENGTH: 23
<212> TYPE: DNA
<213> ORGANISM: Artificial sequence
<220> FEATURE:
<223> OTHER INFORMATION: synthetic

<400> SEQUENCE: 339
gccagtatgc aatggagctc atg                                           23

<210> SEQ ID NO 340
<211> LENGTH: 25
<212> TYPE: PRT
<213> ORGANISM: Artificial sequence
<220> FEATURE:
<223> OTHER INFORMATION: synthetic

<400> SEQUENCE: 340

Gly Ala Ser Thr Ala Met Gly Ala Thr Cys Ala Asn Cys Ala Met Gly
1               5                   10                  15

Gly Glu Gly Cys Leu Cys Ala Thr Gly
            20                  25

<210> SEQ ID NO 341
<211> LENGTH: 9
<212> TYPE: PRT
<213> ORGANISM: Artificial sequence
<220> FEATURE:
<223> OTHER INFORMATION: synthetic

<400> SEQUENCE: 341

Ala Ser Met Thr Asn Met Glu Leu Met
1               5